United States Patent
Csjernyik et al.

(10) Patent No.: US 8,415,483 B2
(45) Date of Patent: Apr. 9, 2013

(54) COMPOUNDS AND THEIR USE AS BACE INHIBITORS

(75) Inventors: Gabor Csjernyik, Södertälje (SE); Sofia Karlström, Södertälje (SE); Annika Kers, Södertälje (SE); Karin Kolmodin, Södertälje (SE); Martin Nylöf, Södertälje (SE); Liselotte Öhberg, Södertälje (SE); Laszlo Rakos, Södertälje (SE); Lars Sandberg, Södertälje (SE); Fernando Sehgelmeble, Södertälje (SE); Peter Söderman, Södertälje (SE); Britt-Marie Swahn, Södertälje (SE); Stefan Von Berg, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 13/331,284

(22) Filed: Dec. 20, 2011

(65) Prior Publication Data
US 2012/0165347 A1     Jun. 28, 2012

Related U.S. Application Data

(60) Provisional application No. 61/425,852, filed on Dec. 22, 2010, provisional application No. 61/529,620, filed on Aug. 31, 2011.

(51) Int. Cl.
*A61K 31/4184* (2006.01)
*C07D 235/02* (2006.01)
*A61K 31/4439* (2006.01)

(52) U.S. Cl.
USPC ............ 548/301.1; 548/110; 546/15; 514/64; 514/278; 514/393

(58) Field of Classification Search ................ 548/301.1
See application file for complete search history.

(56) References Cited

FOREIGN PATENT DOCUMENTS
| | | |
|---|---|---|
| WO | 2010013794 | 2/2010 |
| WO | 2010021680 | 2/2010 |
| WO | 2010105179 | 9/2010 |

OTHER PUBLICATIONS

Thompson et al., Current Medicinal Chemistry, Oct. 2002, 9(19), pp. 1751-1762.*

* cited by examiner

*Primary Examiner* — Laura L. Stockton
(74) *Attorney, Agent, or Firm* — Kenneth F. Mitchell

(57) ABSTRACT

The present invention relates to compounds of formula (I) and their pharmaceutical compositions. In addition, the present invention relates to therapeutic methods for the treatment and/or prevention of Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

8 Claims, 8 Drawing Sheets

COMPOUNDS AND THEIR USE AS BACE INHIBITORS

CROSS-REFERENCE TO RELATED APPLICATIONS

This application claims priority to Application Nos. 61/425,852 (filed 22 Dec. 2010) and 61/529,620 (filed 31 Aug. 2011). The entire text of each of the above-referenced patent applications is incorporated by reference into this patent.

The present invention relates to compounds and therapeutically acceptable salts thereof, their pharmaceutical compositions, processes for making them and their use as medicaments for treatment and/or prevention of various diseases. In particular the invention relates to compounds, which are inhibitors of β-secretase and hence inhibit the formation of amyloid β (Aβ) peptides and will be used for treatment and/or prevention of Aβ-related pathologies such as Alzheimer's disease, Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

BACKGROUND

The prime neuropathological event distinguishing Alzheimer's disease (AD) is deposition of the 40-42 residue amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Since soluble Aβ can be found in both plasma and cerebrospinal fluid (CSF), and in the medium from cultured cells, APP has to undergo proteolysis. There are three main cleavages of APP that are relevant to the pathobiology of AD, the so-called α-, β-, and γ-cleavages. The α-cleavage, which occurs roughly in the middle of the Aβ domain in APP is executed by the metalloproteases ADAM10 or ADAM17 (the latter also known as TACE). The β-cleavage, occurring at the N terminus of Aβ, is generated by the transmembrane aspartyl protease Beta site APP Cleaving Enzyme1 (BACE1). The γ-cleavage, generating the Aβ C termini and subsequent release of the peptide, is effected by a multi-subunit aspartyl protease named γ-secretase. ADAM10/17 cleavage followed by γ-secretase cleavage results in the release of the soluble p3 peptide, an N-terminally truncated Aβ fragment that fails to form amyloid deposits in humans. This proteolytic route is commonly referred to as the non-amyloidogenic pathway. Consecutive cleavages by BACE1 and γ-secretase generates the intact Aβ peptide, hence this processing scheme has been termed the amyloidogenic pathway. With this knowledge at hand, it is possible to envision two possible avenues of lowering Aβ production: stimulating non-amyloidogenic processing, or inhibit or modulate amyloidogenic processing. This application focuses on the latter strategy, inhibition or modulation of amyloidogenic processing.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630). β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease or Asp2 or Beta site APP Cleaving Enzyme (BACE), as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324). BACE is a membrane bound type 1 protein that is synthesized as a partially active proenzyme, and is abundantly expressed in brain tissue. It is thought to represent the major β-secretase activity, and is considered to be the rate-limiting step in the production of amyloid-β-peptide (Aβ).

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof. BACE is therefore an important candidate for the development of drugs as a treatment and/or prophylaxis of Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, presenile dementia, senile dementia and dementia associated with Parkinson's disease, progressive supranuclear palsy or cortical basal degeneration. It would therefore be useful to inhibit the deposition of Aβ and portions thereof by inhibiting BACE through inhibitors such as the compounds provided herein.

The therapeutic potential of inhibiting the deposition of Aβ has motivated many groups to isolate and characterize secretase enzymes and to identify their potential inhibitors.

DISCLOSURE OF THE INVENTION

The present invention is directed to compounds according to formula (I):

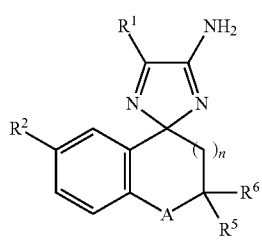

wherein
A is —O— or —CH$_2$—;
n is 0 or 1;
R$^1$ is C$_{1-6}$alkyl or C$_{1-6}$haloalkyl;
R$^2$ is hydrogen, C$_{0-6}$alkylaryl, C$_{0-6}$alkylheteroaryl, C$_{2-6}$alkynyl, C$_{2-6}$alkenyl, C$_{1-6}$alkyl, halogen, cyano, C$_{1-6}$haloalkyl, NHC(O)R$^9$ or OR$^8$, wherein said C$_{0-6}$alkylaryl, C$_{0-6}$alkylheteroaryl, C$_{2-6}$alkynyl, C$_{2-6}$alkenyl, C$_{1-6}$alkyl, or C$_{1-6}$haloalkyl is optionally substituted with one to three R$^7$;
R$^5$ and R$^6$ are independently hydrogen, heterocyclyl, C$_{3-6}$cycloalkyl, aryl, heteroaryl or C$_{1-6}$alkyl, wherein said heterocyclyl, C$_{3-6}$cycloalkyl, aryl, heteroaryl or C$_{1-6}$alkyl is optionally substituted with one or two substituents independently selected from halogen, C$_{1-6}$alkyl, C$_{1-6}$haloalkyl, cyano, or OR$^8$;
or R$^5$ and R$^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, C$_{1-6}$alkyl, C$_{1-6}$haloalkyl, cyano, or OR$^8$; and ring B is optionally fused with an aryl or heteroaryl to form a bi- or polycyclic system;
R$^7$ is independently C$_{1-6}$alkyl, halogen, cyano, C$_{0-6}$alkyl C$_{3-6}$cycloalkyl, C$_{1-6}$haloalkyl, OC$_{1-6}$alkyl, OC$_{1-6}$haloalkyl, C$_{2-6}$alkynyl or C$_{2-6}$alkenyl, wherein said C$_{1-6}$alkyl, C$_{0-6}$alkylC$_{3-6}$cycloalkyl, C$_{1-6}$haloalkyl, OC$_{1-6}$alkyl, OC$_{1-6}$haloalkyl, C$_{2-6}$alkynyl or C$_{2-6}$alkenyl is optionally substituted with 1-3 substituents independently selected from halogen, cyano, C$_{1-6}$alkyl, C$_{1-6}$haloalkyl, OC$_{1-6}$alkyl, and OC$_{1-6}$haloalkyl;
R$^8$ is independently hydrogen, C$_{1-6}$alkyl, C$_{2-6}$alkynyl, C$_{1-6}$haloalkyl, aryl or heteroaryl; wherein said C$_{1-6}$alkyl, C$_{1-6}$haloalkyl, aryl or heteroaryl is optionally substituted with a group selected from halogen, cyano, and C$_{1-6}$alkyl;
R$^9$ is a heteroaryl; wherein said heteroaryl is optionally substituted with halogen, cyano, OR$^8$, C$_{1-6}$haloalkyl or C$_{1-6}$alkyl;
as a free base or a pharmaceutically acceptable salt thereof.

In one embodiment of the present invention, A is —CH$_2$—.
In one embodiment of the present invention, n is 0.
In one embodiment of the present invention, R$^1$ is C$_{1-3}$alkyl. In another embodiment of the invention, R$^1$ is methyl or ethyl. In yet another embodiment, R$^1$ is methyl.
In one embodiment of the present invention, R$^2$ is aryl, heteroaryl, C$_{2-6}$alkynyl, halogen, NHC(O)R$^9$ or OR$^8$, wherein said aryl, heteroaryl or C$_{2-6}$alkynyl is optionally substituted with one to three R$^7$. In another embodiment of the invention, R$^2$ is aryl, heteroaryl, C$_{2-6}$alkynyl or OR$^8$, wherein said aryl, heteroaryl or C$_{2-6}$alkynyl is optionally substituted with one to three R$^7$.

In one embodiment of the present invention, R$^5$ and R$^6$ are independently hydrogen or heterocyclyl wherein said heterocyclyl is optionally substituted with one or two substituents independently selected from C$_{1-6}$alkyl or OR$^8$.

In one embodiment of the present invention, R$^5$ and R$^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, C$_{1-6}$alkyl or OR$^8$; and ring B is optionally fused with an aryl or heteroaryl to form a bi- or polycyclic system.

In another embodiment of the invention, R$^5$ and R$^6$ together with the carbon to which they are attached, form a ring B, which is a 3-14 membered cycloalkyl monocyclic ring; and wherein ring B is optionally substituted by one or two substituents independently selected from oxo, halogen, C$_{1-6}$alkyl or OR$^8$. In yet another embodiment, R$^5$ and R$^6$ together with the carbon to which they are attached form a cyclohexyl ring, which is substituted with OR$^8$.

In one embodiment of the present invention, R$^7$ is independently C$_{1-6}$alkyl, halogen, cyano, C$_{0-6}$alkylC$_{3-6}$cycloalkyl, C$_{1-6}$haloalkyl, OC$_{1-6}$alkyl or C$_{2-6}$alkynyl, wherein said C$_{1-6}$alkyl, C$_{0-6}$alkylC$_{3-6}$cycloalkyl, C$_{1-6}$haloalkyl, OC$_{1-6}$alkyl, or C$_{2-6}$alkynyl is optionally substituted with 1-3 substituents independently selected from halogen, cyano, C$_{1-6}$alkyl, C$_{1-6}$haloalkyl, OC$_{1-6}$alkyl and OC$_{1-6}$haloalkyl. In another embodiment of the invention, R$^7$ is halogen, cyano, C$_{0-6}$alkylC$_{3-6}$cycloalkyl, C$_{1-6}$haloalkyl, OC$_{1-6}$alkyl or C$_{2-6}$alkynyl, wherein said C$_{0-6}$alkylC$_{3-6}$cycloalkyl, C$_{1-6}$haloalkyl, OC$_{1-6}$alkyl, or C$_{2-6}$alkynyl is optionally substituted with 1-3 substituents independently selected from OC$_{1-6}$alkyl and OC$_{1-6}$haloalkyl.

In one embodiment of the present invention, R$^8$ is independently C$_{1-6}$alkyl, C$_{2-6}$alkynyl or C$_{1-6}$haloalkyl. In another embodiment of the invention, R$^8$ is independently C$_{1-6}$alkyl or C$_{1-6}$haloalkyl.

In one embodiment of the present invention, R$^9$ is heteroaryl; wherein said heteroaryl is optionally substituted with halogen, cyano, OR$^8$, C$_{1-6}$haloalkyl or C$_{1-6}$alkyl.

In one embodiment of the present invention,
A is —O— or —CH$_2$—;
n is 0 or 1;
R$^1$ is C$_{1-6}$alkyl;
R$^2$ is C$_{0-6}$alkylaryl, C$_{0-6}$alkylheteroaryl, C$_{2-6}$alkynyl, halogen, NHC(O)R$^9$ or OR$^8$; wherein said C$_{0-6}$alkylaryl, C$_{0-6}$alkylheteroaryl or C$_{2-6}$alkynyl is optionally substituted with one to three R$^7$;
R$^5$ and R$^6$ are independently hydrogen or heterocyclyl, wherein said heterocyclyl, is optionally substituted with one or two substituents independently selected from halogen, C$_{1-6}$alkyl, C$_{1-6}$haloalkyl, cyano or OR$^8$;
or R$^5$ and R$^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, C$_{1-6}$alkyl or OR$^8$; and ring B is optionally fused with an aryl or heteroaryl to form a bi- or polycyclic system;
R$^7$ is independently C$_{1-6}$alkyl, halogen, cyano, C$_{0-6}$alkyl C$_{3-6}$cycloalkyl, C$_{1-6}$haloalkyl, OC$_{1-6}$alkyl or C$_{2-6}$alkynyl, wherein said C$_{1-6}$alkyl, C$_{0-6}$alkylC$_{3-6}$cycloalkyl, C$_{1-6}$haloalkyl, OC$_{1-6}$alkyl or C$_{2-6}$alkynyl is optionally substituted with 1-3 substituents independently selected from halogen, cyano, $C_{1-6}$alkyl, $C_{1-6}$haloalkyl, $OC_{1-6}$alkyl and $OC_{1-6}$haloalkyl;

$R^8$ is independently $C_{1-6}$alkyl, $C_{2-6}$alkynyl or $C_{1-6}$haloalkyl; wherein said $C_{1-6}$alkyl, $C_{1-6}$haloalkyl, aryl or heteroaryl is optionally substituted with a group selected from halogen, cyano, or $C_{1-6}$alkyl;

$R^9$ is heteroaryl, wherein said heteroaryl is optionally substituted with halogen, cyano, $OR^8$, $C_{1-6}$haloalkyl or $C_{1-6}$alkyl.

In one embodiment of the present invention,

A is —O— or —CH$_2$—;

n is 0 or 1;

$R^1$ is $C_{1-3}$alkyl;

$R^2$ is aryl, heteroaryl, $C_{2-6}$alkynyl, halogen, NHC(O)$R^9$ or $OR^8$, wherein said aryl, heteroaryl or $C_{2-6}$alkynyl is optionally substituted with one to three $R^7$;

$R^5$ and $R^6$ are independently hydrogen or heterocyclyl, wherein said heterocyclyl is optionally substituted with two substituents independently selected from $C_{1-6}$alkyl;

or $R^5$ and $R^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, $C_{1-6}$alkyl or $OR^8$; and ring B is optionally fused with an aryl or heteroaryl to form a bicyclic system;

$R^7$ is independently $C_{1-6}$alkyl, halogen, cyano, $C_{0-6}$alkyl $C_{3-6}$cycloalkyl, $C_{1-6}$haloalkyl, $OC_{1-6}$alkyl or $C_{2-6}$alkynyl, wherein said $C_{1-6}$alkyl, $C_{0-6}$alkyl$C_{3-6}$cycloalkyl, $C_{1-6}$haloalkyl, $OC_{1-6}$alkyl or $C_{2-6}$alkynyl, is optionally substituted with 1-3 substituents independently selected from halogen, cyano, $C_{1-6}$alkyl, $C_{1-6}$haloalkyl, $OC_{1-6}$alkyl and $OC_{1-6}$haloalkyl;

$R^8$ is independently $C_{1-6}$alkyl, $C_{2-6}$alkynyl or $C_{1-6}$haloalkyl; wherein said $C_{1-6}$alkyl, $C_{1-6}$haloalkyl, aryl or heteroaryl is optionally substituted with a group selected from halogen, cyano or $C_{1-6}$alkyl; and $R^9$ is heteroaryl, wherein said heteroaryl is optionally substituted with halogen, cyano, $OR^8$, $C_{1-6}$haloalkyl or $C_{1-6}$alkyl.

In one embodiment of the present invention,

A is —CH—;

n is 0;

$R^1$ is methyl or ethyl;

$R^2$ is aryl, heteroaryl or $C_{2-6}$alkynyl, wherein said aryl, heteroaryl or $C_{2-6}$alkynyl is optionally substituted with one to three $R^7$;

$R^5$ and $R^6$ together with the carbon to which they are attached form a cyclohexyl ring, which is substituted with $OR^8$;

$R^7$ is independently $C_{1-3}$alkyl, halogen, cyano or $C_{2-6}$alkynyl;

$R^8$ is $C_{1-3}$ alkyl.

In one embodiment of the present invention,

A is —CH$_2$—;

n is 0;

$R^1$ is methyl or ethyl;

$R^2$ is phenyl or pyridinyl, wherein said phenyl or pyridinyl is optionally substituted with one or two $R^7$;

$R^5$ and $R^6$ together with the carbon to which they are attached form a cyclohexyl ring, which is substituted with methoxy;

$R^7$ is independently Chloro, fluoro, cyano or prop-1-yn-1-yl.

In one embodiment, the compound of formula (I) has the following configuration:

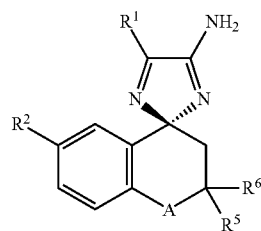

In another embodiment, the invention relates to a compound of formula (I) selected from the group consisting of:

6-(3,5-dichlorophenyl)-5'-methylspiro[chroman-4,2'-imidazol]-4'-amine;

6-(5-chloropyridin-3-yl)-5'-methylspiro[chroman-4,2'-imidazol]-4'-amine;

6-(3,5-difluorophenyl)-5'-methylspiro[chroman-4,2'-imidazol]-4'-amine;

6-(3,5-dimethylphenyl)-5'-methylspiro[chroman-4,2'-imidazol]-4'-amine;

6-(2,5-dimethoxyphenyl)-5'-methylspiro[chroman-4,2'-imidazol]-4'-amine;

6-(2,3-difluorophenyl)-5'-methylspiro[chroman-4,2'-imidazol]-4'-amine;

6-(2,5-dimethylphenyl)-5'-methylspiro[chroman-4,2'-imidazol]-4'-amine;

6-(5-fluoro-2-methoxyphenyl)-5'-methylspiro[chroman-4,2'-imidazol]-4'-amine;

6-(2-fluoro-3-methoxyphenyl)-5'-methylspiro[chroman-4,2'-imidazol]-4'-amine;

6-(2-methoxy-5-methylphenyl)-5'-methylspiro[chroman-4,2'-imidazol]-4'-amine;

6-(2-fluoro-5-methylphenyl)-5'-methylspiro[chroman-4,2'-imidazol]-4'-amine;

6-(2-fluoro-5-methoxyphenyl)-5'-methylspiro[chroman-4,2'-imidazol]-4'-amine;

N-(4'-amino-5'-methyl-spiro[chromane-4,2'-imidazole]-6-yl)-5-chloro-pyridine-2-carboxamide;

N-(4'-amino-5'-methyl-spiro[chromane-4,2'-imidazole]-6-yl)-5-(trifluoromethyl)pyridine-2-carboxamide;

N-(4'-amino-5'-methyl-spiro[chromane-4,2'-imidazole]-6-yl)-5-but-2-ynoxy-pyridine-2-carboxamide;

N-(4'-amino-5'-methyl-spiro[chromane-4,2'-imidazole]-6-yl)-5-but-2-ynoxy-pyrazine-2-carboxamide;

N-(4'-amino-5'-methyl-spiro[chromane-4,2'-imidazole]-6-yl)-5-methyl-thiophene-2-carboxamide;

N-(4'-amino-5'-methyl-spiro[chromane-4,2'-imidazole]-6-yl)-3,5-dichloro-pyridine-2-carboxamide;

6'-bromo-4-(difluoromethoxy)-5"-methyl-3'H-dispiro[cyclohexane-1,2'-indene-1',2"-imidazol]-4"-amine;

6'-bromo-4-methoxy-5"-methyl-3'H-dispiro[cyclohexane-1,2'-indene-1',2"-imidazol]-4"-amine;

4-methoxy-5"-methyl-6'-[5-(prop-1-yn-1-yl)pyridin-3-yl]-3'H-dispiro[cyclohexane-1,2'-indene-1',2"-imidazol]-4"-amine;

4-methoxy-5"-methyl-6'-[4-(prop-1-yn-1-yl)pyridin-2-yl]-3'H-dispiro[cyclohexane-1,2'-indene-1',2"-imidazol]-4"-amine;

5-(4"-amino-4-methoxy-5"-methyl-3'H-dispiro[cyclohexane-1,2'-indene-1',2"-imidazol]-6'-yl)benzene-1,3-dicarbonitrile;

3-(4"-amino-4-methoxy-5"-methyl-3'H-dispiro[cyclohexane-1,2'-indene-1',2"-imidazol]-6'-yl)-5-chlorobenzonitrile;

6'-(5-chloropyridin-3-yl)-4-methoxy-5"-methyl-3'H-dispiro[cyclohexane-1,2'-indene-1',2"-imidazol]-4"-amine;

6'-(5-fluoropyridin-3-yl)-4-methoxy-5''-methyl-3'H-dispiro[cyclohexane-1,2'-indene-1',2''-imidazol]-4''-amine;

5-(4''-amino-4-methoxy-5''-methyl-3'H-dispiro[cyclohexane-1,2'-indene-1',2''-imidazol]-6'-yl)-2-fluorobenzonitrile;

6'-(3,3-dimethylbut-1-yn-1-yl)-4-methoxy-5''-methyl-3'H-dispiro[cyclohexane-1,2'-indene-1',2''-imidazol]-4''-amine;

6'-(cyclopropylethynyl)-4-methoxy-5''-methyl-3'H-dispiro[cyclohexane-1,2'-indene-1',2''-imidazol]-4''-amine;

N-(4''-amino-4-methoxy-5''-methyl-3'H-dispiro[cyclohexane-1,2'-indene-1',2''-imidazol]-6'-yl)-5-bromopyrimidine-2-carboxamide;

N-(4''-amino-4-methoxy-5''-methyl-3'H-dispiro[cyclohexane-1,2'-indene-1',2''-imidazol]-6'-yl)-5-(trifluoromethyl)pyridine-2-carboxamide;

N-(4''-amino-4-methoxy-5''-methyl-3'H-dispiro[cyclohexane-1,2'-indene-1',2''-imidazol]-6'-yl)-5-chloro-3-methyl-1-benzofuran-2-carboxamide;

N-(4''-amino-4-methoxy-5''-methyl-3'H-dispiro[cyclohexane-1,2'-indene-1',2''-imidazol]-6'-yl)-3,5-dichloropyridine-2-carboxamide;

N-(4''-amino-4-methoxy-5''-methyl-3'H-dispiro[cyclohexane-1,2'-indene-1',2''-imidazol]-6'-yl)-5-chloropyridine-2-carboxamide;

4-methoxy-5''-methyl-6'-(2-methylpropoxy)-3'H-dispiro[cyclohexane-1,2'-indene-1',2''-imidazol]-4''-amine;

4-methoxy-5''-methyl-6'-(3,3,3-trifluoropropoxy)-3'H-dispiro[cyclohexane-1,2'-indene-1',2''-imidazol]-4''-amine;

6'-(3-fluoropropoxy)-4-methoxy-5''-methyl-3'H-dispiro[cyclohexane-1,2'-indene-1',2''-imidazol]-4''-amine;

6'-bromo-5-methyl-2'',3'',5'',6''-tetrahydro-3'H-dispiro[imidazole-2,1'-indene-2',4''-pyran]-4-amine;

6'-(3-chlorophenyl)-5-methyl-2'',3'',5'',6''-tetrahydro-3'H-dispiro[imidazole-2,1'-indene-2',4''-pyran]-4-amine;

6'-(3-chloro-4-fluorophenyl)-5-methyl-2'',3'',5'',6''-tetrahydro-3'H-dispiro[imidazole-2,1'-indene-2',4''-pyran]-4-amine;

6'-bromo-4,4-difluoro-5''-methyl-3'H-dispiro[cyclohexane-1,2'-indene-1',2''-imidazol]-4''-amine;

6'-(5-chloropyridin-3-yl)-4,4-difluoro-5''-methyl-3'H-dispiro[cyclohexane-1,2'-indene-1',2''-imidazol]-4''-amine;

N-(4''-amino-4,4-difluoro-5''-methyl-3'H-dispiro[cyclohexane-1,2'-indene-1',2''-imidazol]-6'-yl)-5-chloropyridine-2-carboxamide;

5'-bromo-4-methoxy-5''-methyldispiro[cyclohexane-1,2'-[1]benzofuran-3',2''-imidazol]-4''-amine;

5'-(3-chlorophenyl)-4-methoxy-5''-methyldispiro[cyclohexane-1,2'-[1]benzofuran-3',2''-imidazol]-4''-amine;

6'-bromo-5-methyl-5'',6''-dihydro-4''H-dispiro[imidazole-2,4'-chromene-2',3''-pyran]-4-amine;

6'-(3-chlorophenyl)-5-methyl-5'',6''-dihydro-4''H-dispiro[imidazole-2,4'-chromene-2',3''-pyran]-4-amine;

6'-(3-chloro-4-fluorophenyl)-5-methyl-5'',6''-dihydro-4''H-dispiro[imidazole-2,4'-chromene-2',3''-pyran]-4-amine;

6-bromo-5'-methyl-2-tetrahydropyran-3-yl-spiro[chromane-4,2'-imidazole]-4'-amine;

6-(3-chlorophenyl)-5'-methyl-2-(tetrahydro-2H-pyran-3-yl)-2,3-dihydrospiro[chromene-4,2'-imidazol]-4'-amine;

6-bromo-2-(2,2-dimethyltetrahydropyran-4-yl)-5'-methyl-spiro[chromane-4,2'-imidazole]-4'-amine;

6-(3-chlorophenyl)-2-(2,2-dimethyltetrahydro-2H-pyran-4-yl)-5'-methyl-2,3-dihydrospiro[chromene-4,2'-imidazol]-4'-amine;

N-(4''-amino-4-methoxy-5''-methyl-3'H-dispiro[cyclohexane-1,2'-indene-1',2''-imidazol]-6'-yl)-5-chloro-3-methylpyridine-2-carboxamide;

N-(4''-amino-4-methoxy-5''-methyl-3'H-dispiro[cyclohexane-1,2'-indene-1',2''-imidazol]-6'-yl)-5-fluoropyridine-2-carboxamide;

4-methoxy-5''-methyl-6'-[2-(prop-1-yn-1-yl)pyridin-4-yl]-3'H-dispiro[cyclohexane-1,2'-indene-1',2''-imidazol]-4''-amine 4-methoxy-5''-methyl-6'-[3-(prop-1-yn-1-yl)phenyl]-3'H-dispiro[cyclohexane-1,2'-indene-1',2''-imidazol]-4''-amine;

6'-(5-bromopyridin-3-yl)-4-methoxy-5''-methyl-3'H-dispiro[cyclohexane-1,2'-indene-1',2''-imidazol]-4''-amine;

4,4-difluoro-5''-methyl-6'-[5-(prop-1-yn-1-yl)pyridin-3-yl]-3'H-dispiro[cyclohexane-1,2'-indene-1',2''-imidazol]-4''-amine;

5'-(5-chloropyridin-3-yl)-4-methoxy-5''-methyldispiro[cyclohexane-1,2'-[1]benzofuran-3',2''-imidazol]-4''-amine;

4-methoxy-5''-methyl-5'-[5-(prop-1-yn-1-yl)pyridin-3-yl]dispiro[cyclohexane-1,2'-[1]benzofuran-3',2''-imidazol]-4''-amine;

7'-bromo-5-methyl-3',4'-dihydro-2'H-spiro[imidazole-2,1'-naphthalen]-4-amine;

7'45-chloropyridin-3-yl)-5-methyl-3',4'-dihydro-2'H-spiro[imidazole-2,1'-naphthalen]-4-amine;

5-methyl-7'-(5-(prop-1-ynyl)pyridin-3-yl)-3',4'-dihydro-2'H-spiro[imidazole-2,1'-naphthalen]-4-amine; 6'-bromo-5''-methyl-3'H-dispiro[cyclobutane-1,2'-indene-1',2''-imidazol]-4''-amine;

6'-(5-chloropyridin-3-yl)-5''-methyl-3'H-dispiro[cyclobutane-1,2'-indene-1',2''-imidazol]-4''-amine;

5''-methyl-6'-[5-(prop-1-yn-1-yl)pyridin-3-yl]-3'H-dispiro[cyclobutane-1,2'-indene-1',2''-imidazol]-4''-amine;

5'-(6'-(cyclopropylethynyl))-5''-methyl-3'H-dispiro[cyclobutane-1,2'-indene-1',2''-imidazol]-4''-amine;

6'-(3,3-dimethylbut-1-yn-1-yl)-5''-methyl-3'H-dispiro[cyclobutane-1,2'-indene-1',2''-imidazol]-4''-amine;

6'-(5-chloro-6-methylpyridin-3-yl)-4-methoxy-5''-methyl-3'H-dispiro[cyclohexane-1,2'-indene-1',2''-imidazol]-4''-amine;

6'-(5-chloro-2-methylpyridin-3-yl)-4-methoxy-5''-methyl-3'H-dispiro[cyclohexane-1,2'-indene-1',2''-imidazol]-4''-amine;

4-methoxy-5''-methyl-6'-[4-methyl-5-(prop-1-yn-1-yl)pyridin-3-yl]-3'H-dispiro[cyclohexane-1,2'-indene-1',2''-imidazol]-4''-amine;

6'-bromo-5''-ethyl-4-methoxy-3'H-dispiro[cyclohexane-1,2'-indene-1',2''-imidazol]-4''-amine;

6'-(5-chloropyridin-3-yl)-5''-ethyl-4-methoxy-3'H-dispiro[cyclohexane-1,2'-indene-1',2''-imidazol]-4''-amine;

5''-ethyl-4-methoxy-6'-[5-(prop-1-yn-1-yl)pyridin-3-yl]-3'H-dispiro[cyclohexane-1,2'-indene-1',2''-imidazol]-4''-amine;

5-(4''-amino-5''-ethyl-4-methoxy-3'H-dispiro[cyclohexane-1,2'-indene-1',2''-imidazol]-6'-yl)pyridine-3-carbonitrile;

3-(4''-amino-5''-ethyl-4-methoxy-3'H-dispiro[cyclohexane-1,2'-indene-1',2''-imidazol]-6'-yl)benzonitrile;

6'-[5-(but-1-yn-1-yl)pyridin-3-yl]-4-methoxy-5''-methyl-3'H-dispiro[cyclohexane-1,2'-indene-1',2''-imidazol]-4''-amine;

4''-amino-5''-methyl-6'-[5-(prop-1-yn-1-yl)pyridin-3-yl]-3'H-dispiro[cyclohexane-1,2'-indene-1',2''-imidazol]-4-ol;

3-(4''-amino-4-methoxy-5''-methyl-3'H-dispiro[cyclohexane-1,2'-indene-1',2''-imidazol]-6'-yl)-5-methylbenzonitrile;

3-(4"-amino-4-methoxy-5"-methyl-3'H-dispiro[cyclohex-
 ane-1,2'-indene-1',2"-imidazol]-6'-yl)-5-fluorobenzoni-
 trile;
6'-bromo-5"-methyl-3'H-dispiro[cyclopropane-1,2'-indene-
 1',2"-imidazol]-4"-amine;
3-(4"-amino-5"-methyl-3'H-dispiro[cyclopropane-1,2'-in-
 dene-1',2"-imidazol]-6'-yl)-5-chlorobenzonitrile;
4"-amino-4-methoxy-5"-methyl-3'H-dispiro[cyclohexane-1,
 2'-indene-1',2"-imidazole]-6'-carbonitrile;
4-methoxy-6'-[3-(methoxymethyl)phenyl]-5"-methyl-3'H-
 dispiro[cyclohexane-1,2'-indene-1',2"-imidazol]-4"-
 amine;
6'-[3-fluoro-5-(methoxymethyl)phenyl]-4-methoxy-5"-me-
 thyl-3'H-dispiro[cyclohexane-1,2'-indene-1',2"-imida-
 zol]-4"-amine;
4-methoxy-5"-methyl-6'-{5-[(2,2,2-trifluoroethoxy)methyl]
 pyridin-3-yl}-3'H-dispiro[cyclohexane-1,2'-indene-1',2"-
 imidazol]-4"-amine;
4-methoxy-5"-methyl-6'-(5-methylpyridin-3-yl)-3'H-dispiro
 [cyclo hexane-1,2'-indene-1',2"-imidazol]-4"-amine;
4-methoxy-5"-methyl-6'-[5-(trifluoromethyl)pyridin-3-yl]-
 3'H-dispiro[cyclohexane-1,2'-indene-1',2"-imidazol]-4"-
 amine;
3-(4"-amino-4-methoxy-5"-methyl-3'H-dispiro[cyclohex-
 ane-1,2'-indene-1',2"-imidazol]-6'-yl)-5-(trifluoromethyl)
 benzonitrile;
3-(4"-amino-4-methoxy-5"-methyl-3'H-dispiro[cyclohex-
 ane-1,2'-indene-1',2"-imidazol]-6'-yl)-5-(difluoromethyl)
 benzonitrile;
5-(4"-amino-4-methoxy-5"-methyl-3'H-dispiro[cyclohex-
 ane-1,2'-indene-1',2"-imidazol]-6'-yl)-2-fluoro-3-meth-
 oxybenzonitrile;
6'-(3,5-difluorophenyl)-4-methoxy-5"-methyl-3'H-dispiro
 [cyclohexane-1,2'-indene-1',2"-imidazol]-4"-amine;
6'-(2-fluoro-3-methoxyphenyl)-4-methoxy-5"-methyl-3'H-
 dispiro[cyclohexane-1,2'-indene-1',2"-imidazol]-4"-
 amine;
4-methoxy-5"-methyl-6'-phenyl-3'H-dispiro[cyclohexane-1,
 2'-indene-1',2"-imidazol]-4"-amine;
3-(4"-amino-4-methoxy-5"-methyl-3'H-dispiro[cyclohex-
 ane-1,2'-indene-1',2"-imidazol]-6'-yl)-5-methoxyben-
 zonitrile;
3-(4"-amino-4-methoxy-5"-methyl-3'H-dispiro[cyclohex-
 ane-1,2'-indene-1',2"-imidazol]-6'-yl)-5-bromobenzoni-
 trile;
3-(4"-amino-4-methoxy-5"-methyl-3'H-dispiro[cyclohex-
 ane-1,2'-indene-1',2"-imidazol]-6'-yl)-5-ethylbenzoni-
 trile;
3-(4"-amino-4-methoxy-5"-methyl-3'H-dispiro[cyclohex-
 ane-1,2'-indene-1',2"-imidazol]-6'-yl)-5-(methoxym-
 ethyl)benzonitrile;
6'-(2-fluoro-5-methoxyphenyl)-4-methoxy-5"-methyl-3'H-
 dispiro[cyclohexane-1,2'-indene-1',2"-imidazol]-4"-
 amine;
6'-(2,5-difluorophenyl)-4-methoxy-5"-methyl-3'H-dispiro
 [cyclohexane-1,2'-indene-1',2"-imidazol]-4"-amine;
5-(4"-amino-4-methoxy-5"-methyl-3'H-dispiro[cyclohex-
 ane-1,2'-indene-1',2"-imidazol]-6'-yl)-3-chloro-2-fluo-
 robenzonitrile;
6'-(2,3-difluorophenyl)-4-methoxy-5"-methyl-3'H-dispiro
 [cyclohexane-1,2'-indene-1',2"-imidazol]-4"-amine;
3-(4"-amino-4-methoxy-5"-methyl-3'H-dispiro[cyclohex-
 ane-1,2'-indene-1',2"-imidazol]-6'-yl)-4-fluorobenzoni-
 trile;
6'-(2,4-difluorophenyl)-4-methoxy-5"-methyl-3'H-dispiro
 [cyclohexane-1,2'-indene-1',2"-imidazol]-4"-amine;
6'-(2,3-dichlorophenyl)-4-methoxy-5"-methyl-3'H-dispiro
 [cyclohexane-1,2'-indene-1',2"-imidazol]-4"-amine;
3-(4"-amino-4-(difluoromethoxy)-5"-methyl-3'H-dispiro
 [cyclohexane-1,2'-indene-1',2"-imidazol]-6'-yl)-5-fluo-
 robenzonitrile;
3-(4"-amino-4-(difluoromethoxy)-5"-methyl-3'H-dispiro
 [cyclohexane-1,2'-indene-1',2"-imidazol]-6'-yl)-5-meth-
 oxybenzonitrile;
4-(difluoromethoxy)-5"-methyl-6'-[5-(trifluoromethyl)pyri-
 din-3-yl]-3'H-dispiro[cyclohexane-1,2'-indene-1',2"-imi-
 dazol]-4"-amine;
3-(4"-amino-4-(difluoromethoxy)-5"-methyl-3'H-dispiro
 [cyclohexane-1,2'-indene-1',2"-imidazol]-6'-yl)-5-chlo-
 robenzonitrile;
4-(difluoromethoxy)-6'-(3,5-difluorophenyl)-5"-methyl-
 3'H-dispiro[cyclohexane-1,2'-indene-1',2"-imidazol]-4"-
 amine;
5-(4"-amino-4-(difluoromethoxy)-5"-methyl-3'H-dispiro
 [cyclohexane-1,2'-indene-1',2"-imidazol]-6'-yl)-2-fluoro-
 3-methoxybenzonitrile;
4-methoxy-4,5"-dimethyl-6'-[5-(prop-1-yn-1-yl)pyridin-3-
 yl]-3'H-dispiro[cyclohexane-1,2'-indene-1',2"-imidazol]-
 4"-amine;
6'-(cyclobutylethynyl)-4-methoxy-5"-methyl-3'H-dispiro
 [cyclohexane-1,2'-indene-1',2"-imidazol]-4"-amine;
4-methoxy-5"-methyl-6'-(3-methylbut-1-yn-1-yl)-3'H-
 dispiro[cyclohexane-1,2'-indene-1',2"-imidazol]-4"-
 amine;
4-methoxy-5"-methyl-6'-{5-[($^2$H$_3$)prop-1-yn-1-yl]pyridin-
 3-yl}-3'H-dispiro[cyclohexane-1,2'-indene-1',2"-imida-
 zol]-4"-amine;
3-(4"-amino-5"-methyl-4-oxodispiro[cyclohexane-1,2'-[1H]
 indene-1'(3'H),2"-[2H]imidazol]-6'-yl)-5-fluorobenzoni-
 trile;
4-methoxy-5"-methyl-6'-(3-methyl-1H-pyrrolo[2,3-b]pyri-
 din-5-yl)-3'H-dispiro[cyclohexane-1,2'-indene-1',2"-imi-
 dazol]-4"-amine;
6'-bromo-5"-methyl-4-[($^2$H$_3$)methyloxy]-3'H-dispiro[cyclo-
 hexane-1,2'-indene-1',2"-imidazol]-4"-amine;
3-(4"-amino-5"-methyl-4-[($^2$H$_3$)methyloxy]-3'H-dispiro[cy-
 clohexane-1,2'-indene-1',2"-imidazol]-6'-yl)-5-fluoroben-
 zonitrile;
6'-(5-chloropyridin-3-yl)-5"-methyl-4-[($^2$H$_3$)methyloxy]-
 3'H-dispiro[cyclohexane-1,2'-indene-1',2"-imidazol]-4"-
 amine;
6'-[5-(difluoromethyl)pyridin-3-yl]-4-methoxy-5"-methyl-
 3'H-dispiro[cyclohexane-1,2'-indene-1',2"-imidazol]-4"-
 amine;
4-methoxy-5"-methyl-6'-(3-methyl-1H-indol-5-yl)-3'H-
 dispiro[cyclohexane-1,2'-indene-1',2"-imidazol]-4"-
 amine;
5"-methyl-4-[($^2$H$_3$)methyloxy]-6'-[5-(prop-1-yn-1-yl)pyri-
 din-3-yl]-3'H-dispiro[cyclohexane-1,2'-indene-1',2"-imi-
 dazol]-4"-amine;
6'-[2-chloro-3-(prop-1-yn-1-yl)phenyl]-4-methoxy-5"-me-
 thyl-3'H-dispiro[cyclohexane-1,2'-indene-1',2"-imida-
 zol]-4"-amine;
6'-bromo-5"-methyl-4-(trifluoromethyl)-3'H-dispiro[cyclo-
 hexane-1,2'-indene-1',2"-imidazol]-4"-amine;
3-(4"-amino-5"-methyl-4-[($^2$H$_3$)methyloxy]-3'H-dispiro[cy-
 clohexane-1,2'-indene-1',2"-imidazol]-6'-yl)-5-chlo-
 robenzonitrile;
6'-(cyclobutylmethoxy)-4-methoxy-5"-methyl-3'H-dispiro
 [cyclohexane-1,2'-indene-1',2"-imidazol]-4"-amine;
5-(4"-amino-4-methoxy-5"-methyl-3'H-dispiro[cyclohex-
 ane-1,2'-indene-1',2"-imidazol]-6'-yl)-2-fluoro-3-(meth-
 oxymethyl)benzonitrile;

6'-bromo-4-(difluoromethyl)-5"-methyl-3'H-dispiro[cyclohexane-1,2'-indene-1',2"-imidazol]-4"-amine;

6'-(5-chloropyridin-3-yl)-4-(difluoromethyl)-5"-methyl-3'H-dispiro[cyclohexane-1,2'-indene-1',2"-imidazol]-4"-amine;

6'-bromo-4-ethoxy-5"-methyl-3'H-dispiro[cyclohexane-1,2'-indene-1',2"-imidazol]-4"-amine;

4-ethoxy-5"-methyl-6'-[5-(trifluoromethyl)pyridin-3-yl]-3'H-dispiro[cyclohexane-1,2'-indene-1',2"-imidazol]-4"-amine;

3-(4"-amino-4-ethoxy-5"-methyl-3'H-dispiro[cyclohexane-1,2'-indene-1',2"-imidazol]-6'-yl)-5-fluorobenzonitrile;

6'-(5-chloropyridin-3-yl)-4-ethoxy-5"-methyl-3'H-dispiro[cyclohexane-1,2'-indene-1',2"-imidazol]-4"-amine;

3-(4"-amino-4-ethoxy-5"-methyl-3'H-dispiro[cyclohexane-1,2'-indene-1',2"-imidazol]-6'-yl)-5-(difluoromethyl)benzonitrile; and 4-ethoxy-5"-methyl-6'-[5-(prop-1-yn-1-yl)pyridin-3-yl]-3'H-dispiro[cyclohexane-1,2'-indene-1',2"-imidazol]-4"-amine, or a pharmaceutically acceptable salt of any foregoing compound.

In another embodiment, the invention relates to a compound of formula (I) selected from the group consisting of:

4-methoxy-5"-methyl-6'-(5-prop-1-yn-1-ylpyridin-3-yl)-3'H-dispiro[cyclohexane-1,2'-indene-1',2"-imidazol]-4"-amine;

3-(4"-amino-4-methoxy-5"-methyl-3'H-dispiro[cyclohexane-1,2'-indene-1',2"-imidazol]-6'-yl)-5-chlorobenzonitrile; and 4-methoxy-5"-methyl-6'-(2-methylpropoxy)-3'H-dispiro[cyclohexane-1,2'-indene-1',2"-imidazol]-4"-amine, or a pharmaceutically acceptable salt of any foregoing compound.

In another embodiment, the invention relates to a compound of formula (I) selected from the group consisting of:

(1r,4r)-4-methoxy-5"-methyl-6'-(5-prop-1-yn-1-ylpyridin-3-yl)-3'H-dispiro[cyclohexane-1,2'-indene-1',2"-imidazol]-4"-amine;

3-[(1r,4r)-4"-amino-4-methoxy-5"-methyl-3'H-dispiro[cyclohexane-1,2'-indene-1',2"-imidazol]-6'-yl]-5-chlorobenzonitrile; and (1r,4r)-4-methoxy-5"-methyl-6'-(2-methylpropoxy)-3'H-dispiro[cyclohexane-1,2'-indene-1',2"-imidazol]-4"-amine, or a pharmaceutically acceptable salt of any foregoing compound.

In another embodiment, the invention relates to a compound of formula (I) selected from the group consisting of:

(1r,1'R,4R)-4-methoxy-5"-methyl-6'-[5-(prop-1-yn-1-yl)pyridin-3-yl]-3'H-dispiro[cyclohexane-1,2'-indene-1',2"-imidazol]-4"-amine;

3-[(1r,1'R,4R)-4"-amino-4-methoxy-5"-methyl-3'H-dispiro[cyclohexane-1,2'-indene-1',2"-imidazol]-6'-yl]-5-chlorobenzonitrile; and (1r,4r)-4-methoxy-5"-methyl-6'-(2-methylpropoxy)-3'H-dispiro[cyclohexane-1,2'-indene-1',2"-imidazol]-4"-amine (isomer 1);

or a pharmaceutically acceptable salt of any foregoing compound.

In yet another embodiment, the invention relates to a compound of formula (I), or a pharmaceutically acceptable salt thereof, with the proviso that any of the specific Examples are individually disclaimed.

Thus, in a further embodiment the invention relates to a compound of formula (I), or a pharmaceutically acceptable salt thereof, with the proviso that the compound is not 4-methoxy-5"-methyl-6'-(5-prop-1-yn-1-ylpyridin-3-yl)-3'H-dispiro[cyclohexane-1,2'-indene-1',2"-imidazol]-4"-amine.

In yet a further embodiment the invention relates to a compound of formula (I), or a pharmaceutically acceptable salt thereof, with the proviso that the compound is not 3-(4"-amino-4-methoxy-5"-methyl-3'H-dispiro[cyclohexane-1,2'-indene-1',2"-imidazol]-6'-yl)-5-chlorobenzonitrile.

In yet a further embodiment the invention relates to a compound of formula (I), or a pharmaceutically acceptable salt thereof, with the proviso that the compound is not 4-methoxy-5"-methyl-6'-(2-methylpropoxy)-3'H-dispiro[cyclohexane-1,2'-indene-1',2"-imidazol]-4"-amine.

The present invention relates to the use of compounds of formula (I) as hereinbefore defined as well as to the salts thereof. Salts for use in pharmaceutical compositions will be pharmaceutically acceptable salts, but other salts may be useful in the production of the compounds of formula (I).

The compounds of the formula (I) may be administered in the form of a prodrug which is broken down in the human or animal body to give a compound of the formula (I). Examples of prodrugs include in vivo hydrolysable esters of a compound of the formula (I). An in vivo hydrolysable (or cleavable) ester of a compound of the formula (I) that contains a carboxy or a hydroxy group is, for example, a pharmaceutically acceptable ester which is hydrolysed in the human or animal body to produce the parent acid or alcohol. Various forms of prodrugs are known in the art.

The definitions set forth in this application are intended to clarify terms used throughout this application. The term "herein" means the entire application.

A variety of compounds in the present invention may exist in particular geometric or stereoisomeric forms. The present invention takes into account all such compounds, including tautomers, cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds.

As used in this application, the term "optionally substituted" means that substitution is optional and therefore it is possible for the designated atom or moiety to be unsubstituted.

As used herein, "alkyl", used alone or as a suffix or prefix, is intended to include both branched and straight chain saturated aliphatic hydrocarbon groups having from 1 to 12 carbon atoms or if a specified number of carbon atoms is provided then that specific number would be intended. For example "$C_{0-6}$alkyl" denotes alkyl having 0, 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. In the case where a subscript is the integer 0 (zero) the group to which the subscript refers to indicates that the group may be absent, i.e. there is a direct bond between the groups.

As used herein, "alkenyl" used alone or as a suffix or prefix is intended to include both branched and straight-chain alkene or olefin containing aliphatic hydrocarbon groups having from 2 to 12 carbon atoms or if a specified number of carbon atoms is provided then that specific number would be intended. For example "$C_{2-6}$alkenyl" denotes alkenyl having 2, 3, 4, 5 or 6 carbon atoms. Examples of alkenyl include, but are not limited to, vinyl, allyl, 1-propenyl, 1-butenyl, 2-butenyl, 3-butenyl, 2-methylbut-2-enyl, 3-methylbut-1-enyl, 1-pentenyl, 3-pentenyl and 4-hexenyl.

As used herein, "alkynyl" used alone or as a suffix or prefix is intended to include to include both branched and straight-chain alkynyl or olefin containing aliphatic hydrocarbon groups having from 2 to 12 carbon atoms or if a specified number of carbon atoms is provided then that specific number would be intended. For example ethynyl, propynyl (e.g. 1-propynyl, 2-propynyl), 3-butynyl, pentynyl, hexynyl and 1-methylpent-2-ynyl.

As used herein, "aromatic" refers to hydrocarbonyl groups having one or more unsaturated carbon ring(s) having aromatic characters, (e.g. 4n+2 delocalized electrons) and comprising up to 14 carbon atoms. In addition "heteroaromatic" refers to groups having one or more unsaturated rings containing carbon and one or more heteroatoms such as nitrogen, oxygen or sulphur having aromatic character (e.g. 4n+2 delocalized electrons).

As used herein, the term "aryl" refers to an aromatic ring structure made up of from 5 to 14 carbon atoms. Ring structures containing 5, 6, 7 and 8 carbon atoms would be single-ring aromatic groups, for example, phenyl. Ring structures containing 8, 9, 10, 11, 12, 13, or 14 would be polycyclic, for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls. Examples of polycyclic rings include, but are not limited to, 2,3-dihydro-1,4-benzodioxine and 2,3-dihydro-1-benzofuran.

As used herein, the terms "cycloalkyl" or "carbocyclyl" are intended to include saturated ring groups, having the specified number of carbon atoms. These may include fused or bridged polycyclic systems. Cycloalkyls have from 3 to 14 carbon atoms in their ring structure. In one embodiment, cycloalkyls have 3, 4, 5, or 6 carbons in the ring structure. For example, "$C_{3-6}$cycloalkyl" denotes such groups as cyclopropyl, cyclobutyl, cyclopentyl, or cyclohexyl.

As used herein, the term "cycloalkenyl" is intended to include unsaturated ring groups, having the specified number of carbon atoms. These may include fused or bridged polycyclic systems. Cycloalkenyls may have from 3 to 10 carbon atoms in their ring structure. In one embodiment, cycloalkenyls have 3, 4, 5, or 6 carbons in the ring structure. For example, "$C_{3-6}$cycloalkenyl" denotes such groups as cyclopropenyl, cyclobutenyl, cyclopentenyl, or cyclohexenyl.

As used herein, "halo" or "halogen" refers to fluoro, chloro, bromo, and iodo.

"Counterion" is used to represent a small, negatively or positively charged species such as chloride, bromide, hydroxide, acetate, sulfate, tosylate, benezensulfonate, ammonium, lithium ion and sodium ion and the like.

As used herein, the term "heterocyclyl" or "heterocyclic" or "heterocycle" refers to a saturated, unsaturated or partially saturated, monocyclic, bicyclic or tricyclic ring (unless otherwise stated) containing 3 to 20 atoms of which 1, 2, 3, 4 or 5 ring atoms are chosen from nitrogen, sulphur or oxygen, which may, unless otherwise specified, be carbon or nitrogen linked, wherein a —$CH_2$— group is optionally be replaced by a —C(O)—; and where unless stated to the contrary a ring nitrogen or sulphur atom is optionally oxidised to form the N-oxide or S-oxide(s) or a ring nitrogen is optionally quarternized; wherein a ring —NH is optionally substituted with acetyl, formyl, methyl or mesyl; and a ring is optionally substituted with one or more halo. It is understood that when the total number of S and O atoms in the heterocyclyl exceeds 1, then these heteroatoms are not adjacent to one another. If the said heterocyclyl group is bi- or tricyclic then at least one of the rings may optionally be a heteroaromatic or aromatic ring provided that at least one of the rings is non-heteroaromatic. If the said heterocyclyl group is monocyclic then it must not be aromatic. Examples of heterocyclyls include, but are not limited to, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, tetrahydroisoquinolinyl, tetrahydroquinolinyl, indolinyl, tetrahydropyranyl, dihydro-2H-pyranyl, tetrahydrofuranyl, tetrahydro-thiopyranyl, tetrahydro-thiopyran 1-oxide, tetrahydro-thiopyran 1,1-dioxide, 1H-pyridin-2-one, and 2,5-dioxoimidazolidinyl.

As used herein, "heteroaryl" refers to a heteroaromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, benzoxazolyl, aza-benzoxazolyl imidazothiazolyl, benzo[1,4]dioxinyl, benzo[1,3]dioxolyl and the like. In some embodiments, the heteroaryl group has from 1 to 20 carbon atoms, and in further embodiments from 3 to 20 carbon atoms. In some embodiments, the heteroaryl group contains 3 to 14, 4 to 14, 3 to 7, or 5 to 6 ring-forming atoms. In some embodiments, the heteroaryl group has 1 to 4, 1 to 3, or 1 to 2 heteroatoms. In some embodiments, the heteroaryl group has 1 heteroatom.

As used herein, "haloalkyl", used alone or as a suffix or prefix, is intended to include both branched and straight chain saturated aliphatic hydrocarbon groups, having at least one halogen substituent and having from 1 to 12 carbon atoms or if a specified number of carbon atoms is provided then that specific number would be intended. For example "$C_{0-6}$haloalkyl" denotes alkyl having 0, 1, 2, 3, 4, 5 or 6 carbon atoms.

Examples of haloalkyl include, but are not limited to, fluoromethyl, difluoromethyl, trifluoromethyl, chlorofluoromethyl, 1-fluoroethyl, 3-fluoropropyl, 2-chloropropyl, 3,4-difluorobutyl.

As used herein, the phrase "protecting group" means temporary substituents which protect a potentially reactive functional group from undesired chemical transformations. Examples of such protecting groups include esters of carboxylic acids, silyl ethers of alcohols, and acetals and ketals of aldehydes and ketones respectively. The field of protecting group chemistry has been reviewed (Greene, T. W.; Wuts, P. G. M. *Protective Groups in Organic Synthesis*, 3$^{rd}$ ed.; Wiley: New York, 1999).

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the non-toxic salts or the quaternary ammonium salts of the parent compound formed, for example, from non-toxic inorganic or organic acids. For example, such non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

The present invention further includes all tautomeric forms of compounds of the invention. As used herein, "tautomer" means other structural isomers that exist in equilibrium resulting from the migration of a hydrogen atom. For example, keto-enol tautomerism where the resulting compound has the properties of both a ketone and an unsaturated alcohol. Other examples of tautomerism include 2H-imidazole-4-amine and its tautomer 1,2-dihydroimidazol-5-imine, and 2H-imidazol-4-thiol and its tautomer 1,2-dihydroimidazol-5-thione. It is understood that in compound representations throughout this description, only one of the possible tautomers of the compound is drawn or named.

As used herein "stable compound" and "stable structure" are meant to indicate a compound that is sufficiently robust to survive isolation to a useful degree of purity from a reaction mixture, and formulation into an efficacious therapeutic agent.

Compounds of the invention further include hydrates and solvates.

The present invention further includes isotopically-labelled compounds of the invention. An "isotopically" or "radio-labelled" compound is a compound of the invention where one or more atoms are replaced or substituted by an atom having an atomic mass or mass number different from the atomic mass or mass number typically found in nature (i.e., naturally occurring). Suitable isotopes that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$C, $^{17}$C, $^{18}$C, $^{18}$F, $^{35}$S, $^{36}$Cl, $^{82}$Br, $^{75}$Br, $^{76}$Br, $^{123}$I, $^{124}$I, $^{125}$I and $^{131}$I. The radionuclide that is incorporated in the instant radiolabelled compounds will depend on the specific application of that radio-labelled compound. For example, for in vitro receptor labelling and competition assays, compounds that incorporate $^3$H, $^{14}$C, $^{82}$Br, $^{125}$I, $^{131}$I or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labelled compound" is a compound that has incorporated at least one radionuclide. In some embodiments the radionuclide is selected from the group consisting of $^3$H, $^{14}$C, $^{125}$I, $^{35}$S and $^{82}$Br.

Compounds of the present invention may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

In another aspect, the invention relates to a compound of formula (I), or a pharmaceutically acceptable salt thereof, for use as a medicament, e.g. for treatment or prevention of Aβ-related pathologies.

In another aspect, the invention relates to the use of a compound of formula (I), or a pharmaceutically acceptable salt thereof, in the manufacture of a medicament for treatment or prevention of Aβ-related pathologies.

In another aspect, the invention relates to a method of treating or preventing Aβ-related pathologies in a mammal, such as a human being, comprising administering to a mammal in need thereof a therapeutically effective amount of a compound of Formula (I), or a pharmaceutically acceptable salt thereof.

The compounds of the invention, and their pharmaceutically acceptable salts, thereby provide methods of treatment of Aβ-related pathologies, such as, but not limited to, Alzheimer's disease, Down's syndrome, β-amyloid angiopathy, cerebral amyloid angiopathy, hereditary cerebral hemorrhage, a disorder associated with cognitive impairment, MCI ("mild cognitive impairment"), memory loss, attention deficit symptoms associated with Alzheimer's disease, neurodegeneration associated with Alzheimer's disease, dementia of mixed vascular origin, dementia of degenerative origin, presenile dementia, senile dementia, dementia associated with Parkinson's disease, progressive supranuclear palsy traumatic brain injury and cortical basal degeneration.

In another aspect, the invention relates to a pharmaceutical composition comprising as active ingredient a therapeutically effective amount of a compound of formula (I), or a pharmaceutically acceptable salt thereof, in association with at least one pharmaceutically acceptable excipient, carrier or diluent.

In another aspect, the invention relates to a method of inhibiting activity of BACE with a compound according to formula (I).

In another aspect, the invention relates to a method of treating or preventing an Aβ-related pathology in a mammal, such as a human being, comprising administering to said patient a therapeutically effective amount of a compound according to formula (I), or a pharmaceutically acceptable salt thereof, and at least one cognitive enhancing agent, memory enhancing agent, or choline esterase inhibitor, wherein said Aβ-related pathology is Alzheimer's disease.

In another aspect, the invention relates to a pharmaceutical composition comprising (i) a compound of formula (I), or a pharmaceutically acceptable salt thereof, (ii) an additional therapeutic agent, or a pharmaceutically acceptable salt thereof, and (iii) pharmaceutically acceptable excipients, carriers or diluents.

In another aspect, the invention relates to a pharmaceutical composition comprising (i) a compound of formula (I), or a pharmaceutically acceptable salt thereof, (ii) at least one agent selected from the group consisting of cognitive enhancing agents, memory enhancing agents and choline esterase inhibitors, and (iii) pharmaceutically acceptable excipients, carriers or diluents.

The treatment of Aβ-related pathology defined herein may be applied as a mono therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents or atypical antipsychotic agents. Cognitive enhancing agents, memory enhancing agents and acetyl choline esterase inhibitors includes, but not limited to, donepezil (ARICEPT), galantamine (REMINYL or RAZADYNE), rivastigmine (EXELON), tacrine (COGNEX) and memantine (NAMENDA, AXURA or EBIXA). Atypical antipsychotic agents includes, but not limited to, olanzapine (marketed as ZYPREXA), aripiprazole (marketed as ABILIFY), risperidone (marketed as RISPERDAL), quetiapine (marketed as SEROQUEL), clozapine (marketed as CLOZARIL), ziprasidone (marketed as GEODON) and olanzapine/fluoxetine (marketed as SYMBYAX).

Such conjoint treatment may be achieved by way of the simultaneous, sequential or separate dosing of the individual components of the treatment. Such combination products employ the compounds of the invention.

Additional conventional therapy may include one or more of the following categories of agents:
(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, rameltoon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof.
(ii) atypical antipsychotics including for example quetiapine and pharmaceutically active isomer(s) and metabolite(s) thereof.
(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof
(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof.
(v) anticonvulsants including for example carbamazepine, clonazepam, ethosuximide, felbamate, fosphenyloin, gabapentin, lacosamide, lamotrogine, levetiracetam, oxcarbazepine, phenobarbital, phenyloin, pregabaline, rufinamide, topiramate, valproate, vigabatrine, zonisamide and equivalents and pharmaceutically active isomer(s) and metabolite(s) thereof
(vi) Alzheimer's therapies including for example donepezil, rivastigmine, galantamine, memantine, and equivalents and pharmaceutically active isomer(s) and metabolite(s) thereof
(vii) Parkinson's therapies including for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof.
(viii) migraine therapies including for example almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan, zomitriptan, and equivalents and pharmaceutically active isomer(s) and metabolite(s) thereof.
(ix) stroke therapies including for example thrombolytic therapy with eg activase and desmoteplase, abciximab, citicoline, clopidogrel, eptifibatide, minocycline, and equivalents and pharmaceutically active isomer(s) and metabolite(s) thereof.
(x) urinary incontinence therapies including for example darafenacin, falvoxate, oxybutynin, propiverine, robalzotan, solifenacin, tolterodine and equivalents and pharmaceutically active isomer(s) and metabolite(s) thereof.
(xi) neuropathic pain therapies including for example lidocain, capsaicin, and anticonvulsants such as gabapentin, pregabalin, and antidepressants such as duloxetine, venlafaxine, amitriptyline, klomipramine, and equivalents and pharmaceutically active isomer(s) and metabolite(s) thereof
(xii) nociceptive pain therapies such as paracetamol, NSAIDS and coxibs, such as celecoxib, etoricoxib, lumiracoxib, valdecoxib, parecoxib, diclofenac, loxoprofen, naproxen, ketoprofen, ibuprofen, nabumeton, meloxicam, piroxicam and opioids such as morphine, oxycodone, buprenorfin, tramadol, and equivalents and pharmaceutically active isomer(s) and metabolite(s) thereof
(xiii) insomnia therapies including for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof.

(xiv) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combination products employ the compounds of this invention within the dosage range described herein and the other pharmaceutically active compound or compounds within approved dosage ranges and/or the dosage described in the publication reference.

PREPARATION OF COMPOUNDS

Figure 1A:
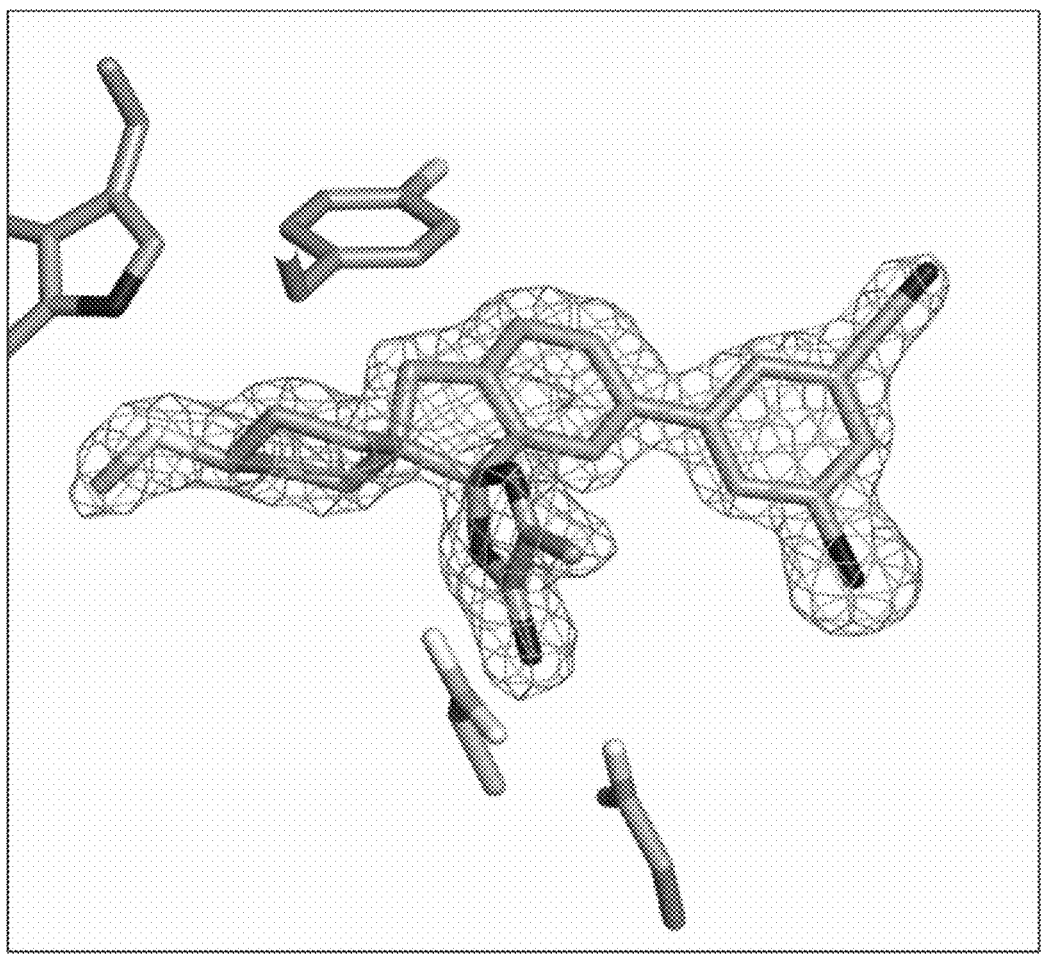
FIG. 1A shows Example 20d Isomer 1 bound to the BACE active site at 1.8 Å resolution. 2Fo-Fc map contoured at 1.7 sigma.

The compounds of the present invention can be prepared as a free base or a pharmaceutically acceptable salt thereof by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 3$^{rd}$ Edition, Wiley-Interscience, New York, 1999. It is understood that microwaves (MW) can alternatively be used for the heating of reaction mixtures. Another aspect of the present invention provides a process for preparing a compound of formula (I), or a pharmaceutically acceptable salt thereof, wherein, unless specified otherwise, $R^1$-$R^9$, n and A are defined as for formula (I) above, or are groups that can be converted into $R^1$-$R^9$, or A in subsequent transformations. A compound of formula (XI) may be equivalent to a compound of formula (I). LG represents a leaving group such as halogen (such as chlorine, bromine or iodine) or an alkyl-, aryl- or haloalkyl-sulfonate (such as triflate) and PG represents a protecting group. Said process comprises of:

Method (i): Formation of a Corresponding Compound of Formula (IIIa):

Scheme 1

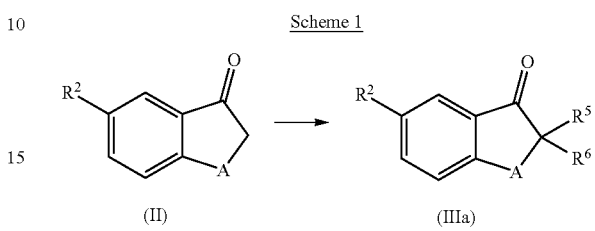

A ketone of formula (II), is treated with a suitable bas such as sodium hydride, KOtBu, or LDA in presence of a (bis-substituted) alkyl halide, triflate or mesylate to give a compound of formula (Ma) (Scheme 1). Said reaction may be performed at a temperature range between −78° C. and +50° C., in a suitable solvent, such as tetrahydrofuran or dimethylformamide. Alkyations could be carried ut in a sequential way with intermediates isolated and purified or in a one-pot stepwise fashion. If the reactions yield a product substituted with a olefin, cyano, sulfone or the like it could optionally be reacted further by Dieckman cyclization, RCM, nucleophilic substitution or cycloaddition to give highly substituted spirocyclic intermediates.

Method (ii): Formation of a Corresponding Compound of Formula (IIIa):

Scheme 2

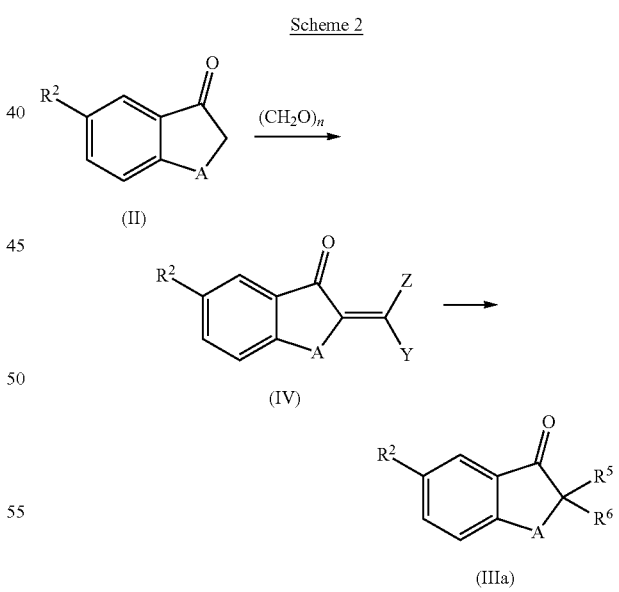

A ketone of formula (II), is reacted with an aldehyde or ketone such as formaldehyde in a temperature range between room temperature and +100° C. in presence of any protic acid such as a boronic acid (such as PhB(OH)$_2$), or in the presence of N-Methylanilinium trifluoroacetate, in a suitable solvent such as benzene or toluene (Scheme 2). The intermediate (IV), wherein Z and Y are defined as for example hydrogen or alkyl, can be reacted with various dienes utilizing the Diels- Alder reaction in a temperature range between room temperature and +220° C. optionally in a sealed tube. The reaction can be carried out neat or in a suitable solvent such as benzene, toluene or THF. A Lewis acid or any other agents that may assist the reaction can be added to yield enriched enantiomers or diastereomers. The resulting spirocyclic ring may optionally contain one or more substituent which may be further converted by known functional group transformations.

Method (iii): Formation of a Corresponding Compound of Formula (IIIa):

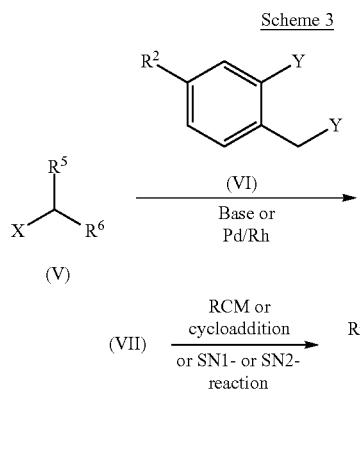

An alkyl or cycloalkyl or heterocycloalkyl derivative (V) containing electron withdrawing groups X such as cyano, carboxylic acid or alkylesters can be alkylated with optionally substituted ortho-halo benzyl bromides or chlorides (VI) (Y=halogen such as bromo or chloro) (Scheme 3). Said reaction is assisted by a base such as LDA, NaH or LiHMDS in a solvent such as benzene, THF or toluene at temperature range between −78° C. and 80° C. An alkylated intermediate (VII) can be isolated and further subjected to a base such as BuLi or LDA in solvents such as THF to effect ring cyclizations. Alternatively one can also utilize transition metal chemistry such as Pd, Cu or Rh containing chelating agents such as phosphine derivatives or amines in solvents such as DMF, THF or toluene in presence of a base such as triethylamine or sodium carbonate at temperature range between room temperature and +100° C. In the event where the product (VII) from the reaction contains a substituent such as olefin, sulfone, cyano, and the like, they can be further manipulated (Scheme 3) by RCM, cycloaddition, nucleophilic substitution or any other known reaction to give highly substituted spirocyclic compounds (IIIa).

Method (iv:) Formation of a Corresponding Compound of Formula (XIa):

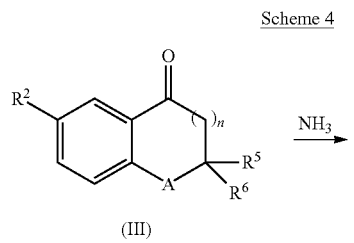

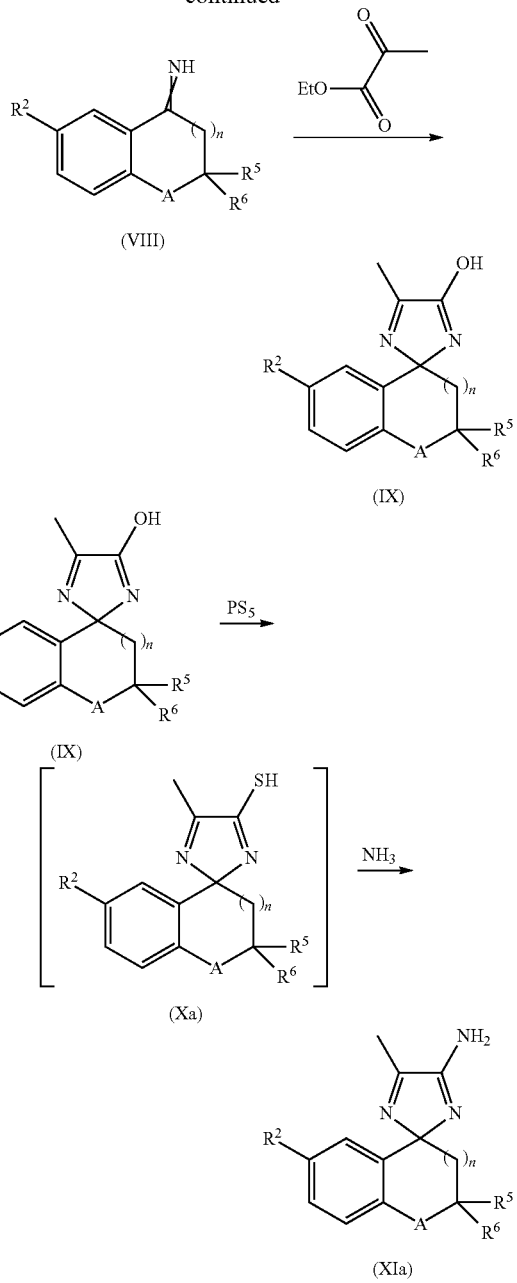

A ketone of formula (III), is reacted with ammonia to form intermediate (VIII) (Scheme 4). The compound of formula (VIII) is optionally not isolated and may be submitted to the next step immediately in a one pot system. Compound (VIII) is further reacted with ethyl 2-oxopropanoate to form an imidazole compound of formula (IX). Said reaction may be performed at a temperature range between room temperature and +160° C., in a suitable solvent, such as methanol, ethanol or isopropyl alcohol.

The amino imidazole compound (XIa) may then be obtained by formation of intermediate (Xa), by reacting the alcohol of formula (IX), with a sulphurating reagent such as phosphorus pentasulfide in the presence of a base such as pyridine (Scheme 4). The transformation to a compound of formula (XIa) may be performed by reacting the intermediate of formula (Xa) with ammonia, optionally in the presence of an oxidation agent, such as tert-butyl hydroperoxide.

Method (v): Formation of a Corresponding Compound of Formula (XI):

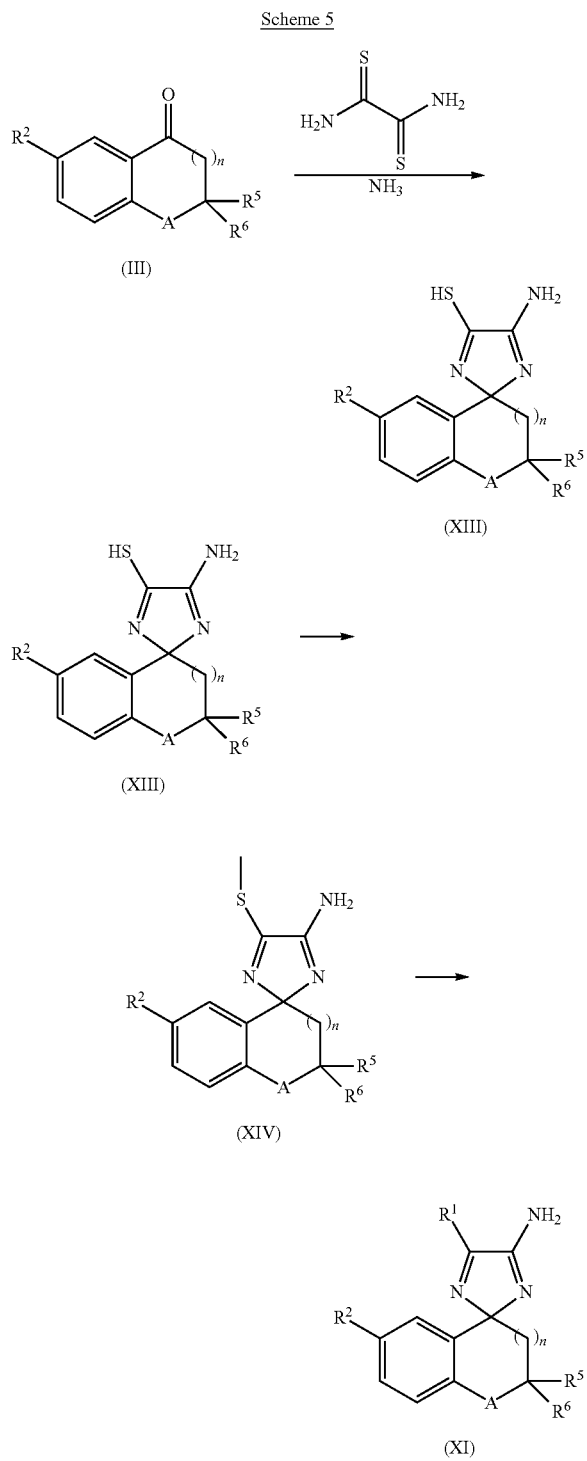

A ketone of formula (III), is reacted with ethanebis(thioamide) in presence of ammonia to form a compound of formula (XIII) (Scheme 5). Said reaction may be performed at a temperature range between room temperature and +180° C., in a suitable solvent, such as methanol, ethanol or isopropyl alcohol.

An alkylating agent, such as methyl iodide and a thioimidazole of formula (XIII) are reacted to form a compound of formula (XIV) (Scheme 5). Said compound (XIV) may be further transformed into a compound of formula (XI), wherein $R^1$ is an alkyl group such as methyl or ethyl, by reacting it with an organometallic reagent, such as methylmagnesium bromide or ethylmagnesium bromide, in the presence of a suitable catalyst, such as [1,3-bis(diphenylphosphino)propane]nickel(II) chloride. Alternatively, the compound of formula (XI) ($R^1$ is an alkyl such as methyl or ethyl) may also be obtained by reacting compound of formula (XIV) with a mixture of zinc iodide and a Grignard reagent such as methylmagnesium bromide, or ethylmagnesium bromide, in the presence of a suitable catalyst such as bis(triphenylphosphine)palladium(II) chloride in a suitable solvent such as THF, 2-methyl-tetrahydrofuran or toluene.

Method (vi) Formation of a Corresponding Compound of Formula (XI):

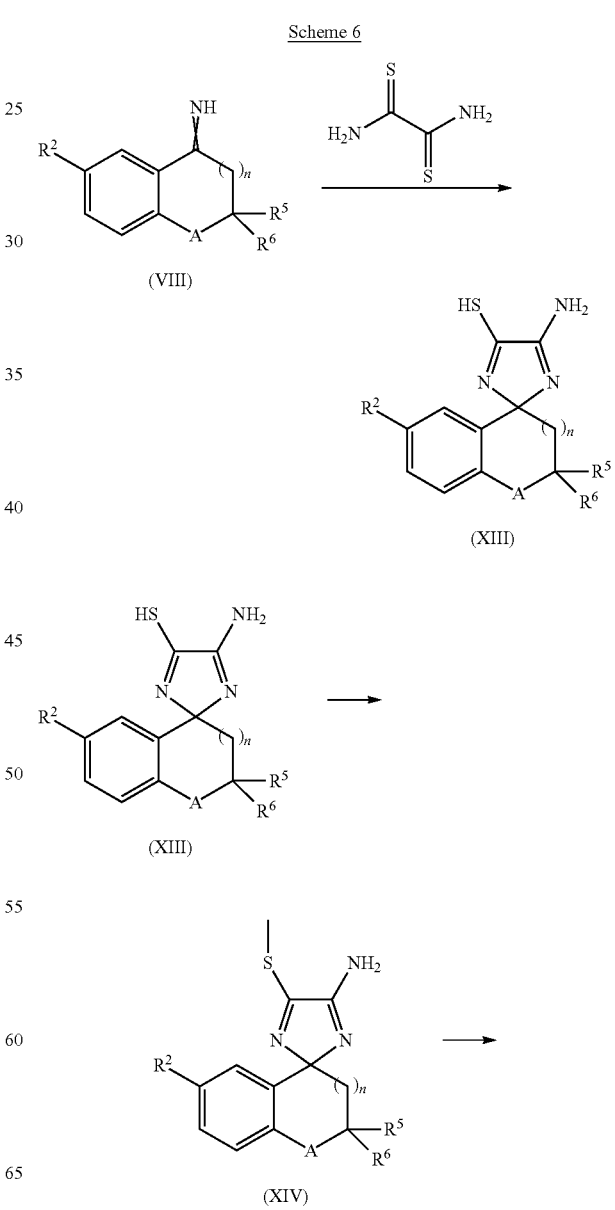

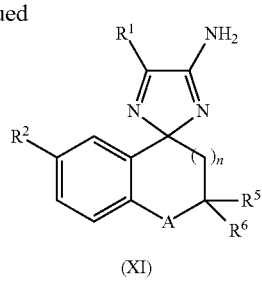

(XI)

An imine of formula (VIII), is reacted with ethanebis(thioamide) to form a compound of formula (XIII) (Scheme 6). Said reaction may be performed at a temperature range between +120° C. and +180° C., in a suitable solvent, such as methanol, ethanol or isopropyl alcohol. An alkylating agent, such as methyl iodide and a thioimidazole of formula (XIII) are reacted to form a compound of formula (XIV) (Scheme 6). Said compound (XIV) may be further transformed into a compound of formula (XI), wherein $R^1$ is an alkyl group such as methyl or ethyl, by reacting it with an organometallic reagent, such as methylmagnesium bromide or ethylmagnesium bromide, in the presence of a suitable catalyst, such as [1,3-bis(diphenylphosphino)propane]nickel(II) chloride. Alternatively, the compound of formula (XI) ($R^1$ is an alkyl such as methyl or ethyl) may also be obtained by reacting compound of formula (XIV) with a mixture of zinc iodide and a Grignard reagent such as methylmagnesium bromide, or ethylmagnesium bromide, in the presence of a suitable catalyst such as bis(triphenylphosphine)palladium(II) chloride in a suitable solvent such as THF, 2-methyl-tetrahydrofuran or toluene.

Method (vii) Formation of a Corresponding Compound of Formula (XV):

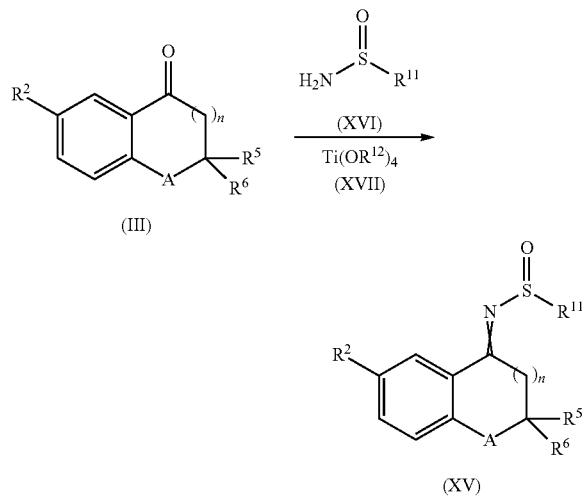

A compound of formula (XV) may be obtained by reacting a compound of formula (III) with a compound of formula (XVI) (Scheme 7), wherein $R^{11}$ is alkyl (such as for example tert-butyl). The reaction is performed in the presence of a suitable Lewis acid, such as a compound of formula (XVII), wherein $R^{12}$ is alkyl (such as ethyl or isopropyl). The reaction is performed in a suitable solvent (such as dichloromethane, 2-methyl-tetrahydrofuran or tetrahydrofuran) at a temperature between room temperature and reflux temperature, optionally with azeotropic distillation to remove an alcohol formed in the reaction.

Method (viii) Formation of a Corresponding Compound of Formula (XVIII):

Scheme 8

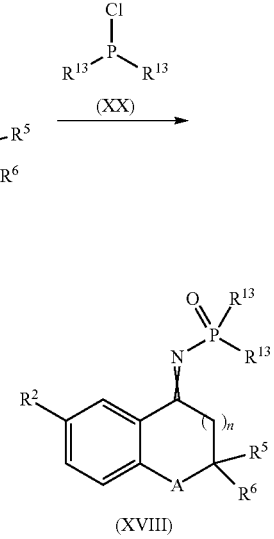

A compound of formula (XIX) may be obtained by reacting a compound of formula (III) with hydroxylamine hydrochloride and a base such as potassium acetate in a suitable solvent such as a mixture of water and a suitable alcohol such as ethanol at reflux temperature (Scheme 8). Said compound (XIX) may be further transformed into a compound of formula (XVIII) by reacting it with a compound of formula (XX), wherein $R^{13}$ is alkyl or aryl. The reaction is performed in a suitable solvent such as dichloromethane in the presence of triethylamine at a temperature between −78° C. and room temperature.

Method (ix) Formation of a Corresponding Compound of Formula (XXI):

Scheme 9

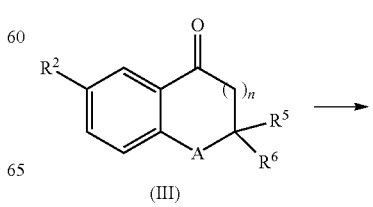

-continued

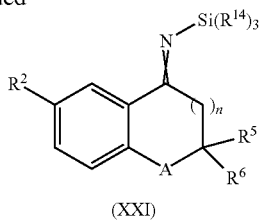

(XXI)

A compound of formula (XXI) wherein $R^{14}$ is an alkyl such as methyl may be obtained by reacting a compound of formula (III) with a silicon compound such as LiHMDS in a suitable solvent such as dichloromethane, 2-methyl-tetrahydrofuran or tetrahydrofuran (Scheme 9).

Method (x) Formation of a Corresponding Compound of Formula (XIa):

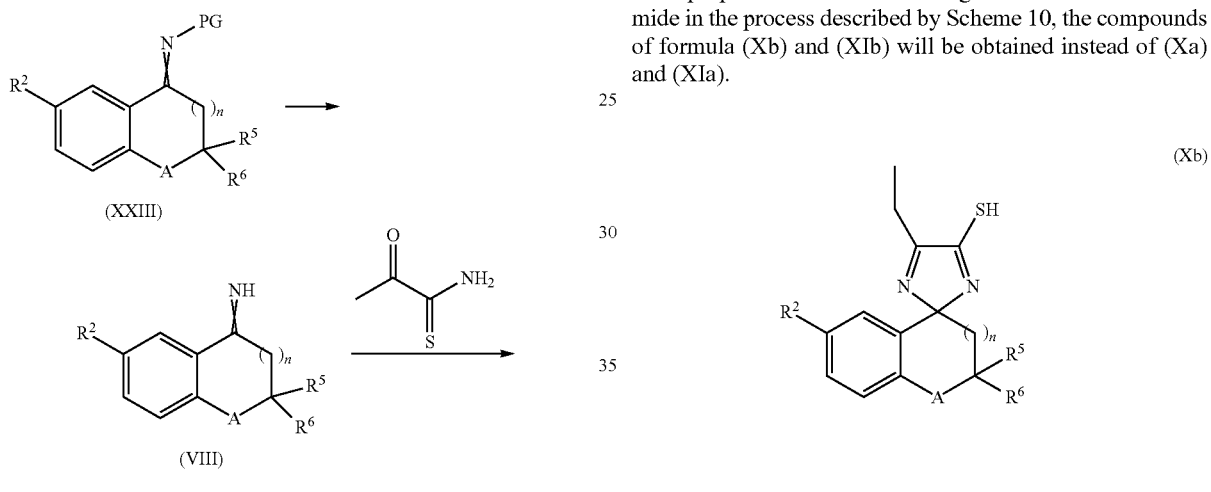

A compound of formula (VIII) may be obtained by reacting a compound (XVIII) (wherein PG is a protecting group such as for example $S(O)R^{11}$ (Method (vii), formula XV), $SiR^{14}$ (such as $SiMe_3$) (Method (ix), formula XXI), P(O)($R^{13})_2$) (Method (viii), formula XVIII), $S(O)_2$alkyl, C(O)Oalkyl, OH or Oalkyl using a suitable method of removing the protecting group PG to form imine (VIII) (Scheme 10). A suitable method may be, but is not limited to, treating said compound XXIII with an acid such as hydrochloric acid under dry conditions in a suitable solvent (such as dioxane or tetrahydrofuran), or treatment with a protic solvent such as methanol (when PG=$SiMe_3$). Compound (VIII) may be isolated or reacted further without isolation. A compound of formula (VIII) is further reacted with 2-oxopropane thioamide (described in Asinger et al. *Justus Liebigs Annalen der Chemie* 1971, vol 744, p. 51-64) optionally in the presence of triethyl orthoformate, in a solvent such as methanol at a temperature between room temperature and reflux temperature, optionally under Dean-Stark conditions, to yield a compound of formula (Xa). The transformation to a compound of formula (XIa) may be performed by reacting the intermediate of formula (Xa) with ammonia, optionally in the presence of an oxidation agent, such as tert-butyl hydroperoxide. If 2-oxopropane thioamide is exchanged for 2-oxobutanethioamide in the process described by Scheme 10, the compounds of formula (Xb) and (XIb) will be obtained instead of (Xa) and (XIa).

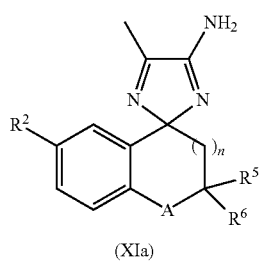

Method (xi) Formation of a Corresponding Compound of Formula (XIa):

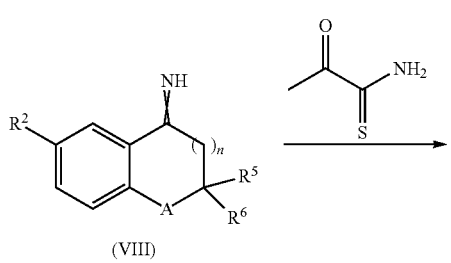

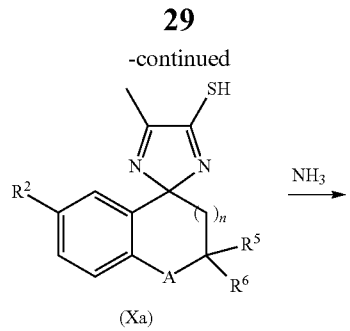

(Xa)

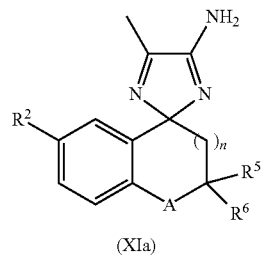

(XIa)

A compound of formula (Xa) may be obtained from a compound of formula (VIII) (Scheme 11). An imine of formula (VIII) is reacted with 2-oxopropane thioamide (described in Asinger et al. *Justus Liebigs Annalen der Chemie* 1971, vol 744, p. 51-64) in a solvent such as methanol at a temperature between room temperature and reflux temperature to yield a compound of formula (Xa). Compound (VIII) may be obtained from a ketone of formula (III) (Scheme 4) or prepared by methods known to the person skilled in the art. The compound of formula (Xa) is subsequently treated with ammonia, to yield the compound of formula (XIa). If 2-oxopropane thioamide is exchanged for 2-oxobutanethioamide in the process described by Scheme 11, the compounds of formula (Xb) and (XIb) will be obtained instead of (Xa) and (XIa) (see above).

Method (xii) Formation of a Corresponding Compound of Formula (XIa):

Scheme 12

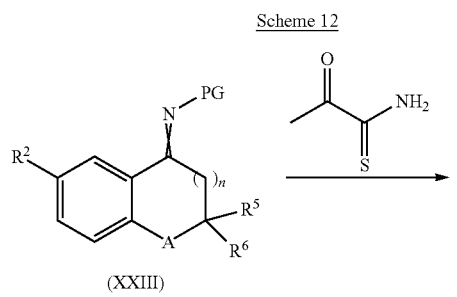

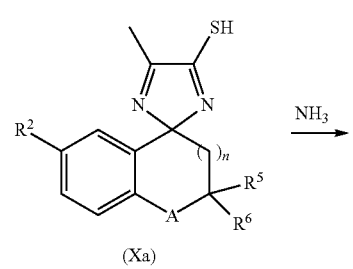

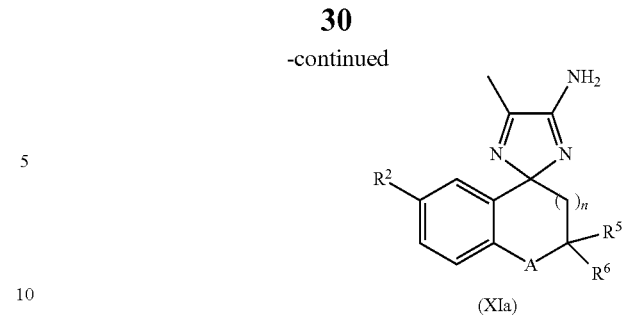

(XIa)

A compound of formula (XXIII) (wherein PG is a protecting group such as for example $S(O)R^{11}$ (Method (vii), formula XV), $SiR^{14}$ (such as $SiMe_3$, Method (ix), formula XXI), $P(O)(R^{13})_2)$ (Method (viii), formula XVIII), $S(O)_2$alkyl, C(O)Oalkyl, OH or Oalkyl is reacted with 2-oxopropane thioamide (described in Asinger et al. Justus Liebigs Annalen der Chemie 1971, vol 744, p. 51-64) in a solvent such as acetonitrile at a temperature range between +100° C. and +160° C. to yield a compound of formula (Xa) (Scheme 12). The compound of formula (Xa) is subsequently treated with ammonia, in a suitable solvent such as methanol, THF, or 2-methyl-tetrahydrofuran optionally in the presence of an oxidation agent, such as tert-butyl hydroperoxide, at a temperature between room temperature and 150° C., optionally in a closed system, to yield the compound of formula (XIa). If 2-oxopropane thioamide is exchanged for 2-oxobutanethioamide in the process described by Scheme 12, the compounds of formula (Xb) and (XIb) (see above) will be obtained instead of (Xa) and (XIa).

Method (xiii) Formation of a Corresponding Compound of Formula (XI):

Scheme 13

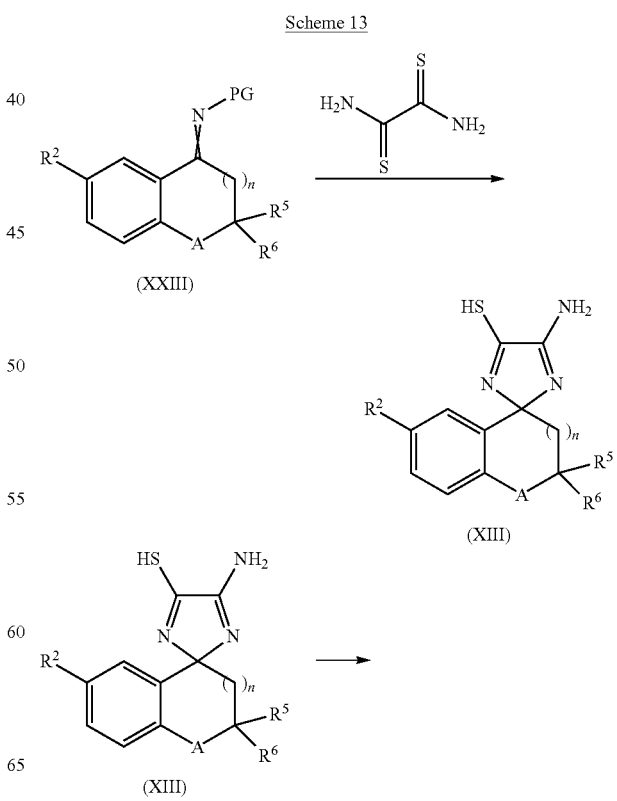

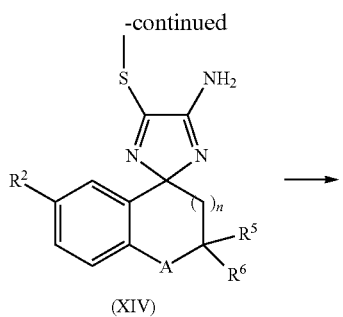

(XIV)

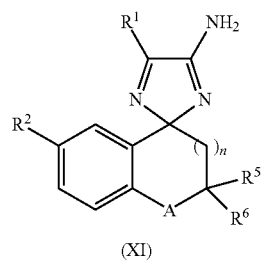

(XI)

A compound of formula (XXIII), wherein PG is a protecting group such as for example S(O)R$^{11}$ (Method (vii), formula XV), SiR$^{14}$ (such as SiMe$_3$) (Method (ix), formula XXI), P(O)(R$^{13}$)$_2$) (Method (viii), formula XVIII), S(O)$_2$alkyl, C(O)Oalkyl, OH or Oalkyl, is reacted with ethanebis(thioamide) to form a compound of formula (XIII) (Scheme 13). Said reaction may be performed at a temperature range between reflux temperature and +180° C., in a suitable solvent, such as methanol, ethanol or isopropyl alcohol, optionally in the presence of ammonia. An alkylating agent, such as methyl iodide and a thioimidazole of formula (XIII) are reacted to form a compound of formula (XIV) (Scheme 13). Said compound (XIV) may be further transformed into a compound of formula (XI), wherein R$^1$ is an alkyl group such as methyl or ethyl, by reacting it with an organometallic reagent, such as methylmagnesium bromide or ethylmagnesium bromide, in the presence of a suitable catalyst, such as [1,3-bis(diphenylphosphino)propane]nickel (II) chloride. Alternatively, the compound of formula (XI) (R$^1$ is an alkyl such as methyl or ethyl) may also be obtained by reacting compound of formula (XIV) with a mixture of zinc iodide and a Grignard reagent such as methylmagnesium bromide, or ethylmagnesium bromide, in the presence of a suitable catalyst such as bis(triphenylphosphine)palladium (II) chloride in a suitable solvent such as THF, 2-methyl-tetrahydrofuran or toluene.

Method (xiv) Formation of a Corresponding Compound of Formula (I):

Scheme 14

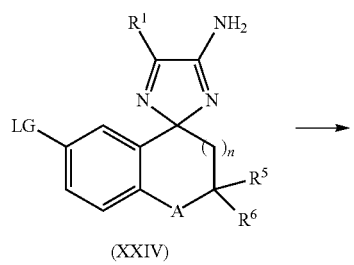

(XXIV)

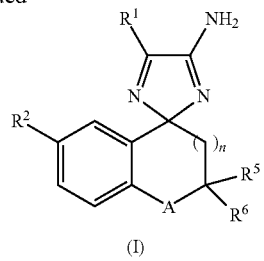

(I)

A compound of formula (I) wherein R$^2$ is an optionally substituted aryl or heteroaryl, may be obtained (Scheme 14) by starting from, for example, a compound of formula (XXIV), and reacting said compound of formula (XXIV) with a boronic acid or a boronic ester or a stannane of formula T-R$^2$, wherein T is for example B(OH)$_2$, B(Oalkyl)$_2$, or SnR$_3$, and R$^2$ is an optionally substituted aryl or a heteroaryl, in the presence of a transition metal catalyst such as a palladium catalyst, such as [1,1'-bis(diphenylphosphino)ferrocene]palladium(II) chloride, tetrakis(triphenylphosphine)-palladium (0), palladium diphenylphosphineferrocene dichloride, palladium(II) acetate or bis(dibenzylideneacetone) palladium (0), or sodium tetrachloropalladate (II). Optionally, a suitable ligand such as triphenylphosphine, tri-tert-butylphosphine or 2-(dicyclohexylphosphino)biphenyl, 3-(di-tert-butylphosphonium)propane sulfonate, or zinc and sodium triphenylphosphinetrimetasulfonate, is used. A suitable base, such as cesium fluoride, an alkyl amine, such as triethyl amine, or an alkali metal or alkaline earth metal carbonate or hydroxide such as potassium carbonate, sodium carbonate, cesium carbonate, or sodium hydroxide, may be used in the reaction. Said reaction may be performed in a suitable solvent, such as toluene, tetrahydrofuran, 2-methyl-tetrahydrofuran, dioxane, dimethoxyethane, water, ethanol, N,N-dimethylacetamide, acetonitrile or N,N-dimethylformamide, or mixtures thereof. Alternatively a compound of formula (I) wherein R$^2$ is an optionally substituted aryl or heteroaryl can be prepared from compound (XXIV) by transformation into a compound (1a) wherein T is as described above (B(OH)$_2$ or B(Oalkyl)$_2$) (Scheme 14a). Compound (1a) is then reacted with a compound R$^2$-LG wherein R$^2$ is an optionally substituted aryl or heteroaryl and LG is a leaving group such as a halogen to yield compound (I).

Scheme 14a

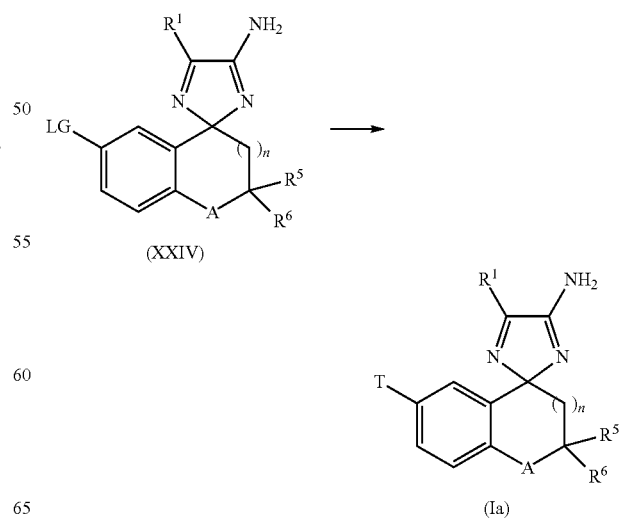

(XXIV)

(Ia)

Method (xv) Formation of a Corresponding Compound of Formula (I):

A compound of formula (I), wherein $R^2$ is cyano, may be obtained (Scheme 14) by starting from, for example, a compound of formula (XXIV), wherein LG is a leaving group such as a halogen, (such as iodide, bromide or chlorine), and reacting said compound of formula (XXIV) with a metal cyano reagent such as copper(I) cyanide.

Method (xvi) Formation of a Corresponding Compound of Formula (I):

A compound of formula (I), wherein $R^2$ is an alkyl group such as methyl may be generated from a compound of formula (XXIV) (Scheme 14), wherein LG represents a leaving group, such as a halogen, (such as iodide, bromide or chlorine), by reaction with an organometallic reagent generated from zinc iodide and methylmagnesium bromide under the influence of a transition metal catalyst such as for example bis(triphenylphosphine)palladium(II) chloride.

Method (xvii) Formation of a Corresponding Compound of Formula (I):

A compound of formula (I), wherein $R^2$ is an alkyne may be generated from a compound of formula (XXIV) (Scheme 14), wherein LG represents a leaving group, such as a halogen, (such as iodide or bromide), by reaction with an alkyne such as such as an alkylethyne or a cycloalkylethyne under the influence of a transition metal catalyst such as for example tetrakis(triphenylphosphine)palladium(0) in presence of a base such as triethylamine and copper(I)iodide. The alkyne is optionally silylated. Said reaction may be performed at a temperature range between room temperature and reflux temperature, in a suitable solvent, such as THF or toluene.

Method (xviii) Formation of a Corresponding Compound of Formula (I):

A compound of formula (I) wherein $R^2$ is $NHC(O)R^9$ may be prepared according to Scheme 14 by reacting a compound of formula (XXIV) with a compound $R^9C(O)NH_2$ in the presence of a suitable palladium catalyst such as palladium (II) acetate, optionally in the presence of a suitable ligand such as Xantphos. Said reaction is preformed in the presence of a suitable base such as cesium carbonate in a suitable solvent such as THF or 2-methyl-tetrahydrofuran at a temperature between reflux temperature and 160° C.

Method (xix) Formation of a Corresponding Compound of Formula (I):

A compound of formula (I) wherein $R^2$ is $NHC(O)R^9$ may be obtained from a compound of formula (XXIV) as shown in Scheme 15.

Scheme 15

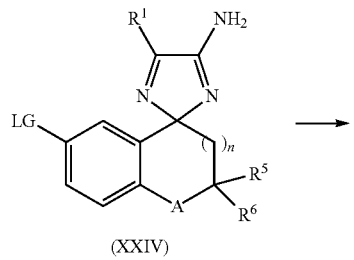

(XXIV)

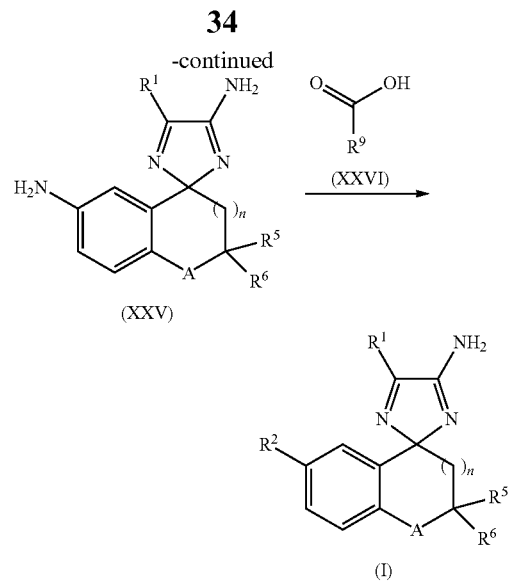

(XXV)

(I)

A compound of formula (XXIV) is reacted with ammonia in the presence of trans-4-hydroxy-L-proline, potassium carbonate and copper(I)iodide in a solvent such as DMSO at a temperature between room temperature and 150° C. to give a compound of formula (XXV). Said compound of formula (XXV) is further reacted with a carboxylic acid of formula (XXVI) wherein $R^9$ is as defined above. The reaction is performed in the presence of a suitable amide coupling agent such as 1-(3-dimethylaminopropyl)-3-ethyl-carbodiimide in a solvent such as DMF, optionally in the presence of hydrochloric acid.

Method (xx) Formation of a Corresponding Compound of Formula (IIIb):

Scheme 16

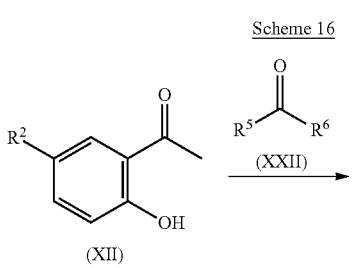

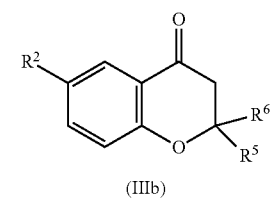

(IIIb)

A compound of formula (IIIb) may be obtained by reacting a ketone of formula (XII) with an aldehyde or ketone of formula (XXII) in presence of a base such as pyrrolidine, piperidine, proline, morpholine or Borax in a suitable solvent such as benzene, toluene, methanol or ethanol or a mixture of water and a suitable alcohol such as methanol or ethanol in a temperature range between room temperature and +180° C. (Scheme 16).

Method (xxi) Formation of a Compound of Formula (I)

Scheme 17

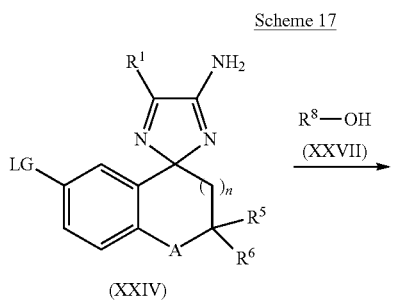

A compound of formula (I) wherein $R^2$ is $OR^8$ may be prepared by reacting a compound of formula (XXIV), wherein LG represents a leaving group, such as a halogen, (such as iodide or bromide), with an alcohol of formula (XXVII) in the presence of a suitable palladium catalyst such as palladium(II) acetate, optionally in the presence of a suitable ligand such as 2-(di-t-butylphosphino)-1,1'-binaphthyl (Scheme 17). Said reaction is performed in the presence of a suitable base such as cesium carbonate in a suitable solvent such as THF, 2-methyl-tetrahydrofuran or toluene at a temperature between 20° C. and 160° C.

Method (xxii) Formation of a Compound of Formula (II)

Scheme 18

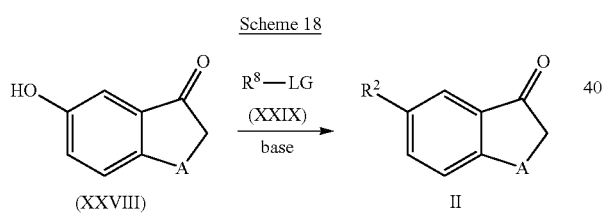

A compound of formula (II) wherein $R^2$ is $OR^8$ may be prepared by reacting a compound of formula (XXVIII), with a compound of formula (XXIX), wherein LG represent a suitable leaving group, such as halogen (such as chloride, bromide, or iodide), or trifluoromethylsulphonate, in the presence of a suitable base such as an alkali carbonate, such as $Cs_2CO_3$, $K_2CO_3$, $Na_2CO_3$, in a suitable solvent such as THF, 2-methyl-THF, DMF, or DMSO, or a mixture thereof, at a temperature between 0-150° C. (Scheme 18).

Method (xxiii) Formation of a Compound of Formula (II)

Scheme 19

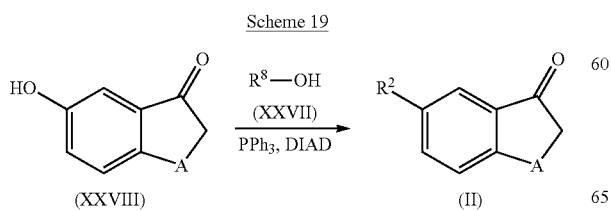

A compound of formula (II) wherein $R^2$ is $OR^8$ may be prepared by reacting a compound of formula (XXVIII), with a compound of formula (XXVII), in the presence of a suitable phosphine source such as triphenyl phosphine, in the presence of a suitable activating reagent such as diethyl azodicarboxylate, in a suitable solvent such as THF, 2-methyl-THF, or DMF or a mixture thereof, at a temperature of 0-100° C. (Scheme 19).

Method (xxiv) Formation of a Compound of Formula (XXX)

Scheme 20

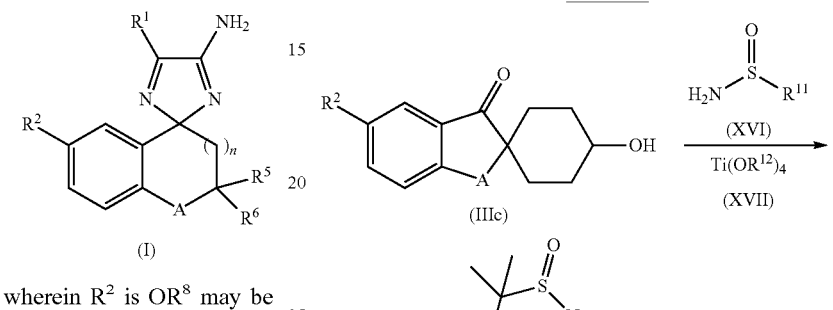

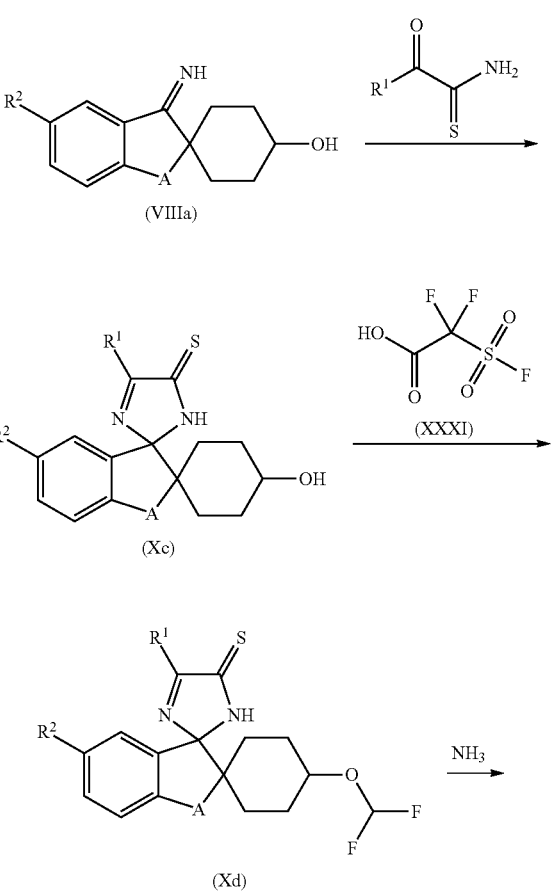

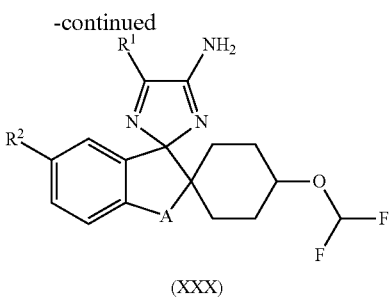

(XXX)

A compound of formula (VIIIa) may be obtained by for example method (vii) and method (x) as shown in Scheme 20. Said compound of formula (VIIIa) may be obtained by reacting a compound (XVa), with an acid such as hydrochloric acid under dry conditions in a suitable solvent (such as dioxane or tetrahydrofuran). Compound (VIIIa) may be isolated or reacted iii further without isolation. The compound of formula (VIIIa) is further reacted with 2-oxopropane thioamide (described in Asinger et al. *Justus Liebigs Annalen der Chemie* 1971, vol 744, p. 51-64) optionally in the presence of triethyl orthoformate, in a solvent such as methanol at a temperature between room temperature and reflux temperature, optionally under azeotropic distillation conditions, to yield a compound of formula (Xc). A compound of formula (Xd) may be obtained by reacting a compound of formula (Xa) with a suitable fluorinating agent such as a compound of formula (XXXI) under the influence of cuprous iodide in a suitable solvent, such as acetonitrile, at a temperature between room temperature and reflux temperature.

The transformation to a compound of formula (XXX) may be performed by reacting the compound of formula (Xd) with ammonia, optionally in the presence of an oxidation agent, such as tert-butyl hydroperoxide.

Compounds of formula (II), (III), (V), (VI), (XII), (XVI), (XVII), (XX), (XXII), (XXVI), and (XXVII) are commercially available compounds, or are known in the literature, or they are prepared by standard processes known in the art.

General Methods

All solvents used were of analytical grade and commercially available anhydrous solvents were routinely used for reactions. Starting materials used were available from commercial sources, or prepared according to literature procedures. Room temperature refers to 20-25° C. Solvent mixture compositions are given as volume percentages or volume ratios.

Microwave heating was performed in a Biotage Creator, Initiator or Smith Synthesizer Single-mode microwave cavity producing continuous irradiation at 2450 MHz. It is understood that microwaves can be used for the heating of reaction mixtures.

Thin layer chromatography (TLC) was performed on Merck TLC-plates (Silica gel 60 $F_{254}$) and spots were UV visualized. Straight phase flash column chromatography ("flash chromatography") was manually performed on Merck Silica gel 60 (0.040-0.063 mm), or automatically using an ISCO Combiflash® Companion™ system using RediSep™ normal-phase flash columns using the solvent system indicated. Phase separation was optionally performed on an Isolute® phase separator.

NMR

NMR spectra were recorded on a 400-600 MHz NMR spectrometer fitted with a probe of suitable configuration. Spectra were recorded at ambient temperature unless otherwise stated. Chemical shifts are given in ppm down- and upfield from TMS (0.00 ppm). The following reference signals were used in $^1$H-NMR: TMS δ 0.00, or the residual solvent signal of DMSO-$d_6$ δ 2.49, $CD_3OD$ δ 3.30, acetone-$d_6$ 2.04 or $CDCl_3$ δ 7.25 (unless otherwise indicated). Resonance multiplicities are denoted s, d, t, q, m, br and app for singlet, doublet, triplet, quartet, multiplet, broad and apparent, respectively. In some cases only diagnostic signals are reported.

HPLC, HPLCMS, and LCMS Analyses:

High pressure liquid chromatography (HPLC) was performed on a reversed phase (RP) column. A linear gradient was applied using for example mobile phase A (10 mM $NH_4OAc$ in 5% $CH_3OH$ or 5% $CH_3CN$ (aq.), or 0.1% $NH_3$ (aq.) or 0.1% formic acid (aq.)) and B ($CH_3OH$ or $CH_3CN$). Mass spectrometry (MS) analyses were performed in positive and/or negative ion mode using electrospray ionization (ESI+/−) and/or atmospheric pressure chemical ionization (APCI+/−).

GCFID and GCMS Analyses:

Gas chromatography (GC) was performed on a GC equipped with a mass spectrometer (MS) or a flame ionization detector (FID). The MS ion source was either an electron impact (EI) or a chemical ionization (CI, reactant gas methane). For separation a capillary column was used for example DB-5MS, (J&W Scientific). A linear temperature gradient was applied.

Preparative Chromatography:

Preparative chromatography was run on a Waters FractionLynx system with a Autosampler combined Automated Fraction Collector (Waters 2767), Gradient Pump (Waters 2525), Column Switch (Waters CFO) and PDA (Waters 2996). Column; XBridge® Prep C8 10 μm OBD™ 19×300 mm, with guard column; XTerra® Prep MS C8 10 μm 19×10 mm Cartridge. A gradient of A (95% 0.1 M $NH_4OAc$ in MilliQ water and 5% MeCN) in B (100% MeCN) or a gradient of A (95% 0.1 M $NH_4OAc$ in MilliQ water and 5% MeOH), A (0.2% $NH_3$ in MilliQ water) or A (0.2% formic acid in MilliQ water) in B (100% MeOH) was applied for LC-separation at flow rate 20 ml/min. Preparative chiral chromatography for separation of isomers was run on for example an LaPrep® system using the specified column and mobile phase system.

SFC Analyses:

Supercritical Fluid Chromatography (SFC) was performed on a straight phase column. A isocratic flow was applied using mobile phase A ($CO_2$) and for example mobile phase B (MeOH, EtOH or IPA).

Straight Phase HPLC Analyses:

High pressure liquid chromatography (HPLC) was performed on a straight phase column. A linear gradient or isocratic flow was applied using for example mobile phase A (Heptane) and B (EtOH or IPA).

High-Resolution Mass Spectrometry (HRMS) for accurate mass measurements was performed on a Waters Synapt-G2 mass spectrometer equipped with a LockSpray source and connected to an Acquity HPLC system with a PDA detector and an Acquity HPLC BEH C18 column. The measured mass confirmed the elemental composition within 3 ppm.

Abbreviations

ACN acetonitrile
aq aqueous
Atm atmospheric pressure
Boc t-butoxycarbonyl
Borax di-sodium tetraborate or sodium borate or sodium tetraborate
Cbz benzyloxycarbonyl
CDI 1,1'-carbonyldiimidazole
dba dibenzylideneacetone DCM dichloromethane
DEA diethylamine
DIBAL-H diisobutylaluminium hydride
DIPEA diisopropylethylamine
DME 1,2-dimethoxyethane
DMF N,N-dimethyl formamide
DMSO dimethyl sulfoxide
dppf 1,1'-bis(diphenylphosphino)ferrocene
$Et_2O$ diethyl ether
EtOAc ethyl acetate
EtOH ethanol
eq. or equiv. equivalent
h hour(s)
HPLC high performance liquid chromatography
IPA isopropanol
LCMS liquid chromatography mass spectrometry
LiHMDS lithium bis(trimethylsilyl)amide
MeOH methanol
min minute(s)
MS mass spectrometry
MW microwave(s)
$NH_4OAc$ ammonium acetate
NMR nuclear magnetic resonance
ox oxidation
Psi pounds per square inch
quant. quantitative
RCM ring closing metathesis
r.t. room temperature
sat. saturated
SFC supercritical fluid chromatography
TFA trifluoroacetic acid
THF tetrahydrofuran
TLC thin layer chromatography
TMEDA tetramethylethylenediamine
HPLC ultra performance liquid chromatography
2-Me THF 2-methyl tetrahydrofuran Compounds have been named using CambridgeSoft MedChem ELN v2.2 or ACD/Name, version 10.0, or 10.06, or version 12.01, software from Advanced Chemistry Development, Inc. (ACD/Labs), Toronto ON, Canada, www.acdlabs.com, or Lexichem, version 1.9, software from OpenEye.

EXAMPLES

Below follows a number of non-limiting examples of compounds of the invention.

Intermediate 1

N-(6-Bromochroman-4-ylidene)-2-methylpropane-2-sulfinamide

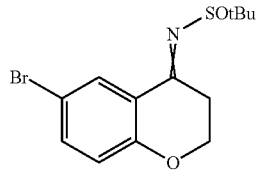

6-Bromochroman-4-one (5.0 g, 22 mmol) and 2-methylpropane-2-sulfinamide (2.6 g, 22 mmol) were dissolved in dry THF (80 mL). Titanium ethoxide (10 g, 44 mmol) was added. The resulting mixture was heated at 60° C. for 2 days. An additional portion of titanium ethoxide (1.0 g, 8.4 mmol) was added after 12 h. The mixture was mixed with heptane and evaporated onto silica gel. Flash chromatography on silica (0-50% EtOAc in heptane) gave the title compound (6.0 g, 83% yield). $^1$H NMR (500 MHz, $CDCl_3$) δ ppm 1.34 (s, 9 H) 3.26-3.32 (m, 1 H) 3.47-3.54 (m, 1 H) 4.28-4.40 (m, 2 H) 6.83 (d, 1 H) 7.46 (dd, 1 H) 8.06 (d, 1 H); MS (ES+) m/z 330 $[M+H]^+$.

Intermediate 2

2-Oxopropanethioamide

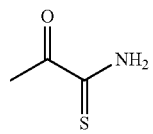

A solution of acetyl cyanide (140 mL, 1764.24 mmol) in 2-methyl-tetrahydrofuran (850 mL) was stirred at −10° C. as hydrogen sulfide (Sigma-Aldrich lecture bottle) was bubbled through the solution. The addition of hydrogen sulfide was stopped after 15 min and to the stirred mixture, triethylamine (1.230 mL, 8.82 mmol) in 2-methyl-tetrahydrofuran (13 mL) was added slowly over 30 min (exothermic reaction). Hydrogen sulfide addition was continued for 3 h at 5° C., 3 h at 10° C. and overnight at 15° C. Nitrogen gas was bubbled though the solution for 30 min, followed by evaporation of the volatiles. To the residue was added a mixture of heptane (100 mL) and EtOAc (100 mL). A solid was filtered off (79 g, 43% yield) and the filtrate was purified by a short-plug silica gel chromatography, eluting with 50% ethylacetate in heptane to give 79 g (43% yield) of the title compound. Both crops (in total 158 g, 87% yield) contained the title product of adequate purity according to GC-MS: MS (ES+) m/z 104 $[M+H]^+$.

Intermediate 3

6-Bromo-4'-methylspiro[chroman-4,2'-imidazole]-5'(1'H)-thione

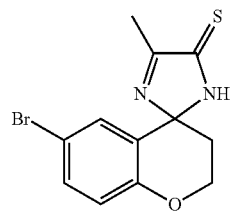 [SMILES: CC1=NC2(CCOc3ccc(Br)cc32)NC1=S]

N-(6-Bromochroman-4-ylidene)-2-methylpropane-2-sulfinamide (2.0 g, 6.0 mmol, Intermediate 1) was dissolved in dry dioxane (2 mL), and 4M HCl in dioxane (15 mL, 60.00 mmol) was added. A white precipitate started to form. The mixture was stirred at r.t. for 12 h. The mixture was diluted with dry $Et_2O$ (50 mL) and vacuum filtered. The filter cake was washed with dry $Et_2O$ (50 mL), then immediately dissolved by shaking in $NaHCO_3$ (aq) and $CH_2Cl_2$. The organic phase was dried ($K_2CO_3$) and evaporated to give 6-bromo-chroman-4-imine (1.3 g, 5.7 mmol). The solid was dissolved together with 2-oxopropanethioamide (Intermediate 2, 1.7 g, 17 mmol, Intermediate 2) in dry methanol (5 mL) and the resulting solution was heated at 60° C. for 12 h. Evaporation onto silica and purification by flash chromatography (EtOAc in heptane) gave the title compound (0.39 g, 21% yield). $^1$H NMR (400 MHz, CDCl$_3$) δ ppm 2.18 (m, 1 H), 2.35 (m, 1 H), 2.42 (s, 3 H), 4.35-4.40 (m, 1 H), 4.60 (m, 1 H), 6.81 (d, 1 H), 6.88 (d, 1 H), 7.33 (dd, 1 H); MS (ES+) m/z 311 [M+H]$^+$.

Intermediate 4

6-Bromo-5'-methylspiro[chroman-4,2'-imidazol]-4'-amine

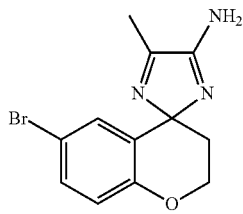 [SMILES: CC1=NC2(CCOc3ccc(Br)cc32)N=C1N]

6-Bromo-4'-methylspiro[chroman-4,2'-imidazole]-5' (1'H)-thione (0.10 g, 0.32 mmol, Intermediate 3) was dissolved in MeOH (1 mL) and 7M ammonia in MeOH (4 mL, 28 mmol) was added. The solution was heated at 60° C. for 12 h in a sealed vial. The solution was evaporated in vacuo. The treatment with 7M ammonia was repeated in the same way one more time. Evaporation in vacuo gave the title compound (73 mg, 77% yield) which was used without further purification in the following step. $^1$H NMR (400 MHz, CDCl$_3$) δ ppm 2.11 (m, 2 H), 2.35 (s, 3 H), 4.53 (m, 2 H), 4.98 (br s, 2 H), 6.66 (m, 1 H), 6.78 (d, 1 H), 7.22 (m, 1 H); MS (ES+) m/z 294 [M+H]$^+$.

Intermediate 5

6'-Bromo-4-methoxy-spiro[cyclohexane-1,2'-indane]-1'-one

Method A

Step 1: 6'-Bromospiro[cyclohexane-1,2'-indene]-1',4 (3'H)-dione

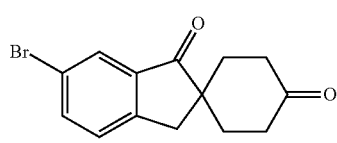 [SMILES: O=C1CCC2(CC1)Cc1ccc(Br)cc1C2=O]

Potassium tert-butoxide (7.50 g, 66.81 mmol) was added in portions to 6-bromo-2,3-dihydro-1H-inden-1-one (11.75 g, 55.67 mmol) and methyl acrylate (11.05 mL, 122.5 mmol) in THF (55 mL) under cooling in an ice-bath. The mixture was stirred for 1.5 h at r.t. Water (80 mL) and KOH (3.12 g, 55.7 mmol) was added and the mixture was heated to 75° C. and then at 60° C. overnight. The mixture was cooled to 0° C., and the formed precipitate was filtered off and dried in vacuo to give the title compound (11.69 g, 72% yield). $^1$H NMR (500 MHz, CDCl$_3$) δ ppm 1.83-1.92 (m, 2 H), 2.15-2.27 (m, 2 H), 2.40-2.50 (m, 2 H), 2.71 (dt, 2 H), 3.17 (s, 2 H), 7.39 (d, 1 H), 7.75 (dd, 1 H), 7.92 (d, 1 H); MS (ES+) m/z 293 [M+H]$^+$.

Step 2: 6'-Bromo-4-hydroxyspiro[cyclohexane-1,2'-inden]-1'(3'H)-one

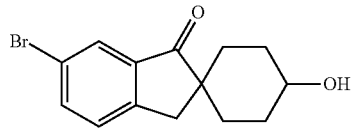 [SMILES: O=C1c2cc(Br)ccc2CC12CCC(O)CC2]

6'-Bromospiro[cyclohexane-1,2'-indene]-1',4(3'H)-dione (Intermediate 5 Step 1, 6.1 g, 20.8 mmol) was dissolved in THF (220 mL) and cooled to −65° C. Sodium borohydride (0.354 g, 9.36 mmol) was added and the cooling bath was removed. The mixture was allowed to reach 0° C. (approx. 30 min). Water (10 mL) was added, and most of the organic solvent was removed by evaporation. The residue was partitioned between EtOAc (100 mL), and an aq. solution of NaCl (50 mL). The organic phase was dried (MgSO$_4$) and evaporated to give a product which was combined with additional product obtained in a similar way starting from 14.6 g of 6'-bromospiro[cyclohexane-1,2'-indene]-1',4(3'H)-dione. Purification was made by flash chromatography (120 g silica, gradient elution: CH$_2$Cl$_2$ to CH$_2$Cl$_2$/MeOH (90:10)) affording 13.6 g (66% yield) of the title compound. The obtained material consisted of an 80:20 mixture of isomer 1 and isomer 2. Analytical samples of the isomers were isolated by flash chromatography (heptane/EtOAc gradient) to yield:

Isomer 1: (1r,4r)-6'-Bromo-4-hydroxyspiro[cyclohexane-1,2'-inden]-1'(3'H)-one:

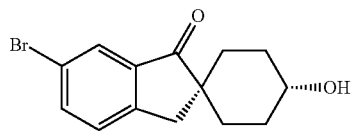 [SMILES: O=C1c2cc(Br)ccc2C[C@]12CC[C@@H](O)CC2]

$^1$H NMR (400 MHz, DMSO-d$_6$) δ ppm 1.20-1.43 (m, 4 H), 1.49-1.62 (m, 2 H), 1.79-1.89 (m, 2 H), 2.99 (s, 2 H), 3.39-3.50 (m, 1 H), 4.68 (d, 1 H), 7.56 (d, 1 H), 7.76 (d, 1 H), 7.85 (dd, 1 H); MS (ES+) m/z 317 [M+Na]$^+$ and Isomer 2: (1s,4s)-6'-bromo-4-hydroxyspiro[cyclohexane-1,2'-inden]-1'(3'H)-one

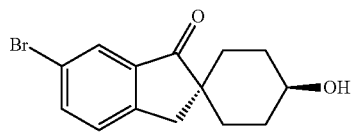

$^1$H NMR (400 MHz, DMSO-d$_6$) δ ppm 1.07-1.20 (m, 2 H), 1.51-1.63 (m, 2 H), 1.65-1.76 (m, 2 H), 1.93 (td, 2 H), 2.98 (s, 2 H), 3.83 (d, 1 H), 4.45 (d, 1 H), 7.51-7.55 (m, 1 H), 7.76 (d, 1 H), 7.84 (dd, 1 H); MS (ES+) m/z 317 [M+Na]$^+$.

Step 3: 6'-Bromo-4-methoxyspiro[cyclohexane-1,2'-inden]-1'(3'H)-one

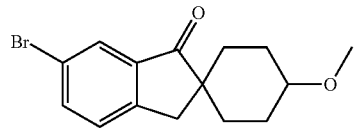 [SMILES: COC1CCC2(CC1)Cc1ccc(Br)cc1C2=O]

A mixture of isomers of 6'-bromo-4-hydroxyspiro[cyclohexane-1,2'-inden]-1'(3'H)-one (Intermediate 5 Step 2, 12.7 g, 43.0 mmol) was dissolved in THF (210 mL) under $N_2$ and cooled to 0° C. Potassium tert-butoxide (5.79 g, 51.6 mmol) was added portionwise and the mixture was stirred at 0° C. for 25 min. Methyl iodide (4.30 mL, 68.8 mmol) was added. The cooling bath was removed, and the mixture was stirred at r.t. Additional potassium tert-butoxide (0.483 g, 4.30 mmol) was added twice, after 2 h and 3 h respectively, and then the mixture was stirred for 2 h. Water (100 mL) was added and the resulting solution was partitioned between aq. NaCl solution (200 mL), and EtOAc (200 mL). The aq. phase was extracted with another portion of EtOAc (100 mL). The combined organic phases were dried ($MgSO_4$) and evaporated to give 12.5 g (94% yield) of a mixture (approx. 80:20) of:

Isomer 1: (1r,4r)-6'-bromo-4-methoxyspiro[cyclohexane-1,2'-inden]-1'(3'H)-one

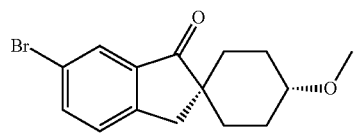 [SMILES: CO[C@H]1CC[C@]2(CC1)Cc1ccc(Br)cc1C2=O]

and Isomer 2: (1s,4s)-6'-bromo-4-methoxyspiro[cyclohexane-1,2'-inden]-1'(3'H)-one:

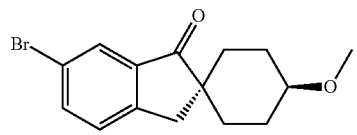 [SMILES: CO[C@H]1CC[C@@]2(CC1)Cc1ccc(Br)cc1C2=O]

$^1$H NMR (400 MHz, DMSO-$d_6$, signals for Isomer 1) δ ppm 1.20-1.32 (m, 2 H), 1.40-1.48 (m, 2 H), 1.51-1.62 (m, 2 H), 1.97-2.07 (m, 2 H), 3.00 (s, 2 H), 3.15-3.23 (m, 1 H), 3.26 (s, 3 H), 7.56 (d, 1 H), 7.77 (d, 1 H), 7.86 (dd, 1 H); MS (ES+) m/z 309 [M+H]$^+$.

Method B

Step 1: 6'-Bromospiro[cyclohexane-1,2'-indene]-1',4(3'H)-dione

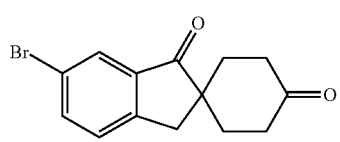 [SMILES: O=C1CCC2(CC1)Cc1ccc(Br)cc1C2=O]

6-Bromo-2,3-dihydro-1H-inden-1-one (800 g, 3.79 mol) and methyl acrylate (787 mL, 8.72 mol) in 2-methyl-tetrahydrofuran (4 L) were stirred at 28° C. Potassium tent-pentoxide solution in toluene (1.7 M, 2.68 L, 4.55 mol) was added dropwise keeping the temperature between 30° C. and 43° C. The mixture was stirred for 0.5 h at 25° C. Water (4 L) was added and after 10 min were KOH (383 g, 6.82 mol) added. The mixture was heated to reflux and the organic solvent was distilled off during 4 h. The mixture was cooled to 10° C., and the formed precipitate was filtered off and dried in vacuo to give the title compound (837 g, 75% yield). $^1$H NMR (500 MHz, DMSO-$d_6$) δ ppm 1.74-1.85 (m, 2 H), 1.94 (m, 2 H), 2.34 (m, 2 H), 2.52-2.60 (m, 2 H), 3.27 (s, 2 H), 7.60 (d, 1 H), 7.79-7.83 (m, 1 H), 7.89 (m, 1 H); MS (ES+) m/z 293 [M+H]$^+$.

Step 2: (1r,4r)-6'-Bromo-4-hydroxyspiro[cyclohexane-1,2'-inden]-1'(3'H)-one

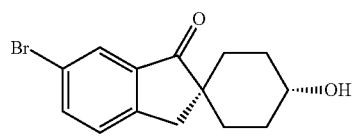

To 6'-bromospiro[cyclohexane-1,2'-indene]-1',4(3'H)-dione (Intermediate 5 Step 1, 50.52 g, 172.3 mmol) in DCM (250 mL), borane tert-butylamine complex (5.70 g, 65.49 mmol) in DCM (50 mL) was slowly charged at 0° C. After 40 min concentrated HCl (20 mL) followed by 20% NaCl (70 mL) were charged. The mixture was allowed to reach r.t. and was stirred for 30 min. The phases were separated and to the water phase were DCM (40 mL) and $H_2O$ (10 mL) charged. The organic phases were combined, concentrated and dried under vacuum overnight to give the title product (52.4 g, 100% yield) as a mixture of the title product (83% yield) and the other diasteromer (1s,4s)-6'-bromo-4-hydroxyspiro[cyclohexane-1,2'-inden]-1'(3'H)-one (17%): $^1$H NMR (500 MHz, CDCl$_3$, signals for both isomers) δ ppm $^1$H NMR (500 MHz, CDCl$_3$) δ ppm 1.39-1.50 (m, 3 H), 1.67-1.85 (m, 3 H) 2.05-2.12 (m, 2 H) 2.96 (s, 0.34 H), 2.98 (s, 1.68 H), 3.76 (m, 0.83 H), 4.04 (m, 0.17 H), 7.34 (m, 1 H) 7.70 (m, 1 H) 7.88 (d, 1 H); MS (ES+) m/z 295 [M+H]$^+$.

Step 3: (1r,4r)-6'-Bromo-4-methoxyspiro[cyclohexane-1,2'-inden]-1'(3'H)-one

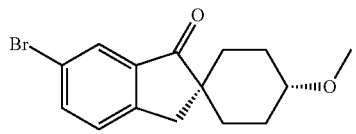 [SMILES: CO[C@H]1CC[C@]2(CC1)Cc1ccc(Br)cc1C2=O]

(1r,4r)-6'-Bromo-4-hydroxyspiro[cyclohexane-1,2'-inden]-1'(3'H)-one (Intermediate 5 Step 2, 50.9 g, 172 mmol) (containing 17% of (1s,4s)-6'-bromo-4-hydroxyspiro[cyclohexane-1,2'-inden]-1'(3'H)-one), methyl iodide (18.33 mL, 293.1 mmol) and 2-Me THF (360 mL) were heated to 30° C. under $N_2$. Potassium tent-pentoxide solution in toluene (1.7 M in toluene, 203 mL, 344 mmol) was added dropwise over 30 min. The mixture was allowed to reach r.t. and was stirred for 1 h. Water (250 mL) was added and after 10 min of stirring the phases were separated. The organic phase was washed with water (140 mL), concentrated and dried in vacuo to give a solid. 300 mL MeOH was added to the solid and the mixture was heated to reflux. Water was added (30 mL) followed by reflux for 5 min. The mixture was slowly allowed to reach r.t. The mixture was stirred overnight at r.t. The solid was filtered off to give the title compound as a single isomer (31 g, 58% yield): $^1$H NMR (500 MHz, CDCl$_3$) δ ppm 1.38 (m, 2 H) 1.52 (m, 2 H) 1.77 (td, 2 H) 2.16 (m, 2 H) 2.98 (s, 2 H) 3.28 (m, 1 H) 3.40 (s, 3 H) 7.35 (d, 1 H) 7.70 (dd, 1 H) 7.88 (d, 1 H); MS (ES+) m/z 309 [M+H]$^+$.

Method C

Step 1: 6'-Bromospiro[cyclohexane-1,2'-indene]-1',4(3'H)-dione

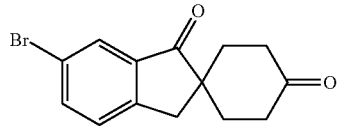 [SMILES: O=C1CCC2(CC1)Cc1ccc(Br)cc1C2=O]

Methyl acrylate (6.6 L, 73 mol) was charged gradually in three equal portions (each 2.2 L, 24.6 mol) to a mixture of 6-bromo-1-indanone (8.00 kg, 37.9 mol), THF (16 L) and potassium tert-butoxide (210 g, 1.87 mol) at approximately 20-30° C. Additional potassium tert-butoxide (86 g, 0.77 mol), dissolved in THF (0.39 L), was charged after the first portion of methyl acrylate. More potassium tert-butoxide (86 g, 0.77 mol), dissolved in THF (0.39 L), was charged after the second portion of methyl acrylate. Further potassium tert-butoxide (4.64 kg, 41.3 mol) solution in THF (21 L) was then charged gradually at approximately 20-30° C. Solvent (21.5 L) was distilled off at approximately 65° C. and then a mixture of water (49 L) and 50%. aq KOH (2.3 L, 30 mol) was added over approximately 10 min. at below 60° C. The reaction was held at 60° C. for approximately 6 h., then cooled to 20° C. over 1 h. and then filtered after holding at 20° C. for approximately 12 h. The solids were washed with a mixture of water (8 L) and THF (4 L), and then dried to give the title compound (7.47 kg, at 92% w/w NMR assay, 23.4 mol, 62% yield):

$^1$H NMR (500 MHz, DMSO-d$_6$) δ ppm 1.78-1.84 (m, 2 H), 1.95 (td, 2 H), 2.32-2.38 (m, 2 H), 2.51-2.59 (m, 2 H), 3.27 (s, 2 H), 7.60 (d, 1 H), 7.81 (m, 1 H), 7.89 (m, 1 H).

Step 2: (1r,4r)-6'-Bromo-4-hydroxyspiro[cyclohexane-1,2'-inden]-1(3'H)-one

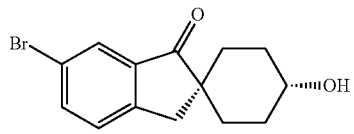

6'-bromospiro[cyclohexane-1,2'-indene]-1',4(3'H)-dione (Intermediate 5 Step 1, 750 g, 2.56 mol) and propan-2-ol (9.855 L) were heated to reflux and ground NaOH (100 g, 2.50 mol) was added in two portions to the mixture. The mixture was heated to reflux for 2 h. 5 L of solvent were removed by vacuum distillation. Toluene (2 L) was added and 2 L of solvent was removed by vacuum distillation. Toluene (3 L) followed by 2 M HCl (1.278 L, 2.56 mol) was added to the mixture under stirring. The phases were separated and the organic phase was washed with water (2.0 L). The organic phase was concentrated and toluene (2 L) was added and then the mixture was concentrated. 2-methyl-tetrahydrofuran (1 L) was added and then 0.5 L of the solvent was removed by vacuum distillation, the resulting mixture was used as such in the next step. The title compound was a mixture with the diastereomer (1s,4s)-6'-bromo-4-hydroxyspiro[cyclohexane-1,2'-inden]-1'(3'H)-one in the ratio 7:3 (established by HPLC and NMR analysis): $^1$H NMR (500 MHz, CDCl$_3$, signals for both isomers) δ ppm 1.40-1.52 (m, 3 H), 1.70-1.84 (m, 3 H), 2.04-2.11 (m, 2 H), 2.97 (s, 0.62 H), 3.00 (s, 1.38 H), 3.73-3.81 (m, 0.7 H), 4.04 (m, 0.3 H), 7.31-7.38 (m, 1 H), 7.67-7.73 (m, 1 H), 7.89 (m, 1 H).

Step 3: (1r,4r)-6'-Bromo-4-methoxyspiro[cyclohexane-1,2'-inden]-1'(3'H)-one

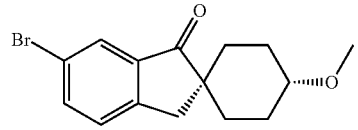 [SMILES: CO[C@H]1CC[C@]2(CC1)Cc1ccc(Br)cc1C2=O]

Borane tert-butylamine complex (820 g, 9.4 mol) dissolved in DCM (3.6 L) was charged to a slurry of 6'-bromospiro [cyclohexane-1,2'-indene]-1',4(3'H)-dione (Intermediate 5 Step 1, 7.46 kg, at 92% w/w NMR assay, 23.4 mol) in DCM (41 L) at approximately 0-5° C. over approximately 40 min. After approximately 1 h., a solution of NaCl (2.68 kg), water (12.9 L) and 37% hydrochloric acid (2.5 L, 31 mol) was charged. The mixture was warmed to approximately 15° C. and the phases separated after settling into layers. The DCM phase, containing (1r,4r)-6'-Bromo-4-hydroxyspiro[cyclohexane-1,2'-inden]-1'(3'H)-one (Intermediate 5 Step 2), was returned to the reactor, together with methyl methanesulfonate (2.59 L, 30.5 mol) and tetrabutyl-ammonium chloride (130 g, 0.47 mol). Aq. 50% NaOH (13 L, 229 mol) was then charged to the vigorously agitated reaction mixture over approximately 1 h. at approximately 20° C. After holding for approximately 16 h., water (19 L) was added and the aq. phase discarded after separation. Solvent (34 L) was distilled off at atmospheric pressure and then more solvent (20 L) was distilled off whilst adding EtOH (20 L) in 5 equal portions. EtOH (14 L) was added and the solution cooled to 25° C. A sample (0.3 L) was taken at 40° C. during the cooling. The sample crystallised spontaneously and was recharged to the reactor at 25° C. After re-heating to approximately 40° C., water (14 L) was charged over approximately 20 min. The slurry was cooled to approximately 20° C. and held for 16 h. before filtering. The solids were washed with a mixture of water (4.8 L) and EtOH (6.4 L) and then dried to give the title compound (containing 4.6% of Isomer 2: (1s,4s)-6'-bromo-4-methoxyspiro[cyclohexane-1,2'-inden]-1'(3'H)-one by HPLC-analysis) (5.57 kg, at 91% NMR assay, 16.4 mol, 70% yield): $^1$H NMR (500 MHz, DMSO-d$_6$) δ ppm 1.22-1.32 (m, 2 H), 1.41-1.48 (m, 2 H), 1.56 (td, 2 H), 1.99-2.07 (m, 2 H), 3.01 (s, 2 H), 3.16-3.23 (m, 1 H), 3.27 (s, 3 H), 7.56 (d, 1 H), 7.77 (d, 1 H), 7.86 (dd, 1 H).

Intermediate 10

6-Bromo-2',3',5',6'-tetrahydrospiro[indene-2,4'-pyran]-1(3 H)-one

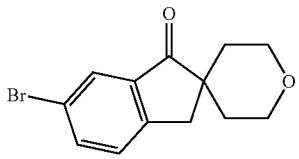 [SMILES: O=C1c2cc(Br)ccc2CC12CCOCC2]

A solution of potassium tert-butoxide (3.94 g, 35.1 mmol) in t-BuOH (35 mL) was added dropwise over 15 min to a solution of 6-bromo-1-indanone (3.53 g, 16.73 mmol) in 2-methyl-tetrahydrofuran (350 mL) at r.t. under a nitrogen atmosphere. After 15 min bis(2-bromoethyl)ether (2.102 mL, 16.73 mmol) was added and the resulting mixture was stirred at r.t. for 5 h. Potassium tert-butoxide (0.938 g, 8.36 mmol) was added and the mixture was stirred at r.t. overnight. The mixture was quenched with saturated aq. NH$_4$Cl (150 mL) and the organic layer was separated. The aqueous layer was extracted with EtOAc (3×50 mL) and Et$_2$O (50 mL). The combined organics were washed with brine (100 mL), dried over MgSO$_4$, filtered and concentrated. The resulting residue was taken up in DCM, concentrated onto silica gel and purified on a silica gel column eluted with 0-40% EtOAc in heptane to give 1.14 g (24% yield) of the title compound; MS (ES+) m/z 281 [M+H]$^1$.

Intermediate 11

6'-Bromo-4,4-difluoro-spiro[cyclohexane-1,2'-indane]-1'-one

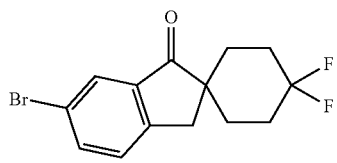 [SMILES: O=C1c2cc(Br)ccc2CC12CCC(F)(F)CC2]

A solution of 6'-bromospiro[cyclohexane-1,2'-indene]-1', 4(3'H)-dione (Intermediate 5 Method A Step 1, 2 g, 6.82 mmol) in DCM (10 mL) was added to a solution of 4-tert-butyl-2,6-dimethylphenylsulfur trifluoride (FLUOLEAD™) (3.24 g, 13.0 mmol) and EtOH (0.159 mL, 2.73 mmol) in DCM (10 mL) at 0° C. The reaction mixture was allowed to reach r.t. and was stirred overnight. The reaction mixture was poured into a cooled aq. 1 M NaOH solution (5 mL) and the mixture was stirred for 60 min at r.t. The water phase was extracted with DCM twice. The combined organic phases were concentrated and the crude product was purified on a silica column (gradient of EtOAc/n-heptane 0-20%). Two batches were collected. Batch 1 gave 2.2 g (purity by HPLC, uv detection 42%) and batch 2 gave 819 mg (purity by HPLC, uv detection 62%). The compound was used as such in next step. $^1$H NMR (500 MHz, CDCl$_3$) δ ppm 1.57-1.66 (m, 2 H), 1.83-1.98 (m, 2 H), 2.00-2.08 (m, 2 H), 2.26-2.38 (m, 2 H), 3.01 (s, 2 H), 7.35 (d, 1 H), 7.72 (dd, 1 H), 7.89 (d, 1 H).

Intermediate 12

5-Bromo-4'-methoxy-3H-spiro[benzofuran-2,1'-cyclohexane]-3-one

Step 1: 2-(5-Bromo-2-fluorophenyl)-2-((trimethylsilyl)oxy)acetonitrile

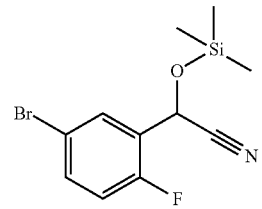 [SMILES: C[Si](C)(C)OC(C#N)c1cc(Br)ccc1F]

To a solution of 5-bromo-2-fluoro-benzaldehyde (30.45 g, 150 mmol) in THF (250 mL), was added DMAP (0.203 g, 1.73 mmol) followed by trimethylsilyl cyanide (18.24 g, 183.8 mmol). The reaction mixture was stirred at r.t. for 4 h and then concentrated in vacuo to afford 45.8 g (quantitative yield) of the title compound which was used directly in the next step without further purification. $^1$H NMR (400 MHz, CDCl$_3$): δ ppm 1.71 (m, 6 H), 2.31 (m, 2 H), 3.32 (m, 1 H), 3.41 (s, 3 H), 7.03 (d, J=9.20 Hz, 1 H), 7.36 (t, J=8.80, 2.00 Hz, 1 H), 7.77 (d, J=2.00 Hz, 1 H).

Step 2: (5-Bromo-2-fluorophenyl)(1-hydroxy-4-methoxycyclohexyl)methanone

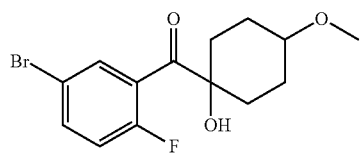 [SMILES: COC1CCC(O)(C(=O)c2cc(Br)ccc2F)CC1]

LiHMDS (1.0 M, 165 mL, 165 mmol) was added dropwise to a solution of 2-(5-bromo-2-fluorophenyl)-2-((trimethylsilyl)oxy)acetonitrile (Intermediate 12 Step 1, 45.80 g, 150 mmol) in acetonitrile (250 mL) at −78° C. The reaction mixture was stirred for 1.5 h and a solution of 4-methoxycyclohexanone (Lee, C. K.; Lee, I.-S. H.; Noland, W. E. Heterocycles, 2007, 71, 419-428) (20.3 g, 150 mmol) in THF (30 mL) was added slowly and the stirring at −78° C. was continued for 3 h. 1M HCl aq. (300 mL) was added at −78° C., and the mixture was allowed to warm slowly to r.t. and stirred overnight. The phases were separated and the aqueous layer was extracted with EtOAc (2×500 mL). The combined extracts were dried over Na$_2$SO$_4$, filtered, and concentrated in vacuo to afford 57 g of the crude material. A portion of the crude product (30 g) was purified by flash chromatography using a gradient of 0 to 50% EtOAc in EtOAc in hexanes to afford 9.24 g of the title compound.

Step 3: 5-Bromo-4'-methoxy-3H-spiro[benzofuran-2,
1'-cyclohexan]-3-one

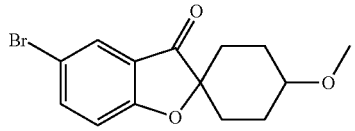

A mixture of (5-bromo-2-fluorophenyl)(1-hydroxy-4-methoxycyclohexyl)methanone (Intermediate 12 Step 2, 1.05 g, 3.17 mmol) and potassium tert-butoxide (0.445 g, 3.80 mmol) in THF (10 mL) was heated in a microwave reactor at 70° C. for 30 min. The solvent was removed in vacuo and the residue was purified by flash chromatography using a gradient of 0 to 15% EtOAc in hexanes to afford 388 mg (39% yield) of the title compound. $^1$H NMR (400 MHz, CDCl$_3$): δ ppm 1.71 (m, 6 H), 2.31 (m, 2 H), 3.32 (m, 1 H), 3.41 (s, 3 H), 7.03 (d, J=9.20 Hz, 1 H), 7.36 (t, J=8.80, 2.00 Hz, 1 H), 7.77 (d, J=2.00 Hz, 1 H); MS (ES+) m/z 312 [M+H]$^+$.

Intermediate 14

3-Bromo-5-(prop-1-ynyl)pyridine

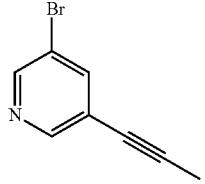

3,5-Dibromopyridine (30 g, 127 mmol), copper(I) iodide (7.24 g, 38.0 mmol) and tetrakis(triphenylphosphine)palladium(0) (4.39 g, 3.80 mmol) were mixed in toluene (120 mL) under nitrogen atmosphere. 1-(Trimethylsilyl)-1-propyne (26.36 mL, 164.5 mmol), triethylamine (53.0 mL, 380 mmol) and tetra-n-butylammonium fluoride (12.66 mL, 12.66 mmol) were added. The mixture was heated to reflux and stirred under nitrogen overnight. Water (100 mL) was added to the reaction mixture was filtered and the phases separated. The organic phase was washed with 1 M HCl aq. (100 mL). The organic phase was concentrated and dissolved in MeOH (200 mL), filtered and concentrated. The mixture was dissolved in DCM and evaporated with silica gel to dryness, and then transferred to a silica gel column (300 g). The product was eluted with a gradient of EtOAc (0-5%) in heptane. The fractions containing the pure product was combined and evaporated to give the title compound (16.39 g, 66% yield): $^1$H NMR (500 MHz, CDCl$_3$) δ ppm 2.08 (s, 3 H), 7.82 (t, 1 H), 8.52 (d, 1 H), 8.55 (d, 1 H); MS (APCI+) m/z 197.0 [M+H]$^+$.

Intermediate 15

5-(Prop-1-ynyl)pyridin-3-ylboronic acid

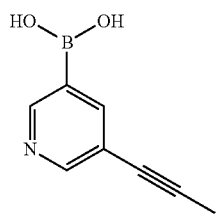

3-Bromo-5-(prop-1-ynyl)pyridine (Intermediate 14, 25 g, 117 mmol), 2-methyl-tetrahydrofuran (60 mL), toluene (200 mL) and triisopropyl borate (33.2 mL, 140.78 mmol) were mixed. The mixture was cooled to −50° C. To the cold mixture was added n-BuLi (59.8 mL, 149.5 mmol) dropwise during 30 min. The mixture was stirred for 60 min. at −50° C. 2M HCl aq. (100 mL) was added. The mixture was then allowed to reach r.t. and stirred for 20 min. The organic and water phase were separated. The organic phase was extracted with NaOH (2M aq.) (2×100 mL). The water phases were combined and the pH was adjusted to pH 5. The product was extracted with 2-methyl-THF (2×100 mL). The organic phase was dried with Na$_2$SO$_4$, filtered and concentrated to give the title compound (16.47 g, 87% yield): $^1$H NMR (500 MHz, CD$_3$OD) δ ppm 2.11 (s, 3 H) 8.21 (br. s., 1 H) 8.53 (m, 2 H); MS (APCI+) m/z 162.2 [M+H]$^+$.

Intermediate 16

2-Bromo-4-(prop-1-ynyl)pyridine

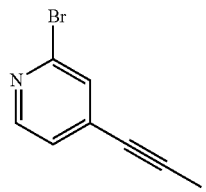

To a solution of 2-bromo-4-iodopyridine (2 g, 7.04 mmol), copper(I) iodide (0.080 mL, 2.11 mmol) and tetrakis(triphenylphosphine)palladium(0) (0.407 g, 0.35 mmol) in toluene (85 mL) was added 1-(trimethylsilyl)-1-propyne (1.054 mL, 7.04 mmol), triethylamine (3.24 mL, 23.25 mmol) and tetrabutylammonium fluoride (1 M in THF, 7.04 mL, 7.04 mmol) and the resulting mixture was stirred under an argon atmosphere at r.t. overnight. The mixture was concentrated and the resulting residue was partitioned between water (10 mL) and DCM (10 mL) and poured into a phase separator. The organic phase was collected, and the aqueous phase was extracted once with DCM (10 mL). The combined organics were concentrated and purified by flash chromatography using 0% to 30% EtOAc in heptane to give the title compound (1.195 g, 87% yield): $^1$H NMR (500 MHz, DMSO-d$_6$) δ ppm 2.11 (s, 3 H), 7.42 (dd, 1 H), 7.65 (s, 1 H), 8.35 (dd, 1 H); MS (ES+) m/z 196 [M+H]$^+$; MS (APCI+) m/z 196 [M+H]$^+$.

Intermediate 17

4-(Prop-1-ynyl)-2-(trimethylstannyl)pyridine

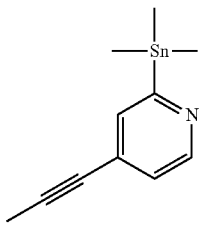

2-Bromo-4-(prop-1-ynyl)pyridine (Intermediate 16, 1.077 g, 5.49 mmol) was dissolved in toluene (30 mL) and 1,1,1,2,2,2-hexamethyldistannane (2.278 mL, 10.99 mmol) and tetrakis(triphenylphosphine)palladium(0) (0.635 g, 0.55 mmol) were added. The reaction was stirred at 80° C. overnight under argon atmosphere. The mixture was cooled to r.t. and filtered through a pad of diatomaceous earth and concentrated in vacuo. Toluene (20 mL) was added and the mixture was concentrated in vacuo to yield the title compound that was used as such in the next step: MS (APCI+) m/z 282 [M+H]$^+$.

Intermediate 18

Methyl 5-(but-2-ynyloxy)picolinate

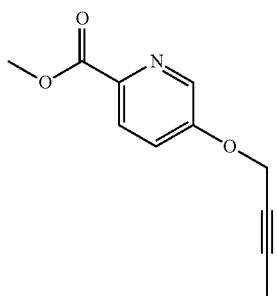

To a solution of but-2-yn-1-ol (0.635 mL, 8.49 mmol) in THF (30 mL) were added methyl 5-hydroxypicolinate (1.3 g, 8.49 mmol), triphenylphosphine (3.34 g, 12.73 mmol) and diisopropyl azodicarboxylate (2.507 mL, 12.73 mmol) at 0° C. The reaction mixture was then allowed to reach r.t and stirred for 2 days. The reaction mixture was concentrated and the product was purified by flash chromatography using a heptane/EtOAc gradient to give 1.42 g (82% yield) of the title compound. $^1$H NMR (400 MHz, CDCl$_3$) δ ppm 1.87 (t, 3 H), 4.00 (s, 3 H), 4.79 (q, 2 H), 7.41 (dd, 1 H), 8.11-8.20 (m, 1 H), 8.49 (d, 1 H).

Intermediate 19

5-(But-2-ynyloxy)picolinic acid

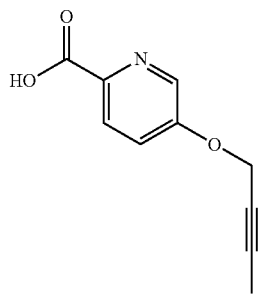

To a solution of methyl 5-(but-2-ynyloxy)picolinate (Intermediate 18, 1.42 g, 6.92 mmol) in THF (15 mL) was added lithium hydroxide (0.871 g, 20.76 mmol) dissolved in water (5 mL) to the reaction mixture at r.t. After 3 days of stirring was the reaction mixture partioned between water and EtOAc. The water was made acidic with aq. solution of HCl (2M) and extracted with EtOAc. The organic phase was dried over MgSO$_4$ and concentrated to give 0.60 g (45% yield) of the title compound: $^1$H NMR (500 MHz, CD$_3$OD) δ ppm 1.84 (t, 3 H), 4.87 (q, 2 H), 7.57 (dd, 1H), 8.14 (d, 1 H), 8.34 (d, 1 H); MS (ES+) m/z 192 [M+H]$^+$.

Intermediate 26

6-Bromo-5',6'-dihydro-4'H-spiro[chromene-2,3'-pyran]-4(3 H)-one

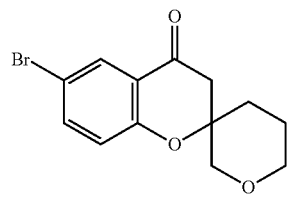

A solution of 1-(5-bromo-2-hydroxyphenyl)ethanone (8.2 g, 38.13 mmol), dihydro-pyran-3-one (4.96 g, 49.57 mmol) and pyrrolidine (4.12 mL, 49.57 mmol) in toluene (80 mL) was stirred at 50° C. for 1 h. The temperature was increased to reflux, and the reaction was refluxed for 22 h. Additional dihydro-pyran-3-one (0.5 g 5 mmol) was added and the mixture was refluxed for an additional 24 h. The mixture was allowed to reach r.t., and then water (50 mL) followed by EtOAc (100 mL) was added. The organic layer was concentrated and the residue was purified by flash chromatography using a gradient of heptane to 40% EtOAc in heptane to give the title compound (9 g, 79% yield): $^1$H NMR (500 MHz, CDCl$_3$) δ ppm 1.57 (m, 1 H), 1.72 (ddd, 1 H), 1.96 (m, 1 H), 2.12 (m, 1 H), 2.71 (m, 2 H), 3.51 (d, 1 H), 3.58 (m, 1 H), 3.86 (m, 2 H), 6.96 (d, 1 H), 7.57 (dd, 5 H), 7.97 (d, 4 H); MS (ES+) m/z 297 [M+H]$^+$.

Intermediate 27

6-Bromo-2-tetrahydropyran-3-yl-chroman-4-one

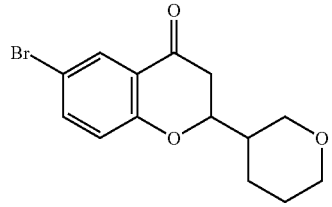 [SMILES: O=C1CC(C2CCCOC2)Oc2ccc(Br)cc21]

A solution of 1-(5-bromo-2-hydroxyphenyl)ethanone (18 g, 83.70 mmol), tetrahydro-2H-pyran-3-carbaldehyde (9.55 g, 83.70 mmol) and pyrrolidine (6.95 mL, 83.70 mmol) in MeOH (125 mL) was heated to reflux for 4.5 h. The mixture was allowed to reach r.t. and concentrated. The residue was dissolved in EtOAc (150 mL) and washed with 1M NaOH (80 mL), 1M HCl (80 mL), and brine (80 mL) successively. The organic phase was concentrated, the residue was purified by flash chromatography with a gradient of 10% EtOAc in heptane to 40% EtOAc in heptane to give the title compound (18 g, 69% yield): $^1$H NMR (500 MHz, DMSO-d$_6$) δ ppm 1.50 (m, 3 H), 1.79 (m, 0.5 H), 1.94 (m, 1.5 H), 2.67 (m, 1 H), 2.86 (m, 1 H), 3.30 (m, 2 H), 3.78 (m, 1 H), 3.84 (m, 0.5 H), 4.04

(dd, 0.5 H), 4.44 (m, 1 H), 7.05 (dd, 1 H), 7.71 (m, 1 H), 7.79 (d, 1 H); MS (ES+) m/z 311 [M+H]+.

Intermediate 28

6-Bromo-2-(2,2-dimethyltetrahydropyran-4-yl)chroman-4-one

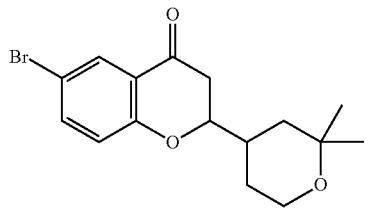 [SMILES: CC1(C)CC(C2CC(=O)c3cc(Br)ccc3O2)CCO1]

A solution of 1-(5-bromo-2-hydroxyphenyl)ethanone (13.5 g, 62.78 mmol), 2,2-dimethyltetrahydro-2H-pyran-4-carbaldehyde (9.40 g, 62.78 mmol) and pyrrolidine (5.22 mL, 62.78 mmol) in MeOH (125 mL) was heated to reflux for 3 h. The mixture was allowed to reach r.t. and then concentrated. The residue was dissolved in EtOAc (100 mL) and washed with 1M NaOH (60 mL), 1M HCl (60 mL), and brine (60 mL) successively. The organic phase was concentrated and the residue was purified by flash chromatography with a gradient of 10% EtOAc in heptane to 40% EtOAc in heptane to give the title compound (16.22 g, 76% yield): $^1$H NMR (500 MHz, DMSO-$d_6$) δ ppm 1.15 (m, 6H), 1.26 (m, 2 H), 1.52 (m, 1 H), 1.76 (m, 1 H), 2.12 (ddd, 1 H), 2.65 (m, 1 H), 2.83 (m, 1 H), 3.57 (m, 1 H), 3.66 (m, 1 H), 4.32 (ddd, 1 H), 7.05 (dd, 1 H), 7.70 (dd, 1 H), 7.78 (d, 1 H); MS (ES−) m/z 337 [M−H]−.

Intermediate 29

2-Oxobutanethioamide

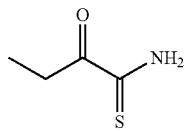

Hydrogen sulfide was bubbled through a solution of propionyl cyanide (25 g, 300.88 mmol) in 2-methyl-tetrahydrofuran (200 mL) at −10° C. for 10 min. The addition of hydrogen sulfide was stopped and triethylamine (0.419 mL, 3.01 mmol, as a solution in 2-methyl-tetrahydrofuran (4 mL)) was added dropwise over 10 min. Hydrogen sulfide addition was continued for 1.5 h at −10° C. before the addition was stopped and the flask was flushed with nitrogen for 2.5 h, during which time the reaction mixture was allowed to reach rt. The mixture was concentrated and the resulting residue was taken up in 1:1 EtOAc:heptane and passed through a short plug of silica to give 30.2 g (86% yield) of the title compound. $^1$H NMR (400 MHz, DMSO-$d_6$) δ ppm 0.99 (t, 3 H), 2.93 (q, 2 H), 9.79 (br. s., 1 H), 10.20 (br. s., 1 H); MS (ES+) m/z 118 [M+H]+.

Intermediate 30

5'-Methylspiro[chroman-4,2'-imidazole]-4',6-diamine

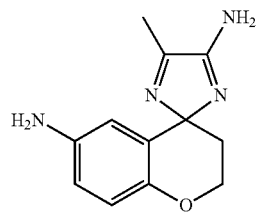 [SMILES: CC1=NC2(CCOc3ccc(N)cc32)N=C1N]

A mixture of 6-bromo-5'-methylspiro[chroman-4,2'-imidazol]-4'-amine (Intermediate 4, 115 mg, 0.39 mmol), trans-4-hydroxy-L-proline (51 mg, 0.39 mmol), CuI (37 mg, 0.20 mmol), and $K_2CO_3$ (162 mg, 1.17 mmol) in DMSO (0.9 mL) was stirred at r.t. for 15 min. Ammonia, (30-33% in $H_2O$, 0.37 mL, 5.86 mmol) was added and the mixture was subjected to microwave irradiation at 110° C. for 3 h. The mixture was diluted with DMSO and water and filtered through a pad of diatomaceous earth. NaCl (s) was added and the aqueous mixture was extracted with EtOAc (5×35 mL). The combined organic phases were dried ($Na_2SO_4$) and evaporated to give a crude product which was purified by flash chromatography (4 g silica, eluent: $CHCl_3$/(MeOH/$NH_3$) gradient) affording the title compound (59 mg, 65% yield). $^1$H NMR (400 MHz, DMSO-$d_6$) δ ppm 1.76-1.92 (m, 2 H), 2.19 (s, 3 H), 4.18-4.34 (m, 2 H), 4.45 (br. s., 2 H), 5.69 (d, 1 H), 6.35 (dd, 1 H), 6.45 (br. s., 2 H), 6.50 (d, 1 H); MS (ES+) m/z 231 [M+H]+.

Intermediate 31

1-Bromo-3-(prop-1-ynyl)benzene

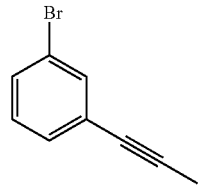

To a solution of 1-bromo-3-iodobenzene (3.0 g, 10.6 mmol), copper(I) iodide (0.61 g, 3.2 mmol) and tetrakis (triphenylphosphine)palladium(0) (0.61 g, 0.53 mmol) in toluene (20 mL) was added 1-(trimethylsilyl)-1-propyne (1.6 mL, 10.6 mmol), triethylamine (4.9 mL, 35.0 mmol) and a 1M solution of tetrabutylammonium fluoride in tetrahydrofuran (10.6 mL, 10.6 mmol). The resulting mixture was stirred under a nitrogen atmosphere at r.t. overnight. The mixture was partitioned between water and $Et_2O$ and the organic phase was dried over magnesium sulfate and concentrated in vacuo. The residue was filtered through a plug of silica and eluted with heptane (4×25 mL) affording the title compound (1.6 g, 80% yield): $^1$H NMR (500 MHz, DMSO-$d_6$) δ ppm 2.05 (s, 3H), 7.30 (t, 1H), 7.39 (d, 1H), 7.52-7.56 (m, 1H), 7.56-7.58 (m, 1H); MS (CI) m/z 195 [M+H]+.

Intermediate 32

2-Chloro-4-(prop-1-ynyl)pyridine

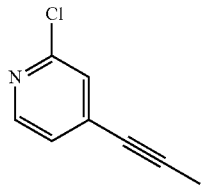

4-Bromo-2-chloropyridine (1.00 g, 5.20 mmol), 1-(trimethylsilyl)-1-propyne (0.846 mL, 5.72 mmol), copper(I) iodide (99 mg, 0.52 mmol), and tetrakis(triphenylphosphine)palladium(0) (90 mg, 0.08 mmol) were taken up in toluene (14 mL) in a microwave vial. Tetra-N-butylammonium fluoride (1M in THF) (6 mL, 6.00 mmol) was added and the reaction vessel was sealed and heated at 100° C. for 20 min in a microwave reactor. After cooling, the mixture was filtered through diatomaceous earth, and then concentrated in vacuo. The product was purified by flash chromatography using a gradient of EtOAc in heptane (0-50%) to give the title compound (530 mg, 67% yield): $^1$H NMR (500 MHz, DMSO-$d_6$) δ ppm 2.11 (s, 3 H), 7.38 (dd, 1 H), 7.51 (s, 1 H), 8.37 (d, 1 H).; MS (ES+) m/z 152 [M+H]$^+$.

Intermediate 33

4-Bromo-2-(prop-1-ynyl)pyridine

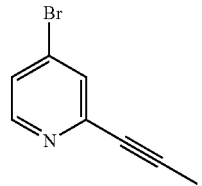

The title compound (0.560 g, 57% yield) was prepared as described for Intermediate 32 starting from 4-bromo-2-iodopyridine (1.42 g, 5.00 mmol): $^1$H NMR (500 MHz, DMSO-$d_6$) δ ppm 2.08 (s, 3 H), 7.63 (dd, 1 H), 7.73 (d, 1 H), 8.39 (d, 1 H); MS (MM-ES+APCI)+m/z 196 [M+H]$^+$.

Intermediate 34

3-(Prop-1-ynyl)phenylboronic acid

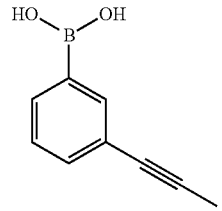

n-Butyl lithium (2.5 M in hexanes, 3.7 mL, 9.4 mmol) was added dropwise to a solution of 1-bromo-3-(prop-1-ynyl) benzene (Intermediate 31, 1.66 g, 8.51 mmol) and triisopropyl borate (2.2 mL, 9.4 mmol) in tetrahydrofuran (5 mL) and toluene (15 mL) at −78° C. under an argon atmosphere. The reaction mixture was stirred for 30 min. and then allowed to reach r.t. and stirred for 1 h. The mixture was cooled to −78° C., and 3 M aq. hydrochloric acid was added and the mixture was stirred at r.t. for 15 min. The mixture was basified by addition of solid KOH. 2-methyl-tetrahydrofuran was added under stirring and the obtained solid was collected by filtration affording the title compound 1.0 g (75% yield). $^1$H NMR (500 MHz, DMSO-$d_6$) δ ppm 2.01 (s, 3 H), 6.92-7.03 (m, 1 H), 7.09-7.20 (m, 1 H), 7.55-7.79 (m, 2 H).

Intermediate 35

3-Chloro-5-(4,4,5,5-tetramethyl-1,3,2-dioxaborolan-2-yl)benzonitrile

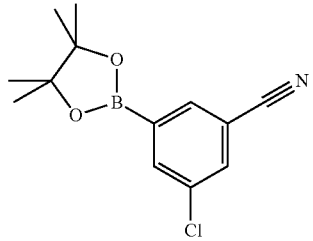 [SMILES: CC1(C)OB(c2cc(Cl)cc(C#N)c2)OC1(C)C]

A suspension of 4,4,4',4',5,5,5',5'-octamethyl-2,2'-bi(1,3,2-dioxaborolane) (665 mg, 2.62 mmol), 3-chloro-5-iodobenzonitrile (345 mg, 1.31 mmol), and potassium acetate (386 mg, 3.93 mmol) in dioxane (5 mL) was degassed with a stream of argon for a couple of min. PdCl$_2$(dppf) CH$_2$Cl$_2$ (53.5 mg, 0.07 mmol) was added and the mixture was heated at reflux under N$_2$ for 4 h. The mixture was allowed to cool and was then filtered. The filter cake was washed with EtOAc. The filtrate was concentrated in vacuo. The residue was purified by flash chromatography (eluent: heptane/EtOAc gradient) affording the title compound (69 mg, 20% yield). $^1$H NMR (400 MHz, DMSO-$d_6$) δ ppm 1.30 (s, 12 H), 7.88 (dd, 1 H), 7.90-7.94 (m, 1 H), 8.19 (dd, 1 H); MS (CI) m/z 264 [M+H]$^+$.

Note: the product has no UV-response but is visualized on TLC by a visualization agent containing phosphomolybdic acid and Ce(SO$_4$)$_2$.

Intermediate 36

5-(But-2-ynyloxy)pyrazine-2-carboxylic acid

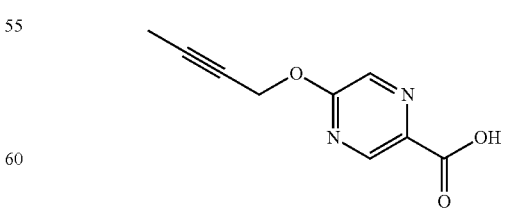

To a slurry of 5-chloro-pyrazine-2-carboxylic acid (0.79 g, 5.00 mmol) in DMF (35 mL) were added 2-butyn-1-ol (3.74 mL, 50.0 mmol) and potassium tert-butoxide (2.24 g, 20.0 mmol). The resulting mixture was heated at 65° C. overnight.

The reaction mixture was neutralized with 2 M HCl and then concentrated in vacuo. A part (400 mg) of the crude material was partitioned between 0.5 M NaOH and a 1:1 mixture of heptane and EtOAc. The aqueous phase was made slightly acidic (pH-3-4) by addition of 1 M HCl. To the obtained suspension was added NaCl (s) and the mixture was extracted twice with EtOAc. The combined organic phases were dried (Na$_2$SO$_4$) and evaporated to give 0.11 g of the title compound. $^1$H NMR (400 MHz, DMSO-d$_6$) δ ppm 1.84 (t, 3 H), 5.06 (q, 2 H), 8.42 (d, 1 H), 8.82 (d, 1 H), 13.38 (br. s., 1 H); MS (ES$^+$) m/z 193 [M+H]$^+$.

Intermediate 37

1-(4-Bromo-2-iodobenzyl)cyclobutanecarbonitrile

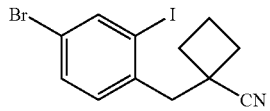

Lithium diisopropylamide (3.34 mL, 6.68 mmol), was added dropwise to a solution of cyclobutanecarbonitrile (0.417 g, 5.14 mmol) in THF (20 mL) at −78° C. under an argon atmosphere. The reaction mixture was stirred at −78° C. for 30 min, then was a solution of 4-bromo-1-(bromomethyl)-2-iodobenzene (see Caruso, A.; Tovar, J., D. *J. Org. Chem.* 2011, 76, 2227-2239., 2.51 g, 6.68 mmol) in THF (8 mL) slowly added dropwise and the reaction was allowed to reach r.t. The mixture was stirred for another 3 h and then quenched with water. The reaction mixture was partitioned between water and EtOAc, the organic layer was dried over MgSO$_4$ and concentrated to give a crude product which was purified by flash chromatography (eluent: heptane/ethylactae 12:1) to afford the title compound (1.71 g, 89% yield): $^1$H NMR (500 MHz, CDCl$_3$) δ ppm 2.08-2.34 (m, 4 H), 2.47-2.58 (m, 2 H), 3.18-3.23 (m, 2 H), 7.29 (s, 1 H), 7.49 (dd, 1 H), 8.03 (d, 1 H); GC MS (EI) m/z 375 M Intermediate 38

6'-Bromospiro[cyclobutane-1,2'-inden]-1'(3'H)-one

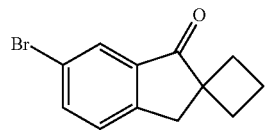 [SMILES: O=C1c2cc(Br)ccc2CC12CCC2]

A dried flask charged with 1-(4-bromo-2-iodobenzyl)cyclobutanecarbonitrile (Intermediate 37, 2.60 g, 6.91 mmol), was dissolved in dry THF (100 mL) under an argon atmosphere. The resulting mixture was cooled to −78° C. and then was tert-butyllithium (1.7 M in pentane, 8.13 mL, 13.83 mmol), added dropwise. The reaction was stirred for 1.5 h at −78° C. and then the reaction was quenched with MeOH (0.5 mL), followed by aq. hydrochloric acid (2M, 10 mL). The resulting solution was concentrated to remove the organic solvent and then partitioned between DCM and water. The organic phase was dried over MgSO$_4$ and concentrated to give a crude product which was purified by flash chromatography (eluent: heptane/EtOAc20:1-15:1-10:1) to afford the title compound (1.1 g, 63% yield): $^1$H NMR (500 MHz, CDCl$_3$) δ ppm 1.97-2.13 (m, 3 H), 2.13-2.24 (m, 1 H), 2.45-2.60 (m, 2 H), 3.24 (s, 2 H), 7.31 (d, 1 H), 7.67 (dd, 1H), 7.88 (d, 1 H); GC MS (EI) m/z 250 M Intermediate 39

6'-(Cyclobutylmethoxy)spiro[cyclohexane-1,2'-indene]-1',4(3'H)-dione

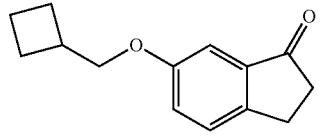 [SMILES: O=C1CCc2ccc(OCC3CCC3)cc21]

To a solution of 6-hydroxy-2,3-dihydro-1H-inden-1-one (3 g, 20.3 mmol) in THF (140 mL) were cyclobutylmethanol (2.10 mL, 22.3 mmol), triphenylphosphine (7.97 g, 30.4 mmol) and diisopropyl azodicarboxylate (5.98 mL, 30.4 mmol) added. The mixture was heated to 45° C. and left stirring over the weekend. The crude product was purified by flash chromatography using a gradient of 0-10% EtOAc in heptane to afford 2.56 g (58% yield) of the title compound: $^1$H NMR (500 MHz, CDCl$_3$) δ ppm 1.81-2.03 (m, 4 H), 2.11-2.20 (m, 2 H), 2.69-2.74 (m, 2 H), 2.78 (dt, 1 H), 3.04-3.12 (m, 2 H), 3.96 (d, 2 H), 7.17-7.22 (m, 2 H), 7.36 (d, 1 H); MS (ES+) m/z 217 [M+H]$^1$.

Intermediate 40

(1r,4r)-6'-(Cyclobutylmethoxy)-4-hydroxyspiro[cyclohexane-1,2'-inden]-1'(3'H)-one

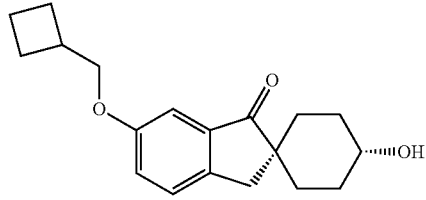 [SMILES: O=C1c2cc(OCC3CCC3)ccc2C[C@]12CC[C@@H](O)CC2]

6'-(Cyclobutylmethoxy)spiro[cyclohexane-1,2'-indene]-1',4(3'H)-dione (Intermediate 39, 2.35 g, 7.88 mmol) was dissolved in tetrahydrofuran (40 mL) and MeOH (3.19 mL, 78.76 mmol). Borane-trimethylamine complex (1.26 g, 17.3 mmol) was added and the mixture was stirred at r.t. overnight. Citric acid monohydrate (23.2 g, 110 mmol) was added in all at once, followed by dropwise addition of water (2.84 mL, 157 mmol). The mixture was stirred for 4 h. before being diluted with water and extracted with EtOAc twice. The combined organic phases were washed with NaHCO$_3$ and brine, and concentrated. The crude product was purified on a silica gel column (gradient elution 0-50% EtOAc in n-heptane) to give the title compound (1.84 g, 78% yield, containing 29% of (1s,4s)-6'-(cyclobutylmethoxy)-4-hydroxyspiro[cyclohexane-1,2'-inden]-1'(3'H)-one). The compound was used as such in the next step: $^1$H NMR (500 MHz, DMSO-d$_6$) δ ppm 1.10 (m, minor isomer), 1.2-1.4 (m, 4H), 1.57 (m, 2H), 1.71 (m, minor isomer), 1.75-1.95 (m, 6H), 2.07 (m, 2H), 2.71 (m, 1H), 2.92 (m, 2H), 3.44 (m, 1H), 3.84 (m, minor isomer), 3.98

(d, 2H), 4.42 (d, minor isomer), 4.66 (d, 1H), 7.07 (d, 1H), 7.26 (m, 1H), 7.44 (m, 1H); MS (ES+) m/z 301.1 [M+H]⁺.

Intermediate 41

3-Bromo-5-chloro-2-methylpyridine

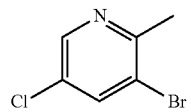

2,3-Dibromo-5-chloropyridine (1.3 g, 4.70 mmol), methylboronic acid (0.30 g, 5.01 mmol), bis(triphenylphosphine)palladium(II) chloride (0.50 g, 0.70 mmol) and dioxane (10 mL) were added. K₂CO₃ (2 M aq. solution, 7.0 mL, 14.0 mmol) was added and the reaction was put under N₂ (g) atmosphere. The reaction was heated to reflux for 5 h. The reaction was stirred at 50° C. overnight and then heated to reflux for additionally 1 h. Methylboronic acid (0.14 g, 2.35 mmol) was added and the reaction was refluxed for 4 h and the allowed to cool down to r.t. The mixture is was filtered through a silica plug. EtOAc and water were added and the phases were separated. The organic phase was washed two more times with water. The organic phase was dried with MgSO₄, filtered and concentrated in vacuo. The crude product was purified by flash chromatography (12 g SiO₂, 0-20% MeOH containing 0.1 M NH₃ in DCM). The fractions containing pure product were pooled and concentrated, yielding the title compound (123 mg, 13% yield): ¹H NMR (DMSO-d₆) δ ppm 2.56 (s, 3 H), 8.29 (d, 1 H), 8.52 (d, 1 H); MS (CI) m/z 206 [M+H]⁺.

Intermediate 42

Diethyl 2-(5-bromo-3-chloropyridin-2-yl)malonate

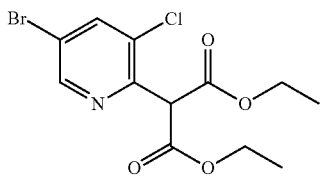 [SMILES: CCOC(=O)C(C(=O)OCC)c1ncc(Br)cc1Cl]

Diethyl malonate (0.87 mL, 5.7 mmol) was added dropwise to a suspension of NaH (55% in mineral oil, 0.27 g, 6.2 mmol) in DMF (6 mL) at 0° C. The ice-bath was removed and the mixture was stirred under N₂ at r.t. for 20 min. 5-Bromo-2,3-dichloropyridine (1.0 g, 4.4 mmol) was added, and the mixture was stirred at 120° C. overnight. The mixture was allowed to cool and was then partitioned between water containing NaCl and EtOAc. The organic phase was dried (MgSO₄) and evaporated to give a crude product which was purified by flash chromatography (25 g SiO₂, heptane/EtOAc gradient) affording the title compound (0.8 g, 2 mmol, 52% yield) containing a residue of unreacted malonic ester. MS (ES+) m/z 350 [M+H]⁺. A part of this material was used as such in the subsequent step.

Intermediate 43

5-Bromo-3-chloro-2-methylpyridine

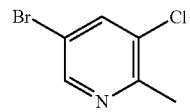

A solution of impure diethyl 2-(5-bromo-3-chloropyridin-2-yl)malonate (Intermediate 42, 0.41 g, 1.2 mmol) and conc. aq. HCl (3 mL) was heated at reflux for 3 h. The volatiles were removed in vacuo, and the residue was co-evaporated with acetonitrile. The residual solid (mono-decarboxylated acid) was dissolved in dioxane (4.5 mL) and heated at reflux overnight. The volatiles were removed in vacuo. The residue was purified by flash chromatography (4 g SiO₂, heptane/EtOAc gradient) affording the title compound (0.12 g, 51% yield): ¹H NMR (500 MHz, CDCl₃) δ ppm 2.60 (s, 3 H), 7.82 (d, 1 H), 8.46 (d, 1 H); MS (CI) m/z 206 [M+H]⁺.

Intermediate 44

3-Chloro-2-methyl-5-(4,4,5,5-tetramethyl-1,3,2-dioxaborolan-2-yl)pyridine

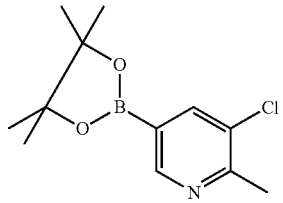

A suspension of 4,4,4',4',5,5,5',5'-octamethyl-2,2'-bi(1,3,2-dioxaborolane) (0.836 g, 3.29 mmol), 5-bromo-3-chloro-2-methylpyridine (Intermediate 43, 0.34 g, 1.65 mmol), and potassium acetate (0.485 g, 4.94 mmol) in dioxane (5 mL) was degassed with a stream of N₂ (g) for a couple of min. PdCl₂(dppf) CH₂Cl₂ (0.067 g, 0.08 mmol) was added and the mixture was heated at reflux under N₂ (g) for 1.5 h. The mixture was allowed to cool to r.t. and was then filtered. The filter cake was washed with EtOAc. The filtrate was concentrated in vacuo. The residue was purified by flash chromatography (40 g SiO₂, gradient elution with 0-80% EtOAc in heptane to yield the title compound (0.44 g, quantitative yield): ¹H NMR (500 MHz, CDCl₃) δ ppm 1.35 (s, 12 H), 2.65 (s, 3 H), 7.95-8.03 (m, 1 H), 8.69 (d, 1 H); MS (ES+) m/z 172 [M+H]⁺(mass corresponding to the boronic acid).

Intermediate 45

3-Bromo-4-methyl-5-(prop-1-ynyl)pyridine

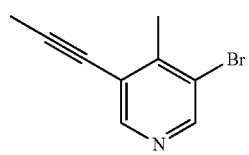

3,5-Dibromo-4-methylpyridine (0.50 g, 2.0 mmol), 1-(trimethylsilyl)-1-propyne (0.35 mL, 2.4 mmol), copper(I) iodide (0.11 g, 0.60 mmol), tetrakis(triphenylphosphine)palladium(0) (0.023 g, 0.02 mmol) were mixed in toluene (2 mL). The mixture was degassed by a stream of argon for a couple of min. Tetra-n-butylammonium fluoride (1 M in THF) (2.4 mL, 2.4 mmol) was added, and the reaction was heated under $N_2$ at 70° C. overnight. The mixture was partitioned between water containing sat aq. $NaHCO_3$ and EtOAc. The organic phase was dried ($MgSO_4$) and evaporated to give a crude product which was purified by flash chromatography (40 g $SiO_2$, heptane/EtOAc gradient) affording the title compound (0.067 g, 16% yield): $^1$H NMR (500 MHz, DMSO-$d_6$) δ ppm 2.15 (s, 3 H), 2.46 (s, 3 H), 8.48 (s, 1 H), 8.61 (s, 1 H); MS (ES$^+$) m/z 210 [M+H]$^+$.

Intermediate 46

(1r,4r)-6'-(Cyclobutylmethoxy)-4-methoxyspiro[cyclohexane-1,2'-inden]-1'(3'H)-one

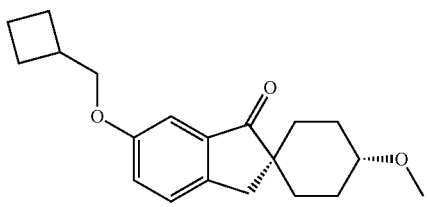 [SMILES: CO[C@H]1CC[C@]2(CC1)Cc1ccc(OCC3CCC3)cc1C2=O]

(1r,4r)-6'-(Cyclobutylmethoxy)-4-hydroxyspiro[cyclohexane-1,2'-inden]-1'(3'H)-one (Intermediate 40, containing 29% of an isomer, 1.84 g, 6.13 mmol) was dissolved in 2-Me THF (17 mL) under an inert atmosphere and the solution was cooled to 0° C. Methyl iodide (0.498 mL, 7.96 mmol) was added followed by portionwise addition of potassium tert-butoxide (0.962 g, 8.58 mmol). The resulting mixture was stirred at 35° C. for 1 h. Potassium tert-butoxide (0.962 g, 8.58 mmol) was added and stirring continued. After another 30 min, a new portion of potassium tert-butoxide (0.103 g, 0.92 mmol) was added and stirring continued. After a total of 4 h, full conversion was obtained. Water (6 mL) and brine (3 mL) was added. The phases were separated and the organic layer was dried and concentrated. The crude product was purified on a silica gel column (gradient elution of 0-50% EtOAc in n-heptane) to give the title compound (1.480 g, 77%). The product contained 29% of (1s,4s)-6'-(cyclobutylmethoxy)-4-methoxyspiro[cyclohexane-1,2'-inden]-1'(3'H)-one and was used as such in next step: $^1$H NMR (500 MHz, DMSO-$d_6$) δ ppm 1.11 (m, minor isomer), 1.26 (m, 2H), 1.40 (d, 1H), 1.57 (m, 2H), 1.75-1.95 (m, 5H), 2.0-2.1 (m, 3H), 2.71 (m, 1H), 2.95 (s, 3H), 2.95 (s, minor isomer), 3.19 (m, 1H), 3.24 (s, minor isomer), 3.26 (s, 3H), 3.45 (m, minor isomer), 3.99 (d, 2H), 7.07 (d, 1H), 7.26 (m, 1H), 7.45 (m, 1H); MS (ES+) m/z 315.1 [M+H]$^1$.

Intermediate 47

6-(3,3,3-trifluoropropoxy)-2,3-dihydro-1H-inden-1-one

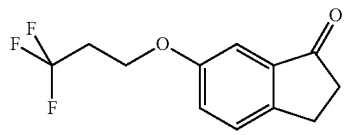 [SMILES: O=C1CCc2ccc(OCCC(F)(F)F)cc21]

To a solution of 6-hydroxy-2,3-dihydro-1H-inden-1-one (3.0 g, 20.3 mmol) in THF (140 mL) were triphenylphosphine (7.97 g, 30.4 mmol) and 3,3,3-trifluoropropan-1-ol (1.963 mL, 22.27 mmol) added. Diisopropyl azodicarboxylate (5.98 mL, 30.4 mmol) was added dropwise and the mixture was left stirring at r.t. overnight. Since there was starting material remaining, 3,3,3-trifluoro-1-propanol (0.892 mL, 10.1 mmol) was added dropwise and stirring was continued. After 30 min the mixture was heated to 40° C. and after 1 h the mixture was concentrated. The crude product was purified by flash chromatography (0-12% EtOAc in heptane as eluent) to afford 1.08 g (22% yield) of the title compound (containing some diisopropyl azodicarboxylate): $^1$H NMR (500 MHz, CDCl$_3$) δ 2.65 (qt, 2 H), 2.71-2.77 (m, 2 H), 3.05-3.13 (m, 2 H), 4.23 (t, 2 H), 7.17-7.23 (m, 2 H), 7.40 (d, 1 H); MS (ES+) m/z 245 [M+H]$^1$.

Intermediate 48

3-Bromo-5-(but-1-ynyl)-pyridine

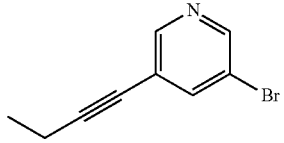

But-1-yne (g) was during 5 min gently bubbled through anhydrous acetonitrile cooled in an ice-water bath. The resulting solution contained about 170 mg but-1-yne per mL. The solution of but-1-yne (4.57 mL, 14.36 mmol) and diisopropylamine (3.72 mL, 26.11 mmol) were added sequentially to a mixture of 3,5-dibromopyridine (3.09 g, 13.06 mmol), bis(triphenylphosphine)-palladium(II) chloride (0.458 g, 0.65 mmol) and CuI (0.249 g, 1.31 mmol) in acetonitrile (15 mL) under an argon atmosphere. The resulting mixture was stirred at r.t. overnight, diluted with EtOAc and passed through a short plug of silica. The solvents were evaporated and the residue was purified by flash chromatography on silica (gradient elution 0-20% EtOAc in heptane) to give 2.40 g of the title compound (87% yield): $^1$H NMR (500 MHz, DMSO-$d_6$) δ ppm 1.17 (t, 4 H), 2.47 (q, 3 H), 8.11 (t, 1 H), 8.57 (d, 1 H), 8.65 (d, 1 H); MS (ES+) m/z 210 [M+H]$^+$.

Intermediate 49

5-(But-1-ynyl)pyridin-3-ylboronic acid

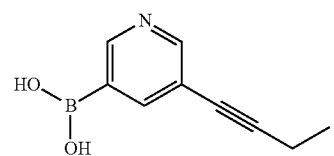

n-BuLi (2.5 M in hexanes, 5.46 mL, 13.7 mmol) was added dropwise to a solution of 3-bromo-5-(but-1-ynyl)pyridine (Intermediate 48, 2.39 g, 11.4 mmol) and triisopropyl borate (3.15 mL, 13.65 mmol) in 2-Me THF (20 mL) at −50° C. The mixture was stirred for 1.5 h while the temperature was kept between −50 and −40° C. The mixture was lifted up from the cooling bath and 2 M aq. HCl (12 mL, 24 mmol) was added followed by stirring for 20 min. The mixture was diluted with EtOAc. Aq. NaOH (2 M) was added until pH about 12 was obtained in the aqueous phase. The phases were separated. The organic phase was extracted with dilute aq. NaOH and with water. The combined aqueous phases were washed with EtOAc, acidified to pH about 5 by the addition of conc. HCl and extracted with DCM. The organic phase was dried over Na₂SO₄ and concentrated to give 1.522 g (76% yield) of the title compound: ¹H NMR (500 MHz, CDCl₃) δ ppm 1.11-1.37 (m, 3 H), 2.26-2.58 (m, 2 H), 7.46-10.34 (m, 3 H); MS (ES+) m/z 176 [M+H]⁺.

Intermediate 50

3-Bromo-5-methylbenzonitrile

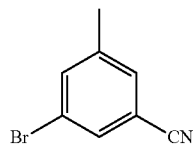

A mixture of 1,3-dibromo-5-methylbenzene (1.0 g, 4.0 mmol), copper cyanide (0.179 g, 2.00 mmol), pyridine (0.323 mL, 4.00 mmol), and DMF (15 mL) were heated at 190° C. for 10 h in microwave reactor. The reaction mixture was allowed to cool to r.t., and then poured into a solution of H₂O (20 mL) and aq. NH₃ solution (25-35% NH₃, 10 mL) and the water phase was extracted with EtOAc. The combined organic extracts were dried (Mg₂SO₄), filtered and concentrated in vacuo. The residue was purified by silica gel chromatograpy (hexane/EtOAc gradient elution) to afford the title compound (0.58 g, 74% yield): ¹H NMR (500 MHz, CDCl₃) δ ppm 2.39 (s, 3 H) 7.41 (s, 1 H) 7.58 (s, 1 H) 7.60 (s, 1 H); MS (EI) m/z 195 M Intermediate 51

1-(4-Bromo-2-iodobenzyl)cyclopropanecarbonitrile

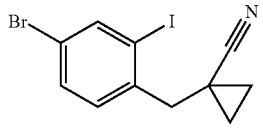 [SMILES: N#CC1(Cc2ccc(Br)cc2I)CC1]

The title compound (2.1 g, 55% yield) was prepared as described for 1-(4-Bromo-2-iodobenzyl)cyclobutanecarbonitrile (Intermediate 37) starting from cyclopropanecarbonitrile (1.96 mL, 26.6 mmol) and 4-bromo-1-(bromomethyl)-2-iodobenzene (see Caruso, A.; Tovar, J., D. *J. Org. Chem.* 2011, 76, 2227-2239) (4.0 g, 10.6 mmol): ¹H NMR (400 MHz, CDCl₃) δ ppm 1.02-1.07 (m, 2 H), 1.33-1.37 (m, 2 H), 2.98 (s, 2 H), 7.35 (d, 1 H), 7.51 (dd, 1 H), 8.02 (d, 1 H); MS (CI) m/z 362 [M+H]

Intermediate 52

6'-Bromospiro[cyclopropane-1,2'-inden]-1'(3'H)-one

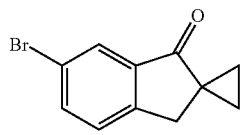

A dried flask was charged with 1-(4-bromo-2-iodobenzyl)cyclopropanecarbonitrile (Intermediate 51, 3.29 g, 9.09 mmol) and dry THF (30 mL) was added under argon atmosphere. The resulting mixture was cooled to −78° C. and n-BuLi (2.5 M in hexanes, 7.27 mL, 18.2 mmol) was added dropwise. The solution was allowed to reach r.t. The reaction was quenched with MeOH (2 mL) and HCl (1M, 5 mL). The mixture was extracted with EtOAc. The water phase was basified with sat NaHCO₃ and extracted with EtOAc twice. The organic phases were combined, dried over MgSO₄, filtered and concentrated in vacuo. HCl (1 M, 4 mL) and DCM (5 mL) were added and the organic phase was collected. This was repeated twice. The water phase was basified with sat NaHCO₃ and extracted with DCM. The combined organic phases were dried through a phase separator and evaporated to dryness to give the title compound (1.1 g, 51% yield): MS (CI) m/z 237 [M+H]⁺.

Intermediate 53

1-Bromo-3-fluoro-5-(methoxymethyl)benzene

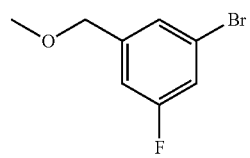

NaH (60% dispersion in mineral oil, 245 mg, 6.12 mmol) was added to a solution of (3-bromo-5-fluorophenyl)methanol (1.195 g, 5.83 mmol) in 2-Me THF (20 mL). After gas evolution had ceased, MeI (0.455 mL, 7.29 mmol) was added and the resulting mixture was stirred at r.t. for 16 h. Another portion of NaH (50 mg, 2.1 mmol) and MeI (0.10 mL, 1.6 mmol) were added and the mixture was heated to 60° C. for 2 h. The cooled mixture was diluted with EtOAc, washed with water, dried over MgSO₄ and concentrated in vacuo. The residue was purified by flash chromatography on silica (gradient of 0-15% EtOAc in heptane) to give 0.810 g (63% yield) of the title compound: ¹H NMR (400 MHz, DMSO-d₆) δ ppm 3.30 (s, 3 H), 4.38-4.46 (m, 2 H), 7.18 (m, 1 H), 7.37 (s, 1 H), 7.44-7.50 (m, 1 H); MS (EI) m/z 218 M⁺.

Intermediate 54

3-Bromo-5-((2,2,2-trifluoroethoxy)methyl)pyridine

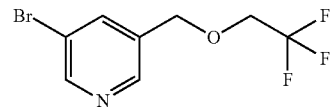 [SMILES: FC(F)(F)COCc1cncc(Br)c1]

2,2,2-Trifluoroethanol (0.434 g, 4.34 mmol) was added to a suspension of NaH (0.198 g, 4.96 mmol) in THF (10 mL). When gas evolution had ceased, a solution of (5-bromopyridin-3-yl)methyl methanesulfonate (see WO2007/076247; 1.10 g, 4.13 mmol) in DMF was added. The resulting mixture was stirred for 2 h at r.t. and then the volatile solvent was evaporated. The remaining solution was diluted with water and extracted with EtOAc (3×30 mL). The combined extracts were dried over MgSO₄ and concentrated. The residue was purified by flash chromatography on silica using gradient elution with EtOAc in heptane to give 227 mg of the title compound (20% yield). ¹H NMR (500 MHz, CDCl₃) δ ppm 3.92 (q, 2 H), 4.70 (s, 2 H), 7.87 (m, 1 H), 8.50 (m, 1 H), 8.66 (d, 1 H); MS (EI) m/z 269 M⁺.

Intermediate 55

3-(4,4,5,5-Tetramethyl-1,3,2-dioxaborolan-2-yl)-5-(trifluoromethyl)benzonitrile

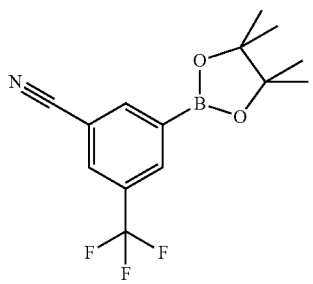 [SMILES: CC1(C)OB(c2cc(C#N)cc(C(F)(F)F)c2)OC1(C)C]

3-bromo-5-(trifluoromethyl)benzonitrile (1.25 mL, 5.00 mmol), 4,4,4',4',5,5,5',5'-octamethyl-2,2'-bi(1,3,2-dioxaborolane) (2.54 g, 10.0 mmol), [1,1'-bis(diphenylphosphino)ferrocene]-palladium(II) chloride (288 mg, 0.35 mmol), and potassium acetate (1.47 g, 15.0 mmol) were mixed in dioxane (15 mL) in a round-bottomed flask. The atmosphere was exchanged for argon, and the mixture was heated to 110° C. for 1 h. The reaction mixture was cooled to r.t., filtered through diatomaceous earth, and the filter cake was washed with EtOAc. The filtrate solution was washed with brine, dried over MgSO₄, and concentrated in vacuo. The residue was purified by flash chromatography using heptane/EtOAc (70/30) as eluent to give the title compound (495 mg, 33% yield): ¹H NMR (400 MHz, CDCl₃) δ ppm 1.37 (s, 12 H), 7.98 (m, 1 H), 8.26 (s, 2 H); MS (ES+) m/z 297 [M+H]⁺.

Intermediate 56

3-(Difluoromethyl)-5-(4,4,5,5-tetramethyl-1,3,2-dioxaborolan-2-yl)benzonitrile

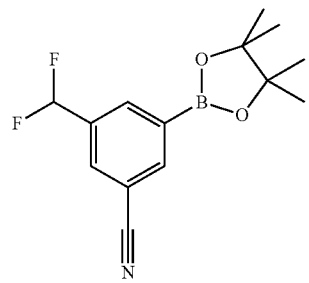 [SMILES: CC1(C)OB(c2cc(C#N)cc(C(F)F)c2)OC1(C)C]

4,4,4',4',5,5,5',5'-Octamethyl-2,2'-bi(1,3,2-dioxaborolane) (643 mg, 2.53 mmol), di-μ-methoxobis(1,5-cyclooctadiene)diiridium(I) (50.4 mg, 0.08 mmol), and 4,4'-di-tert-butyl-2,2'-dipyridyl (82 mg, 0.30 mmol) were mixed. The atmosphere was exchanged for argon. Hexane (5 mL) was added, while the argon atmosphere was maintained. The mixture was stirred for 5 min at r.t. A solution of 3-(difluoromethyl)benzonitrile (776 mg, 5.07 mmol) in hexane (5 mL) was added, and the mixture was stirred at r.t. for 16 h. The reaction mixture was diluted with EtOAc, and washed with brine. The organic layer was dried over MgSO₄, filtered, concentrated in vacuo, and purified by flash chromatography using heptane/EtOAc (85/15) as eluent to give 192 mg (13% yield) of the title compound: ¹H NMR (400 MHz, CDCl₃) δ ppm 1.37 (s, 12 H), 6.68 (s, 1 H) 7.86-7.91 (m, 1 H) 8.14 (s, 1 H) 8.18-8.22 (m, 1 H); MS (ES+) m/z 279 [M+H]⁺.

Intermediate 57

3-Chloro-2-fluoro-5-(4,4,5,5-tetramethyl-1,3,2-dioxaborolan-2-yl)benzonitrile

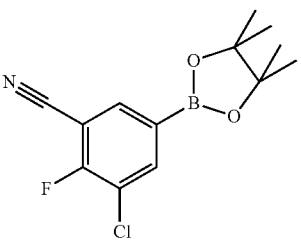 [SMILES: CC1(C)OB(c2cc(Cl)c(F)c(C#N)c2)OC1(C)C]

is A suspension of 5-bromo-3-chloro-2-fluorobenzonitrile (0.959 g, 4.09 mmol), 4,4,4',4',5,5,5',5'-octamethyl-2,2'-bi(1,3,2-dioxaborolane) (2.08 g, 8.18 mmol), [1,1'-bis(diphenylphosphino)-ferrocene]palladium(II) chloride (0.234 g, 0.29 mmol), and potassium acetate (1.20 g, 12.3 mmol) in dioxane (15 mL), was placed in a microwave vial. The mixture was degassed with a stream of argon for a couple of min, and the reaction mixture was then heated to 110° C. for 1 h in a microwave reactor. The reaction mixture was cooled to r.t., filtered through diatomaceous earth, and extracted with EtOAc. The organic phase was washed with brine, dried over MgSO₄ and concentrated in vacuo. The residue was purified by flash chromatography using heptane/EtOAc (70/30) as eluent to give the title compound (1.22 g, quantitative yield): GC MS (EI) m/z 282 M⁺.

Intermediate 58

3-Bromo-5-ethylbenzonitrile

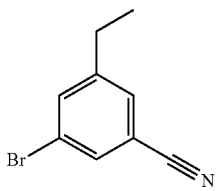

A mixture of 1,3-dibromo-5-ethylbenzene (2.7 g, 10.2 mmol), copper cyanide (0.916 g, 10.2 mmol), pyridine (1.65 mL, 20.5 mmol) in DMF (15 mL) was heated at 150° C. for 3 h. After cooling to r.t., the mixture was poured into a solution of H₂O (30 mL) and ammonia (25% aq. Solution, 20 mL) and extracted with EtOAc. The combined organic layer was dried (MgSO$_4$), filtered and concentrated in vacuo. The product was purified using flash chromatography on silica gel, gradient elution of 0-60% EtOAc in n-heptane. GCMS (CI) m/z 210 [M+1]$^+$.

Intermediate 59

3-Bromo-5-(methoxymethyl)benzonitrile

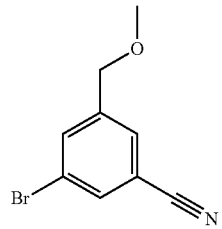

MeOH (0.088 mL, 2.18 mmol) was added to a slurry of NaH (45 mg, 1.13 mmol) in DMF (2 mL). When gas evolution ceased, a solution of 3-bromo-5-(bromomethyl)benzonitrile (see WO2009/100169; 240 mg, 0.87 mmol) in DMF (1 mL) was added. The reaction was quenched by adding aq. sat NH$_4$Cl solution. The mixture was partitioned between toluene (5 mL) and water (3 mL). The toluene layer was collected, washed with water, dried over Na$_2$SO$_4$, and concentrated in vacuo. The crude product was dried at reduced pressure and used in the next step: GCMS (CI) m/z 226 [M+H]$^+$.

Intermediate 60

6'-Bromo-4-hydroxy-4-methylspiro[cyclohexane-1,2'-inden]-1'(3'H)-one

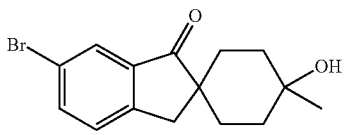 [SMILES: CC1(O)CCC2(CC1)Cc1ccc(Br)cc1C2=O]

Methylmagnesium chloride (3 M in THF, 3.41 mL, 10.2 mmol) was added, at −15° C., and under Ar, to a solution of 6'-bromospiro[cyclohexane-1,2'-indene]-1',4(3'H)-dione (Intermediate 5 Method A Step 1, 3 g, 10.2 mmol) in THF (4 mL). The reaction was allowed to attain r.t. The mixture was cooled to −15° C., methylmagnesium chloride (3 M in THF, 3.41 mL, 10.2 mmol) was added and the mixture was stirred for 1 h at r.t. The reaction was quenched with aq. sat. NH$_4$Cl solution, and then extracted with DCM. The organic layer was dried over Na$_2$SO$_4$ and concentrated in vacuo. The isomeric products were separated using a SFC Berger Multigram II System equipped with a Chiralpak AD-H column (20*250 mm; 5 μm) and a mobile phase consisting of 40% MeOH (with 0.1% DEA) and 60% CO$_2$ at a flow rate of 50 mL/min to give: Isomer 1: (1r,4r)-6'-Bromo-4-hydroxy-4-methylspiro[cyclohexane-1,2'-inden]-1'(3'1)-one, (114 mg, 11% yield) with retention time 3.9 min:

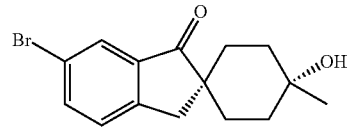

$^1$H NMR (500 MHz, CDCl$_3$) δ ppm 1.17 (s, 3 H), 1.48 (m, 4 H), 1.60 (m, 4 H), 2.98 (s, 2 H), 4.39 (s, 1 H), 7.55 (d, 1 H), 7.75 (d, 1 H), 7.85 (dd, 1 H); MS (ES−) m/z 307 [M−H]$^−$, and
Isomer 2: (1s,4s)-6'-Bromo-4-hydroxy-4-methylspiro[cyclohexane-1,2'-inden]-1'(3'H)-one, (164 mg, 16% yield) with retention time 9.4 min:

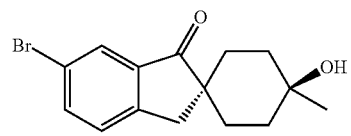 [SMILES: C[C@]1(O)CC[C@@]2(CC1)Cc1ccc(Br)cc1C2=O]

$^1$H NMR (500 MHz, CDCl$_3$) δ ppm 1.10 (d, 2 H), 1.14 (s, 3 H), 1.43 (td, 2 H), 1.56 (d, 2 H), 1.95 (td, 2 H), 2.97 (s, 2 H), 4.11 (s, 1 H), 7.53 (d, 1 H), 7.76 (d, 1 H), 7.85 (dd, 1 H); MS (ES−) m/z 307 [M−H]$^−$.

Intermediate 61

(1r,4r)-6'-Bromo-4-methoxy-4-methylspiro[cyclohexane-1,2'-inden]-1'(3'H)-one

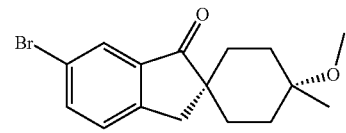 [SMILES: CO[C@]1(C)CC[C@@]2(CC1)Cc1ccc(Br)cc1C2=O]

(1r,4r)-6'-bromo-4-hydroxy-4-methylspiro[cyclohexane-1,2'-inden]-1'(3'H)-one (Intermediate 60, Isomer 1, 0.114 g, 0.37 mmol) and methyl iodide (0.046 mL, 0.74 mmol) were dissolved in THF (5 mL). Potassium tert-pentoxide (1.7 M in toluene, 0.282 mL, 0.48 mmol) was added dropwise, and the mixture was stirred at 30 min. Potassium tert-pentoxide (1.7 M in toluene, 0.217 mL, 0.37 mmol) was added and the mixture was stirred for 15 min. A mixture of water (10 mL) and EtOAc (10 mL) was added and the resulting mixture was stirred for 10 min. The organic phase was collected, dried over Na$_2$SO$_4$ and concentrated in vacuo to give the title compound (119 mg, 87% yield): $^1$H NMR (500 MHz, CDCl$_3$) δ ppm 1.19 (s, 3 H), 1.48 (br. s., 4 H), 1.53 (m, 4 H), 1.66 (m, 2 H), 1.83 (m, 2 H), 2.86 (s, 2 H), 3.17 (s, 3 H), 7.23 (d, 1 H), 7.59 (m, 1 H), 7.77 (m, 1 H); MS (ES+) m/z 323 [M+H]$^+$.

Intermediate 62

6-(3-Fluoropropoxy)-2,3-dihydro-1H-inden-1-one

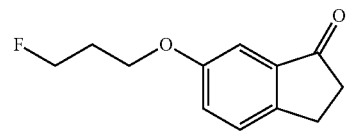 [SMILES: O=C1CCc2ccc(OCCCF)cc21]

To a solution of 6-hydroxy-2,3-dihydro-1H-inden-1-one (3.0 g, 20 mmol) in THF (140 mL) were 3-fluoropropan-1-ol (1.67 mL, 22.3 mmol), triphenylphosphine (7.97 g, 30.4 mmol) and diisopropyl azodicarboxylate (5.98 mL, 30.4 mmol) added. The mixture was stirred at r.t. for two days. More 3-fluoropropanol (0.5 mL) was added and the mixture was heated to 45° C. After 2 h the mixture was concentrated, and the crude product was purified by flash chromatography using 0-20% EtOAc in heptane as eluent, affording 3.42 g (81% yield) of the title compound: $^1$H NMR (500 MHz, CDCl$_3$) δ 2.12-2.26 (m, 2 H), 2.68-2.76 (m, 2 H), 3.04-3.12 (m, 2 H), 4.14 (t, 2 H), 4.61 (t, 1 H), 4.70 (t, 1 H), 7.17-7.22 (m, 2 H), 7.38 (d, 1 H); MS (EI) m/z 208 M$^+$.

Intermediate 63

6'-(3-Fluoropropoxy)spiro[cyclohexane-1,2'-indene]-1',4(3'H)-dione

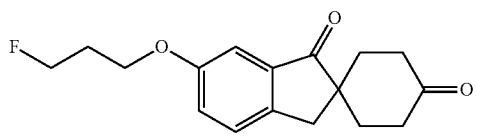 [SMILES: O=C1CCC2(CC1)Cc1ccc(OCCCF)cc1C2=O]

A mixture of 6-(3-fluoropropoxy)-2,3-dihydro-1H-inden-1-one (Intermediate 62, 3.42 g, 16.4 mmol) and methyl acrylate (3.26 mL, 36.1 mmol) in 2-Me THF (15 mL) was cooled to 0° C. Potassium tert-butoxide (2.21 g, 19.71 mmol) was added in portions. After stirring for 1 h at r.t., water (22.5 mL) and KOH (0.921 g, 16.4 mmol) were added and the mixture was heated at reflux for 4.5 h. The mixture was allowed to cool to r.t. and brine was added. The layers were separated and the aqueous layer was extracted with EtOAc. The combined organic layers were dried over Na$_2$SO$_4$, filtered and concentrated in vacuo to yield 3.14 g (66% yield) of the title compound which was used in the next step without further purification: $^1$H NMR (400 MHz, CDCl$_3$) δ 1.82-1.91 (m, 2 H), 2.13-2.27 (m, 4 H), 2.41-2.52 (m, 2 H), 2.70 (dt, 2 H), 3.16 (s, 2 H), 4.11-4.17 (m, 2 H), 4.60 (t, 1 H), 4.72 (t, 1 H), 7.21-7.27 (m, 2 H), 7.39 (dd, 1 H); MS (ES+) m/z 291 [M+H]$^+$.

Intermediate 64

6'-(3-Fluoropropoxy)-4-hydroxyspiro[cyclohexane-1,2'-inden]-1'(3'H)-one

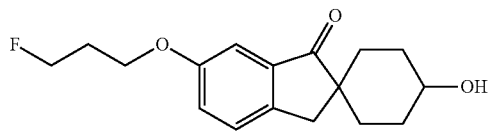 [SMILES: O=C1c2cc(OCCCF)ccc2CC12CCC(O)CC2]

6'-(3-Fluoropropoxy)spiro[cyclohexane-1,2'-indene]-1',4 (3'H)-dione (Intermediate 63, 3.14 g, 10.8 mmol) were dissolved in tetrahydrofuran (50 mL) and MeOH (4.38 mL, 108 mmol). Borane-trimethylamine complex (1.74 g, 23.8 mmol) was added and the resulting mixture was stirred overnight. Citric acid monohydrate (31.8 g, 151 mmol) was added all at once and was followed by dropwise addition of water (3.90 mL, 216 mmol). The mixture was stirred for 3 h before being diluted with water and extracted with EtOAc (×2). The combined organic phases was dried over MgSO$_4$ and concentrated in vacuo. The product was purified using silica gel flash chromatography using a gradient of MeOH (0-10%) in DCM to give 1.94 (61% yield) of the title compound which was used in the next step without further purification: MS (ES+) m/z 307 [M+H]$^+$.

Intermediate 65

6'-(3-Fluoropropoxy)-4-methoxyspiro[cyclohexane-1,2'-inden]-1'(3'H)-one

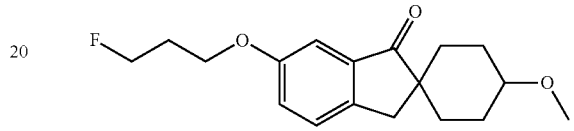

6'-(3-Fluoropropoxy)-4-hydroxyspiro[cyclohexane-1,2'-inden]-1'(3'H)-one (Intermediate 64, 1.94 g, 6.64 mmol) was dissolved in tetrahydrofuran (35 mL) under argon and cooled to 0° C. Potassium tert-butoxide (2.23 g, 19.9 mmol) was added portion wise and the mixture was stirred at 0° C. for 15 min. Methyl iodide (0.83 mL, 13.3 mmol) was added. The cooling bath was removed, and the mixture was stirred at r.t. overnight. Water (200 mL) was added and the resulting solution was partitioned between additional water (200 mL) and EtOAc (400 mL). The organic phases were dried over MgSO$_4$ and concentrated in vacuo. The product was isolated using flash chromatography using a gradient of EtOAc (0-50%) in heptane to give 0.611 g (30% yield) of the title compound: MS (ES+) m/z 307 [M+H]$^+$.

Intermediate 66

6-Isobutoxy-2,3-dihydro-1H-inden-1-one

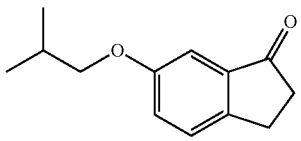

To a mixture of 6-hydroxy-2,3-dihydro-1H-inden-1-one (5.0 g, 33.8 mmol) in DMF (170 mL) was added K$_2$CO$_3$ (9.33 g, 67.5 mmol) and 1-bromo-2-methylpropane (5.50 mL, 50.6 mmol). The resulting orange mixture was stirred at r.t. overnight and was then heated to 60° C. for 2 days. The mixture was cooled to r.t., water was added and the mixture was extracted with EtOAc (×4). The combined organic layers were dried over MgSO$_4$ and concentrated in vacuo. Purification by flash chromatography using 0-20% EtOAc in heptane as eluent afforded 4.98 g (72% yield) of the title compound: $^1$H NMR (500 MHz, CDCl$_3$) δ ppm 1.03 (d, 6 H), 2.10 (dt, 1

H), 2.69-2.75 (m, 2 H), 3.04-3.11 (m, 2 H), 3.75 (d, 2 H), 7.17-7.22 (m, 2 H), 7.37 (d, 1 H); MS (ES+) m/z 205 [M+H]$^+$.

Intermediate 67

6'-Isobutoxyspiro[cyclohexane-1,2'-indene]-1',4(3'H)-dione

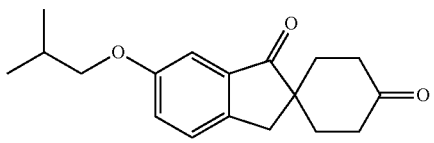 [SMILES: CC(C)COc1ccc2c(c1)C(=O)C1(CCC(=O)CC1)C2]

The title compound (3.02 g, 72% yield) was prepared using the method described for Intermediate 63 starting from 6-isobutoxy-2,3-dihydro-1H-inden-1-one (Intermediate 66, 3.0 g, 14.7 mmol) and methyl acrylate (2.92 mL, 32.3 mmol): $^1$H NMR (400 MHz, CDCl$_3$) δ ppm 1.04 (m, 8 H) 1.86 (m, 2 H) 2.11 (dt, 1 H) 2.21 (m, 2 H) 2.47 (m, 3 H) 2.70 (m, 2 H) 3.15 (s, 2 H) 3.76 (m, 3 H) 7.20 (m, 1 H) 7.25 (m, 1 H) 7.38 (d, 1 H); MS (ES+) m/z 287 [M+H]$^+$.

Intermediate 68

(1r,4r)-4-Hydroxy-6'-isobutoxyspiro[cyclohexane-1,2'-inden]-1'(3'H)-one

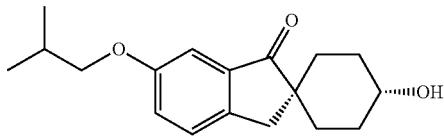 [SMILES: CC(C)COc1ccc2c(c1)C(=O)[C@]1(CC[C@H](O)CC1)C2]

The title compound (1.20 g, 40% yield, containing 5% of another isomer) was prepared using the method described for 6'-(3-Fluoropropoxy)-4-hydroxyspiro[cyclohexane-1,2'-inden]-1'(3'H)-one (Intermediate 64) starting from 6'-isobutoxyspiro[cyclohexane-1,2'-indene]-1',4(3'H)-dione (Intermediate 67, 3.02 g, 10.6 mmol) and borane-trimethylamine complex (1.69 g, 23.2 mmol). The product was purified by flash chromatography with gradient elution of 0-100% EtOAc in heptane as eluent: $^1$H NMR (400 MHz, CDCl$_3$) δ 1.03 (d, J=6.82 Hz, 7 H), 1.38-1.52 (m, 5 H), 1.76-1.87 (m, 2 H), 2.02-2.16 (m, 4 H), 2.97 (s, 2 H), 3.70-3.82 (m, 4 H), 7.17 (d, J=2.53 Hz, 1 H), 7.19-7.24 (m, 1 H), 7.34 (dd, J=8.34, 0.51 Hz, 1 H); MS (ES+) m/z 289 [M+H]$^+$.

Intermediate 69

(1r,4r)-6'-Isobutoxy-4-methoxyspiro[cyclohexane-1,2'-inden]-1'(3'H)-one

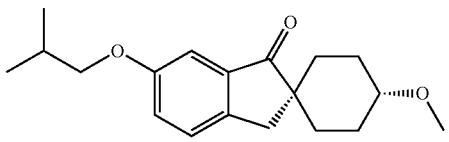 [SMILES: CO[C@H]1CC[C@]2(CC1)Cc1ccc(OCC(C)C)cc1C2=O]

(1r,4r)-4-Hydroxy-6'-isobutoxyspiro[cyclohexane-1,2'-inden]-1'(3'H)-one (Intermediate 68, 1.2 g, 4.16 mmol) was dissolved in 2-Me THF (12 mL) under an inert atmosphere, and the solution was cooled to 0° C. Methyl iodide (0.338 mL, 5.41 mmol) was added followed by portionwise addition of potassium tert-butoxide (0.654 g, 5.83 mmol). The resulting mixture was stirred at 35° C. for 1 h. Potassium tert-butoxide (0.233 g, 2.08 mmol) was added and stirring continued. After another 30 min, a new portion of potassium tert-butoxide (0.070 g, 0.62 mmol) was added and stirring continued. After a total of 4 h, full conversion was obtained and water (6 mL) and brine (3 mL) were added. The phases were separated and the organic layer was dried over Na$_2$SO$_4$ and concentrated to yield 1.23 g (98% yield) of the title compound: $^1$H NMR (400 MHz, CDCl$_3$) δ ppm 1.03 (d, 6 H) 1.38 (m, 2 H) 1.50 (dt, 2 H) 1.78 (m, 2 H) 2.09 (m, 1 H) 2.15 (m, 2 H) 2.96 (s, 2 H) 3.27 (m, 1 H) 3.41 (s, 3 H) 3.75 (d, 2 H) 7.17 (d, 1 H) 7.21 (m, 1 H) 7.34 (dd, 1 H). MS (ES+) m/z 303 [M+H]$^+$.

Intermediate 70

3-Bromo-5-[($^2$H$_3$)prop-1-yn-1-yl]pyridine

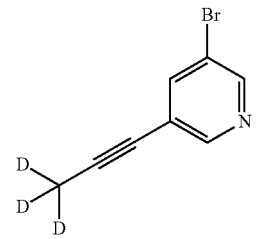 [SMILES: [2H]C([2H])([2H])C#Cc1cncc(Br)c1]

n-BuLi (2.5 M in hexanes, 0.44 mL, 1.10 mmol) was added dropwise, under Ar and at 0° C., to a solution of 3-bromo-5-ethynylpyridine (see WO2005/094822, 200 mg, 1.10 mmol) in THF (2 mL). The mixture was stirred for 1 h. Iodomethane-d3 (0.56 mL, 1.32 mmol) was added at 0° C. and the reaction was stirred at r.t. for 1 h. The reaction was quenched with ammonium chloride solution (aq sat, 2 mL) and extracted with DCM (15 mL). The organic layer was dried over Na$_2$SO$_4$ and concentrated in vacuo. The product was purified by flash chromatography with gradient elution of 0-30% EtOAc in n-heptane to yield the title compound (77 mg, 35% yield): $^1$H NMR (500 MHz, CDCl$_3$) δ ppm 7.84 (t, 1 H), 8.53 (d, 1 H), 8.56 (d, 1 H); MS (ES+) m/z 199 [M+H]$^+$.

Intermediate 71

6''-Bromodispiro[1,3-dioxolane-2,1'-cyclohexane-4',2''-inden]-1''(3''H)-one

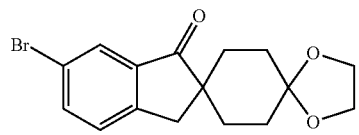 [SMILES: O=C1c2cc(Br)ccc2CC12CCC1(CC2)OCCO1]

Ethane-1,2-diol (0.968 mL, 17.4 mmol), 6'-bromospiro[cyclohexane-1,2'-indene]-1',4(3'H)-dione (Intermediate 5 Method A Step 1, 5.09 g, 17.4 mmol) and p-toluenesulfonic acid monohydrate (0.165 g, 0.87 mmol) in toluene (100 mL), were heated to reflux overnight. The mixture was cooled to r.t. before transferred to a separation funnel and washed with NaHCO₃ (sat aq). The aqueous phase was extracted with EtOAc. The combined organic phases were washed with brine. The formed solid was filtered off and the filtrate concentrated. The filtrate residue was dissolved in EtOAc and washed with water. More solid was formed that was collected by filtration. This process was repeated three more times until no more solid was formed. The combined solids were dried overnight under vacuum to yield 3.76 g of the title compound. The remaining organic phase was concentrated to yield 1.9 g of the title compound. Combination of the solids gave the title compound (5.66 g, 97% yield): $^1$H NMR (500 MHz, CDCl$_3$) δ ppm 1.50 (dt, 2 H) 1.66-1.74 (m, 2 H) 1.92 (dt, 2 H) 2.06 (td, 2 H) 3.01 (s, 2 H) 3.97-4.03 (m, 4 H) 7.34 (d, 1 H) 7.70 (dd, 1 H) 7.89 (d, 1 H); MS (ES+) m/z 337 [M+H]$^+$.

Intermediate 72

6'-Bromo-4-[($^2$H$_3$)methyloxy]spiro[cyclohexane-1,2'-inden]-1'(3'H)-one

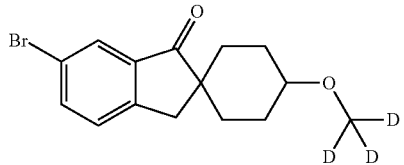 [SMILES: [2H]C([2H])([2H])OC1CCC2(CC1)Cc1ccc(Br)cc1C2=O]

6'-Bromo-4-hydroxyspiro[cyclohexane-1,2'-inden]-1'(3'H)-one (Intermediate 5 Step 2, 3 g, 10.2 mmol) (64:36 ratio of isomers (1r,4r) and (1s,4s)) was dissolved in 2-Me THF (30 mL) under an inert atmosphere and the solution was cooled to 0° C. Iodomethane-d3 (0.633 mL, 10.1 mmol) was added followed by portionwise addition of potassium tert-butoxide (1.60 g, 14.2 mmol). The resulting mixture was stirred at r.t. for 1 h. Potassium tert-butoxide (0.456 g, 4.07 mmol) was added and stirring continued. After another 30 min, potassium tert-butoxide (0.342 g, 3.05 mmol) was added and stirring continued. After a total of 4 h, water and brine were added. The phases were separated and the organic layer was extracted with EtOAc. The combined organic layers were dried over MgSO₄ and concentrated. Purification by flash chromatography using 0-15% EtOAc in heptane as eluent afforded 1.66 g (52% yield) of the title compound as a mixture is of isomers (1r,4r) major and (1s,4s) minor. Major isomer: $^1$H NMR (500 MHz, CDCl$_3$) δ 1.20-1.28 (m, 1 H), 1.32-1.43 (m, 1 H), 1.48-1.64 (m, 3 H), 1.77 (td, 1 H), 2.00-2.11 (m, 1 H), 2.12-2.20 (m, 1 H), 2.98 (s, 2 H), 3.23-3.32 (m, 1 H), 7.31-7.38 (m, 1 H), 7.66-7.73 (m, 1 H), 7.87-7.90 (m, 1 H); MS (ES+) m/z 312 [M+H]$^+$.

Intermediate 73

3-Bromo-5-(difluoromethyl)pyridine

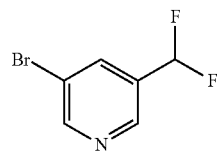

5-Bromonicotinaldehyde (5.0 g, 26.9 mmol) was dissolved in DCM (25 mL). The atmosphere was exchanged to argon, and diethylaminosulfur trifluoride (4.29 mL, 32.3 mmol) was added. The reaction mixture was stirred at 21° C. for 2 h. The reaction was quenched with 15 mL sat NaHCO₃. The phases were separated, and the organic layer was collected, washed with brine, dried over MgSO₄, filtered, and concentrated in vacuo. The residue was purified by flash chromatography using heptane/EtOAc 90/10 as eluent to give the title compound (3.66 g, 65% yield): $^1$H NMR (500 MHz, DMSO-d$_6$) δ ppm 7.15 (t, 1 H) 8.32 (s, 1 H) 8.80 (s, 1 H) 8.91 (s, 1 H); MS (EI) m/z 207 M$^+$.

Intermediate 74

3-(Difluoromethyl)-5-(4,4,5,5-tetramethyl-1,3,2-dioxaborolan-2-yl)pyridine

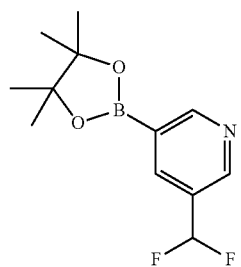 [SMILES: CC1(C)OB(c2cncc(C(F)F)c2)OC1(C)C]

A suspension of 4,4,4',4',5,5,5',5'-octamethyl-2,2'-bi(1,3,2-dioxaborolane) (8.95 g, 35.2 mmol), 3-bromo-5-(difluoromethyl)pyridine (Intermediate 73, 3.67 g, 17.6 mmol), potassium acetate (5.19 g, 52.9 mmol) in dioxane (70 mL) was degassed with a stream of argon for a couple of to min. PdCl₂(dppf) CH₂Cl₂ (0.179 g, 0.22 mmol) was added and the mixture was heated at reflux under N₂ for 4 h. The mixture was allowed to cool and was filtered. The filter cake was washed with EtOAc and the filtrate was concentrated in vacuo. The residue was purified with flash chromatography on silica gel, gradient elution with EtOAc in n-heptane. The title compound (2.0 g) that still contained some impurities was used as such in the next step: MS (EI) m/z 207 Mt Intermediate 75

1-Bromo-2-chloro-3-(prop-1-ynyl)benzene

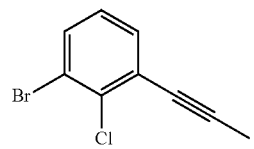

To a microwave vial were added 1,3-dibromo-2-chlorobenzene (780 mg, 2.89 mmol), trimethyl(prop-1-ynyl)silane (0.645 mL, 4.33 mmol), copper iodide (28 mg, 0.14 mmol), PdCl₂(dppf) CH₂Cl₂ (118 mg, 0.14 mmol), tetrabutylammonium fluoride (1 M in THF, 8.66 mL, 8.66 mmol), diisopropylamine (1.23 mL, 8.66 mmol) and anhydrous DMF (5 mL). The vial was capped and purged with argon and the mixture was irradiated at 100° C. for 1 h in a microwave reactor. The mixture was diluted with water and extracted with DCM three times, dried through a phase separator and concentrated in vacuo. The product was purified by flash chromatography (100% heptanes as eluent) to give 146 mg (22% yield) of the title compound. $^1$H NMR (500 MHz, DMSO-d$_6$) δ ppm 2.13 (s, 3 H) 7.24 (t, J=7.88 Hz, 1 H) 7.53 (dd, J=7.57, 1.26 Hz, 1 H) 7.74 (dd, J=8.04, 1.42 Hz, 1 H); MS (CI) m/z 231 [M+H][1].

Intermediate 76

4-(Trifluoromethyl)cyclohexanecarboxylate

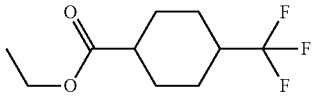

4-(Trifluoromethyl)cyclohexanecarboxylic acid (5.00 g, 25.5 mmol) was dissolved in toluene (100 mL), and sulfuric acid (0.014 mL, 0.25 mmol) was added. The reaction mixture was reacted under Dean-Stark conditions for 16 h. The reaction mixture was cooled to r.t., and diluted with EtOAc. The solution was washed with sat aq. NaHCO$_3$. The organic layer was washed with brine, and concentrated in vacuo providing the title compound (5.64 g, 99% yield): $^1$H NMR (500 MHz, DMSO-d$_6$) δ ppm 0.96 (d, 1 H) 1.19-1.30 (m, 2 H) 1.38-1.50 (m, 3 H) 1.83 (d, 2 H) 2.18 (s, 3 H) 2.91-3.12 (m, 3 H) 3.20 (s, 3 H) 6.55 (br. s., 2 H) 6.89 (d, 1 H) 7.01-7.26 (m, 1 H) 7.43 (d, 1 H) 7.60 (dd, 1 H) 8.01 (d, 2 H) 8.22 (s, 1 H); MS (ES+) m/z 449 [M+H][1] and (ES−) m/z 447 [M−H][−].

Intermediate 77

Ethyl 1-(4-bromo-2-iodobenzyl)-4-(trifluoromethyl)cyclohexanecarboxylate

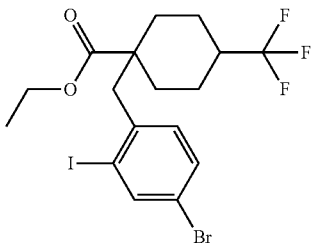 [SMILES: CCOC(=O)C1(Cc2ccc(Br)cc2I)CCC(C(F)(F)F)CC1]

Ethyl 4-(trifluoromethyl)cyclohexanecarboxylate (Intermediate 76, 1.492 g, 6.65 mmol) was dissolved in THF (25 mL). The atmosphere was exchanged to argon, and the solution was cooled to −78° C. Lithium diisopropylamide (1.8 M in THF/heptane/ethylbenzene) (4.07 mL, 7.32 mmol) was added, while the temperature was kept at −78° C. The solution was stirred for 30 min at −78° C. 4-Bromo-1-(bromomethyl)-2-iodobenzene (see Caruso, A.; Tovar, J., D. *J. Org. Chem.* 2011, 76, 2227-2239., 2.50 g, 6.65 mmol) in THF (25 mL) was added via a syringe. The mixture was allowed to reach r.t., while stirred for 2 h. Water (10 mL) was added to the reaction mixture, followed by EtOAc (40 mL). The phases were separated. The organic layer was dried over MgSO$_4$, filtered, and concentrated in vacuo. The residue was purified by flash chromatography (eluent: heptane/EtOAc 95/5) to give the title compound (2.41 g, 69% yield): $^1$H NMR (400 MHz, CDCl$_3$) δ ppm 1.22-1.27 (m, 3 H) 1.29-1.43 (m, 4 H) 1.82-1.90 (m, 2 H) 1.82-1.90 (m, 3 H) 1.97 (br. s., 2 H) 2.28-2.36 (m, 3 H) 3.01 (s, 3 H) 4.18 (q, 3 H) 6.91 (m, 1 H) 7.38 (m, 1 H) 7.99 (m, 1 H); MS (ES+) m/z 520 [M+H][+].

Intermediate 78

6'-Bromo-4-(trifluoromethyl)spiro[cyclohexane-1,2'-inden]-1'(3'H)-one

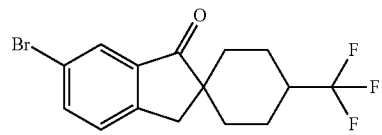 [SMILES: O=C1c2cc(Br)ccc2CC12CCC(C(F)(F)F)CC2]

Ethyl 1-(4-bromo-2-iodobenzyl)-4-(trifluoromethyl)cyclohexanecarboxylate (Intermediate 77, 2.41 g, 4.64 mmol) was dissolved in THF (40 mL). The atmosphere was exchanged to argon, and the solution was cooled to −78° C. Isopropylmagnesium chloride-lithium chloride (1.3 M in THF) (2.86 mL, 3.71 mmol) was added dropwise. The reaction mixture was stirred at −78° C. for 15 min. The reaction mixture left to warm up to r.t., while stirred for 30 min. The reaction is mixture was quenched with sat. NH$_4$Cl. Brine was added, and the phases were separated. The organic layer was washed with brine, dried over MgSO$_4$, filtered, and concentrated in vacuo. The residue was purified by preparative chromatography (XBridge C18 (10 µm, 50×250 mm) column with a gradient of 50-100% MeCN) in (95% 0.05M NH$_4$OAc in MilliQ water and 5% MeCN) over 15 min at a flow rate of 100 mL/min). The purification provided the title compound (0.849 g, 52% yield): $^1$H NMR (400 MHz, CDCl$_3$) δ ppm 1.51-1.61 (m, 3 H) 1.75-1.84 (m, 2 H) 1.97 (m, 2 H) 2.18 (m, 2 H) 2.90 (s, 2 H) 7.29 (dd, 1 H) 7.69 (dd, 1 H) 7.84 (d, 1 H); MS (ES+) 346 [M+H][+].

Intermediate 79

2-Fluoro-3-methoxy-5-(4,4,5,5-tetramethyl-1,3,2-dioxaborolan-2-yl)benzonitrile

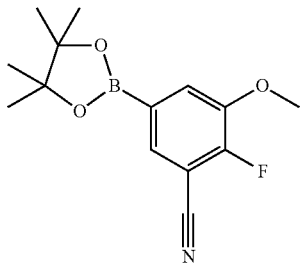

A flask containing 2-fluoro-3-methoxybenzonitrile (302 mg, 2.00 mmol), 4,4'-di-tert-butyl-2,2'-dipyridyl (8 mg, 0.03 mmol) and bis(pinacolato)diboron (254 mg, 1.0 mmol) was flushed with argon, and then charged with hexane (6 mL). The mixture was then stirred at 25° C. overnight. The reaction mixture was diluted with EtOAc and washed with brine. The organic phase was concentrated and the crude product was purified on a silica column (0-50% EtOAc/n-heptane) to give the title compound (362 mg with 73% purity according to HPLC): $^1$H NMR (500 MHz, DMSO-$d_6$) δ ppm 7.63-7.55 (m, 2 H), 3.93 (s, 3 H), 1.31 (s, 12 H); MS (EI) m/z 277 M$^+$.

Intermediate 80

6'-Bromo-4-ethoxyspiro[cyclohexane-1,2'-inden]-1'(3'H)-one

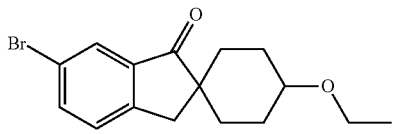 [SMILES: CCOC1CCC2(CC1)Cc1ccc(Br)cc1C2=O]

6'-Bromo-4-hydroxyspiro[cyclohexane-1,2'-inden]-1'(3'H)-one as a 2:1 mixture of isomers (Intermediate 5 Step 2, 10.4 g, 34.1 mmol) and ethyl iodide (3.6 mL, 44.3 mmol) were dissolved in 2-MeTHF (100 mL) under N$_2$. KOt-Bu (7.65 g, 68.2 mmol) was added portionwise to the reaction mixture, keeping the internal temperature below 30° C. The solution was stirred at r.t. overnight. Water (40 mL) and brine (25 mL) were added and the mixture was further stirred for 5 min. The mixture was diluted with brine and 2-Me-THF until two layers formed. The phases were separated. Activated charcoal was added to the organic layer which was then stirred for 10 min. Diatomaceous earth was added and the mixture was further stirred for 5 min. The mixture was filtered through a plug of silica gel and diatomaceous earth, which was rinsed with heptane/EtOAc 7:3. The filtrate was concentrated. The filtration sequence was repeated, affording 4.0 g (36% yield) of the title compound (as a 2:1 mixture of isomers): $^1$H NMR (300 MHz, CDCl$_3$) ppm 1.22 (t, 3 H), 1.32-1.45 (m, 2 H), 1.45-1.52 (m, 2 H), 1.77 (dt, 2 H), 2.07-2.16 (m, 2 H), 2.98 (s, 2 H), 3.30-3.40 (m, 1 H), 3.57 (q, 2 H), 7.34 (d, 1 H), 7.69 (dd, 1 H), 7.87 (d, 1 H).

Intermediate 81

6'-(3,3,3-Trifluoropropoxy)spiro[cyclohexane-1,2'-indene]-1',4(3'H)-dione

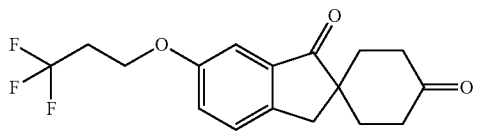 [SMILES: O=C1CCC2(CC1)Cc1ccc(OCCC(F)(F)F)cc1C2=O]

The title compound (854 mg, 58% yield) was prepared using the method described for Intermediate 63 starting from 6-(3,3,3-trifluoropropoxy)-2,3-dihydro-1H-inden-1-one (Intermediate 47, 1.08 g, 4.42 mmol) and methyl acrylate (878 μL, 9.73 mmol): $^1$H NMR (500 MHz, CDCl$_3$) δ ppm 1.82-1.92 (m, 2 H), 2.17-2.27 (m, 2 H), 2.42-2.53 (m, 2 H), 2.60-2.75 (m, 4 H), 3.14-3.20 (m, 2 H), 4.22-4.27 (m, 2 H), 7.19-7.22 (m, 1 H), 7.25 (dd, 1 H), 7.41 (d, 1 H): MS (ES+) m/z 327 [M+H]$^+$.

Intermediate 82

(1r,4r)-4-Hydroxy-6'-(3,3,3-trifluoropropoxy)spiro[cyclohexane-1,2'-inden]-1'(3'H)-one

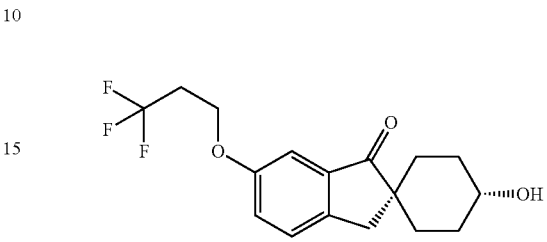

The title compound (357 mg, 51% yield, containing 16% of another isomer) was prepared using the method described for Intermediate 64 starting from 6'-(3,3,3-trifluoropropoxy)spiro-[cyclohexane-1,2'-indene]-1',4(3'H)-dione (Intermediate 81, 689 mg, 2.11 mmol) and borane-trimethylamine complex (339 mg, 4.65 mmol). The product was purified by flash chromatography using 0-100% EtOAc in heptane as eluent: $^1$H NMR (500 MHz, CDCl$_3$) δ ppm 1.40-1.52 (m, 4 H), 1.82 (td, 2 H), 2.03-2.13 (m, 2 H), 2.65 (qt, 2 H), 2.99 (s, 2 H), 3.73-3.82 (m, 1 H), 4.23 (t, 2 H), 7.16-7.20 (m, 1 H), 7.22 (dd, 1 H), 7.38 (d, 1 H); MS (ES+) m/z 329 [M+H]$^+$.

Intermediate 83

((1r,4r)-4-Methoxy-6'-(3,3,3-trifluoropropoxy)spiro[cyclohexane-1,2'-inden]-1'(3'H)-one

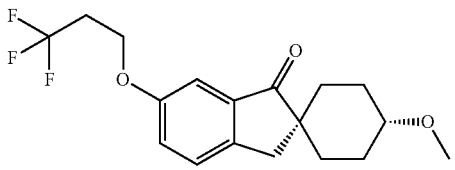 [SMILES: CO[C@H]1CC[C@]2(CC1)Cc1ccc(OCCC(F)(F)F)cc1C2=O]

(1r,4r)-4-Hydroxy-6'-(3,3,3-trifluoropropoxy)spiro[cyclohexane-1,2'-inden]-1'(3'H)-one (Intermediate 82, 357 mg, 1.09 mmol) was dissolved in 2-Me THF (7 mL) under an inert atmosphere, and the solution was cooled to 0° C. Methyl iodide (88 μL, 1.41 mmol) was added followed by portionwise addition of potassium tert-butoxide (171 mg, 1.52 mmol). The resulting mixture was stirred at r.t. for 1 h. Some alcohol remained so more potassium tert-butoxide (61 mg, 0.54 mmol) was added and stirring continued. After 30 min, water and brine were added.

The phases were separated and the organic layer was dried over MgSO$_4$ and concentrated. Purification by flash chromatography using 0-25% EtOAc in heptane as eluent afforded 201 mg (54% yield) of the title compound (containing 11% of another isomer): $^1$H NMR (500 MHz, CDCl$_3$) δ 1.32-1.44 (m, 2 H), 1.51 (d, 2 H), 1.78 (td, 2 H), 2.12-2.21 (m, 2 H), 2.59-2.70 (m, 2 H), 2.97 (s, 2 H), 3.24-3.32 (m, 1 H), 3.41 (s, 3 H), 4.23 (t, 2 H), 7.16-7.23 (m, 2 H), 7.37 (d, 1 H); MS (ES+) m/z 343 [M+H]$^+$.

Intermediate 84

3-(Bromomethyl)-2-fluorobenzonitrile

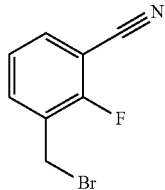 [SMILES: N#Cc1cccc(CBr)c1F]

NBS (1.729 g, 9.71 mmol) was added to a solution of 2-fluoro-3-methylbenzonitrile (1.25 g, 9.25 mmol) in acetonitrile (25 mL). The obtained mixture was refluxed, and then benzoic peroxyanhydride (0.045 g, 0.18 mmol) was added. The reaction mixture was refluxed overnight, then cooled to r.t. and water was added. The aqueous phase was discarded and the organic phase was dried over MgSO$_4$ and concentrated. The crude product was purified by flash chromatography using a gradient of EtOAc in heptane as eluent to give the title compound (1.39 g, 70% yield): $^1$H NMR (500 MHz, DMSO-d$_6$) δ ppm 4.75 (s, 2 H) 7.43 (t, 1 H) 7.93 (t, 2 H); MS (EI) m/z 213 M.

Intermediate 85

2-Fluoro-3-(methoxymethyl)benzonitrile

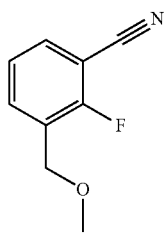

3-(Bromomethyl)-2-fluorobenzonitrile (Intermediate 84, 1.39 g, 6.49 mmol) was dissolved in MeOH (10 mL) and sodium methoxide (1.238 mL, 6.49 mmol) was added. The mixture was stirred at r.t. for 2 h. This mixture was concentrated and then partitioned between water and EtOAc. The organic layer was separated and then concentrated in vacuo. The resulting residue was purified by flash chromatography using EtOAc/heptanes as eluent to give the title compound (0.900 g, 84% yield): $^1$H NMR (500 MHz, DMSO-d$_6$) δ ppm 3.32 (s, 3 H) 4.52 (br. s, 2 H) 7.42 (t, 1 H) 7.77-7.84 (m, 1 H) 7.86-7.92 (m, 1 H); MS (EI) m/z 166 M$^+$.

Intermediate 86

2-Fluoro-3-(methoxymethyl)-5-(4,4,5,5-tetramethyl-1,3,2-dioxaborolan-2-yl)benzonitrile

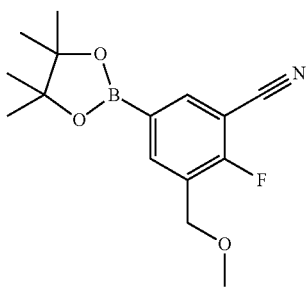 [SMILES: COCc1cc(B2OC(C)(C)C(C)(C)O2)cc(C#N)c1F]

4,4,4',4',5,5,5',5'-Octamethyl-2,2'-bi(1,3,2-dioxaborolane) (1.15 g, 4.53 mmol), di-g-methoxobis(1,5-cyclooctadiene)diiridium(I) (45 mg, 0.07 mmol), and 4,4'-di-tert-butyl-2,2'-dipyridyl (72.9 mg, 0.27 mmol) were added to a reaction flask. The atmosphere was exchanged to argon. Hexane (10 mL) was added, while the argon atmosphere was maintained. The mixture was stirred for 5 min at r.t. The color of the reaction mixture turned red. A solution of 2-fluoro-3-(methoxymethyl)benzonitrile (Intermediate 85, 748 mg, 4.53 mmol) in hexane (10 mL) was added, and the mixture was refluxed for 2 h. The reaction mixture was diluted with EtOAc and is washed with brine. The organic layer was collected, dried over MgSO$_4$, filtered and concentrated. The residue was purified by flash chromatography using EtOAc/heptane eluent system to give 254 mg (19% yield) of the title compound: MS (EI) m/z 291 M$^+$.

Intermediate 87

Methyl 4-(hydroxymethyl)cyclohexanecarboxylate

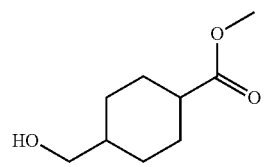

To a solution of 4-(methoxycarbonyl)cyclohexanecarboxylic acid (5.44 g, 29.2 mmol) in dry THF at −78° C., was added borane-methyl sulfide complex (19.0 mL, 38.0 mmol) dropwise over 20 min. The mixture was stirred for 3 h and was then allowed to slowly attain r.t. The reaction was quenched with water (20 mL) and the mixture was extracted with EtOAc. The organic phase was washed once with brine, dried over MgSO$_4$ and concentrated in vacuo to give the title compound (4.80 g, 95% yield) as a mixture of two diastereomers: MS (EI) m/z 172 M.

Intermediate 88

Methyl 4-formylcyclohexanecarboxylate

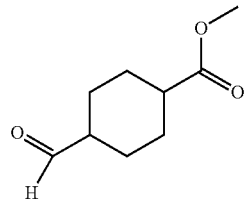

To a solution of methyl 4-(hydroxymethyl)cyclohexanecarboxylate (Intermediate 87, 4.08 g, 23.7 mmol) in DCM was added NaHCO$_3$ (9.95 g, 118 mmol), followed by Dess-Martin Periodinane (12.1 g, 28.4 mmol). The mixture was stirred at r.t. for 2.5 h. Et$_2$O (60 mL) was added followed by an aq. solution of NaHCO$_3$ (1 M, 60 mL) and a 20% aq. solution of sodium thiosulfate (40 mL). The resulting mixture was stirred overnight. The phases were separated and the aqueous phase was extracted with Et$_2$O. The organic phase was washed with brine and dried over MgSO$_4$, filtered and concentrated in vacuo to yield the title compound (4.0 g, 99% yield): MS (EI) m/z 170 M$^+$.

Intermediate 89

Methyl 4-(difluoromethyl)cyclohexanecarboxylate

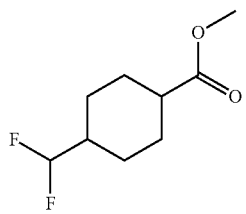

Methyl 4-formylcyclohexanecarboxylate (Intermediate 88, 4.0 g, 23.5 mmol) was dissolved in dry DCM (80 mL). Bis(2-methoxyethyl)amino-sulfur trifluoride (3.42 mL, 25.9 mmol) was added dropwise over 20 min. The reaction mixture was stirred for 1.5 h. Water (40 mL) was added dropwise and the reaction mixture was stirred for 2 min. The organic phase was separated from the water phase with a phase separator and evaporated in vacuo to give the title compound (4.28 g, 95% yield): MS (CI) m/z 193 [M+H]$^+$.

Intermediate 90

Methyl 1-(4-bromo-2-iodobenzyl)-4-(difluoromethyl)cyclohexanecarboxylate

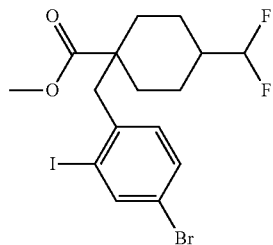 [SMILES: COC(=O)C1(Cc2ccc(Br)cc2I)CCC(C(F)F)CC1]

Methyl 4-(difluoromethyl)cyclohexanecarboxylate (Intermediate 89, 2.46 g, 12.8 mmol) was dissolved in THF (25 mL). The atmosphere was exchanged to N$_2$ (g), and the solution was cooled to −78° C. Lithium diisopropylamide (1.8M in THF/heptane/ethylbenzene) (8.51 mL, 15.3 mmol) was added, while the temperature was kept at −78° C. The solution was stirred for 60 min at −78° C. A solution of 4-bromo-1-(bromomethyl)-2-iodobenzene (see Caruso, A.; Tovar, J., D. *J. Org. Chem.* 2011, 76, 2227-2239., 4.8 g, 12.8 mmol) in THF (5.0 mL) was added via syringe. The reaction was removed from the cooling bath, and allowed to reach r.t., while stirred for 2.5 h. Water (30 mL) was added, followed by DCM (30 mL). The organic layer was collected and dried over MgSO$_4$, filtered and evaporated in vacuo. The residue was purified by flash chromatography, (0-100% EtOAc in heptanes, 220 g SiO$_2$) to give the title compound (3.29 g, 53% yield): $^1$H NMR (500 MHz, CDCl$_3$) δ ppm 1.11-1.20 (m, 2 H), 1.39 (td, 2 H), 1.67-1.80 (m, 3 H), 2.30 (d, 2 H), 3.01 (s, 2 H), 3.70 (s, 3 H), 5.49 (d, 1 H), 6.89 (d, 1 H), 7.38 (dd, 1 H), 7.99 (d, 1 H), MS (CI) m/z 487 [M+H]$^1$.

Intermediate 91

6'-Bromo-4-(difluoromethyl)spiro[cyclohexane-1,2'-inden]-1'(3'H)-one

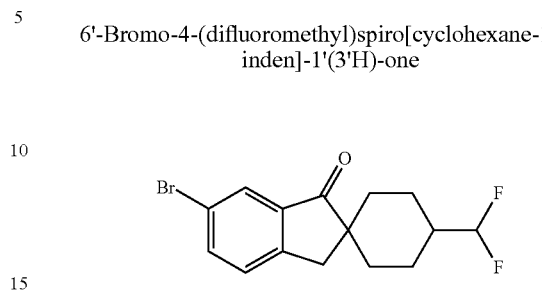

Methyl 1-(4-bromo-2-iodobenzyl)-4-(difluoromethyl)cyclohexanecarboxylate (Intermediate 90, 2.3 g, 4.72 mmol) was dissolved in THF (30 mL). The atmosphere was exchanged to N$_2$ (g), and the solution was cooled to −20° C. Isopropylmagnesium chloride-lithium chloride (1.3M in THF, 4.00 mL, 5.19 mmol) was added dropwise over one h. The reaction mixture was stirred at −20° C. for 40 min. The reaction mixture was removed from the cooling bath, and left to warm up to r.t., while stirred for 1.5 h. The reaction was stirred at r.t. overnight and then heated at 40° C. for 3 h. The reaction was cooled to r.t. and quenched with sat. NH$_4$Cl. The resulting mixture was stirred overnight. The organic layer was collected and dried over MgSO$_4$, filtered, and concentrated. The residue was purified by flash chromatography (0-10% EtOAc in heptane) followed by preparative chromatography to give the title compound (0.562 g, 24% yield): $^1$H NMR (500 MHz, DMSO-d$_6$) δ ppm 1.46-1.65 (m, 4 H), 1.75-1.96 (m, 5 H), 2.93 (s, 2 H), 6.00 (dt, 1 H), 7.51 (d, 1 H), 7.73 (d, 1 H), 7.83 (dd, 1 H).

Example 1

6-(3,5-Dichlorophenyl)-5'-methylspiro[chroman-4,2'-imidazol]-4'-amine

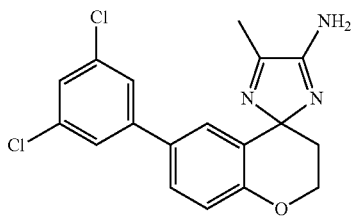 [SMILES: CC1=NC2(CCOc3ccc(-c4cc(Cl)cc(Cl)c4)cc32)N=C1N]

6-Bromo-5'-methylspiro[chroman-4,2'-imidazol]-4'-amine (73 mg, 0.25 mmol, Intermediate 4), 3,5-dichlorophenylboronic acid (95 mg, 0.50 mmol) and K$_2$CO$_3$ (83 mg, 0.60 mmol) were mixed in dioxane (2 mL) and degassed by passing nitrogen through for 5 min. Then (1,1'-bis(diphenyl-phosphino)ferrocene)-dichloropalladium(II) (10 mg, 0.01 mmol) was added and the mixture was heated in a sealed vial at 100° C. overnight. (1,1'-Bis(diphenylphosphino)ferrocene)-dichloro-palladium(II) (10 mg, 0.01 mmol) was added and heating continued in a microwave oven at 130° C. for 2×1 h. Purification by preparative HPLC gave the title compound (13 mg, 14% yield): $^1$H NMR (400 MHz, CDCl$_3$) δ ppm 2.04-2.30 (m, 2 H), 2.38 (s, 3 H), 4.50-4.69 (m, 2 H), 4.88 (br s, 2 H), 6.69 (s, 1 H), 6.98 (d, 1 H), 7.22-7.35 (m, 4 H); MS (ES+) m/z 360 [M+H]$^1$.

Example 2

6-(5-Chloropyridin-3-yl)-5'-methylspiro[chroman-4,2'-imidazol]-4'-amine

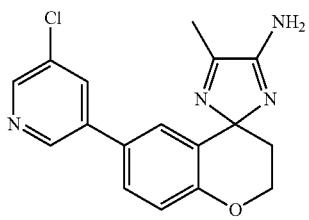 [SMILES: CC1=NC2(CCOc3ccc(-c4cncc(Cl)c4)cc32)N=C1N]

6-Bromo-5'-methylspiro[chroman-4,2'-imidazol]-4'-amine (60 mg, 0.20 mmol, Intermediate 4), 5-chloropyridin-3-ylboronic acid (62 mg, 0.40 mmol) and 2M $K_2CO_3$ (aq, 0.20 mL, 0.41 mmol) were mixed in dioxane (5 mL) and degassed by passing nitrogen through for 5 min. Then (1,1'-bis(diphenylphosphino)ferrocene)-dichloropalladium(II) (8 mg, 10 µmol) was added and the mixture was heated in a microwave oven at 130° C. for 1 h. Purification by preparative chromatography HPLC gave the title compound (42 mg, 63% yield): $^1$H NMR (400 MHz, $CDCl_3$) δ ppm 2.17 (m, 2 H), 2.37 (s, 3 H), 4.59 (m, 2 H), 5.04 (br s, 2 H), 6.73 (d, 1 H), 7.01 (d, 1 H), 7.34 (dd, 1 H), 7.70 (m, 1 H), 8.45 (m, 1 H), 8.55 (m, 1 H); MS (ES+) m/z 327 [M+H]$^+$.

Example 3

6-(3,5-Difluorophenyl)-5'-methylspiro[chroman-4,2'-imidazol]-4'-amine

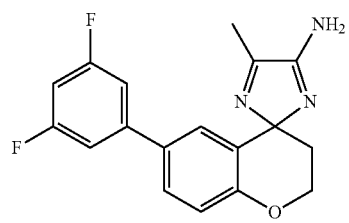 [SMILES: CC1=NC2(CCOc3ccc(-c4cc(F)cc(F)c4)cc32)N=C1N]

6-Bromo-5'-methylspiro[chroman-4,2'-imidazol]-4'-amine (Intermediate 4, 0.10 g, 0.34 mmol), 3,5-difluorophenylboronic acid (0.11 g, 0.68 mmol) and 2M $K_2CO_3$ (aq., 0.34 mL, 0.69 mmol) were mixed in dioxane (3 mL) and degassed by passing through nitrogen for 5 min. Then (1,1'-bis(diphenylphosphino)ferrocene)-dichloropalladium(II) (14 mg, 20 µmol) was added and the mixture was heated in a microwave oven at 130° C. for 1 h. Purification by preparative chromatography gave the title compound (17 mg, 15% yield): $^1$H NMR (400 MHz, $CDCl_3$) δ ppm 2.25 (m, 2 H), 2.41 (s, 3 H), 4.57 (m, 2 H), 6.66-6.86 (m, 2 H), 6.89-7.05 (m, 3 H), 7.38 (d, 1 H), 8.1-9.0 (br m, 2 H); MS (ES+) m/z 328 [M+H]$^+$.

Examples 4-12

To a mixture of 6-bromo-5'-methylspiro[chroman-4,2'-imidazol]-4'-amine (Intermediate 4, 0.20 mmol, 1.0 eq) and the corresponding boronic acid $R^2$—$B(OH)_2$ (0.40 mmol, 2.0 eq) in a mixture of 1,4-dioxane, EtOH and water (2 mL, v:v:v=4:1:1) was added $Pd_2(dba)_3$ (0.02 mmol, 0.1 eq) and X-Phos (0.02 mmol, 0.1 eq) followed by $Na_2CO_3$ (0.40 mmol, 2.0 eq) under nitrogen. The reaction mixture was stirred at 90° C. overnight. The crude product was purified by preparative TLC to afford the respective compound in Table 1.

TABLE 1

| Example | $R^2$ | Name | Yield (mg) | Yield (%) | LC MS (ES+) observed ion m/z [M + H]$^+$ |
|---|---|---|---|---|---|
| 4 | | 6-(3,5-Dimethylphenyl)-5'-methylspiro[chroman-4,2'-imidazol]-4'-amine | 20 | 32 | 320.1 |

TABLE 1-continued

| Example | R² | Name | Yield (mg) | Yield (%) | LC MS (ES+) observed ion m/z [M + H]⁺ |
|---|---|---|---|---|---|
| 5 | | 6-(2,5-Dimethoxyphenyl)-5'-methylspiro]chroman-4,2'-imidazol]-4'-amine | 25 | 36 | 352.1 |
| 6 | | 6-(2,3-Difluorophenyl)-5'-methylspiro[chroman-4,2'-imidazol]-4'-amine | 17 | 26 | 328.1 |
| 7 | | 6-(2,5-Dimethylphenyl)-5'-methylspiro[chroman-4,2'-imidazol]-4'-amine | 15 | 23 | 320.1 |
| 8 | | 6-(5-Fluoro-2-methoxyphenyl)-5'-methylspiro[chroman-4,2'-imidazol]-4'-amine | 23 | 35 | 340.1 |
| 9 | | 6-(2-Fluoro-3-methoxyphenyl)-5'-methylspiro[chroman-4,2'-imidazol]-4'-amine | 24 | 35 | 340.1 |
| 10 | | 6-(2-Methoxy-5-methylphenyl)-5'-methylspiro[chroman-4,2'-imidazol]-4'-amine | 29 | 43 | 336.1 |
| 11 | | 6-(2-Fluoro-5-methylphenyl)-5'-methylspiro[chroman-4,2'-imidazol]-4'-amine | 22 | 34 | 324.1 |

TABLE 1-continued

| Example | R² | Name | Yield (mg) | Yield (%) | LC MS (ES+) observed ion m/z [M + H]⁺ |
|---|---|---|---|---|---|
| 12 | 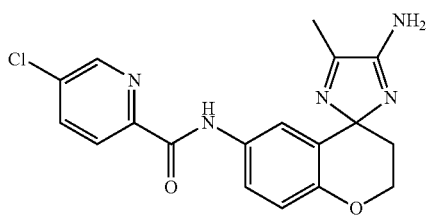 | 6-(2-Fluoro-5-methoxyphenyl)-5'-methylspiro[chroman-4,2'-imidazol]-4'-amine | 20 | 29 | 340.1 |

Example 13a

N-(4'-Amino-5'-methylspiro[chroman-4,2'-imidazole]-6-yl)-5-chloropicolinamide

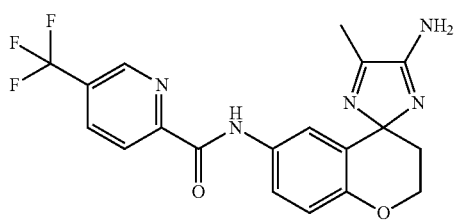 [SMILES: CC1=NC2(CCOc3ccc(NC(=O)c4ccc(C(F)(F)F)cn4)cc32)N=C1N]

N-(3-Dimethylaminopropyl)-N'-ethylcarbodiimide hydrochloride (58 mg, 0.30 mmol) was added to a suspension of 5-chloropyridine-2-carboxylic acid (37 mg, 0.23 mmol) in DCM (1.5 mL). The obtained solution was stirred for 10 min and added dropwise over 2 min to an ice-cooled solution of 5'-methylspiro[chroman-4,2'-imidazole]-4',6-diamine (Intermediate 30, 54 mg, 0.23 mmol) and 2 M HCl (0.117 mL, 0.23 mmol) in DMF (1.5 mL). The mixture was stirred at 0° C. for 5 min. Volatiles were removed in vacuo, and the residue was purified by preparative chromatography. Fractions containing the product were combined, and the organic solvent was removed in vacuo. The aqueous residue was alkalized with (sat) NaHCO₃ and then extracted twice with EtOAc. The combined organic phases were dried (Na₂SO₄) and evaporated to give a product which was purified by flash chromatography (4 g, gradient elution (EtOAc/MeOH/conc. NH₃) in heptane) affording the title compound (27 mg, 31% yield). ¹H NMR (400 MHz, DMSO-d₆) δ ppm 1.92 (br. s., 2 H), 2.23 (s, 3 H), 4.23-4.54 (m, 2 H), 6.56 (br. s., 2 H), 6.80 (d, 1 H), 7.05 (br. s., 1 H), 7.54-7.72 (m, 1 H), 8.04-8.12 (m, 1 H), 8.13-8.23 (m, 1 H), 8.72 (br. s., 1 H), 10.41 (s, 1 H); HPLC, MS (APCI¹) m/z 370 [M+H]¹.

Example 13c

N-(4'-Amino-5'-methylspiro[chroman-4,2'-imidazole]-6-yl)-5-(trifluoromethyl)picolinamide

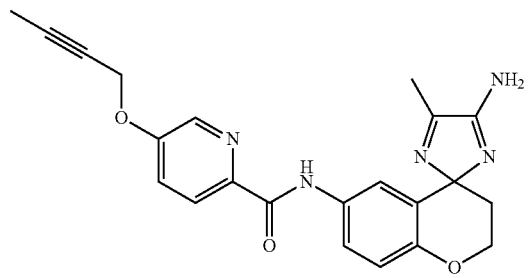 [SMILES: CC#CCOc1ccc(C(=O)Nc2ccc3c(c2)C2(CCO3)N=C(C)C(N)=N2)nc1]

The title compound (44 mg, 46% yield) was prepared as described for Example 13a starting from 5-(trifluoromethyl)picolinic acid (45 mg, 0.23 mmol) and 5'-methylspiro[chroman-4,2'-imidazole]-4',6-diamine (Intermediate 30, 54 mg, 0.23 mmol): ¹H NMR (400 MHz, DMSO-d₆) δ ppm 1.85-1.98 (m, 2 H), 2.24 (s, 3 H), 4.30-4.50 (m, 2 H), 6.56 (s, 2 H), 6.81 (d, 1 H), 7.02-7.10 (m, 1 H), 7.62-7.71 (m, 1 H), 8.28 (d, 1 H), 8.46 (dd, 1 H), 9.01-9.10 (m, 1 H), 10.57 (s, 1 H); MS (APCI⁺) m/z 404 [M+H]¹.

Example 13d

N-(4'-amino-5'-methylspiro[chroman-4,2'-imidazole]-6-yl)-5-(but-2-ynyloxy)picolinamide

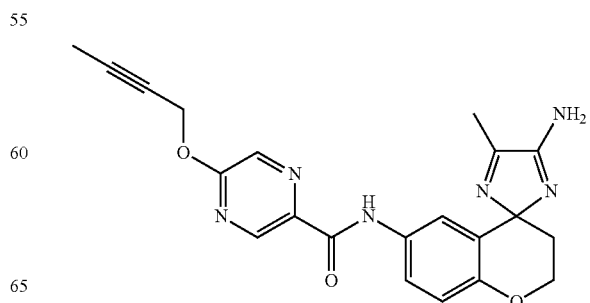

The title compound (15 mg, 16% yield) was prepared as described for Example 13a starting from 5-(but-2-ynyloxy)picolinic acid (Intermediate 19, 45 mg, 0.24 mmol) and 5'-methylspiro[chroman-4,2'-imidazole]-4',6-diamine (Intermediate 30, 54.7 mg, 0.24 mmol): ¹H NMR (500 MHz, CDCl₃) δ ppm 1.87 (t, 3 H), 2.03 (m, 1 H), 2.30 (m, 1 H), 2.39 (m, 3 H), 4.50 (m, 1 H), 4.62 (m, 1 H), 4.76 (m, 2 H), 6.92 (d, 1 H), 6.98 (m, 1 H), 7.41 (dd, 1 H), 7.49 (m, 1 H), 8.18 (d, 1 H), 8.28 (d, 1 H), 9.61 (s, 1 H); MS (ES+) m/z 404 [M+H]⁺.

Example 13e

N-(4'-Amino-5'-methylspiro[chroman-4,2'-imidazole]-6-yl)-5-(but-2-ynyloxy)pyrazine-2-carboxamide The title compound (28 mg, 24% yield) was prepared as described for Example 13a starting from 5-(but-2-ynyloxy)pyrazine-2-carboxylic acid (Intermediate 36, 58 mg, 0.30 mmol) and 5'-methylspiro[chroman-4,2'-imidazole]-4',6-diamine (Intermediate 30, 63 mg, 0.27 mmol). The crude product was purified by flash chromatography (4 g silica, gradient elution of (EtOAc/MeOH/conc. NH$_3$ (80/20/1) in heptane) followed by preparative chromatography. The pure fractions were combined and evaporated. The residual oil was solidified by evaporation with EtOAc and heptanes: $^1$H NMR (400 MHz, DMSO-d$_6$) δ ppm 1.85 (t, 3 H), 1.88-1.96 (m, 2 H), 2.23 (s, 3 H), 4.28-4.48 (m, 2 H), 5.07 (q, 2 H), 6.55 (s, 2 H), 6.79 (d, 1 H), 7.02-7.10 (m, 1 H), 7.55-7.64 (m, 1 H), 8.39 (d, 1 H), 8.84 (d, 1 H), 10.26 (s, 1 H); MS (APCI$^+$) m/z 405 [M+H]$^+$.

Example 13f

N-(4'-Amino-5'-methylspiro[chroman-4,2'-imidazole]-6-yl)-5-methylthiophene-2-carboxamide

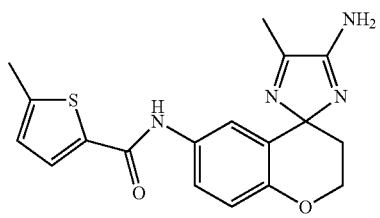 [SMILES: CC1=NC2(CCOc3ccc(NC(=O)c4ccc(C)s4)cc32)N=C1N]

The title compound (45.5 mg, 57% yield) was prepared as described for Example 13a starting from 5-methylthiophene-2-carboxylic acid (32.1 mg, 0.23 mmol) and 5'-methylspiro[chroman-4,2'-imidazole]-4',6-diamine (Intermediate 30, 52 mg, 0.23 mmol): $^1$H NMR (500 MHz, DMSO-d$_6$) δ ppm 1.91 (m, 2 H), 2.23 (s, 3 H), 2.47 (s, 3 H), 4.39 (m, 2 H), 6.55 (s, 2 H), 6.73 (d, 1 H), 6.78 (d, 1 H), 6.86 (dd, 1 H), 7.50 (dd, 1 H), 7.73 (d, 1 H), 9.86 (s, 1 H); MS (ES+) m/z 355 [M+H]$^+$.

Example 13i

N-(4'-Amino-5'-methylspiro[chroman-4,2'-imidazole]-6-yl)-3,5-dichloropicolinamide

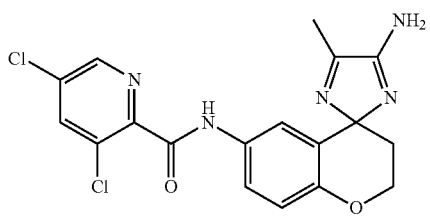 [SMILES: CC1=NC2(CCOc3ccc(NC(=O)c4ncc(Cl)cc4Cl)cc32)N=C1N]

The title compound (59 mg, 62% yield) was prepared as described for Example 13a starting from 3,5-dichloropicolinic acid (45 mg, 0.23 mmol) and 5'-methylspiro[chroman-4,2'-imidazole]-4',6-diamine (Intermediate 30, 54 mg, 0.23 mmol): $^1$H NMR (400 MHz, DMSO-d$_6$) δ ppm 1.82-2.01 (m, 2 H), 2.22 (s, 3 H), 4.29-4.49 (m, 2 H), 6.57 (s, 2 H), 6.75-6.85 (m, 2 H), 7.48-7.57 (m, 1 H), 8.41 (d, 1 H), 8.68 (d, 1 H), 10.39 (s, 1 H); MS (APCI$^+$) m/z 404 [M+H]$^+$.

Example 15

6'-Bromo-4-(difluoromethoxy)-5"-methyl-3'H-dispiro[cyclohexane-1,2'-indene-1',2"-imidazol]-4"-amine

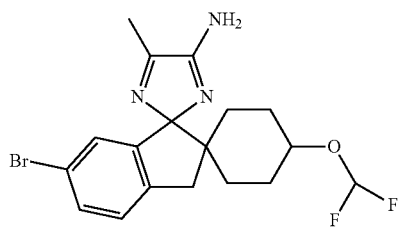 [SMILES: CC1=NC2(N=C1N)c1cc(Br)ccc1CC21CCC(OC(F)F)CC1]

Step 1: N-01r,40-5'-Bromo-4-hydroxyspiro[cyclohexane-1,2'-indene]-3'(1'H)-ylidene)-2-methylpropane-2-sulfinamide

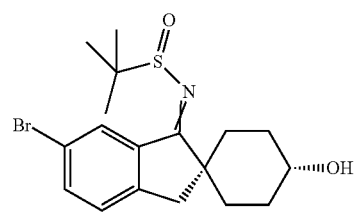 [SMILES: CC(C)(C)S(=O)N=C1c2cc(Br)ccc2C[C@]12CC[C@@H](O)CC2]

Titanium ethoxide (0.733 mL, 3.56 mmol), 2-methyl-2-propanesulfinamide (0.411 g, 3.39 mmol) and (1r,4r)-6'-bromo-4-hydroxyspiro[cyclohexane-1,2'-inden]-1'(3'H)-one (Intermediate 5 Step 2 Isomer 1) (0.5 g, 1.69 mmol) in dry 2-methyl-tetrahydrofuran (7.5 mL) were refluxed for 3 days. 2-Methyl-2-propanesulfinamide (0.411 g, 3.39 mmol), titanium ethoxide (0.733 mL, 3.56 mmol) and 2-methyl-tetrahydrofuran (3 mL) were added and the mixture was refluxed for four more days. The cooled mixture was added to a mixture of MeOH (12.5 mL), NaHCO$_3$ (aq sat) (5 mL) and EtOAc (50 mL). The resulting slurry was stirred for 90 min and was then filtered through a mixture of diatomaceous earth and Na$_2$SO$_4$ and then concentrated in vacuo. Purification by flash chromatography using a gradient of CHCl$_3$/MeOH (40:1-30:1-20:1) gave the title compound (0.398 g, 59% yield): $^1$H NMR (500 MHz, DMSO-d$_6$) δ ppm 1.21-1.78 (m, 15 H), 1.83 (m, 2 H), 2.96-3.01 (m, 2 H), 3.44 (m, 1 H), 4.63-4.72 (m, 1 H), 7.50 (d, 1 H), 7.73-7.82 (m, 1 H), 8.51 (br. s., 1 H); MS (ES+) m/z 398 [M+H]$^+$.

Step 2: (1r,4r)-6'-Bromo-4-hydroxy-5"-methyl-3'H-dispiro[cyclohexane-1,2'-indene-1,2"-imidazole]-4"(3"H)-thione

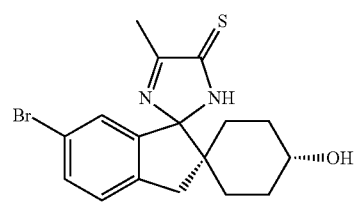

To N-((1r,4r)-5'-bromo-4-hydroxyspiro[cyclohexane-1,2'-indene]-3'(1'H)-ylidene)-2-methyl-propane-2-sulfinamide (Example 15 Step 1) (2.21 g, 5.55 mmol) in dioxane (10 mL) under N$_2$ (g) was added HCl (4 M in 1,4-dioxane) (13.87 mL, 55.48 mmol). The mixture was stirred at r.t for 2 h and was then concentrated. DCM and Et$_2$O were added resulting in the formation of a solid. The solid was filtered off and washed with Et$_2$O. The solid was dissolved in DCM. NaHCO$_3$ (sat. aq) was added and the mixture was poured into a phase separator. The organic phase was collected and concentrated. The residue, containing (1r,4r)-6'-bromo-1'-imino-1',3'-dihydrospiro[cyclohexane-1,2'-inden]-4-ol, and 2-oxopropanethioamide (Intermediate 2, 1.55 g, 15.0 mmol) was dissolved in dry MeOH (25 mL) and heated at 60° C. under N$_2$ (g) overnight. A solid formed and was filtered off. The filtrate was concentrated. Purification by flash chromatography using a gradient of 0-100% EtOAc in n-heptane gave the title compound (1.334 g, 63% yield): $^1$H NMR (400 MHz, DMSO-d$_6$) δ 1.05-1.32 (m, 4 H), 1.43 (m, 2 H), 1.70 m, 2 H), 2.26 (s, 3 H), 2.98 (d, 1 H), 3.06 (d, 1 H), 3.26 (m, 1 H), 4.58 (d, 1 H), 6.97 (d, 1 H), 7.35 (d, 1 H), 7.51 (dd, 1 H), 12.34 (s, 1 H); MS (ES+) m/z 379 [M+H]$^+$.

Step 3: (1r,4r)-6'-Bromo-4-(difluoromethoxy)-5"-methyl-3'H-dispiro[cyclohexane-1,2'-indene-1',2"-imidazol]-4"-amine

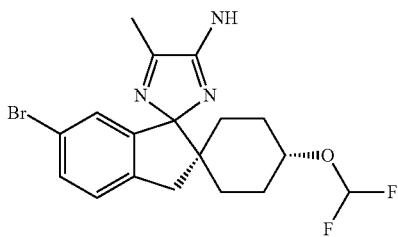

(1r,4r)-6'-Bromo-4-hydroxy-5"-methyl-3'H-dispiro[cyclohexane-1,2'-indene-1',2"-imidazole]-4"(3"H)-thione (Example 15 Step 2, 500 mg, 1.32 mmol) was co-evaporated with dry MeCN twice after which it was suspended in dry MeCN (19 mL), cuprous iodide (25.1 mg, 0.13 mmol) was added and the resulting mixture was heated at 60° C. for 5 min under argon. 2-(fluoro-sulphonyl)difluoroacetic acid (0.217 mL, 1.98 mmol) was added in a stream and the reaction mixture was heated at 60° C. After 1 h more 2-(fluorosulphonyl)difluoroacetic acid (0.217 mL, 1.98 mmol) was added. After heating for another hour, water, Et$_2$O and EtOAc were added. The phases were separated and the aqueous phase was extracted once with EtOAc. The combined organic phases were dried (Na$_2$SO$_4$), filtered and concentrated. To the residue, containing (1r,4r)-6'-bromo-4-(difluoromethoxy)-5"-methyl-3'H-dispiro[cyclohexane-1,2'-indene-1',2"-imidazole]-4"(3"H)-thione, was added ammonia (7 M in MeOH) (18 mL, 126 mmol) and the mixture was microwaved for 40 min. at 100° C. The mixture was concentrated and re-dissolved in ammonia (7 M in MeOH) (18 mL, 126 mmol) and microwaved again for 40 min. at 100° C. The mixture was concentrated. Purification by flash chromatography using a gradient of CHCl$_3$/MeOH 30:1-20:1 gave the title compound (411 mg, 76% yield): $^1$H NMR (500 MHz, DMSO-d$_6$) δ ppm 0.95-1.06 (m, 1 H), 1.35-1.54 (m, 5 H), 1.79 (m, 2 H), 2.17 (s, 3 H), 2.93 (d, 1 H), 3.04 (d, 1 H), 3.87 (m, 1 H), 6.61 (s, 2 H), 6.65 (m, 2 H), 7.26 (d, 1 H), 7.35 (dd, 1 H); MS (ES+) m/z 412 [M+H]$^+$.

Example 19

6'-Bromo-4-methoxy-5"-methyl-3'H-dispiro[cyclohexane-1,2'-indene-1',2"-imidazol]-4"-amine Method A Step 1: (N-(5'-Bromo-4-methoxyspiro[cyclohexane-1,2'-indene]-3'(1'H)-ylidene)-2-methylpropane-2-sulfinamide)

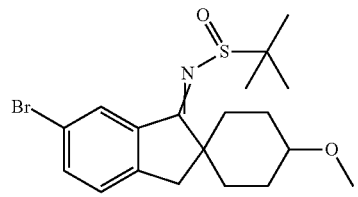 [SMILES: COC1CCC2(CC1)Cc1ccc(Br)cc1C2=NS(=O)C(C)(C)C]

6'-Bromo-4-methoxyspiro[cyclohexane-1,2'-inden]-1'(3'H)-one (Intermediate 5 Method A Step 3, mixture of isomers, 1.14 g, 3.69 mmol), 2-methylpropane-2-sulfinamide (0.670 g, 5.53 mmol) and titanium ethoxide (1.519 mL, 7.37 mmol) were dissolved in 2-Me THF (8 mL) and heated to reflux for 26 h. The reaction was left to cool down to r.t. EtOAc (80 mL) and NaHCO$_3$ (sat, 15 mL) was added under stirring. The mixture was then standing without stirring for 15 min. The organic phase was collected by filtration, dried over MgSO$_4$ and concentrated. Flash chromatography with a gradient of 0-20% EtOAc in n-heptane gave the title compound (1.00 g, 66% yield). $^1$H NMR (500 MHz, CD$_3$CN, signals for the major isomer) δ ppm 0.85-0.91 (m, 1 H), 1.27 (s, 9 H), 1.25-1.86 (multiplets, 5 H), 2.01-2.10 (m, 2 H), 3.02 (br. s, 2 H), 3.18-3.26 (m, 1 H), 3.31 (s, 3 H), 7.37 (d, 1 H), 7.67 (dd, 1 H), 8.59 (br. s., 1 H), MS (ES+) m/z 413 [M+H]$^+$.

Step 2: 6'-Bromo-4-methoxyspiro[cyclohexane-1,2'-inden]-1'(3'H)-imine

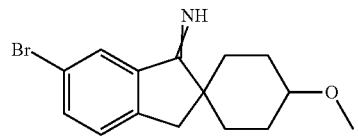 [SMILES: COC1CCC2(CC1)Cc1ccc(Br)cc1C2=N]

To a solution of N-(5'-bromo-4-methoxyspiro[cyclohexane-1,2'-indene]-3'(1'H)-ylidene)-2-methylpropane-2-sulfinamide (Example 19 Step 1, mixture of isomers, 2 g, 4.85 mmol) in anhydrous 1,4-dioxane (25 mL) was added 4M HCl in 1,4-dioxane (12.12 mL, 48.50 mmol). A white precipitate was formed immediately and the resulting cloudy mixture was stirred under a nitrogen atmosphere at r.t. for 90 min. Et$_2$O (30 mL) was added and the solid was filtered off and washed with Et$_2$O. The solid was partitioned between DCM (40 mL) and sat. aq. NaHCO$_3$ (40 mL). The phases were separated and the organic layer concentrated. The crude title compound (1.41 g) was used directly in the next step. MS (EI) m/z 307 M+.

Step 3: 6'-Bromo-4-methoxy-5"-methyl-3'H-dispiro[cyclohexane-1,2'-indene-1',2"-imidazole]-4"(3"H)-thione

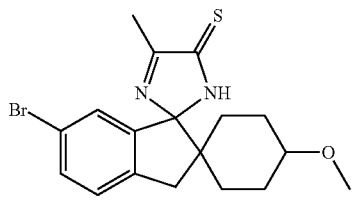 [SMILES: COC1CCC2(CC1)Cc1ccc(Br)cc1C21N=C(C)C(=S)N1]

6'-Bromo-4-methoxyspiro[cyclohexane-1,2'-inden]-1'(3'H)-imine (Example 19 Step 2, 1.41 g, 4.57 mmol) and 2-oxopropanethioamide (Intermediate 2, 1.42 g, 13.7 mmol) were dissolved in dry MeOH (30 mL) and the resulting solution was heated at 60° C. under an atmosphere of nitrogen. After 15 h the reaction was allowed to cool to r.t. A precipitate had formed which was filtered off and dried in vacuo, yielding the title compound (1.16 g, 64% yield) as a mixture of isomers. $^1$H NMR (500 MHz, DMSO-d$_6$) δ ppm 1.18 (m, 4 H), 1.47 (m, 2 H), 1.87 (m, 2 H), 2.27 (m, 3 H), 3.03 (m, 3 H), 3.20 (s, 3 H), 6.98 (d, 1 H), 7.34 (d, 1 H), 7.51 (dd, 1 H); MS (APCI+) m/z 394 [M+H]+.

Step 4: 6'-Bromo-4-methoxy-5"-methyl-3'H-dispiro[cyclohexane-1,2'-indene-1',2"-imidazol]-4"-amine

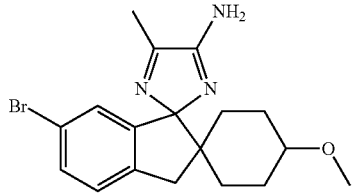 [SMILES: COC1CCC2(CC1)Cc1ccc(Br)cc1C21N=C(C)C(N)=N1]

6'-Bromo-4-methoxy-5"-methyl-3'H-dispiro[cyclohexane-1,2'-indene-1',2"-imidazole]-4"(3"H)-thione (Example 19 Step 3, 0.936 g, 2.38 mmol) was taken up in ammonia (7M in MeOH, 10 mL, 70.00 mmol) and the resulting mixture was bubbled with argon and then heated in the microwave reactor at 120° C. for 1 h. The solvent was evaporated. Ammonia (7M in MeOH, 6 mL, 42 mmol) was added and the reaction was bubbled with argon and heated again using MW for 60 min at 120° C. The solvent was evaporated and ammonia (7M in MeOH, 10 mL, 70 mmol) was added. The reaction was bubbled with argon and then heated using MW for 2 h at 120° C. The solvent was evaporated and ammonia (7M in MeOH, 15 mL, 105 mmol) was added and the reaction was heated again for 2 h at 120° C. The solvent was evaporated and ammonia (7M in MeOH, 15 mL, 105 mmol) was added and the reaction was heated again for 2 h at 120° C. The solvent was evaporated and ammonia (7M in MeOH, 20 mL, 140 mmol) was added. The reaction was heated again using MW for 1 h at 120° C. The solvent was evaporated and the resulting residue was taken up in DCM (60 mL) and brine (×2) and poured into a phase separator. The organic phase was dried with MgSO$_4$, filtered and evaporated to give the title compound (0.736 g, 82% yield) as a mixture of isomers: $^1$H NMR (500 MHz, CDCl$_3$) δ ppm 1.09 (td, 1 H), 1.27-1.49 (m, 3 H), 1.62-1.74 (m, 2 H), 1.93-2.01 (m, 2 H), 2.37 (s, 3 H), 3.04-3.18 (m, 3 H), 3.34 (s, 3 H), 6.90 (d, 1 H), 7.20 (d, 1 H), 7.38 (dd, 1 H); MS (MM−ES+APCI)+m/z 376 [M+H]+.

Separation of the isomers of 6'-bromo-4-methoxy-5"-methyl-3'H-dispiro[cyclohexane-1,2'-indene-1',2"-imidazol]-4"-amine 6'-Bromo-4-methoxy-5"-methyl-3'H-dispiro[cyclohexane-1,2'-indene-1',2"-imidazol]-4"-amine (Example 19 Step 4, 80 mg, 0.21 mmol) was purified using preparative chromatography (Waters FractionLynx system equipped with a XBridge® Prep C8 10 µm OBD™ 19×250 mm column and a guard column; XTerra® Prep MS C8 10 µm 19×10 mm Cartridge. A linear gradient of 35-70% MeOH in 0.2% NH$_3$ in MilliQ water was applied at flow rate of 20 mL/min) to give:
Isomeric Mixture 1
(1s,4s)-6'-Bromo-4-methoxy-5"-methyl-3'H-dispiro[cyclohexane-1,2'-indene-1',2"-imidazol]-4"-amine (the first to elute, minor isomer, 2.0 mg, 2.5% yield):

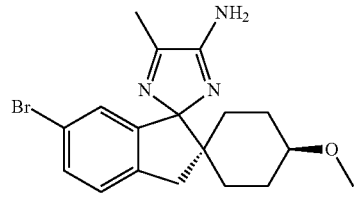

$^1$H NMR (500 MHz, CD$_3$CN) δ ppm 1.15-1.25 (m, 2 H), 1.36 (td, 1 H), 1.45-1.59 (m, 2 H), 1.63-1.74 (m, 3 H), 2.19 (s, 3 H), 2.98-3.06 (dd, 2 H), 3.20 (s, 3 H), 3.32 (t, 1 H), 5.19-5.39 (m, 2 H), 6.75 (d, 1 H), 7.20 (d, 1 H), 7.34 (dd, 1 H); MS (ES+) m/z 378 [M+H]+.
and
Isomeric Mixture 2
(1r,4r)-6'-Bromo-4-methoxy-5"-methyl-3'H-dispiro[cyclohexane-1,2'-indene-1',2"-imidazol]-4"-amine (the second to elute, major isomer, yield not determined):

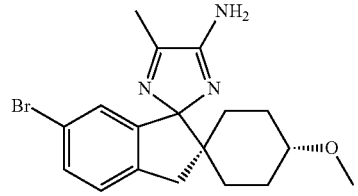

$^1$H NMR (500 MHz, CDCl$_3$) δ ppm 1.09 (td, 3.47 Hz, 1 H), 1.27-1.49 (m, 3 H), 1.62-1.74 (m, 2 H), 1.93-2.01 (m, 2 H), 2.37 (s, 3 H), 3.04-3.18 (m, 3 H), 3.34 (s, 3 H), 6.90 (d, 1 H), 7.20 (d1 H), 7.38 (dd, 1.73 Hz, 1 H), MS (MM−ES+APCI)+ m/z 378 [M+H]+.

Separation of the isomers of (1r,4r)-6'-bromo-4-methoxy-5"-methyl-3'H-dispiro-[cyclohexane-1,2'-indene-1',2"-imidazol]-4"-amine The isomers of Isomeric mixture 2 were separated using SFC Berger Multigram II, with a LuxC4; 4.6*250 mm; 5 µm column, and a mobile phase consisting of 15% MeOH (containing 0.1% DEA) and 85% $CO_2$ at a flow rate of 50 mL/min to give:

Isomer 1: (1r,1'R,4R)-6'-Bromo-4-methoxy-5''-methyl-3'H-dispiro[cyclohexane-1,2'-indene-1',2''-imidazol]-4''-amine (9 mg, 11% yield) with retention time 6.1 min:

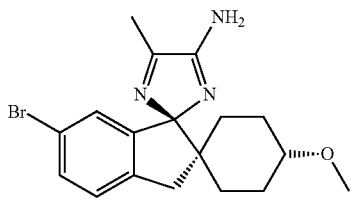

$^1$H NMR (500 MHz, $CD_3CN$) δ ppm 1.05 (dd, 1 H), 1.23 (dt, 2 H), 1.39 (d, 1 H), 1.49 (ddd, 2 H), 1.81-1.89 (m, 2 H), 2.17 (s, 3 H), 2.94-3.10 (m, 3 H), 3.23 (s, 3 H), 5.32 (br. s., 2 H), 6.75 (d, 1 H), 7.19 (d, 1 H), 7.33 (dd, 1 H), MS (MM–ES+APCI)+m/z 378 [M+H]$^+$; and Isomer 2: (1r,1'S,4S)-6'-Bromo-4-methoxy-5''-methyl-3'H-dispiro[cyclohexane-1,2'-indene-1',2''-imidazol]-4''-amine (15 mg, 19% yield) with retention time 9.5 min:

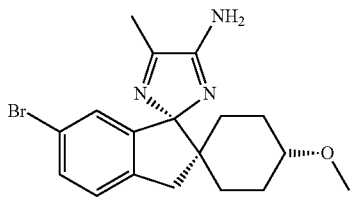

$^1$H NMR (500 MHz, $CD_3CN$) δ ppm 1.00-1.09 (m, 1 H), 1.17-1.31 (m, 2 H), 1.39 (td, 1 H), 1.50 (ddd, 2 H), 1.86 (dt, 2 H), 2.18 (s, 3 H), 2.94-3.10 (m, 3 H), 3.24 (s, 3 H), 5.32 (br. s., 2 H), 6.76 (d, 1 H), 7.20 (d, 1 H), 7.34 (dd, 1 H), MS (MM–ES+APCI)+m/z 378 [M+H]$^+$.

Separation of the isomers of (1s,4s)-6'-bromo-4-methoxy-5''-methyl-3'H-dispiro-[cyclohexane-1,2'-indene-1',2''-imidazol]-4''-amine 1.7 g of a mixture containing (1r,4r)-6'-bromo-4-methoxy-5''-methyl-3'H-dispiro[cyclohexane-1,2'-indene-1',2''-imidazol]-4''-amine (major) and (1s,4s)-6'-bromo-4-methoxy-5''-methyl-3'H-dispiro[cyclohexane-1,2'-indene-1',2''-imidazol]-4''-amine (minor) was purified by preparative chromatography using the following conditions: Column: XBridge C18; 50*300 mm; 10 μm, Mobile phase: 20-60% MeCN in 0.1% aq. $NH_3$ over 20 min, Flow rate: 120 mL/min. The obtained minor isomer (equivalent to Isomeric mixture 1 above) with retention time 15 min, was then separated into its isomers by preparative SFC using the following system: Berger Multigram II SFC system, Column: Chiralcel OD-H; 20*250 mm; 5 μm, Mobile phase: 10% MeOH (containing 0.1% DEA)/90% $CO_2$, Flow rate: 50 mL/min resulting in:

Isomer 3 with undetermined absolute configuration (77 mg, 5% yield) with retention time 6.5 min: $^1$H NMR (400 MHz, DMSO-$d_6$) δ ppm 1.05-1.17 (m, 2 H), 1.24 (td, 1 H), 1.36-1.54 (m, 2 H), 1.57-1.74 (m, 3 H), 2.16 (s, 3 H), 2.85-3.07 (m, 2 H), 3.12 (s, 3 H), 3.29 (br. s., 1 H), 6.58 (s, 3 H), 6.63 (d, 1 H), 7.24 (d, 1 H), 7.33 (dd, 1 H); MS (APCI$^+$) m/z 376 [M+H]$^+$, and Isomer 4 with undetermined absolute configuration (64 mg, 4% yield) with retention time 12 min: $^1$H NMR (400 MHz, DMSO-$d_6$) δ ppm 1.05-1.17 (m, 2 H), 1.24 (td, 1 H), 1.36-1.55 (m, 2 H), 1.57-1.74 (m, 3 H), 2.16 (s, 3 H), 2.85-3.06 (m, 2 H), 3.12 (s, 3 H), 3.29 (br. s., 1 H), 6.58 (s, 2 H), 6.63 (d, 1 H), 7.24 (d, 1 H), 7.33 (dd, 1 H); MS (APCI$^+$) m/z 376 [M+H]$^+$.

Method B

Step 1: N-01r,40-5'-Bromo-4-methoxyspiro[cyclohexane-1,2'-indene]-3'(1'H)-ylidene)-2-methylpropane-2-sulfinamide

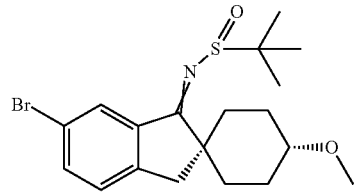 [SMILES: CO[C@H]1CC[C@]2(CC1)Cc1ccc(Br)cc1C2=NS(=O)C(C)(C)C]

(1r,4r)-6'-Bromo-4-methoxyspiro[cyclohexane-1,2'-inden]-1'(3'H)-one (Intermediate 5 Method B Step 3, 31 g, 100 mmol), 2-methylpropane-2-sulfinamide (15.8 g, 130 mmol), 2-methyl-tetrahydrofuran (200 mL) and titanium ethoxide (41.3 mL, 200 mmol) were heated to 100° C. to give an azeotrope at 74° C. The azeotropic distillation was continued for 8 h and then the mixture was reflux overnight. The azeotropic distillation was continued for an additional 8 h and then the mixture was refluxed overnight. The mixture was cooled to r.t. Additional 2-Me THF was added to give the original concentration of the mixture. A solution of sulfuric acid (11.14 mL, 200.5 mmol) and $Na_2SO_4$ (35.6 g, 250 mmol) in water (150 mL) was prepared. The reaction mixture was then added over 20 min to ⅘ of the volume of the acidic solution. The phases were separated, and the organic phase was washed with the remaining acidic solution, followed by ammonium acetate (15.46 g, 200.5 mmol) in water (75 mL) and water (75 mL). The organic phase was concentrated and dried in vacuo overnight to give the title compound (40.8 g, 99% yield): MS (ES+) m/z 412 [M+H]$^+$.

Step 2: (1r,4r-6'-Bromo-4-methoxyspiro[cyclohexane-1,2'-inden]-1'(3'H)-imine hydrochloride

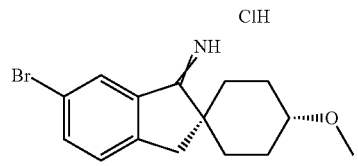 [SMILES: Cl ; CO[C@H]1CC[C@]2(CC1)Cc1ccc(Br)cc1C2=N]

HCl (2 M in $Et_2O$, 99 mL, 197 mmol) was added dropwise over 5 min to N-((1r,40-5'-bromo-4-methoxyspiro[cyclohexane-1,2'-indene]-3'(1'H)-ylidene)-2-methylpropane-2-sulfinamide (Example 19 Step 1, 40.8 g, 98.9 mmol) dissolved in $Et_2O$ (30 mL) and DCM (30 mL). The mixture was stirred for 60 min before it was filtered. The filter cake was washed with $Et_2O$ and dried in vacuo to give the title compound (31.3 g, 92% yield): $^1$H NMR (500 MHz, DMSO-$d_6$) δ ppm 1.28 (m, 2 H) 1.70 (d, 2 H) 2.04 (m, 4 H) 3.17 (s, 2 H) 3.23 (m, 1 H) 3.28 (s, 3 H) 7.61 (d, 1 is H) 8.04 (dd, 1 H) 8.81 (s, 1 H); MS (EI) m/z 307 Mt Step 3: (1r,4r)-6'-Bromo-4-methoxy-5"-methyl-3'H-dispiro[cyclohexane-1,2'-inden-1',2'-imidazole]-4" (3"H)-thione

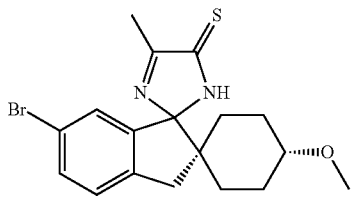

(1r,4r)-6'-Bromo-4-methoxyspiro[cyclohexane-1,2'-inden]-1'(3'H)-imine hydrochloride (Example 19 Step 2, 95 g, 200 mmol) (containing 30% (1s,4s)-6'-bromo-4-methoxyspiro-[cyclohexane-1,2'-inden]-1'(3'H)-imine hydrochloride) was portioned between DCM (600 mL) and 2 M aq. NaOH (400 mL). The organic phase was concentrated and 2-propanol (200 mL) was added and the mixture was concentrated. The resulting (1r,4r)-6'-bromo-4-methoxyspiro-[cyclohexane-1,2'-inden]-1'(3'H)-imine, trimethyl orthoformate (66 mL, 602 mmol) and 2-propanol (300 mL) was heated to 80° C. 2-oxopropanethioamide (51.5 g, 500 mmol) in 2-propanol (250 mL) was added during 40 min while keeping the temperature above 65° C. The reaction was stirred at 75° C. for 2 h. The mixture was concentrated to ~½ the volume and was left at 0° C. overnight. A solid was formed that was filtered off, and dried in a vacuum cabinet at 40° C. for 3 h to give the title compound (61.24 g, 78% yield, containing 14% of (1s,4s)-6'-bromo-4-methoxy-5"-methyl-3'H-dispiro[cyclohexane-1,2'-inden-1',2'-imidazole]-4"(3"H)-thione): MS (EI) m/z 392 M.

Step 4: (1r,40-6'-Bromo-4-methoxy-5"-methyl-3'H-dispiro[cyclohexane-1,2'-indene-1',2"-imidazol]-4"-amine

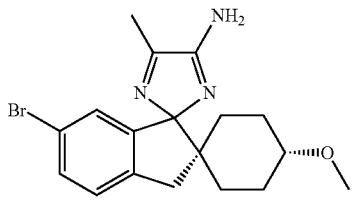

(1r,4r)-6'-Bromo-4-methoxy-5"-methyl-3'H-dispiro[cyclohexane-1,2'-indene-1',2"-imidazole]-4"(3"H)-thione (Example 19 Step 3, 22.7 g, 57.7 mmol) and ammonia (7 M in MeOH, 180 mL, 1.26 mol) was put in a pressure reactor and heated to 74° C. overnight. The residue was allowed to reach r.t. and the mixture was concentrated. The residue was partitioned between 2 M citric acid (400 mL) and EtOAc (400 mL). Any insoluble material was filtered off and was determined is to be unreacted starting material. The organic phase (org 1) was concentrated in vacuo to give additional unreacted starting material. To the aqueous phase was EtOAc (300 mL) added and then 50% NaOH was added until pH ~12, and the mixture was stirred for 10 min. The resulting organic phase (org 2) was saved. The residue from org 1, and the solid filtered off were combined and suspended in ammonia (7 M in MeOH, 180 mL, 1.26 mmol) and put in a pressure reactor and heated 100° C. overnight. The obtained solution was concentrated in vacuo. The residue was partitioned between 2 M citric acid (300 mL) and EtOAc (300 mL). To the aqueous phase was EtOAc (300 mL) added and then 50% NaOH was added until pH ~12, and the mixture was stirred for 10 min. The organic phase was combined with org 2 from above. Activated charcoal was added to the organic phase and the mixture was stirred for 30 min before it was filtered through diatomaceous earth. The organic phase was concentrated and dried in vacuo overnight to give a solid. To the solid was diisopropyl ether (125 mL) added and the mixture was refluxed overnight. The mixture was allowed to reach r.t. and the solid was filtered off to give the title compound (equivalent to Example 19 Isomeric Mixture 2 above) (15 g, 69% yield): $^1$H NMR (500 MHz, DMSO-$d_6$) δ ppm 0.93 (m, 1 H) 1.1-1.25 (m, 2 H) 1.35-1.45 (m, 3 H) 1.81 (br. d, 2 H) 2.16 (s, 3 H) 2.87-3.03 (m, 3 H) 3.18 (s, 3 H) 6.59 (br. s., 2 H), 6.64 (d, 1 H), 7.25 (d, 1 H), 7.34 (dd, 1 H); ES+) m/z 376 [M+H]$^+$.

Step 5: (1r,1'R,4R)-6'-Bromo-4-methoxy-5"methyl-3'H-dispiro[cyclohexane-1',2"-indene-1',2"imidazol]-4"-amine

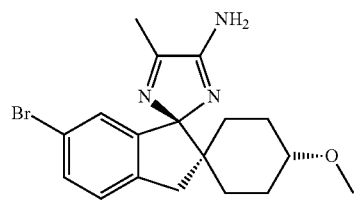

To a 1 L round-bottomed flask was added (1r,4r)-6'-bromo-4-methoxy-5"-methyl-3'H-dispiro[cyclohexane-1,2'-indene-1',2"-imidazol]-4"-amine (Example 19 Method B Step 4, 61 g, 162 mmol), EtOH (99.5%, 600 mL) and water (60 mL) to give a homogeneous mixture which was heated to 70° C. The mixture was stirred for 30 min at the elevated temperature followed by addition of D(+)-10-camphorsulfonic acid (18.8 g, 81.0 mmol). The mixture was stirred at 70° C. for 3 h and then allowed to reach 20° C. over 2 h followed by stirring at 20° C. for 12 h. The mixture was filtered to give a solid that was dried in a vacuum oven at 50° C. for 10 h to give the title compound as a D(+)-10-camphorsulfonic salt (37 g; 37% yield). Enantiomeric ratio was determined by analysis on a SFC Berger Analytix system equipped with a Chiralpak AD-H column (4.6*250 mm; 5 μm) and a mobile phase consisting of 10% MeOH (containing 0.1% DEA) and 90% $CO_2$ at a flow rate of 3 mL/min. The first peak with retention time 3.68 min (area 2.5%) corresponded to (1r,1'S,4S)-6'-bromo-4-methoxy-5"-methyl-3'H-dispiro[cyclohexane-1,2'-indene-1',2"-imidazol]-4"-amine, equivalent to Isomer 2. The second peak with retention time 4.58 min (area 97.5%) corresponded to the title compound (1r,1'R,4R)-6'-bromo-4-methoxy-5"methyl-3'H-dispiro[cyclohexane-1',2"-indene-1',2"imidazol]-4"-amine, equivalent to Isomer 1. The liberation of the title compound from the salt was carried out by stirring the camphorsulfonic acid salt (0.32 g, 0.53 mmol) suspended in dichloromethane (4 mL) with an aqueous solution (4 mL) of KOH (0.32 g, 5.7 mmol) at r.t. during 30 min. The organic phase was separated and concentrated in vacuo to give title compound quantitatively with an enantiomeric excess of 95% (determined as above).

Method C (1r,4r)-6'-Bromo-4-methoxyspiro[cyclohexane-1,2'-inden]-1'(3'H)-imine hydrochloride

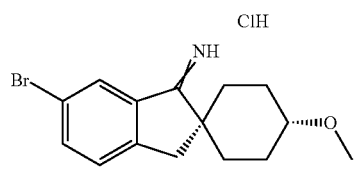 [SMILES: Cl ; CO[C@H]1CC[C@]2(CC1)Cc1ccc(Br)cc1C2=N]

(1r,4r)-6'-Bromo-4-methoxyspiro[cyclohexane-1,2'-inden]-1'(3'H)-one (Intermediate 5 Step 3 Method C, 19.20 g at 91% NMR assay, 56.5 mmol) is reacted with 2-methylpropane-2-sulfinamide (8.90 g, 73.5 mmol) by heating with titanium (IV) ethoxide (24 mL, 115 mmol) and 2-methyl-tetrahydrofuran (44 mL) at approximately 82° C. Three portions of solvent (approximately 26 mL per portion) were distilled off after 0.5 h, 7.5 h and 8 h periods of heating respectively, and more 2-methyl-tetrahydrofuran (26 mL per portion, three portions) added after completing each distillation. A further portion of solvent (approximately 26 mL) was distilled off after 17.5 h. The reaction mixture was cooled to r.t., diluted with DCM (52.5 mL) and then added gradually to a solution (92 mL, 113 g) prepared from $Na_2SO_4$ (17.9% w/w), water (72.2% w/w) and sulfuric acid (9.9% w/w) over approximately 4 min. DCM (52.5 mL) was used to wash the reaction flask and addition funnel and then added to the work-up flask. After separating the layers, the organic phase was washed with a mixture of water (17.5 mL) and a solution (18.5 mL, 23 g) prepared from $Na_2SO_4$ (17.9% w/w), water (72.2% w/w) and sulfuric acid (9.9% w/w). The mixture was stirred with $Na_2SO_4$ (8.75 g) for approximately 6 h. The slurry was filtered and the filter cake washed with DCM (17.5 mL). The combined filtrates were concentrated by distilling off the solvent (approximately 108 mL). Further DCM (52.5 mL) was added and the same volume of solvent (52.5 mL) was distilled off. The dry solution was cooled to approximately 20° C. and diluted with DCM (17.5 mL) and EtOH (8.7 mL). HCl (2 M in $Et_2O$) (34 mL, 68 mmol), was then added gradually over approximately 20 min. The resulting slurry was held at approximately 20° C. for about 45 min before filtering. The filter cake was washed with a solution (17.5 mL per portion, three portions) prepared from equal volumes of DCM and $Et_2O$ and then dried in vacuo to give the title compound containing approximately 4% of another isomer (17.41 g at 88% w/w NMR assay, 44.4 mmol, 79% yield) (residual DCM was detected at 6.8% w/w and ammonium chloride 2.9% w/w in the NMR assay): $^1$H NMR (500 MHz, DMSO-$d_6$) δ ppm 1.30 (m, 2 H), 1.70 (d, 2 H), 1.98 (m, 2 H), 2.10 (m, 2 H), 3.17 (s, 2 H), 3.23 (m, 1 H), 3.29 (s, 3 H), 7.61 (d, 1 H), 8.04 (dd, 1 H), 8.75 (d, 1 H), 12.90 (br s, 2 H).

Example 20a 1r,4r)-4-Methoxy-5"-methyl-6'-(5-prop-1-yn-1-ylpyridin-3-yl)-3'H-dispiro[cyclohexane-1,2'-indene-1',2"-imidazol]-4"-amine

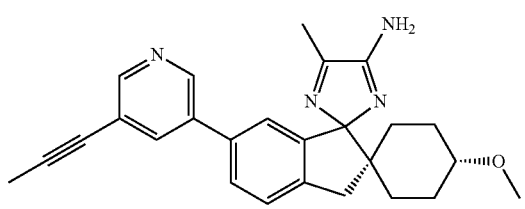

Method A 5-(Prop-1-ynyl)pyridin-3-ylboronic acid (Intermediate 15, 0.044 g, 0.27 mmol), (1r,4r)-6'-bromo-4-methoxy-5"-methyl-3'H-dispiro[cyclohexane-1,2'-indene-1',2"-imidazol]-4"-amine (Example 19 Method A Step 4, 0.085 g, 0.23 mmol), [1,1'-bis(diphenylphosphino)-ferrocene]palladium (II) chloride (9.29 mg, 0.01 mmol), $K_2CO_3$ (2M aq., 1.355 mL, 0.68 mmol) and 2-methyl-tetrahydrofuran (0.5 mL) were mixed and heated to 100° C. using MW for 2×30 min. 2-methyl-tetrahydrofuran (5 mL) and $H_2O$ (5 mL) were added and the layers were separated. The organic layer was dried with $MgSO_4$ and then concentrated. The crude was dissolved in DCM and washed with $H_2O$. The organic phase was separated through a phase separator and dried in vacuo. The crude product was purified with preparative chromatography. The solvent was evaporated and the $H_2O$-phase was extracted with DCM. The organic phase was separated through a phase separator and dried to give the title compound (0.033 g, 36% yield), $^1$H NMR (500 MHz, $CD_3CN$) δ ppm 1.04-1.13 (m, 1 H), 1.23-1.35 (m, 2 H), 1.44 (td, 1 H), 1.50-1.58 (m, 2 H), 1.84-1.91 (m, 2 H), 2.07 (s, 3 H), 2.20 (s, 3 H), 3.00 (ddd, 1 H), 3.08 (d, 1 H), 3.16 (d, 1 H), 3.25 (s, 3 H), 5.25 (br. s., 2 H), 6.88 (d, 1 H), 7.39 (d, 1 H), 7.49 (dd, 1 H), 7.85 (t, 1 H), 8.48 (d, 1 H), 8.64 (d, 1 H), MS (MM−ES+APCI)+m/z 413 [M+H]$^+$.

Separation of the isomers of (1r,4r)-4-methoxy-5"-methyl-6'-(5-prop-1-yn-1-ylpyridin-3-yl)-3'H-dispiro[cyclohexane-1,2'-indene-1',2"-imidazol]-4"-amine (1r,4r)-4-Methoxy-5"-methyl-6'-(5-prop-1-yn-1-ylpyridin-3-yl)-3'H-dispiro[cyclohexane-1,2'-indene-1',2"-imidazol]-4"-amine (Example 20a, 0.144 g, 0.35 mmol) was purified using preparative chromatography (SFC Berger Multigram II, Column: Chiralcel OD-H; 20*250 mm; 5 μm, mobile phase: 30% MeOH (containing 0.1% DEA); 70% $CO_2$, Flow: 50 mL/min, total number of injections: 4). Fractions which contained the product were combined and the MeOH was evaporated to give:
Isomer 1: (1r,1'R,4R)-4-methoxy-5"-methyl-6'-(5-prop-1-yn-1-ylpyridin-3-yl)-3'H-dispiro-[cyclohexane-1,2'-indene-1',2"-imidazol]-4"-amine (49 mg, 34% yield) with retention time 2.5 min:

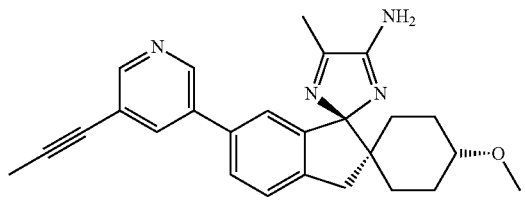

$^1$H NMR (500 MHz, $CD_3CN$) δ ppm 1.07-1.17 (m, 1 H), 1.23-1.39 (m, 2 H), 1.47 (td, 1 H), 1.57 (ddq, 2 H), 1.86-1.94 (m, 2 H), 2.09 (s, 3 H), 2.23 (s, 3 H), 2.98-3.07 (m, 1 H), 3.11 (d, 1 H), 3.20 (d, 1 H), 3.28 (s, 3 H), 5.30 (br. s., 2 H), 6.91 (d, 1 H), 7.42 (d, 1 H), 7.52 (dd, 1 H), 7.88 (t, 1 H), 8.51 (d, 1 H), 8.67 (d, 1 H), MS (MM−ES+APCI)+m/z 413.2 [M+H]$^+$; and
Isomer 2: (1r,1'S,4S)-4-methoxy-5"-methyl-6'-(5-prop-1-yn-1-ylpyridin-3-yl)-3'H-dispiro[cyclohexane-1,2'-indene-1',2"-imidazol]-4"-amine (50 mg, 35% yield) with retention

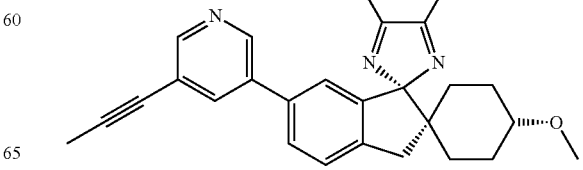

¹H NMR (500 MHz, CD₃CN) δ ppm 1.02-1.13 (m, 1 H), 1.20-1.35 (m, 2 H), 1.44 (d, 1 H), 1.54 (ddd, 2 H), 1.84-1.91 (m, 2 H), 2.06 (s, 3 H), 2.20 (s, 3 H), 3.00 (tt, 1 H), 3.08 (d, 1 H), 3.16 (d, 1 H), 3.25 (s, 3 H), 5.26 (br. s., 2 H), 6.88 (d, 1 H), 7.39 (d, 1 H), 7.49 (dd, 1 H), 7.84 (t, 1 H), 8.48 (d, 1 H), 8.63 (d, 1 H), MS (MM–ES+APCI)+m/z 413.2 [M+H]⁺.

Method B

A vessel was charged with (1r,4r)-6'-bromo-4-methoxy-5"-methyl-3'H-dispiro[cyclohexane-1,2'-indene-1',2"-imidazol]-4"-amine (Example 19 Method B Step 4, 7.5 g, 19.9 mmol), 5-(prop-1-ynyl)pyridin-3-ylboronic acid (Intermediate 15, 3.37 g, 20.9 mmol), 2.0 M aq. K₂CO₃ (29.9 mL, 59.8 mmol), and 2-methyl-tetrahydrofuran (40 mL). The vessel was purged under vacuum and the atmosphere was replaced with argon. Sodium tetrachloropalladate (II) (0.147 g, 0.50 mmol) and 3-(di-tert-butyl phosphonium) propane sulfonate (0.267 g, 1.00 mmol) were added and the contents were heated to reflux for a period of 16 h. The contents were cooled to 30° C. and the phases were separated. The aqueous phase was extracted with 2-methyl-tetrahydrofuran (2×10 mL), then the organics were combined, washed with brine and treated with activated charcoal (2.0 g). The mixture was filtered over diatomaceous earth, and then washed with 2-methyl-tetrahydrofuran (20 mL). The filtrate was concentrated to a volume of approximately 50 mL, then water (300 µL) was added, and the contents were stirred vigorously as seed material was added to promote crystallization. The product began to crystallize and the mixture was stirred for 2 h at r.t., then 30 min. at 0-5° C. in an ice bath before being filtered. The filter cake was washed with 10 mL cold 2-methyl-tetrahydrofuran and then dried in the vacuum oven at 45° C. to give the racemic title compound (5.2 g, 12.6 mmol, 63% yield): MS (ES+) m/z 413 [M+H]⁺.

(1r,1'R,4R)-4-Methoxy-5"-methyl-6'-[5-(prop-1-yn-1-yl)pyridin-3-yl]-3'H-dispiro-[cyclohexane-1,2'-indene-1',2"-imidazol]-4"-amine (isomer 1)

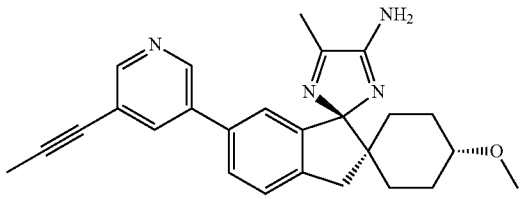 [SMILES: CC#Cc1cncc(-c2ccc3c(c2)[C@@]2(N=C(C)C(N)=N2)[C@]2(CC[C@H](OC)CC2)C3)c1]

Method C

A solution of (1r,4r)-4-methoxy-5"-methyl-6'-(5-prop-1-yn-1-ylpyridin-3-yl)-3'H-dispiro-[cyclohexane-1,2'-indene-1',2"-imidazol]-4"-amine (Example 20a method B, 4.85 g, 11.76 mmol) and EtOH (75 mL) was stirred at 55° C. A solution of (+)-di-p-toluoyl-D-tartaric acid (2.271 g, 5.88 mmol) in EtOH (20 mL) was added and stirring continued. After 2 min. a precipitate began to form. The mixture was stirred for 2 h before being slowly cooled to 30° C. and then stirred for a further 16 h. The heat was removed and the mixture was stirred at r.t. for 30 min. The mixture was filtered and the filter cake washed with chilled EtOH (45 mL). The solid was dried in the vacuum oven at 45° C. for 5 h, then the material was charged to a vessel and DCM (50 mL) and 2.0 M aq. NaOH solution (20 mL) were added. The mixture was stirred at 25° C. for 15 min. The phases were separated and the aqueous layer was extracted with 10 mL DCM. The organic phase was concentrated in vacuo to a residue and 20 mL EtOH was added. The resulting solution was stirred at r.t. as water (15 mL) was slowly added to the vessel. A precipitate slowly began to form, and the resulting mixture was stirred for 10 min. before additional water (20 mL) was added. The mixture was stirred at r.t. for 1 h and then filtered. The filter cake was washed with water (15 mL) and dried in a vacuum oven at 45° C. for a period of 16 h to give the title compound (1.78 g, 36% yield): MS (ES+) m/z 413 [M+H]⁺. This material is equivalent to Example 20a Isomer 1 above.

Method D

To a 500 mL round-bottomed flask was added (1r,1'R,4R)-6'-bromo-4-methoxy-5"-methyl-3'H-dispiro[cyclohexane-1, 2'-inden-1',2"-imidazole]-4"-amine as the D(+)-10-camphor sulfonic acid salt (Example 19 Method B Step 5, 25.4 g, 41.7 mmol), 2 M aq. KOH (100 mL) and 2-methyl-tetrahydrofuran (150 mL). The mixture was stirred for 30 min at r.t. after which the mixture was transferred to a reparatory funnel and allowed to settle. The phases were separated and the organic phase was washed with 2 M aq. K₂CO₃ (100 mL). The organic phase was transferred to a 500 mL round-bottomed flask followed by addition of 5-(prop-1-ynyl)pyridin-3-ylboronic acid u) (Intermediate 15, 6.72 g, 41.74 mmol), K₂CO₃ (2.0 M, 62.6 mL, 125.21 mmol). The mixture was degassed by means of bubbling Ar through the solution for 5 min. To the mixture was then added sodium tetrachloropalladate(II) (0.307 g, 1.04 mmol) and 3-(di-tert-butylphosphonium)propane sulfonate (0.560 g, 2.09 mmol) followed by heating the mixture at reflux (80° C.) overnight. The reaction mixture was allowed to cool down to r.t. and the phases were separated. The aqueous phase was extracted with 2-Me-THF (2×100 mL). The organics were combined, washed with brine and treated with activated charcoal. The mixture was filtered over diatomaceous earth and the filter cake was washed with 2-Me-THF (2×20 mL), and the filtrate was concentrated to give 17.7 g that was combined with 2.8 g from other runs. The material was dissolved in 2-Me-THF under warming and put on silica (~500 g). Elution with 2-Me-THF/Et₃N (100:0-97.5:2.5) gave the product. The solvent was evaporated, then co-evaporated with EtOH (absolute, 250 mL) to give (9.1 g, 53% yield). The HCl-salt was prepared to purify the product further: The product was dissolved in CH₂Cl₂ (125 mL) under gentle warming, HCl in Et₂O (~15 mL) in Et₂O (100 mL) was added, followed by addition of Et₂O (~300 mL) to give a precipitate that was filtered off and washed with Et₂O to give the HCl-salt. CH₂Cl₂ and 2 M aq. NaOH were added and the phases separated. The organic phase was concentrated and then co-evaporated with MeOH. The formed solid was dried in a vacuum cabinet at 45° C. overnight to give the title compound (7.4 g, 43% yield): ¹H NMR (500 MHz, DMSO-d₆) δ ppm 0.97 (d, 1 H) 1.12-1.30 (m, 2 H) 1.37-1.51 (m, 3 H) 1.83 (d, 2 H) 2.09 (s, 3 H) 2.17 (s, 3 H) 2.89-3.12 (m, 3 H) 3.20 (s, 3 H) 6.54 (s, 2 H) 6.83 (s, 1 H) 7.40 (d, 1 H) 7.54 (d, 1 H) 7.90 (s, 1 H) 8.51 (d, 1 H) 8.67 (d, 1 H); HRMS-TOF (ES+) m/z 413.2338 [M+H]¹ (calculated 413.2341); enantiomeric purity >99.5%; NMR Strength 97.8±0.6% (not including water).

Example 20b (1r,4r)-4-Methoxy-5"-methyl-6'-[4-(prop-1-yn-1-yl)pyridin-2-yl]-3'H-dispiro[cyclohexane-1,2'-indene-1', 2"-imidazol]-4"-amine

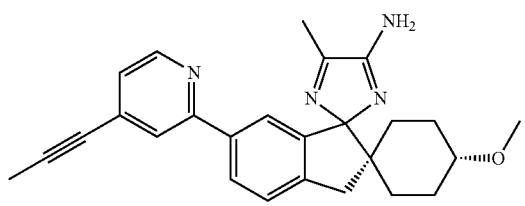

(1r,4r)-6'-Bromo-4-methoxy-5"-methyl-3'H-dispiro[cyclohexane-1,2'-indene-1',2"-imidazol]-4"-amine (Example 19 Method B Step 4, 50 mg, 0.13 mmol), potassium acetate (26.1 mg, 0.27 mmol), bis(pinacolato)diboron (37.1 mg, 0.15 mmol) and PdCl₂(dppf)-CH₂Cl₂ adduct (5.43 mg, 6.64 µmol) were taken up in dioxane (1 mL) in a microwave vial. The reaction vessel was sealed and heated at 110° C. for 20 min in a Biotage Initiator. After cooling, K₂CO₃ (36.7 mg, 0.27 mmol), Pd(Ph₃P)₄ (7.68 mg, 6.64 µmol), and water (0.300 mL) were added followed by 2-chloro-4-(prop-1-ynyl)pyridine (Intermediate 32, 22.16 mg, 0.15 mmol) in dioxane (0.5 mL). The reaction vessel was sealed and heated at 110° C. for 30 min in a Biotage Initiator. After cooling, the mixture was filtered and concentrated in vacuo. The product was purified by flash chromatography using a gradient of EtOAc in heptane (0-100%), then EtOAc:MeOH (9:1) to give the title compound (18 mg, 32% yield): ¹H NMR (500 MHz, DMSO-d₆) δ ppm 0.95 (m, 1 H), 1.12-1.31 (m, 2 H), 1.39-1.54 (m, 3 H), 1.77-1.87 (m, 2 H), 2.11 (s, 3 H), 2.19 (s, 3 H), 2.90-3.12 (m, 3 H), 3.20 (s, 3 H), 6.56 (m, 2 H), 7.25 (dd, 1 H), 7.31 (s, 1 H), 7.38 (d, 1 H), 7.78 (m, 1 H), 7.88 (m, 1 H), 8.55 (d, 1 H); MS (MM−ES+APCI)+m/z 413 [M+H]⁺.

Example 20c

5-[(1r,4r)-4''-Amino-4-methoxy-5''-methyl-3'H-dispiro[cyclohexane-1,2'-indene-1',2''-imidazol]-6'-yl]benzene-1,3-dicarbonitrile

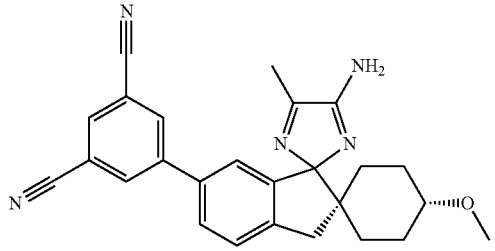

The title compound (79 mg, 53% yield) was prepared as described for Example 20d starting from (1r,4r)-6'-bromo-4-methoxy-5''-methyl-3'H-dispiro[cyclohexane-1,2'-indene-1',2''-imidazol]-4''-amine (Example 19 Method B Step 4, 133 mg, 0.35 mmol), and 5-(4,4,5,5-tetramethyl-1,3,2-dioxaborolan-2-yl)isophthalonitrile (L. Echegoyen, F. Diederich et al. Eur. J. Org. Chem. 2007, 4659-4673) (135 mg, 0.53 mmol): ¹H NMR (400 MHz, DMSO-d₆) δ ppm 0.90-1.04 (m, 1 H), 1.10-1.30 (m, 2 H), 1.34-1.52 (m, 3 H), 1.83 (d, 2 H), 2.18 (s, 3 H), 2.86-3.13 (m, 3 H), 3.19 (s, 3 H), 6.54 (s, 2 H), 6.96 (d, 1 H), 7.43 (d, 1 H), 7.63 (dd, 1 H), 8.34-8.42 (m, 3 H); MS (APCI⁺) m/z 424 [M+H]⁺.

Example 20d

3-[(1r,4r)-4''-Amino-4-methoxy-5''-methyl-3'H-dispiro[cyclohexane-1,2'-indene-1',2''-imidazol]-6'-yl]-5-chlorobenzonitrile

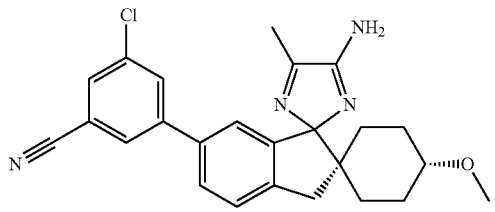

Method A

Sodium tetrachloropalladate(II) (3 mg, 10 µmol), 3-(di-tert-butylphosphonium)propane sulfonate (5 mg, 0.02 mmol), (1r,4r)-6'-bromo-4-methoxy-5''-methyl-3'H-dispiro[cyclohexane-1,2'-indene-1',2''-imidazol]-4''-amine (Example 19 Method B Step 4, 71 mg, 0.19 mmol), 3-chloro-5-(4,4,5,5-tetramethyl-1,3,2-dioxaborolan-2-yl)benzonitrile (Intermediate 35, 75 mg, 0.28 mmol), and 2 M aq. K₂CO₃ (0.29 mL, 0.57 mmol) were mixed in dioxane (2 mL) and the mixture was degassed for a couple of min. by a stream of N₂ (g). The reaction mixture was heated at reflux for 2 h. Water and EtOAc were added and the phases were separated. The aqueous phase was extracted with EtOAc and the combined organic layers were dried over Na₂SO₄, filtered and evaporated. The material was purified by flash chromatography (25 g silica, gradient eluent of EtOAc to a mixture of EtOAc/MeOH/conc. NH₃). The obtained material was purified by preparative chromatography. The pure fractions were combined and the organic solvent was evaporated. The residue was partitioned between 1 M aq. NaOH and EtOAc. The organic phase was dried (Na₂SO₄) and concentrated in vacuo to give the title compound (31 mg, 38% yield). ¹H NMR (400 MHz, DMSO-d₆) δ ppm 0.90-1.03 (m, 1 H), 1.10-1.31 (m, 2 H), 1.34-1.53 (m, 3 H), 1.74-1.89 (m, 2 H), 2.18 (s, 3 H), 2.87-3.14 (m, 3 H), 3.19 (s, 3 H), 6.55 (br. s., 2 H), 6.89 (s, 1 H), 7.41 (d, 1 H), 7.58 (dd, 1 H), 7.95 (d, 2 H), 8.01 (s, 1 H); MS (APCI⁺) m/z 433 [M+H]⁺.

3-[(1r,1'R,4R)-4''-Amino-4-methoxy-5''-methyl-3'H-dispiro[cyclohexane-1,2'-indene-1',2''-imidazol]-6'-yl]-5-chlorobenzonitrile (isomer 1)

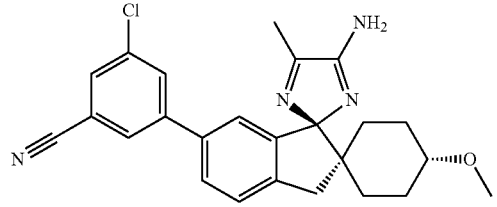 [SMILES: CO[C@H]1CC[C@]2(CC1)Cc1ccc(-c3cc(Cl)cc(C#N)c3)cc1[C@@]21N=C(C)C(N)=N1]

Method B

The title compound was prepared as described for Example 20d above starting from (1r,1'R,4R)-6'-bromo-4-methoxy-5''-methyl-3'H-dispiro[cyclohexane-1,2'-indene-1',2''-imidazol]-4''-amine (Example 19 Isomer 1) in two separate batches (143 mg, 0.38 mmol and 48 mg, 0.13 mmol). After purification by flash chromatography and preparative chromatography the product was freeze-dried from acetonitrile and water. The obtained product was further dried in vacuo at 40° C. affording the title compound as a single enantiomer (127 mg, 58% yield). ¹H NMR (400 MHz, DMSO-d₆) δ ppm 0.97 (td, 1 H), 1.10-1.30 (m, 2 H), 1.34-1.51 (m, 3 H), 1.83 (d, 2 H), 2.18 (s, 3 H), 2.88-3.13 (m, 3 H), 3.19 (s, 3 H), 6.55 (s, 2 H), 6.89 (d, 1 H), 7.41 (d, 1 H), 7.58 (dd, 1 H), 7.95 (dt, 2 H), 8.02 (t, 1 H); MS (APCI⁺) m/z 433 [M+H]⁺.

Method C (1r,1'R,4R)-6'-bromo-4-methoxy-5''-methyl-3'H-dispiro[cyclohexane-1,2'-indene-1',2''-imidazol]-4''-amine as a D(+)-10-camphorsulfonic acid salt (Example 19 Step 5, 36.6 g, 60.1 mmol), 2-methyl-tetrahydrofuran (440 mL) and 2 M aq. KOH (330 mL) were stirred for 30 min. The organic phase was washed with 2 M aq. K₂CO₃ (148 mL). 3-Chloro-5-(4,4,5,5-tetramethyl-1,3,2-dioxaborolan-2-yl)benzonitrile (Intermediate 35, 24.97 g, 62.5 mmol) and 2 M aqueous K₂CO₃

(90 mL, 180.4 mmol) was added to the organic phase. The mixture was degassed. Sodium tetrachloropalladate(II) (0.456 g, 1.50 mmol) and 3-(di-tert-butylphosphinium)propane sulfonate (0.832 g, 3.01 mmol) was added followed by heating to reflux under $N_2$(g). The mixture was stirred at reflux temperature for 220 min. To the mixture was added additional 3-chloro-5-(4,4,5,5-tetramethyl-1,3,2-dioxaborolan-2-yl)benzonitrile (0.600 g, 1.50 mmol) followed by reflux under $N_2$(g) for an additional 140 min. The mixture was then allowed to attain 20° C. followed by stirring of the mixture for 30 min. at 20° C. To the mixture was added water (210 mL) and 2-Me-THF (211 mL) followed by stirring for 10 min. The organic phase was washed with brine (211 mL) and water (211 mL). The organic phase was distilled several times adding additional 2-Me-THF. The mixture was then concentrated to give a solid. The crude product was purified by flash chromatography ($SiO_2$; 2% $NH_3$ in MeOH, 2% MeOH, 96% DCM; Rf=0.35) to give product as a solid. To the solid was added 99.5% EtOH (150 mL) followed by distillation of the mixture under reduced pressure to give a solid. The procedure was repeated 4 times. To the solid was added 99.5% EtOH (270 mL). The mixture was heated to internal T=70° C. The mixture was cooled during 2 h to 45° C. during which crystallization took place followed by stirring at 45° C. for 6 h. The mixture was then allowed to reach 22° C. during 1 h and stirred at 22° C. for 2 h. The mixture was cooled to 5° C. and stirred for 3 h followed by filtration to give a solid which was washed with cold 99.5% EtOH (70 mL) to give the product as a solid which was dried in a vacuum oven at 50° C. for 20 h to give the title compound (15.66 g; 60% yield). The enantiomeric excess was measured to 99.5% on a SFC Berger Analytix system equipped with a Chiralpak OD-H column (4.6*250 mm; 5 μm) and a mobile phase consisting of 35% MeOH (containing 0.1% DEA) and 65% $CO_2$. The first peak with retention time 1.87 min (area 99.75%) corresponded to the title compound 3-[(1r,1'R,4R)-4''-amino-4-methoxy-5''-methyl-3'H-dispiro[cyclohexane-1,2'-indene-1',2''-imidazol]-6'-yl]-5-chlorobenzonitrile. The second peak with retention time 4.08 min (area 0.25%) corresponded to 3-[(1r,1'S,4S)-4''-amino-4-methoxy-5''-methyl-3'H-dispiro[cyclohexane-1,2'-indene-1',2''-imidazol]-6'-yl]-5-chlorobenzonitrile: HRMS-TOF (ES+) m/z 433.1801 [M+H]$^+$ (calculated: 433.1795); NMR strength 90.0±0.2% (residual solvent ethanol was detected at 7.2±0.1%). Other analytical data (NMR, MS, HPLC) where in accordance to those previously described for the compound.

Example 20e (1r,4r)-6'-(5-Chloropyridin-3-yl)-4-methoxy-5''-methyl-3'H-dispiro[cyclohexane-1,2'-indene-1',2''-imidazol]-4''-amine

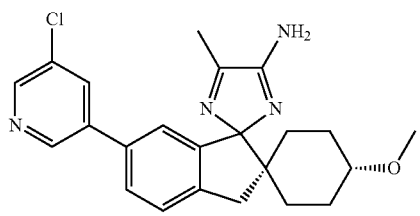

Method A

Sodium tetrachloropalladate(II) (3.13 mg, 10.63 μmol), 3-(di-tert-butylphosphonium)propane sulfonate (5.71 mg, 0.02 mmol), (1r,4r)-6'-bromo-4-methoxy-5''-methyl-3'H-dispiro[cyclohexane-1,2'-indene-1',2''-imidazol]-4''-amine (Example 19) (80 mg, 0.21 mmol) and 5-chloropyridin-3-ylboronic acid (35.2 mg, 0.21 mmol), was added to a vial. 2-Methyl-tetrahydrofuran (1 mL) and $K_2CO_3$ (2M aq) (0.319 mL, 0.64 mmol) was added and the vial was flushed with Ar (g) and capped. The mixture was heated in a microwave reactor at 90° C. for 30 min. Water was added and the residue was extracted with EtOAc (×3). The organic phases were dried using a phase separator and concentrated. The crude product was purified with preparative chromatography. The desired fractions were concentrated. Water and DCM were added and the phases were poured in to a phase separator. The organic phase was collected and concentrated in vacuo to yield the title compound (32 mg, 37% yield). $^1$H NMR (500 MHz, DMSO-$d_6$) δ ppm 0.98 (td, 1 H), 1.13-1.29 (m, 2 H), 1.37-1.50 (m, 3 H), 1.83 (d, 2 H), 2.17 (s, 3 H), 2.91-2.98 (m, 1 H), 3.00 (d, 1 H), 3.09 (d, 1 H), 3.20 (s, 3 H), 6.54 (br. s., 2 H), 6.85-6.90 (m, 1 H), 7.42 (d, 1 H), 7.57 (dd, 1 H), 8.09 (t, 1 H), 8.56 (d, 1 H), 8.71 (d, 1 H); MS (ES+) m/z 409 [M+H]$^+$.

(1r,1'R,4R)-6'-(5-chloropyridin-3-yl)-4-methoxy-5''-methyl-3'H-dispiro[cyclohexane-1,2'-indene-1',2''-imidazol]-4''-amine (isomer 1)

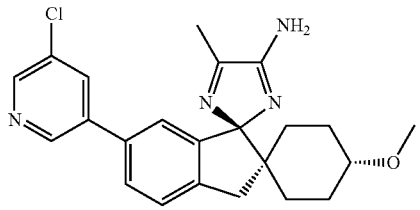 [SMILES: CO[C@H]1CC[C@]2(CC1)Cc1ccc(-c3cncc(Cl)c3)cc1[C@@]21N=C(C)C(N)=N1]

Method B

Sodium tetrachloropalladate(II) (0.015 g, 0.05 mmol), 3-(di-tert-butylphosphonium)propane sulfonate (0.014 g, 0.05 mmol), (1r,1'R,4R)-6'-bromo-4-methoxy-5''-methyl-3'H-dispiro[cyclo-hexane-1,2'-indene-1',2''-imidazol]-4''-amine (Example 19 Isomer 1, 0.190 g, 0.50 mmol) and 5-chloropyridin-3-ylboronic acid (0.100 g, 0.61 mmol) were added to a vial. 2-Methyl-tetrahydrofuran (3 mL) and potassium carbonate (2M aq) (0.757 mL, 1.51 mmol) were added and the vial was flushed with Ar (g) and capped. The mixture was heated in a microwave reactor at 90° C. for 30 min. Water was added and the residue was extracted with EtOAc (×3). The organic phases were combined and dried with $MgSO_4$ and concentrated. The crude product was purified using flash chromatography (25 g $SiO_2$, 5% isocratic 0.1 M $NH_3$ in MeOH in DCM). The fractions containing product were combined and the solvent was evaporated to give the title compound (0.085 g, 41% yield). $^1$H NMR (500 MHz, $CD_3OD$) δ ppm 1.06-1.21 (m, 1 H), 1.27-1.44 (m, 2 H), 1.44-1.56 (m, 1 H), 1.56-1.70 (m, 2 H), 1.96 (d, 2 H), 2.33 (s, 3 H), 3.09 (t, 1 H), 3.17 (d, 1 H), 3.26 (d, 1 H), 7.05 (s, 1 H), 7.50 (d, 1 H), 7.59 (d, 1 H), 8.03-8.09 (m, 1 H), 8.49 (s, 1 H), 8.65 (s, 1 H), MS (ES+) m/z 409 [M+H]+.

Example 20f (1r,4r)-6'-(5-Fluoropyridin-3-yl)-4-methoxy-5"-methyl-3'H-dispiro[cyclohexane-1,2'-indene-1',2"-imidazol]-4"-amine

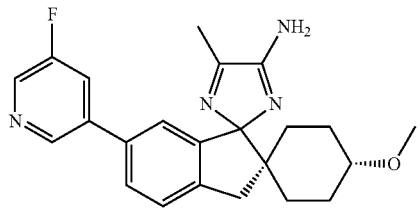

Figure 1B:
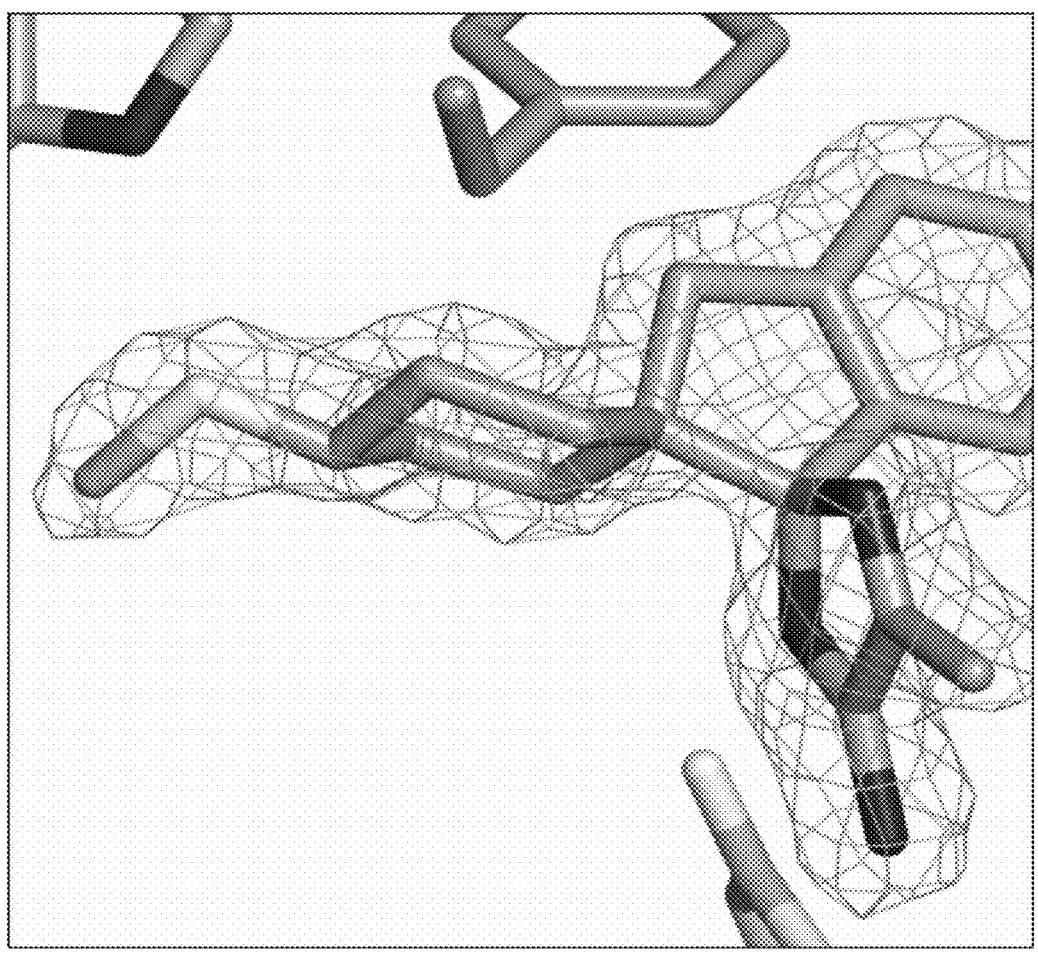
FIG. 1B shows Example 20d Isomer 1 bound to the BACE active site at 1.8 Å resolution. 2Fo-Fc is map contoured at 1.7 sigma.
Figure 2A:
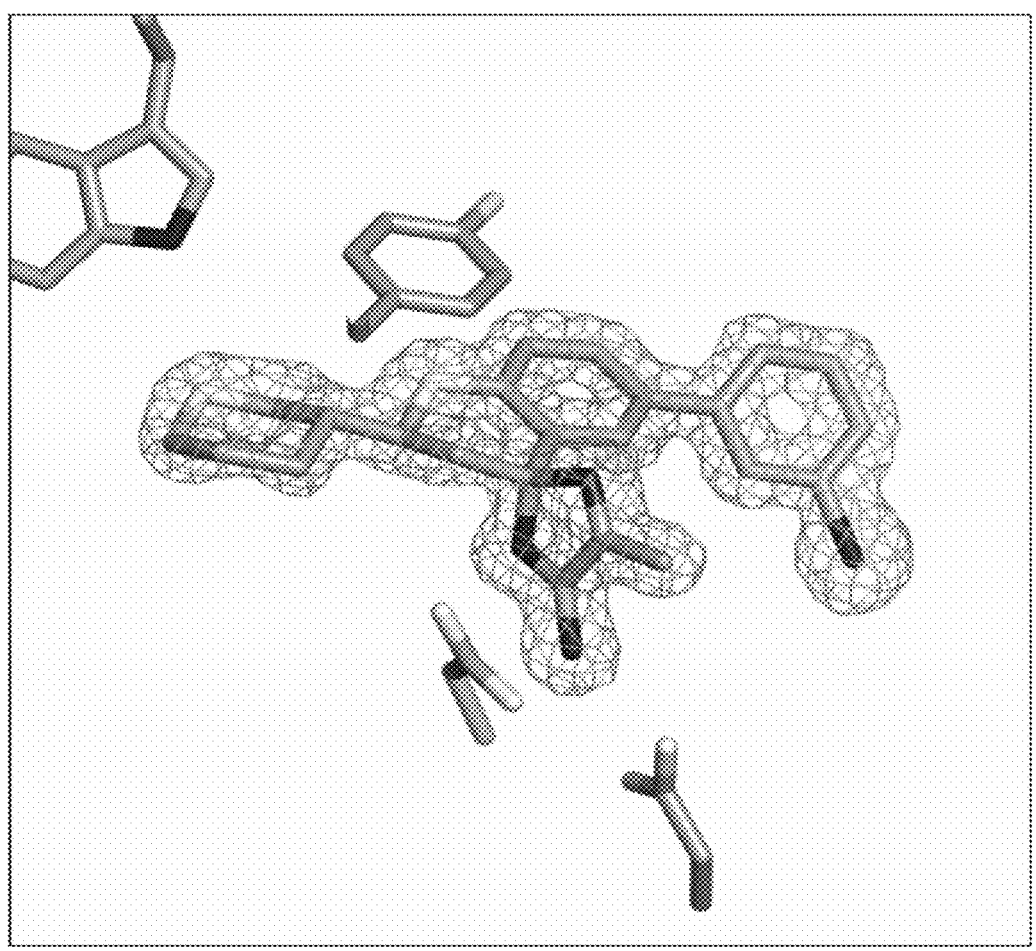
FIG. 2A shows Example 48 Isomer 1 bound to the BACE active site at 1.40 Å resolution. 2Fo-Fc map contoured at 1.3 sigma.
Figure 2B:
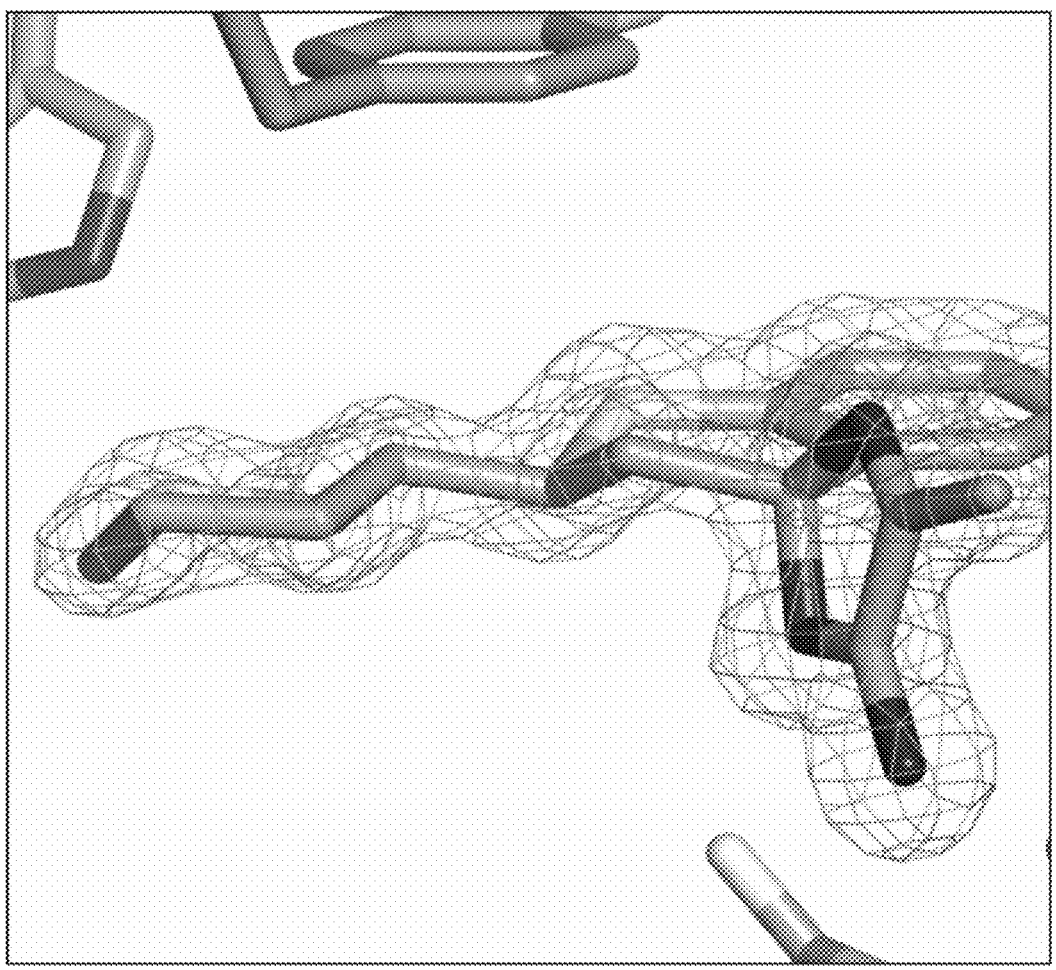
FIG. 2B shows Example 48 Isomer 1 bound to the BACE active site at 1.40 Å resolution. 2Fo-Fc map contoured at 1.3 sigma.
Figure 3A:
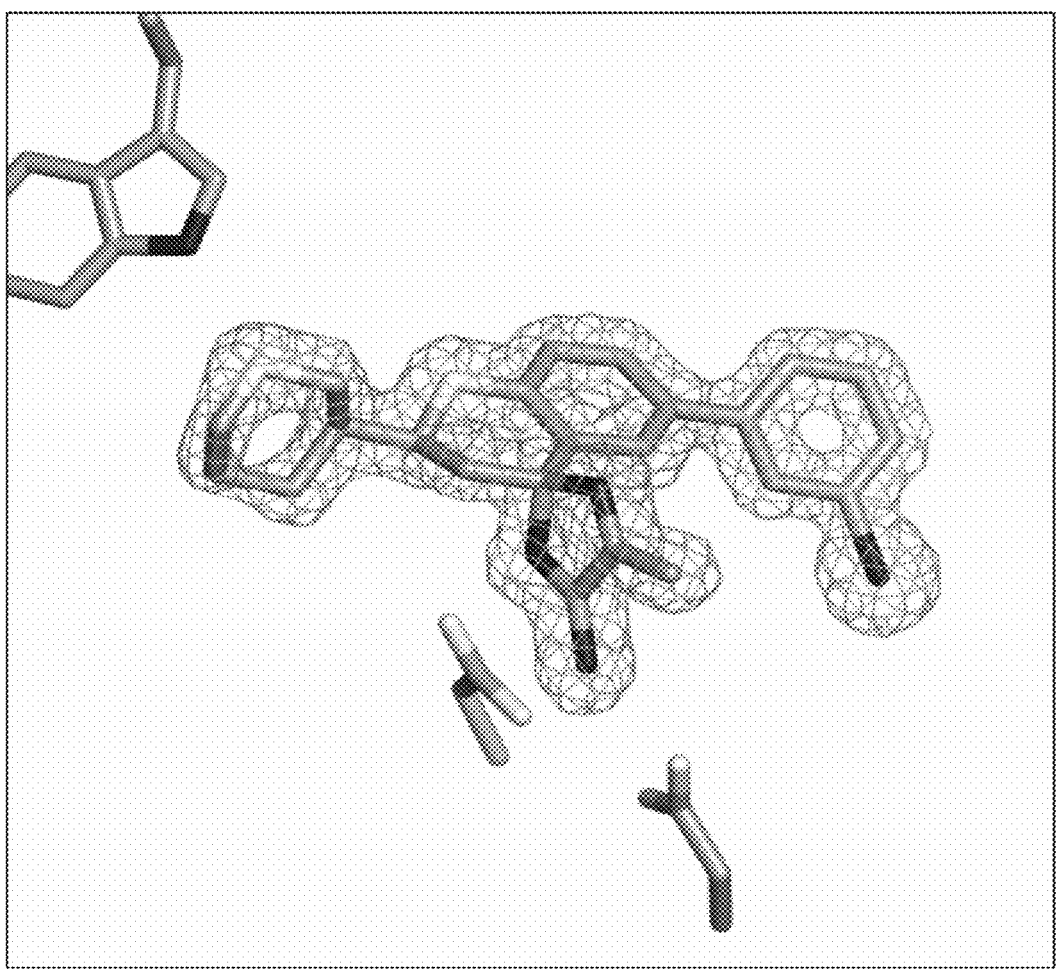
FIG. 3A shows Example 48 Isomer 8 bound to the BACE active site at 1.45 Å resolution. 2Fo-Fc map contoured at 1.1 sigma.
Figure 3B:
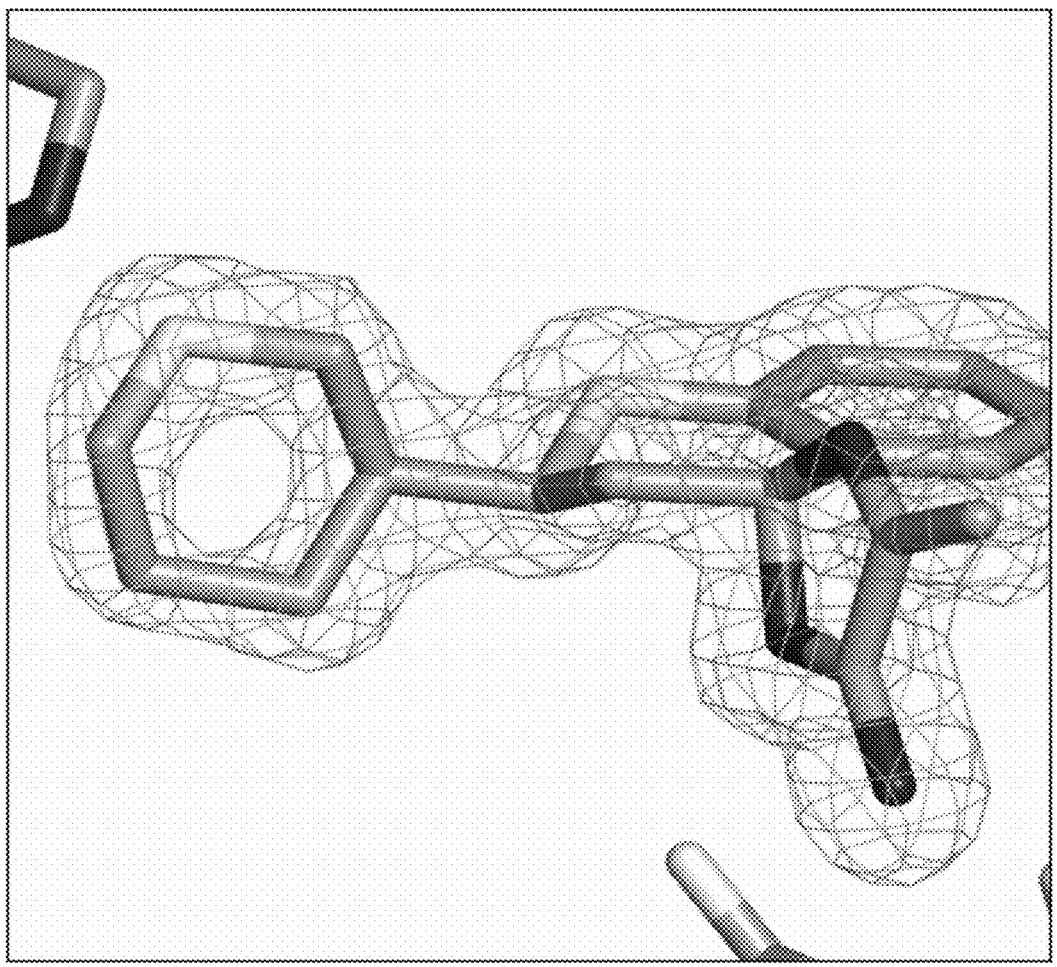
FIG. 3B shows Example 48 Isomer 8 bound to the BACE active site at 1.45 Å resolution. 2Fo-Fc map contoured at 1.1 sigma.
Figure 4A:
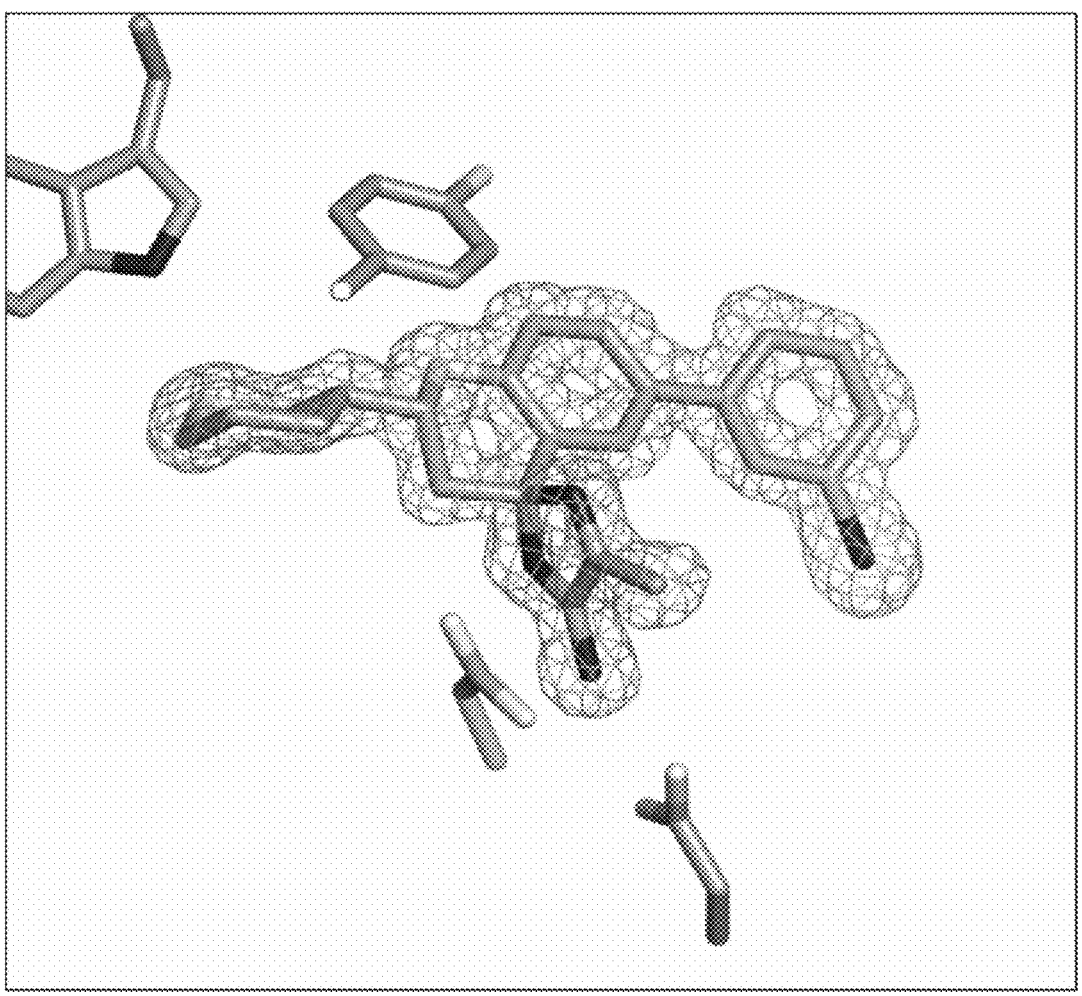
FIG. 4A shows Example 48 Isomer 7 bound to the BACE active site at 1.35 Å resolution. 2Fo-Fc map contoured at 1.3 sigma.
Figure 4B:
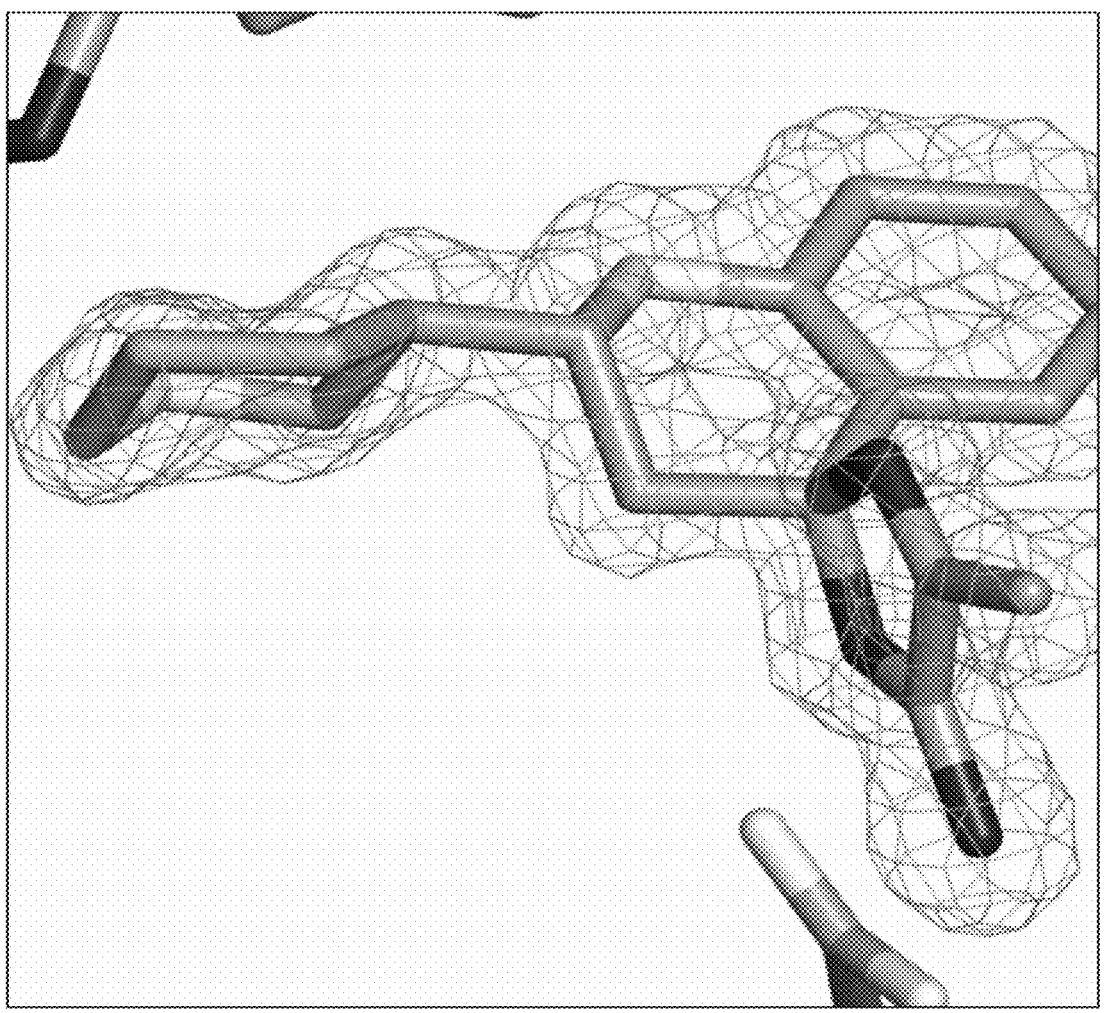
FIG. 4B shows Example 48 Isomer 7 bound to the BACE active site at 1.35 Å resolution. 2Fo-Fc map contoured at 1.3 sigma.

5-Fluoropyridin-3-ylboronic acid (48 mg, 0.34 mmol) and precatalyst 13 (see below) 8.36 mg, 10.63 µmol) was added to a microwave vial. The vial was sealed and evacuated with argon (repeated 3 times). (1r,4r)-6'-Bromo-4-methoxy-5"-methyl-3'H-dispiro[cyclohexane-1,2'-indene-1',2"-imidazol]-4"-amine (Example 19 Method B Step 4, 80.0 mg, 0.21 mmol) dissolved in degassed THF (0.5 mL) was added via a syringe. Degassed 0.5 M K$_3$PO$_4$ solution (1.276 mL, 0.64 mmol) was added via a syringe. The vial was heated in a microwave reactor at 120° C. for 15 min. THF (1.5 mL) and precatalyst 13 (FIG. 1) (8.36 mg, 10.63 µmol) was added. The is reaction was evacuated and backfilled with argon. The solution was stirred in r.t. for approx. 10 min and then heated using MW for 15 min at 120° C. The solvent was evaporated. The crude product was purified using preparative chromatography to give the title compound (34.5 mg, 41% yield), $^1$H NMR (500 MHz, CD$_3$CN) δ ppm 1.05-1.14 (m, 1 H), 1.23-1.35 (m, 2 H), 1.44 (td, 1 H), 1.50-1.57 (m, 2 H), 1.84-1.91 (m, 2 H), 2.20 (s, 3 H), 3.00 (tt, 1 H), 3.09 (d, 1 H), 3.17 (d, 1 H), 3.25 (s, 3 H), 5.27 (br. s., 2 H), 6.92 (d, 1 H), 7.41 (d, 1 H), 7.51 (dd, 1 H), 7.65-7.71 (m, 1 H), 8.40 (d, 1 H), 8.60 (t, 1 H), MS (MM-ES+APCI)+m/z 393.2 [M+H]+.

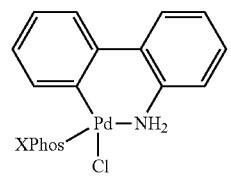

precatalyst 13

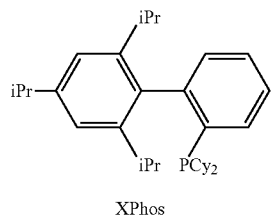

XPhos

For preparation of precatalyst 13 see: Kinzel, T.; Yong Zhang, Y.; Buchwald, S. L. *J. Am. Chem. Soc.* 2010, 132, 14073-14075.

Example 20g

5-[(1r,4r)-4"-Amino-4-methoxy-5"-methyl-3'H-dispiro[cyclohexane-1,2'-indene-1',2"-imidazol]-6'-yl]-2-fluorobenzonitrile

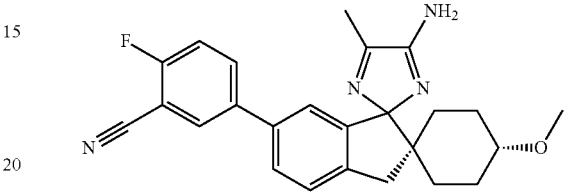

Method A: The title compound (18 mg, 20% yield) was prepared as described for Example 20e starting from (1r,4r)-6'-bromo-4-methoxy-5"-methyl-3'H-dispiro[cyclohexane-1,2'-indene-1',2"-imidazol]-4"-amine (Example 19 Method B Step 4, 84 mg, 0.22 mmol) and 3-cyano-4-fluorophenylboronic acid (40.5 mg, 0.25 mmol). $^1$H NMR (500 MHz, DMSO-d$_6$) δ ppm 0.97 (td, 1 H), 1.13-1.28 (m, 2 H), 1.37-1.50 (m, 3 H), 1.83 (d, 2 H), 2.17 (s, 3 H), 2.90-2.96 (m, 1 H), 2.98 (d, 1 H), 3.05-3.11 (m, 1 H), 3.20 (s, 3 H), 6.53 (br s, 2 H), 6.81-6.84 (m, 1 H), 7.40 (d, 1H), 7.49-7.57 (m, 2 H), 7.89-7.95 (m, 1 H), 8.10 (dd, 1 H) MS (ES+) m/z 417 [M+H]+.

5-[(1r,1'R,4R)-4"-Amino-4-methoxy-5"-methyl-3'H-dispiro[cyclohexane-1,2'-indene-1',2"-imidazol]-6'-yl]-2-fluorobenzonitrile (isomer 1)

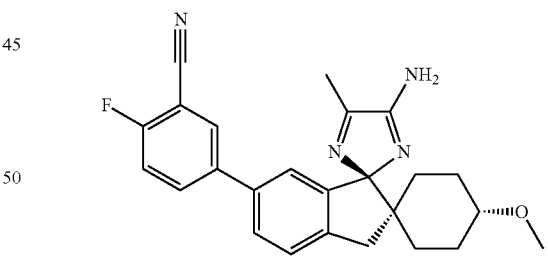

Method B: The title compound (34 mg, 20% yield) was prepared using the procedure in Example 83 starting from (1r,1'R,4R)-6'-bromo-4-methoxy-5"-methyl-3'H-dispiro[cyclohexane-1,2'-indene-1',2"-imidazol]-4"-amine as the D(+)-10-camphor sulfonic acid salt (Example 19 Step 5, 230 mg, 0.38 mmol) and 3-cyano-4-fluorophenylboronic acid (74.8 mg, 0.45 mmol): $^1$H NMR (500 MHz, DMSO-d$_6$) δ ppm 0.97 (m, 1 H), 1.21 (m, 2 H), 1.46 (m, 3 H), 1.83 (d, 2 H), 2.17 (s, 3 H), 3.01 (m, 3 H), 3.20 (s, 3 H), 6.53 (br. s, 2 H), 6.83 (d, 1 H), 7.40 (d, 1 H), 7.53 (m, 2 H), 7.92 (m, 1 H), 8.10 (dd, 1 H); MS (ES+) m/z 417 [M+H]+.

Example 20h (1r,4r)-6'-(3,3-Dimethylbut-1-yn-1-yl)-4-methoxy-5"-methyl-3'H-dispiro[cyclohexane-1,2'-indene-1',2"-imidazol]-4"-amine

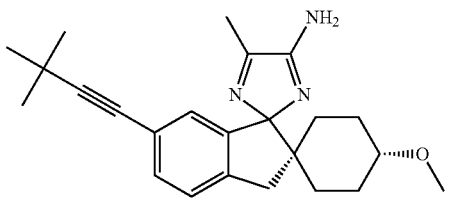

To a solution of (1r,4r)-6'-bromo-4-methoxy-5"-methyl-3'H-dispiro[cyclohexane-1,2'-indene-1',2"-imidazol]-4"-amine (Example 19 Method B Step 4, 0.157 g, 0.42 mmol) in DMF (8 mL) under an argon atmosphere was 3,3-dimethyl-but-1-yne (0.045 g, 0.54 mmol), tetrakis(triphenylphosphine)palladium(0) (0.048 g, 0.04 mmol) and triethylamine (1.75 mL, 12.5 mmol) added. The reaction mixture was stirred at r.t. for 5 min. Cuprous iodide (0.012 g, 0.06 mmol) was added and the reaction mixture was stirred overnight at 65° C. The reaction mixture was allowed to reach r.t. and then partitioned between brine and EtOAc. The organic phase was dried over $MgSO_4$ and concentrated in vacuo. The residue was purified by preparative chromatography to give the title compound (0.047 g, 30% yield): $^1$H NMR (500 MHz, DMSO-$d_6$) δ ppm 0.82-0.97 (m, 1 H), 1.24 (m, 11 H), 1.34-1.48 (m, 3 H), 1.81 (d, 2 H), 2.15 (s, 3 H), 2.86-3.08 (m, 3 H), 3.18 (s, 3 H), 6.47 (s, 1 H), 6.54 (s, 2 H), 7.14 (dd, 1 H), 7.23 (d, 1 H); MS (ES+) m/z 378 [M+H][1].

Separation of the isomers of (1r,4r)-6'-(3,3-dimethyl-but-1-yn-1-yl)-4-methoxy-5"-methyl-3'H-dispiro[cyclohexane-1,2'-indene-1',2"-imidazol]-4"-amine The isomers of (1r,4r)-6'-(3,3-dimethylbut-1-yn-1-yl)-4-methoxy-5"-methyl-3'H-dispiro-[cyclohexane-1,2'-indene-1',2"-imidazol]-4"-amine (Example 20h, 0.047 g, 0.13 mmol) were separated using a SFC Berger Multigram II preparative HPLC, with a Chiralpak OD-H column (20*250 mm; 5 μm), and a mobile phase consisting of 10% IPA (containing 0.1% DEA) and 90% $CO_2$ at a flow rate of 50 mL/min to give:

Isomer 1 with undetermined absolute configuration (16 mg, 33% yield) with retention time 4.9 Mill: $^1$H NMR (500 MHz, DMSO-$d_6$) δ ppm 0.84-0.98 (m, 1 H), 1.24 (m, 11 H), 1.34-1.47 (m, 3 H), 1.81 (d, 2 H), 2.16 (s, 3 H), 2.88-3.06 (m, 3 H), 3.18 (s, 3 H), 6.47 (s, 1 H), 6.54 (s, 2 H), 7.14 (dd, 1 H), 7.23 (d, 1 H); MS (ES+) m/z 378 [M+H][1]; and Isomer 2 with undetermined absolute configuration (16.0 mg, 34% yield) with retention time 6.7 min: $^1$H NMR (500 MHz, DMSO-$d_6$) δ ppm 0.81-0.99 (m, 1 H), 1.24 (m, 11 H), 1.34-1.50 (m, 3 H), 1.81 (d, 2 H), 2.15 (s, 3 H), 2.87-3.07 (m, 3 H), 3.18 (s, 3 H), 6.47 (s, 1 H), 6.54 (s, 2 H), 7.09-7.18 (m, 1 H), 7.23 (d, 1 H); MS (ES+) m/z 378 [M+H]+.

Example 20i (1r,4r)-6'-(cyclopropylethynyl)-4-methoxy-5"-methyl-3'H-dispiro[cyclohexane-1,2'-indene-1',2"-imidazol]-4"-amine

Step 1: (1r,4r)-6'-(Cyclopropylethynyl)-4-methoxyspiro[cyclohexane-1,2'-inden]-1'(3'H)-one

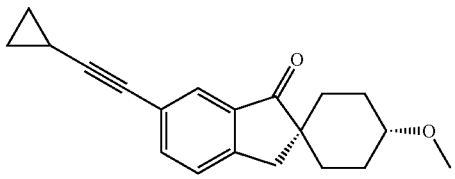 [SMILES: CO[C@H]1CC[C@]2(CC1)Cc1ccc(C#CC3CC3)cc1C2=O]

CuI (46.8 mg, 0.25 mmol) and bis(triphenylphosphine)palladium(II) chloride (43.1 mg, 0.06 mmol) were weighed into a microwave vial. The vial was capped and a solution of 6'-bromo-4-methoxyspiro[cyclohexane-1,2'-inden]-1'(3'H)-one (Intermediate 5 Method A Step 3, 760 mg, 2.46 mmol) in THF (4 mL) was added, the vial was flushed with argon followed by sequential addition of ethynylcyclopropane (487 mg, 7.37 mmol) and triethylamine (1.028 mL, 7.37 mmol). The reaction mixture was heated to 100° C. using MW for 1 h. CuI (56 mg), bis(triphenyl-phosphine)palladium(II) chloride (52 mg) and ethynylcyclopropane (0.5 mL) were added and the mixture was heated to 100° C. for 3 h. The reaction mixture was diluted with EtOAc and passed through a short plug of silica and further eluted with EtOAc. The eluates were concentrated and the residue was dissolved in THF (15 mL) and added to a microwave vial containing CuI (62 mg), bis(triphenylphosphine)palladium(II) chloride (54 mg) and $Cs_2CO_3$ (1708 mg, 5.24 mmol). The vial was flushed with argon and ethynylcyclopropane (0.5 mL) was added. The resulting mixture was heated to 100° C. using MW for 90 min. CuI (60 mg), bis(triphenylphosphine)-palladium(II) chloride (57 mg) and ethynylcyclopropane (0.5 mL) were added and the mixture was heated to 100° C. for 1 h. The reaction mixture was diluted with EtOAc, passed through a short plug of silica and concentrated. The residue was combined with a crude product from a previous batch of the same reaction (starting from 243 mg of 6'-bromo-4-methoxyspiro-[cyclohexane-1,2'-inden]-1'(3'H)-one). The combined batches were purified by flash chromatography on silica using a gradient elution with 0-30% EtOAc in heptane. The product was further purified by preparative chromatography to afford 498 mg (52% yield) of the title compound: $^1$H NMR (400 MHz, CDCl$_3$) δ ppm 0.78-0.84 (m, 2 H), 0.85-0.92 (m, 2 H), 1.29-1.54 (m, 5 H), 1.71-1.82 (m, 2 H), 2.10-2.20 (m, 2 H), 3.01 (s, 2 H), 3.21-3.32 (m, 1 H), 3.40 (s, 3 H), 7.36 (dd, 1 H), 7.58 (dd, 1 H), 7.71-7.77 (m, 1 H). MS (ES+) m/z 295 [M+H]+.

Step 2: N-((1r,40-5'-(Cyclopropylethynyl)-4-methoxyspiro[cyclohexane-1,2'-indene]-3V'H)-ylidene)-2-methylpropane-2-sulfinamide

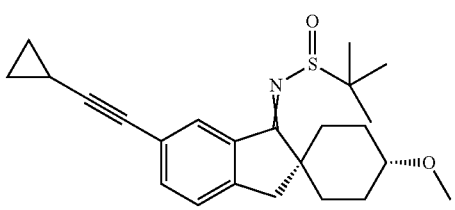 [SMILES: CO[C@H]1CC[C@]2(CC1)Cc1ccc(C#CC3CC3)cc1C2=NS(=O)C(C)(C)C]

(1r,4r)-6'-(Cyclopropylethynyl)-4-methoxyspiro[cyclohexane-1,2'-inden]-1'(3'H)-one (Example 20i Step 1, 494 mg, 1.68 mmol) and 2-methylpropane-2-sulfinamide (366 mg, 3.02 mmol) were dissolved in 2-Me THF (15 mL). Ti(OEt)$_4$ (0.704 mL, 3.36 mmol) was added and the resulting mixture heated to 80° C. for 70 h. The reaction mixture was cooled to r.t. and diluted with EtOAc (85 mL). Water (3 mL) was added under vigorous stirring and then the mixture was allowed to stand for 1 h. The mixture was filtered, the solvent was evaporated and the residue purified by flash chromatography on silica using gradient elution 0-70% EtOAc/heptane to give 470 mg of the title compound (70% yield). $^1$H NMR (500 MHz, CDCl$_3$) δ ppm 0.83 (m, 2 H), 0.87 (m, 2 H), 1.29-1.91 (m, 16 H), 2.12 (m, 2 H), 3.00 (s, 2 H), 3.20-3.33 (m, 1 H), 3.40 (s, 3 H), 7.27 and 7.29 (m overlapping with solvent, 2 H), 7.49 (dd, 1 H). MS (ES+) m/z 398 [M+H]$^+$.

Step 3: 6'-(Cyclopropylethynyl)-4-methoxyspiro [cyclohexane-1,2'-inden]-1'(3'H)-imine

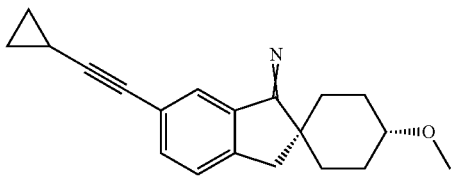 [SMILES: CO[C@H]1CC[C@]2(CC1)Cc1ccc(C#CC3CC3)cc1C2=N]

4 M HCl in dioxane (1.5 mL, 6.00 mmol) was added to a solution of N-(5'-(cyclopropylethynyl)-4-methoxyspiro[cyclohexane-1,2'-indene]-3'(1'H)-ylidene)-2-methylpropane-2-sulfinamide (Example 20i Step 2, 470 mg, 1.18 mmol) in dry dioxane (5 mL) at 5° C. The reaction mixture was allowed to come to r.t. and stirred for 1 h, then it was stored at 0° C. overnight and then concentrated. The product (as the hydrochloride salt) was dissolved in DCM and washed with aq. sat. NaHCO$_3$, dried over Na$_2$SO$_4$ and concentrated to give 363 mg of the title compound (quantitative yield). $^1$H NMR (500 MHz, CDCl$_3$) δ ppm 0.78-0.85 (m, 2 H), 0.85-0.91 (m, 2 H), 1.34-1.49 (m, 3 H), 1.54-1.63 (m, 2 H), 1.68-1.84 (m, 2 H), 2.08-2.19 (m, 2 H), 2.98 (s, 2 H), 3.23-3.33 (m, 1 H), 3.38-3.43 (m, 3 H), 7.27 (m, 2 H), 7.46 (dd, 1 H), 7.69 (br. s., 1 H). MS (ES+) m/z 294 [M+H]$^+$.

Step 4: (1r,4r)-6'-(cyclopropylethynyl)-4-methoxy-5''-methyl-3'H-dispiro[cyclohexane-1,2'-indene-1', 2''-imidazol]-4''-amine

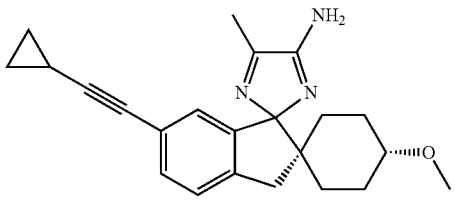

A mixture of 6'-(cyclopropylethynyl)-4-methoxyspiro[cyclohexane-1,2'-inden]-1'(3'H)-imine (Example 20i Step 3, 360 mg, 1.23 mmol) and 2-oxopropanethioamide (Intermediate 2, 380 mg, u) 3.68 mmol) in anhydrous MeOH (10 mL) was heated to 60° C. under an argon atmosphere for 18 h. The mixture was concentrated and 7 M solution of ammonia in MeOH (20 mL, 140 mmol) was added. The resulting mixture was heated to 120° C. using MW for 45 min. The reaction mixture was concentrated, another portion of 7 M ammonia in MeOH (20 mL, 140 mmol) was added to the residue and the mixture was heated using MW to 120° C. for 45 min. This cycle of concentration, ammonia addition and heating was repeated twice more. The reaction mixture was concentrated, the residue was dissolved in DCM and passed through a plug of silica which was further eluted with DCM/EtOAc (50:50). The fractions containing the desired product were concentrated and the residue was further purified by HPLC to give 85 mg (19% yield) of the title compound: $^1$H NMR (500 MHz, CDCl$_3$) δ ppm 0.71-0.76 (m, 2 H), 0.79-0.85 (m, 2 H), 1.09 (td, 1 H), 1.26-1.42 (m, 3 H), 1.42-1.50 (m, 1 H), 1.60-1.71 (m, 2 H), 1.87-2.00 (m, 2 H), 2.27 (s, 3 H), 3.02-3.10 (m, 1 H), 3.10-3.19 (m, 2 H), 3.33 (s, 3 H), 6.76 (s, 1 H), 7.20 (d, 1 H), 7.24 (dd, 1 H); MS (ES+) m/z 362 [M+H]$^1$, (ES−) m/z 360 [M−H]$^-$.

Separation of the isomers of (1r,4r)-6'-(cyclopropylethynyl)-4-methoxy-5''-methyl-3'H-dispiro[cyclohexane-1,2'-indene-1',2''-imidazol]-4''-amine The isomers of (1r,4r)-6'-(cyclopropylethynyl)-4-methoxy-5''-methyl-3'H-dispiro[cyclohexane-1,2'-indene-1',2''-imidazol]-4''-amine (Example 20i Step 4, 65 mg, 0.18 mmol) were separated using a SFC Berger Multigram II preparative HPLC, with a Chiralpak OD-H; 20*250 mm; 5 μm column, and a mobile phase consisting of 20% MeOH (containing 0.1% DEA) and 80% CO$_2$ at a flow rate of 50 mL/min to give:
Isomer 1 with undetermined absolute configuration (22 mg, 35% yield) with retention time 2.9 min: $^1$H NMR (500 MHz, DMSO-d$_6$) δ ppm 0.67 (m, 2 H), 0.83 (m, 2 H), 0.93 (br. s., 1 H), 1.18 (m, 2 H), 1.43 (m, 4 H), 1.80 (m, 2 H), 2.15 (s, 3 H), 2.96 (m, 3 H), 3.18 (s, 3 H), 6.48 (s, 1 H), 6.53 (s, 2 H), 7.15 (dd, 1 H), 7.23 (d, 1 H); MS (APCI+) m/z 362 [M+H]$^+$.
and
Isomer 2 with undetermined absolute configuration (22 mg, 35% yield) with retention time 4.0 min: $^1$H NMR (500 MHz, DMSO-d$_6$) δ ppm 0.67 (m, 2 H), 0.83 (m, 2 H), 0.93 (m, 1 H), 1.18 (m, 2 H), 1.42 (m, 4 H), 1.80 (m, 2 H), 2.15 (s, 3 H), 2.97 (m, 3 H), 3.18 (s, 3 H), 6.48 (s, 1 H), 6.53 (s, 2 H), 7.15 (dd, 1 H), 7.23 (d, 1 H); MS (APCI+) m/z 362 [M+H]$^+$.

Example 20j

N-[(1r,4r)-4''-Amino-4-methoxy-5''-methyl-3'H-dispiro[cyclohexane-1,2'-indene-1',2''-imidazol]-6'-yl]-5-bromopyrimidine-2-carboxamide Step 1: (1r,4r)-4-Methoxy-5''-methyl-3'H-dispiro [cyclohexane-1,2'-indene-1',2''imidazole]-4'',6'-diamine

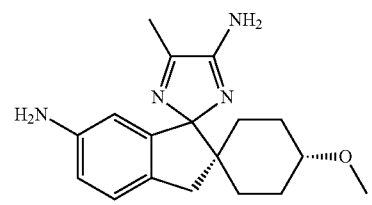

(1r,4r)-6'-Bromo-4-methoxy-5''-methyl-3'H-dispiro[cyclohexane-1,2'-indene-1',2''-imidazol]-4''-amine (Example 19 Method B Step 4, 156 mg, 0.41 mmol), trans-4-hydroxypyrrolidine-2-carboxylic acid (54.4 mg, 0.41 mmol), copper (I) iodide (39.5 mg, 0.21 mmol) and K$_2$CO$_3$ (172 mg, 1.24 mmol) were mixed in dry dimethylsulfoxide (3 mL) in a microwave vial. The mixture was stirred under argon at r.t. for 30 min. Ammonia, 30-33% in H₂O (0.389 mL, 6.22 mmol) was added, the vial was sealed and heated at 110° C. for 3 h in a microwave synthesizer. The reaction was diluted with EtOAc (25 mL) and washed with brine (25 mL). The aqueous layer was extracted with EtOAc (2×25 mL). The organics were combined, dried (Na₂SO₄), filtered and concentrated in vacuo. The crude product was purified by flash chromatography on silica gel using a gradient of 0%-100% (10% MeOH in DCM containing 0.1 N NH₃) in DCM to give the title compound (99 mg, 76% yield). ¹H NMR (500 MHz, DMSO-d₆) δ ppm 0.86 (td, 1 H), 1.07-1.25 (m, 2 H), 1.33-1.50 (m, 2 H), 1.79 (m, 2 H), 2.12 (s, 3 H), 2.80 (m, 2 H), 2.91 (m, 1 H), 3.18 (s, 3 H), 4.71 (s, 2 H), 5.82 (d, 1 H), 6.35 (dd, 1 H), 6.41 (s, 2 H), 6.89 (d, 1 H); MS (ES+) m/z 313 [M+H]⁺.

Step 2: N-[(1r,4r)-4"-Amino-4-methoxy-5"-methyl-3'H-dispiro[cyclohexane-1,2'-indene-1',2"-imidazol]-6'-yl]-5-bromopyrimidine-2-carboxamide

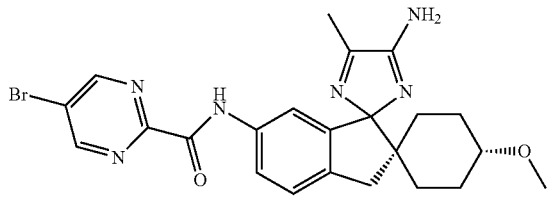

N-(3-Dimethylaminopropyl)-N'-ethylcarbodiimide hydrochloride (45.5 mg, 0.24 mmol) was added to a suspension of 5-bromopyrimidine-2-carboxylic acid (44.4 mg, 0.22 mmol) in DCM (0.5 mL). The obtained solution was stirred for 5 min and added dropwise over 2 min to an ice-cooled solution of (1r,4r)-4-methoxy-5"-methyl-3'H-dispiro[cyclohexane-1,2'-indene-1',2"-imidazole]-4",6'-diamine (Example 20j Step 1, 57 mg, 0.18 mmol) and 2M HCl (0.091 mL, 0.18 mmol) in DMF (0.500 mL). The mixture was stirred at 0° C. for 10 min and then allowed to reach r.t. overnight. The solvent was evaporated. The crude was purified using preparative chromatography to give the title compound (10 mg, 11% yield). ¹H NMR (500 MHz, DMSO-d₆) δ ppm 0.85-1.00 (m, 1 H), 1.08-1.31 (m, 2 H), 1.38-1.52 (m, 3 H), 1.77-1.87 (m, 2 H), 2.16 (s, 3 H), 2.87-3.06 (m, 3 H), 3.19 (s, 3 H), 6.50-6.60 (m, 2 H), 7.15-7.20 (m, 1 H), 7.22-7.29 (m, 1 H), 7.50-7.63 (m, 1 H), 9.18 (s, 2 H), 10.53-10.64 (m, 1 H). MS (ES+) m/z 497.1 [M+H]⁺.

Example 20k

N-[(1r,4r)-4"-Amino-4-methoxy-5"-methyl-3'H-dispiro[cyclohexane-1,2'-indene-1',2"-imidazol]-6'-yl]-5-(trifluoromethyl)pyridine-2-carboxamide

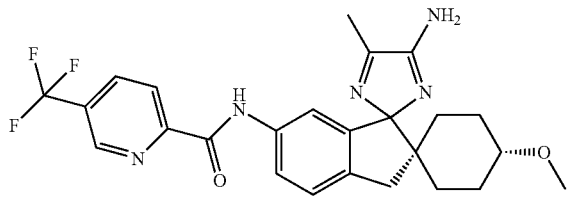

Xantphos (20.76 mg, 0.04 mmol), cesium carbonate (156 mg, 0.48 mmol), palladium(II) acetate (8.05 mg, 0.04 mmol) and 5-(trifluoromethyl)picolinamide (79 mg, 0.42 mmol) were added to a microwave vial. The vial was flushed with argon. A solution of 6'-bromo-4-methoxy-5"-methyl-3'H-dispiro[cyclohexane-1,2'-indene-1',2"-imidazol]-4"-amine (Example 19 Method A Step 4, 90 mg, 0.24 mmol) in dry THF (1.4 mL) was added. The reaction was heated using MW at 150° C. for 1 h. Xantphos (20.76 mg, 0.04 mmol) and palladium(II) acetate (8.05 mg, 0.04 mmol) were added and the reaction was heated again for 1 h at 150° C. The same procedure with addition of Xantphos and Pd(OAc)₂ and heating was repeated once more. The solvent was evaporated and the crude product was dissolved in DCM. The mixture was extracted with brine and filtered through a phase separator. The solvent was evaporated. The crude product was purified using flash chromatography (12 g SiO₂, 0-10% 0.1 M NH₃ in MeOH in DCM). The fractions containing product were combined and the solvent was evaporated. The product was further purified using preparative chromatography to give the title compound (10 mg, 9% yield). ¹H NMR (500 MHz, CDCl₃) δ ppm 1.09 (td, 1 H), 1.30-1.42 (m, 2 H), 1.52-1.62 (m, 1 H), 1.63-1.78 (m, 2 H), 1.91-2.01 (m, 2 H), 2.34 (s, 3 H), 3.03-3.13 (m, 1 H), 3.13-3.24 (m, 2 H), 3.34 (s, 3 H), 7.35 (d, 1 H), 7.54 (dd, 1 H), 8.15 (dd, 1 H), 8.37 (d, 1 H), 8.85 (s, 1 H), 9.87 (s, 1 H); MS (ES+) m/z 486 [M+H]⁺.

Example 20n

N-[(1r,4r)-4"-Amino-4-methoxy-5"-methyl-3'H-dispiro[cyclohexane-1,2'-indene-1',2"-imidazol]-6'-yl]-6-chloro-3-methyl-1-benzofuran-2-carboxamide

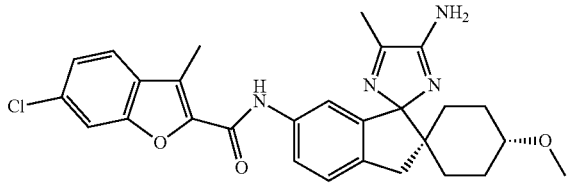

N-(3-Dimethylaminopropyl)-N'-ethylcarbodiimide hydrochloride (45.5 mg, 0.24 mmol) was added to a suspension of 5-chloro-3-methylbenzofuran-2-carboxylic acid (46.1 mg, 0.22 mmol) in DCM (0.5 mL). The obtained solution was stirred for 5 min and then added dropwise over 2 min to an ice-cooled solution of (1r,4r)-4-methoxy-5"-methyl-3'H-dispiro[cyclohexane-1,2'-indene-1',2"-imidazole]-4",6'-diamine (Example 20j Step 1, 57 mg, 0.18 mmol) and 2M HCl (0.091 mL, 0.18 mmol) in DMF (0.500 mL). The mixture was stirred at 0° C. for 10 min and was then allowed to reach r.t. overnight. The solvent was evaporated. The crude product was purified using preparative chromatography to give the title compound (7 mg, 8% yield). ¹H NMR (500 MHz, DMSO-d₆) δ ppm 0.86-0.97 (m, 1 H), 1.08-1.32 (m, 2 H), 1.41-1.51 (m, 3 H), 1.79-1.87 (m, 2 H), 2.18 (s, 3 H), 2.54 (s, 3 H), 2.89-3.08 (m, 3 H), 3.21 (s, 3 H), 6.57 (br. s, 2 H), 7.15 (s, 1 H), 7.23-7.29 (m, 1 H), 7.51-7.55 (m, 1 H), 7.56-7.60 (m, 1 H), 7.66 (s, 1 H), 7.91 (d, 1 H), 10.28 (s, 1 H). MS (ES+) m/z 505.2 [M+H]⁺.

Example 20o

N-[(1r,4r)-4"-Amino-4-methoxy-5"-methyl-3'H-dispiro[cyclohexane-1,2'-indene-1',2"-imidazol]-6'-yl]-3,5-dichloropyridine-2-carboxamide

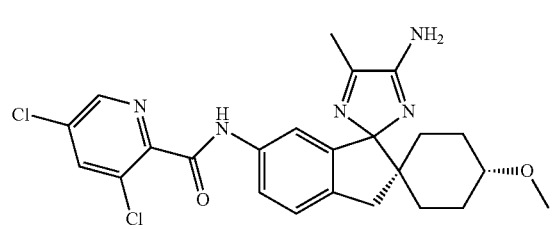

N-(3-Dimethylaminopropyl)-N'-ethylcarbodiimide hydrochloride (55.8 mg, 0.29 mmol) was added to a suspension of 3,5-dichloropicolinic acid (43.0 mg, 0.22 mmol) in DCM (0.5 mL). The obtained solution was stirred for 5 min and added dropwise over 2 min to an ice-cooled solution of 4-methoxy-5"-methyl-3'H-dispiro[cyclohexane-1,2'-indene-1',2"-imidazole]-4",6'-diamine (Example 20j Step 1, 70 mg, 0.22 mmol) and 2M HCl (0.112 mL, 0.22 mmol) in DMF (0.5 mL). The mixture was stirred at 0° C. for 60 min. The mixture was stirred at r.t. for 2 days before the mixture was concentrated and diluted with DMSO and purified by preparative chromatography. The fractions were pooled and extracted with DCM (×3), and the organic phase was passed through a phase separator. Removal of the solvent provided the title compound (19.5 mg, 18% yield): $^1$H NMR (500 MHz, CDCl$_3$) ppm 1.06 (td, J=13.56, 3.78 Hz, 1 H), 1.26-1.43 (m, 2 H), 1.56 (td, J=13.56, 3.15 Hz, 1 H), 1.61-1.73 (m, 2 H), 1.89-1.99 (m, 2 H), 2.31 (s, 3 H), 3.03-3.10 (m, 1 H), 3.10-3.20 (m, 2 H), 3.33 (s, 3 H), 7.25 (d, J=1.89 Hz, 1 H), 7.31 (d, J=8.20 Hz, 1 H), 7.41 (d, J=8.20 Hz, 1 H), 7.87 (d, J=1.89 Hz, 1 H), 8.44 (d, J=2.21 Hz, 1 H), 9.66 (s, 1 H); MS (ES+) m/z 486 [M+H]$^+$.

Example 20q

N-[(1r,4r)-4"-Amino-4-methoxy-5"-methyl-3'H-dispiro[cyclohexane-1,2'-indene-1',2"-imidazol]-6'-yl]-5-chloropyridine-2-carboxamide

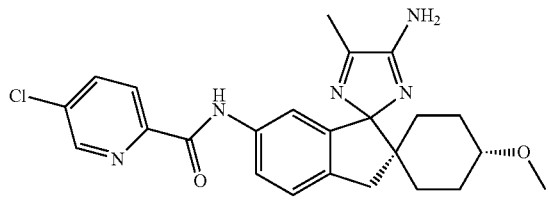

N-(3-Dimethylaminopropyl)-N'-ethylcarbodiimide hydrochloride (37.5 mg, 0.20 mmol) was added to a suspension of 5-chloropicolinic acid (28.4 mg, 0.18 mmol) in DCM (0.5 mL). The solution was stirred for 5 min at r.t. and then dropwise added over 2 min to an ice-cooled solution of 4-methoxy-5"-methyl-3'H-dispiro[cyclohexane-1,2'-indene-1',2"-imidazole]-4",6'-diamine (Example 20j, step 1, 47 mg, 0.15 mmol) and 2M HCl (0.075 mL, 0.15 mmol) in DMF (0.500 mL). The mixture was stirred at 0° C. for 2 min. The solvent was evaporated. The crude product was purified using preparative chromatography. The fractions containing the pure product were collected and extracted with DCM, dried through a phase separator and evaporated to give the title compound (31.5 mg, 46% yield). $^1$H NMR (500 MHz, CD$_3$CN) δ ppm 1.04 (td, 1H), 1.17-1.28 (m, 2 H), 1.45 (td, 1 H), 1.53 (d, 2 H), 1.83-1.89 (m, 2 H), 2.19 (s, 3 H), 2.93-3.06 (m, 2 H), 3.06-3.18 (m, 1 H), 3.24 (s, 3 H), 5.27 (br. s., 2 H), 7.14 (d, 1 H), 7.27 (d, 1 H), 7.48 (dd, 1 H), 7.99 (dd, 1 H), 8.15 (d, 1 H), 8.63 (d, 1 H), 9.80 (br. s., 1 H), MS (ES+) m/z 452 [M+H]$^+$.

Example 20t (1r,4r)-4-Methoxy-5"-methyl-6'-(2-methylpropoxy)-3'H-dispiro[cyclohexane-1,2'-indene-1',2"-imidazol]-4"-amine Step 1: N-01r,40-5'-Isobutoxy-4-methoxyspiro[cyclohexane-1,2'-indene]-3'(1'H)-ylidene)-2-methyl-propane-2-sulfinamide

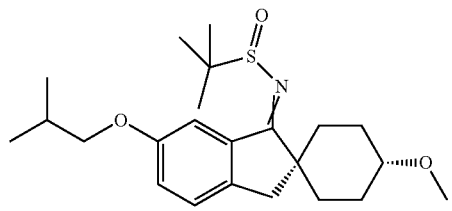 [SMILES: CO[C@H]1CC[C@]2(CC1)Cc1ccc(OCC(C)C)cc1C2=NS(=O)C(C)(C)C]

(1r,4r)-6'-Isobutoxy-4-methoxyspiro[cyclohexane-1,2'-inden]-1'(3'H)-one (Intermediate 69, 1.24 g, 4.10 mmol) and 2-methylpropane-2-sulfinamide (0.895 g, 7.38 mmol) were dissolved in 2-methyl-tetrahydrofuran (15 mL) and titanium (IV) ethoxide (1.72 mL, 8.20 mmol) was added. The resulting mixture was heated to reflux overnight. More 2-methylpropane-2-sulfinamide (0.45 g, 3.7 mmol) was added and the reaction was continued. After another day, the mixture was allowed to cool to r.t. EtOAc (35 mL) was added followed by dropwise addition of water (15 mL) under vigorous stirring. After 10 min of stirring the mixture was allowed to stand still for 1 h before the formed solids were filtered off. The organic layer was dried over Na$_2$SO$_4$ and concentrated in vacuo. Purification by flash chromatography using a gradient of 0-20% EtOAc in heptane as eluent afforded 1.036 g (62% yield) of the title compound: $^1$H NMR (500 MHz, CDCl$_3$) δ 1.01-1.07 (m, 6 H), 1.31-1.36 (s, 9 H), 1.36-1.46 (m, 2 H), 1.52-1.67 (m, 4 H), 2.07-2.14 (m, 3 H), 2.96 (s, 2 H), 3.22-3.33 (m, 1 H), 3.38-3.42 (m, 3 H), 3.73-3.84 (m, 2 H), 7.10 (dd, 1 H), 7.25 (s, 1 H), 7.75-8.03 (m, 1 H); MS (ES+) m/z 406 [M+H]$^+$.

Step 2: (1r,4r)-6'-Isobutoxy-4-methoxyspiro[cyclohexane-1,2'-inden]-1'(3'H)-imine

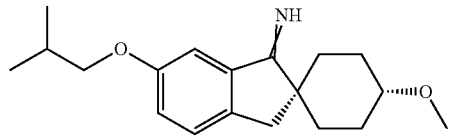 [SMILES: CO[C@H]1CC[C@]2(CC1)Cc1ccc(OCC(C)C)cc1C2=N]

HCl (4 M in 1,4-dioxane, 6.4 mL, 25.5 mmol) was added to a solution of N-((1r,40-5'-isobutoxy-4-methoxyspiro[cyclohexane-1,2'-indene]-3'(1'H)-ylidene)-2-methylpropane-2-sulfinamide (Example 20t, Step 1, 1.036 g, 2.55 mmol) in anhydrous 1,4-dioxane (3 mL). The resulting mixture was stirred under N$_2$ at r.t. for 1 h. The mixture was concentrated to one third of the volume and Et$_2$O (40 mL) was added. The formed solid was filtered off and washed with Et$_2$O. The solid was partitioned between DCM and sat. aq. NaHCO$_3$. The phases were separated and the organic layer dried over Na$_2$SO$_4$ and concentrated in vacuo. The product (635 mg, 82% yield) was used immediately as such in the next step: MS (EI) m/z 301 M.

Step 3: (1r,4r)-4-Methoxy-5"-methyl-6'-(2-methyl-propoxy)-3'H-dispiro[cyclohexane-1,2'-indene-1',2"-imidazole]-4"(3"H)-thione

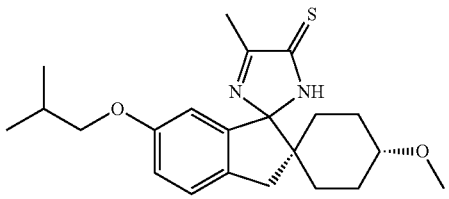

2-Oxopropanethioamide (Intermediate 2, 652 mg, 6.32 mmol) and (1r,4r)-6'-isobutoxy-4-methoxyspiro[cyclohexane-1,2'-inden]-1'(3'H)-imine (Example 20t, Step 2, 635 mg, 2.11 mmol) were dissolved in dry MeOH (10 mL) and the resulting solution was heated at 60° C. under a nitrogen atmosphere overnight. The mixture was allowed to cool to r.t. and the solvent was evaporated in vacuo. Purification by flash chromatography using a gradient of 0-40% EtOAc in heptane as eluent afforded 678 mg (83% yield) of the title compound: $^1$H NMR (400 MHz, CDCl$_3$) δ ppm 1.00 (d, 6 H), 1.12-1.48 (m, 5 H), 1.56-1.80 (m, 3 H), 2.01-2.09 (m, 1 H), 2.40 (s, 3 H), 3.06 (s, 2 H), 3.03-3.14 (m, 1 H), 3.35 (s, 3 H), 3.63 (d, 2 H), 6.43 (d, 1 H), 6.86 (dd, 1 H), 7.21 (d, 1 H), 8.69 (s, 1 H); MS (ES+) m/z 387 [M+H]$^+$.

Step 4: (1r,4r)-4-Methoxy-5"-methyl-6'-(2-methyl-propoxy)-3'H-dispiro[cyclohexane-1,2'-s indene-1',2"-imidazol]-4"-amine

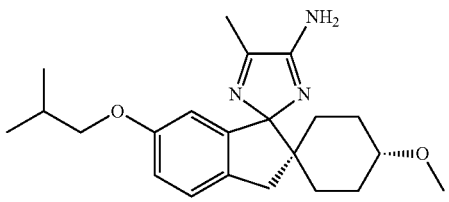

(1r,4r)-4-Methoxy-5"-methyl-6'-(2-methylpropoxy)-3'H-dispiro[cyclohexane-1,2'-indene-1',2"-imidazole]-4"(3"H)-thione (Example 20t Step 3, 678 mg, 1.75 mmol) and ammonia (7 M in MeOH, 15 mL, 105 mmol) were mixed in a microwave vial. The vial was sealed and the reaction was heated at 100° C. for 30 min in a microwave reactor (fixed hold time). The mixture was concentrated in vacuo and the residue was dissolved in ammonia (7 M in MeOH, 15 mL, 105 mmol) and heated at 100° C. for 30 min in a microwave reactor. This (concentration, addition of ammonia and heating) was repeated twice (4 runs in total). After evaporation of the solvent, the residue was partitioned between EtOAc and 2 M citric acid. The phases were separated and the organic layer was extracted with 2 M citric acid. The organic layer was discarded while the combined aqueous phases were basified to pH 12 by addition of 50% NaOH (aq). The product was extracted with EtOAc (×2). The combined organic layers were treated with charcoal and filtered through diatomaceous earth. The filter pad was rinsed with EtOAc and the filtrate was concentrated in vacuo to give 432 mg (67% yield) of the title compound: $^1$H NMR (500 MHz, DMSO-d$_6$) δ ppm 0.89 (d, 1 H), 0.93 (d, 6 H), 1.08-1.26 (m, 2 H), 1.35-1.49 (m, 3 H), 1.80 (d, 2 H), 1.86-1.97 (m, 1 H), 2.15 (s, 3 H), 2.81-2.98 (m, 3 H), 3.18 (s, 3 H), 3.58 (dd, 2 H), 6.05 (d, 1 H), 6.50 (br. s., 2 H), 6.70 (dd, 1 H), 7.15 (d, 1 H); MS (ES+) m/z 370 [M+H]$^+$.

Separation of the isomers of (1r,4r)-4-methoxy-5"-methyl-6'-(2-methylpropoxy)-3'H-dispiro[cyclohexane-1,2'-indene-1',2"-imidazol]-4"-amine The isomers of (1r,4r)-4-methoxy-5"-methyl-6'-(2-methylpropoxy)-3'H-dispiro[cyclohexane-1,2'-indene-1',2"-imidazol]-4"-amine (Example 20t Step 4, 376 mg, 1.02 mmol) were separated using a SFC Berger Multigram II preparative HPLC equipped with a LuxC4 (20*250 mm; 5 μm) column, and a mobile phase consisting of 30% MeOH (containing 0.1% DEA) and 70% CO$_2$ at a flow rate of 50 mL/min to give:
Isomer 1 with undetermined absolute configuration (128 mg, 34% yield) with retention time 2.6 min: $^1$H NMR (500 MHz, DMSO-d$_6$) δ ppm 0.89 (d, 1 H), 0.93 (d, 6 H), 1.08-1.27 (m, 2 H), 1.35-1.47 (m, 3 H), 1.80 (d, 2 H), 1.86-1.98 (m, 1 H), 2.14 (s, 3 H), 2.82-2.99 (m, 3 H), 3.18 (s, 3 H), 3.58 (dd, 2 H), 6.05 (d, 1 H), 6.50 (s, 2 H), 6.70 (dd, 1 H), 7.14 (d, 1 H); MS (ES+) m/z 370 [M+H]$^+$; and
Isomer 2 with undetermined absolute configuration (146 mg, 39% yield) with retention time 3.5 min: $^1$H NMR (500 MHz, DMSO-d$_6$) δ ppm 0.89 (d, 1 H), 0.93 (d, 6 H), 1.08-1.26 (m, 2 H), 1.35-1.47 (m, 3 H), 1.80 (d, 2 H), 1.87-1.98 (m, 1 H), 2.15 (s, 3 H), 2.81-2.98 (m, 3 H), 3.18 (s, 3 H), 3.58 (dd, 2 H), 6.05 (d, 1 H), 6.50 (s, 2 H), 6.70 (dd, 1 H), 7.14 (d, 1 H). MS (ES+) m/z 370 [M+H]$^+$.

Example 20u (1r,4r)-4-methoxy-5"-methyl-6'-(3,3,3-trifluoropropoxy)-3'H-dispiro[cyclohexane-1,2'-indene-1',2"-imidazol]-4"-amine Step 1: N-[(1r,1'E,4r)-4-Methoxy-6'-(3,3,3-trifluoropropoxy)spiro[cyclohexane-1,2'-inden]-1'(3'H)-ylidene]-2-methylpropane-2-sulfinamide

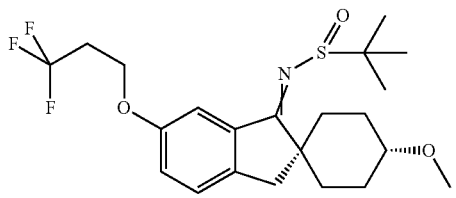 [SMILES: CO[C@H]1CC[C@]2(CC1)Cc1ccc(OCCC(F)(F)F)cc1C2=NS(=O)C(C)(C)C]

(1r,4r)-4-Methoxy-6'-(3,3,3-trifluoropropoxy)spiro[cyclohexane-1,2'-inden]-1'(3'H)-one (Intermediate 83, 320 mg, 0.93 mmol) and 2-methylpropane-2-sulfinamide (204 mg, 1.68 mmol) were dissolved in 2-methyl-tetrahydrofuran (4 mL). Titanium(IV) ethoxide (0.391 mL, 1.87 mmol) was added. The resulting mixture was heated at reflux over the weekend. The mixture was allowed to cool to r.t. and EtOAc (10 mL) was added followed by dropwise addition of water (5 mL) under vigorous stirring. After 10 min of stirring the mixture was allowed to stand still for 1 h before the formed solids were filtered off. The organic layer was dried over Na₂SO₄ and concentrated. Purification of the crude product by flash chromatography using 0-20% EtOAc in heptane as eluent afforded 270 mg (65% yield) of the title compound (containing 5% of another isomer): $^1$H NMR (500 MHz, CDCl₃) δ 1.32-1.35 (m, 9 H), 1.36-1.45 (m, 2 H), 1.52-1.57 (m, 1 H), 1.60-1.68 (m, 1 H), 1.72-2.07 (m, 2 H), 2.13 (d, 2 H), 2.63 (dt, 2 H), 2.97 (s, 2H), 3.21-3.32 (m, 1 H), 3.40 (s, 3 H), 4.26 (td, 2 H), 7.11 (dd, 1 H), 7.29 (d, 1 H), 7.87-8.13 (m, 1 H); MS (ES+) m/z 446 [M+H]⁺.

Step 2: (1r,4r)-4-Methoxy-6'-(3,3,3-trifluoropropoxy)spiro[cyclohexane-1,2'-inden]-1'(3'H)-imine

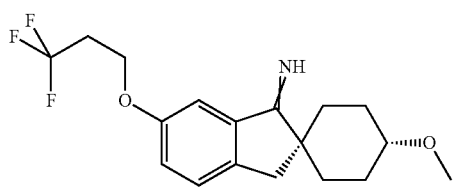 [SMILES: CO[C@H]1CC[C@]2(CC1)Cc1ccc(OCCC(F)(F)F)cc1C2=N]

HCl (4 M in 1,4-dioxane) (1.52 mL, 6.06 mmol) was added to a solution of N-((1r,4r)-4-methoxy-5'-(3,3,3-trifluoropropoxy)spiro[cyclohexane-1,2'-indene]-3'(1'H)-ylidene)-2-methylpropane-2-sulfinamide (Example 20u Step 1, 270 mg, 0.61 mmol) in anhydrous 1,4-m dioxane (1 mL). The resulting mixture was stirred under N₂ at r.t. for 2 h. The mixture was concentrated to ~⅓ of the volume and Et₂O (40 mL) was added. A solid was formed which was filtered off and washed with Et₂O. The solid was partitioned between DCM and sat. aq. NaHCO₃. The phases were separated and the organic layer dried over Na₂SO₄ and concentrated in vacuo. The product (174 mg, 84% yield) containing 9% of another isomer was used is immediately as such in the next step: MS (ES+) m/z 342 [M+H]⁺.

Step 3: (1r,4r)-4-Methoxy-5''-methyl-6'-(3,3,3-trifluoropropoxy)-3'H-dispiro[cyclohexane-1,2'-indene-1',2''-imidazole]-4''(3''H)-thione

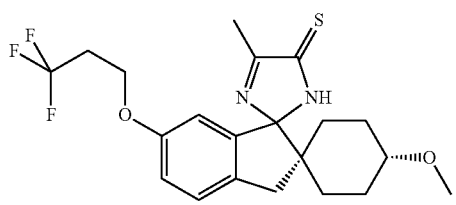

2-Oxopropanethioamide (Intermediate 2, 158 mg, 1.53 mmol) and 4-methoxy-6'-(3,3,3-trifluoropropoxy)spiro[cyclohexane-1,2'-inden]-1'(3'H)-imine (Example 20u, Step 2, 174 mg, 0.51 mmol) were dissolved in dry MeOH (3 mL) and the resulting orange solution was heated at 60° C. under a nitrogen atmosphere overnight. The mixture was allowed to cool to r.t. and the solvent was evaporated in vacuo. Purification by flash chromatography using a gradient of 0-30% EtOAc in heptane as eluent afforded 175 mg (81% yield) of the title compound containing 5% of another isomer: $^1$H NMR (500 MHz, CDCl₃) δ 1.15-1.24 (m, 1 H), 1.34-1.53 (m, 2 H), 1.56-1.69 (m, 2 H), 1.75 (dd, 1 H), 2.02 (dt, 2 H), 2.40 (s, 3 H), 2.53-2.64 (m, 2 H), 3.08 (s, 2 H), 3.09-3.13 (m, 1 H), 3.35 (s, 3 H), 4.12 (t, 2 H), 6.44 (s, 1 H), 6.87 (d, 1 H), 7.24 (d, 1 H), 8.84 (br. s., 1 H); MS (ES+) m/z 387 [M+H]⁺.

Step 4: (1r,4r)-4-methoxy-5''-methyl-6'-(3,3,3-trifluoropropoxy)-3'H-dispiro[cyclohexane-1,2'-indene-1',2''-imidazol]-4''-amine

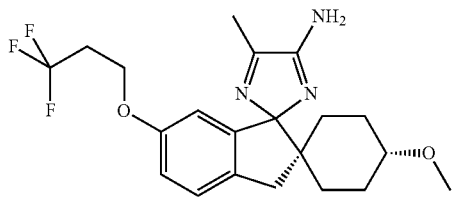

(1r,4r)-4-Methoxy-5''-methyl-6'-(3,3,3-trifluoropropoxy)-3'H-dispiro[cyclohexane-1,2'-indene-1',2''-imidazole]-4''(3''H)-thione (Example 20u Step 3, 175 mg, 0.41 mmol) and ammonia (7 M in MeOH, 3 mL, 21 mmol) were mixed in a microwave vial. The vial was sealed and the reaction was heated at 110° C. for 30 min in a microwave reactor. The mixture was concentrated in vacuo and the residue was dissolved in ammonia (7 M in MeOH, 3 mL, 21 mmol) and heated at 110° C. for 30 min in a microwave reactor. This procedure (concentration, addition of ammonia and heating) was repeated twice (4 runs in total). After evaporation of the solvent, the residue was partitioned between EtOAc and 2 M aq. citric acid. The phases were separated and the organic layer was extracted with 2 M citric acid. The organic layer was discarded while the combined aqueous phases were basified to pH 12 by addition of 50% aq. NaOH. The product was extracted with EtOAc (twice). The combined organic layers were treated with charcoal and filtered through diatomaceous earth. The filter pad was rinsed with EtOAc and the filtrate was concentrated in vacuo. Purification by preparative chromatography afforded 64 mg (38% yield) of the title compound: $^1$H NMR (500 MHz, DMSO-d₆) δ ppm 0.90 (td, 1 H), 1.08-1.27 (m, 2H), 1.34-1.49 (m, 3 H), 1.80 (d, 2 H), 2.15 (s, 3 H), 2.69 (tt, 2 H), 2.82-2.99 (m, 3 H), 3.15-3.22 (m, 3 H), 4.00-4.10 (m, 2 H), 6.08 (d, 1 H), 6.51 (br. s., 2 H), 6.75 (dd, 1 H), 7.18 (d, 1 H); MS (APCI+) m/z 410 [M+H]⁺.

Example 20v (1r,4r)-6'-(3-Fluoropropoxy)-4-methoxy-5''-methyl-3'H-dispiro[cyclohexane-1,2'-indene-1',2''-imidazol]-4''-amine Step 1: N-(5'-(3-Fluoropropoxy)-4-methoxyspiro[cyclohexane-1,2'-indene]-3'(1'H)-ylidene)-2-methylpropane-2-sulfinamide

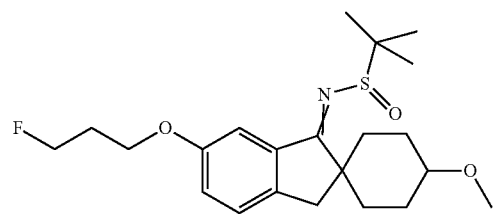 [SMILES: COC1CCC2(CC1)Cc1ccc(OCCCF)cc1C2=NS(=O)C(C)(C)C]

6'-(3-Fluoropropoxy)-4-methoxyspiro[cyclohexane-1,2'-inden]-1'(3'H)-one (Intermediate 65, 611 mg, 1.99 mmol) and 2-methylpropane-2-sulfinamide (435 mg, 3.59 mmol) were dissolved in 2-methyl-tetrahydrofuran (40 mL). Titanium (IV) ethoxide (0.84 mL, 3.99 mmol) was added and the resulting mixture was heated to 80° C. over a weekend. The reaction mixture was cooled to r.t. and diluted with EtOAc (85 mL). Water (3 mL) was added under vigorous stirring and then the mixture was allowed to stand for 1 h. The mixture was filtered, the solvent was evaporated, and the residue was purified by flash chromatography using a gradient of EtOAc (0-70%) in heptane to give 244 mg (30% yield) of the title compound: MS (ES+) m/z 410 [M+H]+.

Step 2: 6'-(3-Fluoropropoxy)-4-methoxyspiro[cyclohexane-1,2'-inden]-1'(3'H)-imine

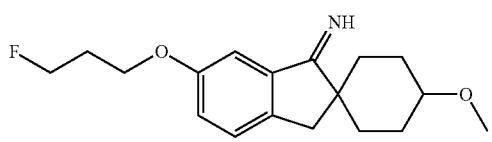 [SMILES: COC1CCC2(CC1)Cc1ccc(OCCCF)cc1C2=N]

HCl (4 M in 1,4-dioxane, 1.489 mL, 5.96 mmol) was added to a solution of N-(5'-(3-fluoro-propoxy)-4-methoxyspiro[cyclohexane-1,2'-indene]-3'(1'H)-ylidene)-2-methylpropane-2-sulfinamide (Example 20v, Step 1, 244 mg, 0.60 mmol) in anhydrous 1,4-dioxane (25 mL). A white precipitate was formed immediately and the resulting cloudy mixture was stirred under a nitrogen atmosphere overnight. The mixture was diluted with NaHCO₃ (aq) and extracted with DCM, dried over MgSO₄ and concentrated in vacuo to give 204 mg (quantitative yield) of the title compound that was used without any purification in the next step: MS (ES+) m/z 306 [M+H]+.

Step 3: 6'-(3-Fluoropropoxy)-4-methoxy-5"-methyl-3'H-dispiro[cyclohexane-1,2'-indene-1',2"-imidazole]-4"(3"H)-thione

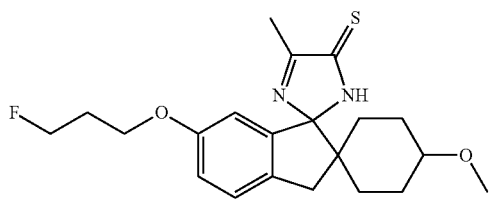 [SMILES: COC1CCC2(CC1)Cc1ccc(OCCCF)cc1C21N=C(C)C(=S)N1]

6'-(3-Fluoropropoxy)-4-methoxyspiro[cyclohexane-1,2'-inden]-1'(3'H)-imine (Example 20v, Step 2, 204 mg, 0.67 mmol), trimethyl orthoformate (0.193 mL, 1.76 mmol) and 2-propanol (5 mL) was added to a MW vial. The vial was sealed and the mixture was heated at 60° C. (oil bath). 2-Oxopropanethioamide (Intermediate 2, 138 mg, 1.34 mmol) in MeOH (15 mL) was added and the resulting mixture was stirred overnight at 60° C. and was then concentrated in vacuo. The product was isolated using flash chromatography (0-50% EtOAc in heptane) to give the title compound (167 mg, 64% yield): MS (ES+) m/z 391 [M+H]¹.

Step 4: (1r,4r)-6'-(3-Fluoropropoxy)-4-methoxy-5"-methyl-3'H-dispiro[cyclohexane-1,2'-indene-1',2"-imidazol]-4"-amine

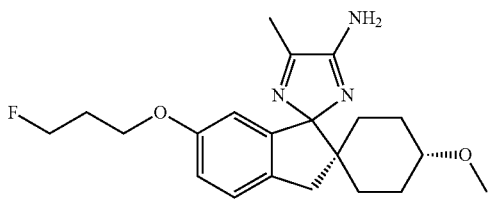

6'-(3-Fluoropropoxy)-4-methoxy-5"-methyl-3'H-dispiro[cyclohexane-1,2'-indene-1',2"-imidazole]-4"(3"H)-thione (Example 20v, Step 3, 167 mg, 0.43 mmol) was placed into a is microwave vial. Ammonia (7M in MeOH, 2 mL, 14 mmol) was added. The mixture was heated for 30 min at 90° C. in a microwave reactor. The mixture was concentrated and ammonia (7M in MeOH, 2 mL, 14 mmol) was added. The mixture was heated at 120° C. for 30 min in a microwave reactor. The cycle of concentration, addition of ammonia and heating at 120° C. with MW was repeated 5 times. The mixture was concentrated in vacuo. The product was isolated using preparative chromatography to give 40 mg (25% yield) of the title compound: ¹H NMR (500 MHz, DMSO-d₆) δ ppm 0.93 (td, J=13.40, 2.84 Hz, 1 H) 1.07-1.27 (m, 2 H) 1.31-1.48 (m, 3 H) 1.81 (d, J=9.46 Hz, 2 H) 1.95-2.10 (m, 2 H) 2.17 (s, 3 H) 2.83-2.99 (m, 3 H) 3.18 (s, 3 H) 3.88-3.95 (m, 2 H) 4.51 (t, J=5.99 Hz, 1 H) 4.61 (t, J=5.99 Hz, 1 H) 6.14 (d, J=2.21 Hz, 1H) 6.75 (dd, J=8.20, 2.52 Hz, 1 H) 7.17 (d, J=8.20 Hz, 1 H) MS (ES+) m/z 374 [M+H]+.

Example 20w

N-[(1r,4r)-4"-Amino-4-methoxy-5"-methyl-3'H-dispiro[cyclohexane-1,2'-indene-1',2"-imidazol]-6'-yl]-5-chloro-3-methylpyridine-2-carboxamide

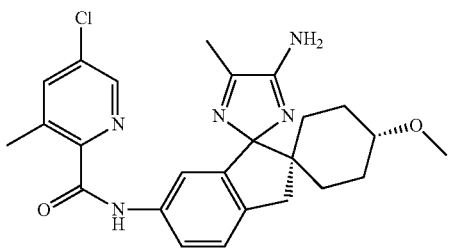

To a slurry of 5-chloro-3-methylpicolinic acid (37.6 mg, 0.22 mmol) in a mixture of DCM/DMF/THF (2.0:2.0:0.5 mL) was added 1-(3-dimethylaminopropyl)-3-ethylcarbodiimide hydrochloride (45.5 mg, 0.24 mmol). The mixture containing the activated acid was stirred for 20 min. under argon before it was added to a cold (0° C., external temp.) stirred solution of (1r,4r)-4-methoxy-5"-methyl-3'H-dispiro[cyclohexane-1,2'-indene-1',2"-imidazole]-4",6'-diamine (Example 20j, step 1, 57.0 mg, 0.18 mmol), hydrochloric acid (3 M) (0.3 mL, 0.90 mmol) and triethylamine (0.099 mL, 0.71 mmol) in DMF (2.0 mL). After 2 h, another portion of activated acid, prepared as above, was added at 0° C. The mixture was stirred at 0° C. for 5 min. and then at r.t. for ~1 h before raising the temperature to 30° C. for 30 min. The reaction was quenched by addition of MeOH (1.5 mL) and the mixture was concentrated at reduced pressure to give a crude product that was purified by preparative chromatography. The isolated

Example 20x

N-[(1r,4r)-4''-Amino-4-methoxy-5''-methyl-3'H-dispiro[cyclohexane-1,2'-indene-1',2''-imidazol]-6'-yl]-5-fluoropyridine-2-carboxamide

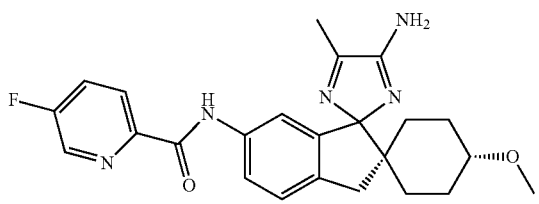

N-(3-Dimethylaminopropyl)-N'-ethylcarbodiimide hydrochloride (39.1 mg, 0.20 mmol) was added to a suspension of 5-fluoropicolinic acid (26.6 mg, 0.19 mmol) in DCM (0.5 mL). The solution was stirred for 10 min at r.t. and then dropwise added to an ice-cooled solution of 4-methoxy-5''-methyl-3'H-dispiro[cyclohexane-1,2'-indene-1',2''-imidazole]-4'',6'-diamine (Example 20j, step 1, 49 mg, 0.16 mmol) and 2M HCl (0.078 mL, 0.16 mmol) in DMF (0.500 mL). The mixture was stirred at 0° C. for 1 h. The solvent was evaporated. The crude product was purified using preparative chromatography. The fractions containing the product were pooled and the MeOH was evaporated. DCM was added and the organic phase was extracted, dried through a phase separator and evaporated to give the title compound (25 mg, 37% yield): $^1$H NMR (500 MHz, CD$_3$CN) δ ppm 0.99-1.10 (m, 1 H), 1.18-1.27 (m, 2 H), 1.45 (td, 1 H), 1.50-1.57 (m, 2 H), 1.83-1.90 (m, 2 H), 2.20 (s, 3 H), 2.94-3.06 (m, 2 H), 3.06-3.15 (m, 1 H), 3.25 (s, 3 H), 5.29 (br. s., 2 H), 7.15 (d, 1 H), 7.28 (d, 1 H), 7.48 (dd, 1 H), 7.72 (td, 1 H), 8.24 (dd, 1 H), 8.52 (d, 1 H), 9.78 (br. s., 1 H); MS (ES+) m/z 436 [M+H]

Example 20y 1r,4r)-4-Methoxy-5''-methyl-6'-[2-(prop-1-yn-1-yl)pyridin-4-yl]-3'H-dispiro[cyclohexane-1,2'-indene-1',2''-imidazol]-4''-amine

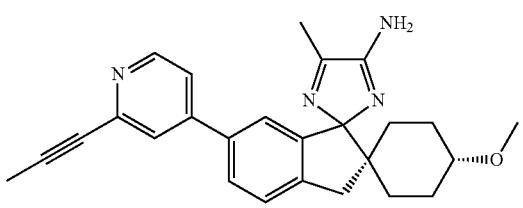

(1r,4r)-6'-Bromo-4-methoxy-5''-methyl-3'H-dispiro[cyclohexane-1,2'-indene-1',2''-imidazol]-4''-amine (Example 19, 75 mg, 0.20 mmol), potassium acetate (39.1 mg, 0.40 mmol), bis(pinacolato)diboron (55.7 mg, 0.22 mmol) and PdCl$_2$(dppf)-CH$_2$Cl$_2$ adduct (8.14 mg, 9.97 μmol) were taken up in dioxane (2 mL) in a microwave vial. The reaction vessel was sealed and heated at 110° C. for 30 min and then at 120° C. for 15 min in a Biotage Initiator. After cooling, K$_2$CO$_3$ (55 mg, 0.40 mmol), Pd(Ph$_3$P)$_4$ (11.5 mg, 9.97 μmol), and water (0.3 mL) were added followed by 4-bromo-2-(prop-1-ynyl)pyridine (Intermediate 33, 39 mg, 0.20 mmol) in dioxane (1 mL). The reaction vessel was sealed and heated at 110° C. for 30 min in a Biotage Initiator. After cooling, the mixture was filtered and concentrated in vacuo. The product was purified by flash chromatography using a gradient of EtOAc in heptane (0-100%), then EtOAc:MeOH (9:1) followed by preparative chromatography to give the title compound (7 mg, 9% yield): $^1$H NMR (500 MHz, DMSO-d$_6$) δ ppm 0.96 (m, 1 H), 1.12-1.29 (m, 2 H), 1.39-1.50 (m, 3 H), 1.83 (m, 2 H), 2.08 (s, 3 H), 2.18 (s, 3 H), 2.90-3.13 (m, 3 H), 3.20 (s, 3 H), 6.56 (s, 2 H), 6.89 (d, 1 H), 7.42 (d, 1 H), 7.50 (dd, 1 H), 7.58 (d, 1 H), 7.62 (dd, 1 H), 8.49 (d, 1 H); MS (MM−ES+APCI)+m/z 413 [M+H]$^+$.

Example 20z (1r,4r)-4-Methoxy-5''-methyl-6'-[3-(prop-1-yn-1-yl)phenyl]-3'H-dispiro[cyclohexane-1,2'-indene-1',2''-imidazol]-4''-amine

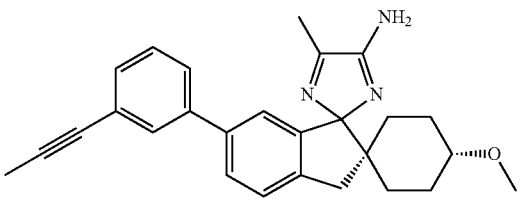

A mixture of sodium tetrachloropalladate(II) (2.9 mg, 9.70 μmol), 3-(di-tert-butylphosphonium)propane sulfonate (5.2 mg, 20.0 μmol), (1r,4r)-6'-bromo-4-methoxy-5''-methyl-3'H-dispiro[cyclohexane-1,2'-indene-1',2''-imidazol]-4''-amine (Example 19, 73 mg, 0.19 mmol) and 3-(prop-1-ynyl)phenylboronic acid (Intermediate 34, 47 mg, 0.29 mmol) in dioxane (2 mL) under argon was heated at reflux overnight. 3-(Prop-1-ynyl)phenylboronic acid (46.6 mg, 0.29 mmol) was added and heating was continued for 4 h. The reaction mixture was partitioned between water and ethyl acetate, the organic layer was dried over MgSO$_4$ and the solvent evaporated. The residue was purified by preparative chromatography to give 4.0 mg (5% yield) of the title compound. $^1$H NMR (500 MHz, DMSO-d$_6$) δ ppm 0.91-1.02 (m, 1 H), 1.10-1.32 (m, 2 H), 1.40-1.54 (m, 3 H), 1.84 (d, 2 H), 2.06 (s, 3 H), 2.18 (s, 3 H), 2.92-3.13 (m, 3 H), 3.21 (s, 3 H), 6.55 (s, 2 H), 6.75 (d, 1 H), 7.30-7.35 (m, 1 H), 7.35-7.42 (m, 2 H), 7.44-7.50 (m, 3 H); MS (MM−ES+APCI)+m/z 412 [M+H]$^+$.

Example 20aa (1r,4r)-6'-(5-Bromopyridin-3-yl)-4-methoxy-5''-methyl-3'H-dispiro[cyclohexane-1,2'-indene-1',2''-imidazol]-4''-amine

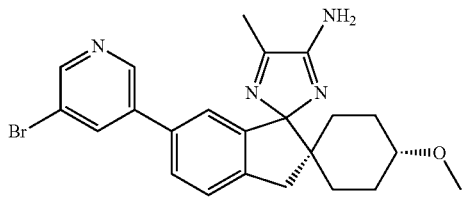

A solution of (1r,4r)-6'-bromo-4-methoxy-5"-methyl-3'H-dispiro[cyclohexane-1,2'-indene-1',2"-imidazol]-4"-amine (Example 19, 130 mg, 0.35 mmol) in MeCN (3.5 mL) and DMF (0.5 mL) was added to a mixture of 4,4,4',4',5,5,5',5'-octamethyl-2,2'-bi(1,3,2-dioxaborolane) (132 mg, 0.52 mmol), PdCl$_2$(dppf)-CH$_2$Cl$_2$ adduct (14.1 mg, 0.02 mmol) and KOAc (136 mg, 1.38 mmol) under argon atmosphere. The mixture was heated to 120° C. using MW for 30 min. PdCl$_2$(dppf)-CH$_2$Cl$_2$ adduct (14.1 mg, 0.02 mmol) and 3,5-dibromopyridine (123 mg, 0.52 mmol) were added and the mixture was heated to 120° C. using MW for 30 min. 3,5-Dibromopyridine (123 mg, 0.52 mmol), KOAc (35 mg, 0.35 mmol), PdCl$_2$(dppf)-CH$_2$Cl$_2$ adduct (14.1 mg, 0.02 mmol) and water (100 µL) were added and the mixture was heated at 120° C. for 30 min. Another cycle of addition of 3,5-dibromopyridine and catalyst and subsequent heating was conducted. The reaction mixture was filtered, the filtrate was concentrated and the residue was purified by flash chromatography using a gradient of EtOAc and heptane (0-100%) and then MeOH and DCM (0-5%). Further purification by preparative chromatography gave 22 mg of the title compound (14% yield). $^1$H NMR (500 MHz, DMSO-d$_6$) δ ppm 0.97 (td, 1 H), 1.13-1.30 (m, 2 H), 1.36-1.52 (m, 3 H), 1.83 (d, 2 H), 2.17 (s, 3 H), 2.91-2.98 (m, 1 H), 3.00 (d, 1 H), 3.09 (d, 1 H), 3.20 (s, 3 H), 6.54 (s, 2 H), 6.86 (d, 1 H), 7.42 (d, 1 H), 7.56 (dd, 1 H), 8.19 (t, 1 H), 8.64 (d, 1 H), 8.73 (d, 1 H). MS (ES+) m/z 453 [M+H]$^+$ and (ES−) m/z 451 [M−H]$^−$.

Example 25

6'-Bromo-5-methyl-2",3",5",6"-tetrahydro-3'H-dispiro[imidazole-2,1'-indene-2',4"-pyran]-4-amine Step 1: N-(5-Bromo-2',3',5',6'-tetrahydrospiro[indene-2,4'-pyran]-3(1 H)-ylidene)-2-methylpropane-2-sulfinamide

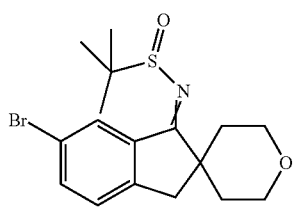 [SMILES: CC(C)(C)S(=O)N=C1c2cc(Br)ccc2CC12CCOCC2]

Titanium(IV) ethoxide (2.119 mL, 10.14 mmol) was added to a solution of 6-bromo-2',3',5',6'-tetrahydrospiro[indene-2,4'-pyran]-1(3 H)-one (Intermediate 10, 1.14 g, 4.05 mmol) and 2-methyl-2-propanesulfinamide (0.688 g, 5.68 mmol) in 2-methyl-tetrahydrofuran (12 mL) and the resulting mixture was stirred at 70° C. overnight. When cooled to r.t., MeOH (1.5 mL), sat. aq. NaHCO$_3$ (5 mL) and EtOAc (10 mL) were added. The mixture was stirred for 1 h, then filtered through diatomaceous earth. The filter cake was washed with EtOAc (3×10 mL). The combined organics were washed with brine (30 mL), dried over MgSO$_4$, filtered, concentrated and purified on a silica gel column eluted with 0-40% EtOAc in heptane to give 545 mg (35% yield) of the title compound; $^1$H NMR (400 MHz, DMSO-d$_6$) δ ppm 8.54 (br. s., 1 H), 7.80 (dd, 1 H), 7.51 (d, 1 H), 3.88 (dd, 2 H), 3.51 (m, 2 H), 3.14 (s, 2 H), 1.38 (m, 2 H), 1.24 (m, 11 H), MS (ES+) m/z 384 [M+H]$^+$.

Step 2: 6-Bromo-2',3',5',6'-tetrahydrospiro[indene-2,4'-pyran]-1(3 H)-imine

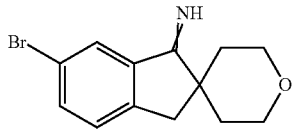 [SMILES: N=C1c2cc(Br)ccc2CC12CCOCC2]

HCl (4M in 1,4-dioxane) (0.683 mL, 2.73 mmol) was added to a solution of N-(5-bromo-2',3',5',6'-tetrahydrospiro[indene-2,4'-pyran]-3(1 H)-ylidene)-2-methylpropane-2-sulfinamide (Example 25 Step 1, 105 mg, 0.27 mmol) in anhydrous 1,4-dioxane (1 mL) and the resulting mixture was stirred under a nitrogen atmosphere at r.t. overnight. Et$_2$O (3 mL) was added, the precipitate was filtered off, washed with Et$_2$O and then dissolved in DCM (5 mL) and sat. aq. NaHCO$_3$ (5 mL). The mixture was poured into a phase separator, the organic layer was collected and concentrated to give the title compound that was used in the next step without any further purification.

Step 3: 6'-Bromo-5-methyl-2",3",5",6"-tetrahydro-3'H-dispiro[imidazole-2,1'-indene-2',4"-pyran]-4(3 H)-thione

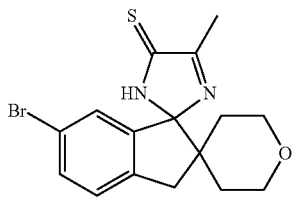 [SMILES: CC1=NC2(NC1=S)c1cc(Br)ccc1CC21CCOCC1]

6-Bromo-2',3',5',6'-tetrahydrospiro[indene-2,4'-pyran]-1(3 H)-imine (Example 25 Step 2, 235 mg, 0.84 mmol) and 2-oxopropanethioamide (Intermediate 2, 173 mg, 1.68 mmol) were taken up in anhydrous MeOH (5 mL) and the resulting mixture was stirred at 60° C. under a nitrogen atmosphere for 3 h. When cooled to r.t. the mixture was concentrated and purified on a silica gel column eluted with 0-50% EtOAc in heptane to give 385 mg (95% yield) of the title compound; $^1$H NMR (500 MHz, DMSO-d$_6$) δ ppm 12.40 (br. s, 1 H), 7.53 (dd, 1 H), 7.36 (d, 1 H), 7.03 (d, 1 H), 3.71 (td, 2 H), 3.44 (m, 2 H), 3.15 (m, 2 H), 2.29 (s, 3 H), 1.64 (s, 1 H), 1.55 (s, 1 H), 1.27 (m, 2 H); MS (ES+) m/z 365 [M+H]$^+$.

Step 4: 6'-Bromo-5-methyl-2",3",5",6"-tetrahydro-3'H-dispiro[imidazole-2,1'-indene-2',4"-pyran]-4-amine

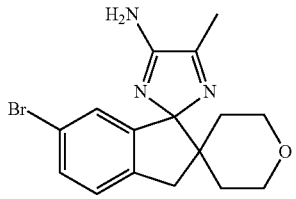 [SMILES: CC1=NC2(N=C1N)c1cc(Br)ccc1CC21CCOCC1]

6'-Bromo-5-methyl-2'',3'',5'',6''-tetrahydro-3'H-dispiro[imidazole-2,1'-indene-2',4''-pyran]-4(3H)-thione (Example 25 Step 3, 415 mg, 1.14 mmol) was taken up in NH₃ (7M in MeOH, 13 mL, 91 mmol) and the resulting mixture was heated in a microwave reactor at 120° C. for 2×1 h. The mixture was concentrated and the resulting residue was taken up in NH₃ (7M in MeOH, 13 mL, 91 mmol) and then heated again for 1 h at 120° C. The mixture was concentrated and the resulting residue was taken up in DCM (10 mL) and sat. aq. NaHCO₃ (5 mL) and poured into a phase separator. The organic layer was collected, concentrated and purified on a silica gel column eluted with 0-10% (0.1M NH₃ in MeOH) in DCM to give 295 mg (75% yield) of the title compound: $^1$H NMR (400 MHz, DMSO-$d_6$) δ ppm 7.36 (dd, 1 H), 7.27 (d, 1 H), 6.68 (d, 1 H), 6.65 (br. s, 1 H), 3.65 (m, 2 H), 3.46 (m, 1 H), 3.38 (m, 1 H), 3.15 (m, 1 H), 3.00 (m, 1 H), 2.18 (s, 3 H), 1.66 (td, 1 H), 1.19 (m, 3 H); MS (ES+) m/z 348[M+H]$^+$.

Example 26a

6'-(3-Chlorophenyl)-5-methyl-2'',3'',5'',6''-tetrahydro-3'H-dispiro[imidazole-2,1'-indene-2',4''-pyran]-4-amine

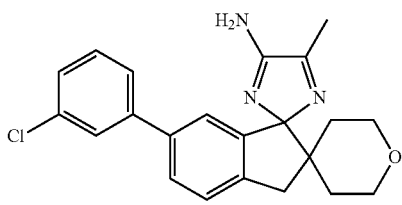 [SMILES: CC1=NC2(N=C1N)c1cc(-c3cccc(Cl)c3)ccc1CC21CCOCC1]

A mixture of 6'-bromo-5-methyl-2'',3'',5'',6''-tetrahydro-3'H-dispiro[imidazole-2,1'-indene-2',4''-pyran]-4-amine (Example 25, 75 mg, 0.22 mmol), 3-chlorophenylboronic acid (40.4 mg, 0.26 mmol), [1,1'-bis(diphenylphosphino)ferrocene]palladium(II) chloride (8.86 mg, 10.77 μmol), 2 M aq. K₂CO₃ (0.215 mL, 0.43 mmol) and 1,4-dioxane (2 mL) were mixed in a vial and heated in a microwave reactor at 130° C. for 15 min. When cooled to r.t., the mixture was diluted with brine (3 mL) and extracted with DCM (3×3 mL). The combined organics were concentrated and the resulting residue was purified by preparative chromatography. The fractions containing the title compound were pooled, the solvent removed in vacuo, and the resulting aqueous residue was extracted with DCM (3×3 mL). The combined organics were passed through a phase separator and concentrated. The resulting residue was taken up in MeOH (2 mL) and dried in a vacuum oven at 40° C. over a weekend to give 36 mg (44% yield) of the title compound; $^1$H NMR (400 MHz, DMSO-$d_6$) δ ppm 7.55 (t, 1 H), 7.49 (m, 2 H), 7.39 (m, 3 H), 6.80 (d, 1 H), 6.61 (br. s, 1 H), 3.66 (m, 2 H), 3.48 (m, 1 H), 3.40 (td, 1 H), 3.22 (d, 1 H), 3.08 (d, 1 H), 2.19 (s, 3 H), 1.72 (td, 1 H), 1.22 (m, 3 H); MS (ES+) m/z 380 [M+H]$^+$.

Example 26c

6'-(3-Chloro-4-fluorophenyl)-5-methyl-2'',3'',5'',6''-tetrahydro-3'H-dispiro[imidazole-2,1'-indene-2',4''-pyran]-4-amine

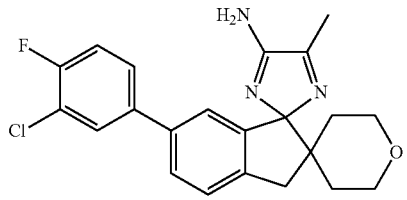 [SMILES: CC1=NC2(N=C1N)c1cc(-c3ccc(F)c(Cl)c3)ccc1CC21CCOCC1]

The title compound was synthesized as described for Example 26a in 42% yield, starting from 6'-bromo-5-methyl-2'',3'',5'',6''-tetrahydro-3'H-dispiro[imidazole-2,1'-indene-2',4''-pyran]-4-amine (Example 25, 75 mg, 0.22 mmol) and 3-chloro-4-fluorobenzeneboronic acid (45.1 mg, 0.26 mmol); $^1$H NMR (400 MHz, DMSO-$d_6$) δ ppm 7.72 (dd, 1 H), 7.52 (m, 2 H), 7.42 (m, 2 H), 6.80 (d, 1 H), 6.60 (br. s, 1 H), 3.66 (m, 2 H), 3.48 (t, 1 H), 3.40 (m, 1 H), 3.20 (m, 1 H), 3.07 (m, 1 H), 2.19 (s, 3 H), 1.71 (td, 1 H), 1.23 (m, 3 H); MS (ES+) m/z 398 [M+H]$^+$.

Example 27

6'-Bromo-4,4-difluoro-5''-methyl-3'H-dispiro[cyclohexane-1,2'-indene-1',2''-imidazol]-4''-amine Step 1: N-(5'-Bromo-4,4-difluorospiro[cyclohexane-1,2'-indene]-3'(1'H)-ylidene)-2-methylpropane-2-sulfinamide

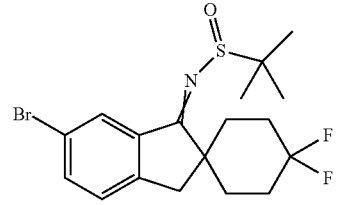 [SMILES: CC(C)(C)S(=O)N=C1c2cc(Br)ccc2CC12CCC(F)(F)CC2]

6'-Bromo-4,4-difluorospiro[cyclohexane-1,2'-inden]-1'(3'H)-one (Intermediate 11, 819 mg, 2.60 mmol), 2-methylpropane-2-sulfinamide (630 mg, 5.20 mmol) and titanium ethoxide (1.874 mL, 9.10 mmol) were dissolved in 2-MeTHF (9 mL) and heated to 120° C. with MW for 1 h. EtOAc (20 mL) and NaHCO₃ (aq., sat, 2 mL) were added under stirring. The mixture was left to stand without stirring for 1 h. The organic phase was collected by filtration, dried over MgSO₄ and concentrated. Flash chromatography with a gradient of 0-50% EtOAc in n-heptane gave the title compound (340 mg, 31% yield). $^1$H NMR (500 MHz, DMSO-$d_6$) δ ppm 1.25 (s, 9 H), 1.56-1.71 (m, 2 H), 2.10 (br. s., 6 H), 3.12 (s, 2 H), 7.49 (d, 1 H), 7.81 (dd, 1 H), 8.43-8.63 (m, 1 H). MS (ES+) m/z 418 [M+H]$^+$.

Step 2: 6'-Bromo-4,4-difluorospiro[cyclohexane-1,2'-inden]-1'(3'H)-imine

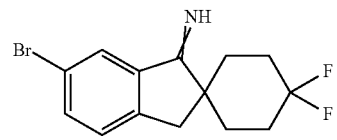 [SMILES: N=C1c2cc(Br)ccc2CC12CCC(F)(F)CC2]

HCl (4M in 1,4-dioxane, 3.38 mL, 13.51 mmol) was added to a solution of N-(5'-bromo-4,4-difluorospiro[cyclohexane-1,2'-indene]-3'(1'H)-ylidene)-2-methylpropane-2-sulfinamide (Example 27 Step 1, 565 mg, 1.35 mmol) in anhydrous 1,4-dioxane (4 mL). The resulting mixture was stirred under a nitrogen atmosphere at r.t. for 90 min. Et$_2$O (2 mL) was added and the precipitate was filtered off and washed with Et$_2$O. The solid was partitioned between DCM (8 mL) and sat. aq. NaHCO$_3$ (8 mL). The phases were separated and the organic layer was dried over MgSO$_4$ and concentrated to give 6'-bromo-4,4-difluorospiro[cyclohexane-1,2'-inden]-1' (3'H)-imine (418 mg, 99% yield), that was used directly in the next step. MS (ES+) m/z 314 [M+H]$^+$.

Step 3: 6'-Bromo-4,4-difluoro-5''-methyl-3'H-dispiro [cyclohexane-1,2'-indene-1,2''-imidazole]-4''(3''H)-thione

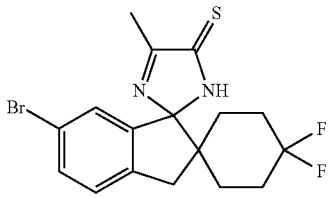 [SMILES: CC1=NC2(NC1=S)c1cc(Br)ccc1CC21CCC(F)(F)CC1]

6'-Bromo-4,4-difluorospiro[cyclohexane-1,2'-inden]-1' (3'H)-imine (Example 27 Step 2, 418 mg, 1.33 mmol) and 2-oxopropanethioamide (Intermediate 2, 412 mg, 3.99 mmol) were dissolved in dry MeOH (6 mL) and the resulting solution was heated at 60° C. under N$_2$(g) overnight. The reaction mixture was allowed to cool to r.t. A precipitate formed which was filtered off and dried in vacuo, yielding the title compound (387 mg, 73% yield). $^1$H NMR (500 MHz, DMSO-d$_6$) δppm 1.29-1.47 (m, 2 H), 1.49-1.62 (m, 2 H), 1.81-2.08 (m, 4 H), 2.28 (s, 3 H), 3.09 (d, 1 H), 3.15 (d, 1 H), 7.02 (d, 1 H), 7.33 (d, 1 H), 7.53 (d, 1 H), 12.42 (s, 1 H); MS (ES+) m/z 399.0 [M+H]$^+$.

Step 4: 6'-Bromo-4,4-difluoro-5''-methyl-3'H-dispiro [cyclohexane-1,2'-indene-1',2''-imidazol]-4''-amine

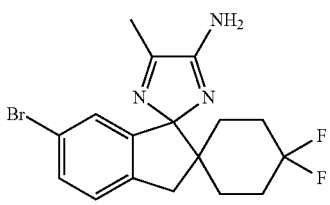 [SMILES: CC1=NC2(N=C1N)c1cc(Br)ccc1CC21CCC(F)(F)CC1]

6'-Bromo-4,4-difluoro-5''-methyl-3'H-dispiro[cyclohexane-1,2'-indene-1',2''-imidazole]-4''(3''H)-thione (Example 27 Step 3, 57 mg, 0.14 mmol) in ammonia (7 M in MeOH) (1.5 mL, 10.5 mmol) was heated in a microwave reactor for 40 min at 100° C. The mixture was concentrated, re-dissolved in ammonia (7 M in MeOH) (1.5 mL, 10.5 mmol) and heated with MW for 40 min at 100° C. The mixture was concentrated. Purification of the crude product by flash chromatography using a gradient of CHCl$_3$/MeOH 40:1-30:1-20:1 gave the title compound (21 mg, 39% yield): $^1$H NMR (500 MHz, DMSO-d$_6$) δ ppm 1.15-1.29 (m, 1 H), 1.47 (m, 2 H), 1.61-1.73 (m, 1 H), 1.73-1.97 (m, 4 H), 2.18 (s, 3 H), 2.98 (d, 1 H), 3.08 (d, 1H), 6.67 (m, 3 H), 7.26 (d, 1 H), 7.37 (dd, 1 H); MS (ES+) m/z 382 [M+H]$^+$.

Example 28c

6'-(5-Chloropyridin-3-yl)-4,4-difluoro-5''-methyl-3'H-dispiro[cyclohexane-1,2'-indene-1',2''-imidazol]-4''-amine

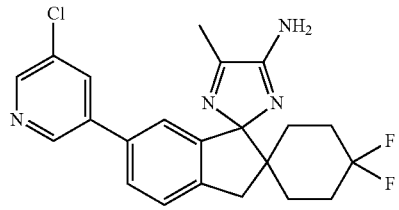 [SMILES: CC1=NC2(N=C1N)c1cc(-c3cncc(Cl)c3)ccc1CC21CCC(F)(F)CC1]

Sodium tetrachloropalladate(II) (7.70 mg, 0.03 mmol), 3-(di-tert-butylphosphonium)propane sulfonate (7.02 mg, 0.03 mmol), 6'-bromo-4,4-difluoro-5''-methyl-3'H-dispiro [cyclohexane-1,2'-indene-1',2''-imidazol]-4''-amine (Example 27, 100 mg, 0.26 mmol) and 5-chloropyridin-3-ylboronic acid (52.0 mg, 0.31 mmol) were added to a microwave vial and dissolved in 2-methyl-tetrahydrofuran (1 mL). K$_2$CO$_3$ (2M aq) (0.392 mL, 0.78 mmol) was added and the vial was flushed with Ar (g) and capped. The mixture was heated in a microwave reactor at 100° C. for 45 min. Additional sodium tetrachloropalladate(II) (7.70 mg, 0.03 mmol), 3-(di-tert-butylphosphonium)propane sulfonate (7.02 mg, 0.03 mmol) and 0.5 equiv. 5-chloropyridin-3-ylboronic acid was added to the reaction mixture and it was heated to 90° C. for 1 h. Water was added and the residue was extracted with EtOAc (×3). The organic phases were dried with MgSO$_4$ and concentrated. The crude product was purified on a silica gel column (4 g SiO$_2$, 7 M NH$_3$ in MeOH in DCM 1:9/DCM 0-100%) to give the title compound (41 mg, 38% yield). $^1$H NMR (500 MHz, DMSO-d$_6$) δ ppm 1.23-1.32 (m, 1 H), 1.52 (br. s., 2 H), 1.72 (br. s., 1 H), 1.79-1.98 (m, 4 H), 2.19 (s, 3 H), 3.08 (d, 1 H), 3.16 (d, 1 H), 6.62 (br. s., 2 H), 6.90 (d, 1 H), 7.43 (d, 1 H), 7.60 (dd, 1 H), 8.10 (t, 1 H), 8.57 (d, 1 H), 8.72 (d, 1 H). MS (APCI+) m/z 415.2 [M+H]$^+$.

Example 28d

N-(4''-Amino-4,4-difluoro-5''-methyl-3'H-dispiro [cyclohexane-1,2'-indene-1',2''-imidazol]-6'-yl)-5-chloropyridine-2-carboxamide Step 1: 4,4-difluoro-5''-methyl-3'H-dispiro[cyclohexane-1,2'-indene-1',2''-imidazole]-4'',6'-diamine

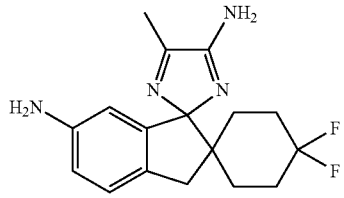 [SMILES: CC1=NC2(N=C1N)c1cc(N)ccc1CC21CCC(F)(F)CC1]

6'-Bromo-4,4-difluoro-5''-methyl-3'H-dispiro[cyclohexane-1,2'-indene-1',2''-imidazol]-4''-amine (Example 27, 116 mg, 0.30 mmol), trans-4-hydroxy-L-proline (40 mg, 0.30 mmol), copper(I) iodide (29 mg, 0.15 mmol) and K$_2$CO$_3$ (126 mg, 0.91 mmol) were mixed in dry dimethylsulfoxide (3 mL) in a microwave vial. The mixture was stirred under argon at r.t. for 30 min. Ammonia (30-33% in H$_2$O) (0.285 mL, 4.55 mmol) was added, the vial was sealed and heated at 110° C. for 3 h in a microwave synthesizer. Additional copper(I)

iodide (29 mg, 0.15 mmol) and trans-4-hydroxy-L-proline (40 mg, 0.30 mmol) were added and the mixture was then heated to 110° C. for 4 h. The mixture was diluted with EtOAc (10 mL) and washed with brine (10 mL). The aqueous layer was extracted with EtOAc (2×10 mL). The organic layers were combined and concentrated in vacuo. The residue was applied on a short column of silica (4 g u) SiO$_2$) and eluted with 0-100% (7 M NH$_3$ in MeOH and DCM 1:9) in DCM to give the title compound (46 mg, 48% yield): $^1$H NMR (500 MHz, DMSO-d$_6$) δ ppm 1.17 (t, 1 H), 1.48 (br. s., 2 H), 1.64-1.96 (m, 5 H), 2.11-2.17 (m, 3 H), 2.83 (d, 1 H), 2.90 (d, 1 H), 4.75 (s, 2 H), 5.83 (d, 1 H), 6.37 (dd, 1 H), 6.50 (s, 2 H), 6.90 (d, 1 H); MS (ES+) m/z 319.1 [M+H]$^+$.

Step 2: N-(4"-Amino-4,4-difluoro-5"-methyl-3'H-dispiro[cyclohexane-1,2'-indene-1,2"-imidazol]-6'-yl)-5-chloropyridine-2-carboxamide

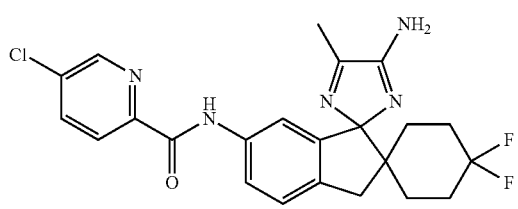 [SMILES: CC1=NC2(N=C1N)c1cc(NC(=O)c3ccc(Cl)cn3)ccc1CC21CCC(F)(F)CC1]

N-(3-Dimethylaminopropyl)-N'-ethylcarbodiimide hydrochloride (36 mg, 0.19 mmol) was added to a suspension of 5-chloropicolinic acid (27 mg, 0.17 mmol) in DCM (0.5 mL). The obtained orange solution was stirred for 5 min and then added dropwise over 2 min to an ice-cooled solution of 4,4-difluoro-5"-methyl-3'H-dispiro[cyclohexane-1,2'-indene-1',2"-imidazole]-4",6'-diamine (Example 28d Step 1, 46 mg, 0.14 mmol) and 2M aq. HCl (0.072 mL, 0.14 mmol) in DMF (0.5 mL). The mixture was stirred at 0° C. for 10 min and was then allowed to reach r.t. overnight. The solvent was evaporated. The crude was purified using preparative chromatography to give the title compound (11 mg, 17% yield): $^1$H NMR (500 MHz, DMSO-d$_6$) δ ppm 1.23 (d, 1 H), 1.51 (d, 2 H), 1.66-1.98 (m, 5 H), 2.18 (s, 3 H), 2.99 (d, 1 H), 3.08 (d, 1 H), 6.63 (br. s., 1 H), 7.23-7.29 (m, 2 H), 7.62 (d, 1 H), 8.10 (d, 1 H), 8.18 (dd, 1 H), 8.74 (s, 1 H), 10.50 (s, 1 H); MS (APCI+) m/z 458.1 [M+H]$^+$.

Example 28h 4,4-Difluoro-5"-methyl-6'-[5-(prop-1-yn-1-yl)pyridin-3-yl]-3'H-dispiro[cyclohexane-1,2'-indene-1',2"-imidazol]-4"-amine

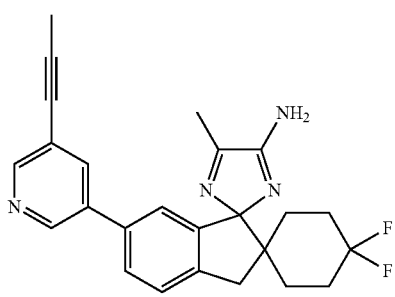 [SMILES: CC#Cc1cncc(-c2ccc3c(c2)C2(N=C(C)C(N)=N2)C2(CCC(F)(F)CC2)C3)c1]

The title compound (26 mg, 24% yield) was prepared as described for Example 28c starting from 6'-bromo-4,4-difluoro-5"-methyl-3'H-dispiro[cyclohexane-1,2'-indene-1',2"-imidazol]-4"-amine (Example 27, 100 mg, 0.26 mmol) and 5-(prop-1-ynyl)pyridin-3-ylboronic acid (Intermediate 15, 50.5 mg, 0.31 mmol). $^1$H NMR (500 MHz, DMSO-d$_6$) δ ppm 1.22-1.30 (m, 1 H), 1.51 (br. s., 2 H), 1.71 (br. s., 1 H), 1.78-1.97 (m, 4 H), 2.09 (s, 3 H), 2.19 (s, 3 H), 3.06 (d, 1 H), 3.15 (d, 1 H), 6.61 (s, 2 H), 6.85 (d, 1 H), 7.41 (d, 1 H), 7.56 (dd, 1 H), 7.91 (t, 1 H), 8.51 (d, 1 H), 8.67 (d, 1 H). MS (APCI+) m/z 419.2 [M+H]$^+$.

Example 29

5'-bromo-4-methoxy-5"-methyldispiro[cyclohexane-1,2'-[1]benzofuran-3',2"-imidazol]-4"-amine Step 1: N-(5-Bromo-4'-methoxy-3H-spiro[benzofuran-2,1'-cyclohexane]-3-ylidene)-2-methylpropane-2-sulfinamide

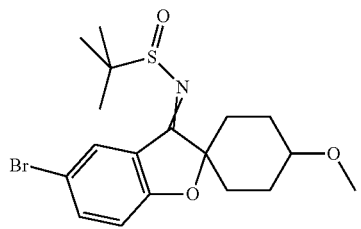 [SMILES: COC1CCC2(CC1)Oc1ccc(Br)cc1C2=NS(=O)C(C)(C)C]

To a mixture of 5-bromo-4'-methoxy-3H-spiro[benzofuran-2,1'-cyclohexan]-3-one (Intermediate 12, 2.8 g, 9.00 mmol) and 2-methylpropane-2-sulfinamide (2.024 g, 16.20 mmol) in methyl THF (15 mL) was added titanium ethoxide (3.71 mL, 18.00 mmol) and the reaction was heated to reflux. After 21 h the reaction was allowed to cool to r.t. whereafter it was diluted with EtOAc (150 mL). Water (12 mL) was added dropwise over 10 min under vigorous stirring and then the mixture was left standing without stirring for 1.5 h. The solids were filtered off and the organics were evaporated. The crude product was purified by flash chromatography using a gradient of 0%-50% EtOAc in heptane, yielding 2.41 g of the title compound (65% yield): $^1$H NMR (500 MHz, CDCl$_3$) δ ppm 1.33 (s, 9 H), 1.81 (m, 6 H), 2.12 (d, 2 H), 3.33 (m, 1 H), 3.42 (s, 3 H), 6.94 (d, 1 H), 7.59 (dd, 1 H), 8.53 (m, 1 H); MS (ES+) m/z 415 [M+H]$^+$.

Step 2: 5-Bromo-4'-methoxy-3H-spiro[benzofuran-2,1'-cyclohexan]-3-imine

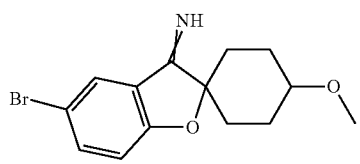 [SMILES: COC1CCC2(CC1)Oc1ccc(Br)cc1C2=N]

To a solution of N-(5-bromo-4'-methoxy-3H-spiro[benzofuran-2,1'-cyclohexane]-3-ylidene)-2-methylpropane-2-sulfinamide (Example 29 Step 1, 2 g, 4.83 mmol) in anhydrous 1,4-dioxane (40 mL) was added 4M HCl in 1,4-dioxane (12.07 mL, 48.27 mmol) and the resulting mixture was stirred under a nitrogen atmosphere at rt overnight. Et$_2$O (30 mL) was added and the precipitate was filtered off and washed with Et$_2$O, then partitioned between DCM (40 mL) and sat. aq. NaHCO$_3$ (40 mL). The phases were separated and the organic layer concentrated, yielding 1.37 g of the crude title compound which was used immediately in the next step: MS (EI) m/z 309 M$^+$.

Step 3: 5'-Bromo-4-methoxy-5"-methyldispiro[cyclohexane-1,2'-[1]benzofuran-3',2"imidazole]-4" (3"H)-thione

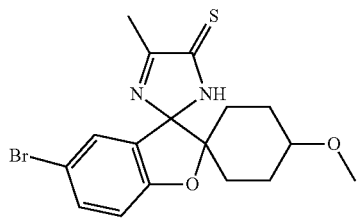 [SMILES: COC1CCC2(CC1)Oc1ccc(Br)cc1C21N=C(C)C(=S)N1]

5-Bromo-4'-methoxy-3H-spiro[benzofuran-2,1'-cyclohexan]-3-imine (Example 29 Step 2, 1.37 g, 4.41 mmol) and 2-oxopropanethioamide (Intermediate 2, 0.909 g, 8.81 mmol) were dissolved in dry MeOH (25 mL) and the resulting orange solution was heated at 60° C. under a nitrogen atmosphere overnight. More 2-oxopropanethioamide (400 mg) was added and stirring continued. After 24 h the mixture was allowed to cool to r.t. and the solvent was evaporated. Purification by flash chromatography using a gradient of 0-100% EtOAc in heptane afforded 373 mg of the title compound (21% yield). $^1$H NMR (500 MHz, DMSO-d$_6$) δ ppm 1.35 (m, 1 H), 1.47 (m, 3 H), 1.87 (m, 2 H), 1.97 (m, 2 H), 2.29 (s, 3 H), 3.13 (s, 3 H), 4.11 (m, 1 H), 6.99 (d, 1 H), 7.16 (d, 1 H), 7.48 (dd, 1 H); MS (ES+) m/z 396 [M+H]$^+$.

Step 4: 5'-Bromo-4-methoxy-5"-methyldispiro[cyclohexane-1,2'-[1]benzofuran-3',2"-imidazol]-4"-amine

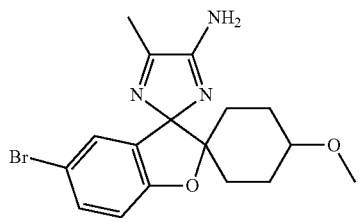 [SMILES: COC1CCC2(CC1)Oc1ccc(Br)cc1C21N=C(C)C(N)=N1]

A mixture of 5'-bromo-4-methoxy-5"-methyldispiro[cyclohexane-1,2'-[1]benzofuran-3',2"-imidazole]-4"(3"H)-thione (Example 29 Step 3, 365 mg, 0.92 mmol) and 7M ammonia in MeOH (10 mL, 70.00 mmol) was prepared in a microwave vial. The vial was sealed and the reaction was heated at 120° C. for 30 min in a microwave reactor. The mixture was concentrated and the residue was dissolved in 7M ammonia in MeOH (4 mL) and heated once more at 120° C. for 30 min using MW. Again, the mixture was concentrated, 7M ammonia in MeOH (10 mL, 70.00 mmol) was added and the mixture was heated at 120° C. The mixture was concentrated and the crude product was dissolved in 20% MeOH in DCM and filtered through a silica pad and eluted is with 20% MeOH in DCM. After concentration of the organic layer, DCM was added to the residue. A solid was formed which was filtered off and washed with DCM, yielding 94 mg of the title compound (27% yield). The mother liquor was concentrated, Et$_2$O was added and the solid was filtered off and dried, yielding a second crop of the title compound (85 mg, 24% yield). $^1$H NMR (500 MHz, DMSO-d$_6$) δ ppm 1.19 (d, 1 H), 1.43 (m, 3 H), 1.80 (d, 2 H), 1.95 (m, 2 H), 2.20 (s, 3 H), 3.07 (d, 1 H), 3.21 (s, 3 H), 6.68 (d, 1 H), 6.74 (br. s., 2 H), 6.87 (d, 1 H), 7.31 (dd, 1 H); MS (ES+) m/z 379 [M+H]$^+$.

Example 30b

5'-(3-Chlorophenyl)-4-methoxy-5"-methyldispiro[cyclohexane-1,2"-[1]benzofuran-3',2"-imidazol]-4"-amine

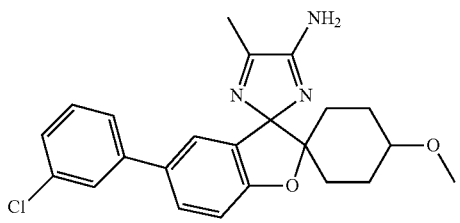 [SMILES: COC1CCC2(CC1)Oc1ccc(-c3cccc(Cl)c3)cc1C21N=C(C)C(N)=N1]

3-Chlorophenylboronic acid (47.7 mg, 0.31 mmol), 5'-bromo-4-methoxy-5"-methyldispiro-[cyclohexane-1,2'-[1]benzofuran-3',2"-imidazol]-4"-amine (Example 29, 77 mg, 0.20 mmol) and (1,1'-bis(diphenylphosphino)ferrocene)-dichloropalladium(II) (8.37 mg, 10.18 μmol) were put in a microwave vial and dissolved in dry dioxane (2 mL). A 2M aq. solution of K$_2$CO$_3$ (0.204 mL, 0.41 mmol) was added, the mixture was degassed with nitrogen gas and the mixture was heated at 120° C. for 20 min in a microwave reactor. The mixture was combined with a second reaction from 10 mg (0.03 mmol) of 5'-bromo-4-methoxy-5"-methyldispiro[cyclohexane-1,2'-[1]benzofuran-3',2"-imidazol]-4"-amine and concentrated. EtOAc (7 mL) and a sat. aq. solution of NaHCO$_3$ (5 mL) was added and the phases were separated. The aqueous phase was extracted with EtOAc (5 mL) and the combined organic layers were dried over MgSO$_4$, filtered and evaporated. The crude product was purified by preparative chromatography, yielding 38.5 mg of the title compound (41% yield). $^1$H NMR (500 MHz, DMSO-d$_6$) δ ppm 1.21 (m, 1 H), 1.46 (m, 3 H), 1.82 (m, 2 H), 1.98 (m, 2 H), 2.21 (s, 3 H), 3.09 (m, 1 H), 3.22 (s, 3 H), 6.71 (br. s., 2 H), 6.85 (d, 1 H), 6.98 (d, 1 H), 7.32 (m, 1 H), 7.40 (s, 1 H), 7.47 (m, 1 H), 7.51 (m, 1 H), 7.54 (s, 1 H); MS (APCI+) m/z 410 [M+H]$^+$.

Example 30d

5'-(5-Chloropyridin-3-yl)-4-methoxy-5"-methyldispiro[cyclohexane-1,2'-[1]benzofuran-3',2"-imidazol]-4"-amine

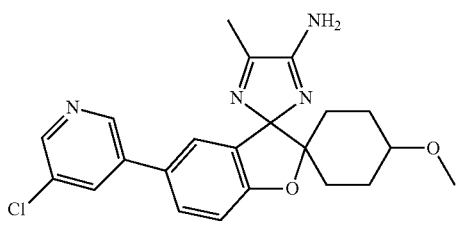 [SMILES: COC1CCC2(CC1)Oc1ccc(-c3cncc(Cl)c3)cc1C21N=C(C)C(N)=N1]

Sodium tetrachloropalladate (II) (2.294 mg, 7.80 μmol), 3-(di-tert-butylphosphonium)propane sulfonate (4.19 mg, 0.02 mmol), 5-chloropyridin-3-ylboronic acid (25.8 mg, 0.16 mmol) and 5'-bromo-4-methoxy-5"-methyldispiro[cyclohexane-1,2'-[1]benzofuran-3',2"-imidazol]-4"-amine (Example 29, 59 mg, 0.16 mmol), was added to a vial. 2-Methyltetrahydrofuran (1 mL) and 2 M aq. $K_2CO_3$ (0.234 mL, 0.47 mmol) was added and the mixture was degassed by bubbling nitrogen gas through the solution. The vial was sealed and heated in a microwave reactor at 90° C. for 30 min and the crude mixture was combined with a second reaction from 20 mg (0.05 mmol) of 5'-bromo-4-methoxy-5"-methyldispiro [cyclohexane-1,2'-[1]benzofuran-3',2"-imidazol]-4"-amine. Water (5 mL) and EtOAc (5 mL) was added and the phases were separated. The aqueous phase was extracted with EtOAc (5 mL) and the combined organic layers were dried over $MgSO_4$, filtered and evaporated. Purification by flash chromatography using a 0-10% gradient of MeOH, containing 1.2% 7M $NH_3$ in MeOH, in DCM afforded 36 mg of the title compound (56% yield): $^1$H NMR (500 MHz, DMSO-$d_6$) δ ppm 1.22 (m, 1 H), 1.46 (m, 3 H), 1.81 (m, 2 H), 1.97 (m, 2 H), 2.21 (s, 3 H), 3.10 (m, 1 H), 3.22 (s, 3 H), 6.71 (br. s., 2 H), 7.01 (m, 2 H), 7.61 (dd, 1 H), 8.08 (t, 1 H), 8.51 (d, 1 H), 8.72 (d, 1 H); MS (APCI+) m/z 411 [M+H]$^+$.

Example 30e

4-Methoxy-5"-methyl-5'-[5-(prop-1-yn-1-yl)pyridin-3-yl]dispiro[cyclohexane-1,2'-[1]benzofuran-3',2"-imidazol]-4"-amine

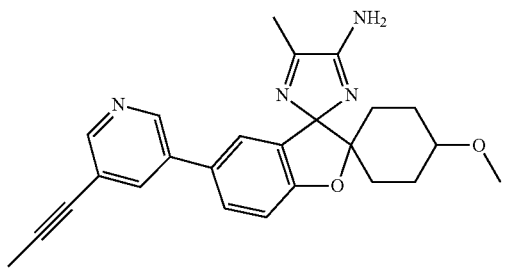 [SMILES: CC#Cc1cncc(-c2ccc3c(c2)C2(N=C(C)C(N)=N2)C2(CCC(OC)CC2)O3)c1]

5-(Prop-1-ynyl)pyridin-3-ylboronic acid (Intermediate 15, 57.4 mg, 0.36 mmol), (1,1'-bis(diphenylphosphino)ferrocene)-dichloropalladium(II) (9.79 mg, 0.01 mmol), cesium carbonate (233 mg, 0.71 mmol) and 5'-bromo-4-methoxy-5"-methyldispiro[cyclohexane-1,2'-[1]benzofuran-3',2"-imidazol]-4"-amine (Example 29, 90 mg, 0.24 mmol) were dissolved in a 6:3:1 mixture of DME:EtOH:water (2 mL) and heated at 150° C. in a microwave reactor for 15 min. The mixture was concentrated and the residue was partitioned between EtOAc (7 mL) and sat. aq. $NaHCO_3$ (5 mL). The layers were separated and the organic layer was dried over $MgSO_4$ and concentrated. Purification of the crude product by preparative chromatography afforded 41 mg of the title compound (42% yield). $^1$H NMR (500 MHz, DMSO-$d_6$) δ ppm 1.22 (m, 1 H), 1.46 (m, 3 H), 1.81 (m, 2 H), 1.98 (m, 2 H), 2.09 (s, 3 H), 2.21 (s, 3 H), 3.10 (m, 1 H), 3.22 (s, 3 H), 6.70 (s, 2 H), 6.95 (d, 1 H), 6.99 (d, 1 H), 7.56 (d, 1 H), 7.91 (t, 1 H), 8.47 (d, 1 H), 8.67 (d, 1 H); MS (APCI+) m/z 415 [M+H]$^+$.

Example 45

6'-Bromo-5-methyl-5",6"-dihydro-4"H-dispiro[imidazole-2,4'-chromene-2',3"-pyran]-4-amine Step 1: N-(6-Bromo-5',6'-dihydro-4'H-spiro [chromene-2,3'-pyran]-4(3H)-ylidene)-2-methylpropane-2-sulfinamide

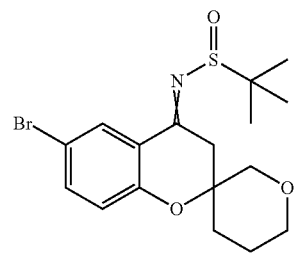 [SMILES: CC(C)(C)S(=O)N=C1CC2(CCCOC2)Oc2ccc(Br)cc21]

6-Bromo-5',6'-dihydro-4'H-spiro[chromene-2,3'-pyran]-4 (3H)-one (Intermediate 26, 2.007 g, 6.75 mmol), 2-methylpropane-2-sulfinamide (1.228 g, 10.13 mmol) and titanium ethoxide (2.78 mL, 13.51 mmol) were dissolved in methyl THF (16 mL) and heated to reflux for 19 h. The reaction was left to cool down to r.t. when EtOAc (80 mL) and $NaHCO_3$ (sat., 5 mL) were added under stirring. The mixture was let standing for 1 h. The organic phase was collected by filtration, dried over $MgSO_4$ and concentrated. The crude product was purified by flash chromatography using a gradient of 0-50% EtOAc in heptane. The desired fractions were evaporated to give the title compound as a mixture of diastereomers in a ratio 1:1 as determined by NMR (2.63 g, 97% yield): $^1$H NMR (500 MHz, CDCl$_3$) δ ppm 1.34 (s, 9H), 1.50-1.57 (m, 0.5H), 1.60-1.68 (m, 1H), 1.73 (m, 0.5H) 1.87-2.09 (m, 2H), 2.99 (d, 0.5H), 3.26 (d, 0.5H), 3.33 (d, 0.5H), 3.45-3.61 (m, 2H), 3.64 (d, 0.5H), 3.77-3.93 (m, 2H), 6.88-6.93 (m, 1H), 7.48 (dd, 1H), 7.98 (dd, 1H); MS (ES+) m/z 401.9 [M+H]$^+$.

Step 2: 6-Bromo-5',6'-dihydro-4'H-spiro[chromene-2,3'-pyran]-4(3H)-imine

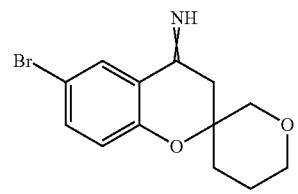 [SMILES: N=C1CC2(CCCOC2)Oc2ccc(Br)cc21]

HCl (4 M in 1,4-dioxane) (0.395 mL, 12.99 mmol) was added to a suspension of N-(6-bromo-5',6'-dihydro-4'H-spiro [chromene-2,3'-pyran]-4(3H)-ylidene)-2-methylpropane-2-sulfinamide (Example 45 Step 1, 520 mg, 1.30 mmol) in anhydrous 1,4-dioxane (6 mL) and the resulting mixture was stirred under a nitrogen atmosphere at r.t. for 2 days. A precipitate was formed. The precipitate was filtered off and washed with Et$_2$O. The solid was then dissolved in DCM and sat. aq. $NaHCO_3$. The mixture was poured into a phase separator, the organic layer was collected and concentrated. The title compound was used directly in the next step without any further purification.

Step 3: 6'-Bromo-5-methyl-5",6"-dihydro-4"H-dispiro[imidazole-2,4'-chromene-2',3"-pyran]-4(3H)-thione

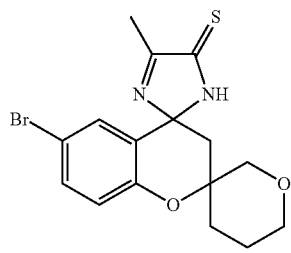 [SMILES: CC1=NC2(CC3(CCCOC3)Oc3ccc(Br)cc32)NC1=S]

2-Oxopropanethioamide (Intermediate 2, 289 mg, 2.80 mmol) and 6-bromo-5',6'-dihydro-4'H-spiro[chromene-2,3'-pyran]-4(3H)-imine (Example 45 Step 2, 331.4 mg, 1.12 mmol) were dissolved in acetonitrile (3 mL) and heated using MW for 20 min to 120° C. The solvent was evaporated under reduced pressure. The crude product was purified by flash chromatography using a gradient of 0-50% EtOAc in heptane but co-eluted with byproducts. The not completely pure product was used as a mixture in the next step.

Step 4: 6'-Bromo-5-methyl-5",6"-dihydro-4"H-dispiro[imidazole-2,4'-chromene-2',3"-pyran]-4-amine

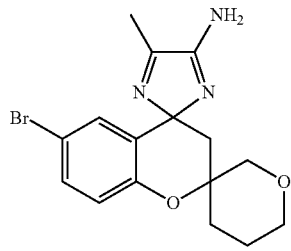 [SMILES: CC1=NC2(CC3(CCCOC3)Oc3ccc(Br)cc32)N=C1N]

6'-Bromo-5-methyl-5",6"-dihydro-4"H-dispiro[imidazole-2,4'-chromene-2',3"-pyran]-4(3H)-thione (Example 45 Step 3, 319 mg, 0.84 mmol) was taken up in ammonia (7M in MeOH, 10 mL, 70.00 mmol) and the resulting mixture was heated in the microwave reactor at 120° C. for 2 h. The solvent was evaporated and ammonia (7M in MeOH, 10 mL, 70.00 mmol) was added and the reaction was heated using MW for 1 h at 120° C. The solvent was evaporated and the resulting residue was taken up in DCM and saturated NaHCO$_3$ and poured into a phase separator. The organic phase was dried and concentrated. The crude product was purified by flash chromatography using a gradient of 0-100% EtOAc in heptane followed by a gradient of 0-40% MeOH with 1% NH$_3$ in DCM. The desired fractions were evaporated to give the title compound (130 mg, 43% yield) as a mixture of diastereomers in a 1:1 ratio as determined by NMR: $^1$H NMR (500 MHz, DMSO-d$_6$) δ ppm 1.41-1.49 (m), 1.76-1.89 (m), 1.89-1.95 (m), 1.95-2.06 (m), 2.21 (s), 2.23 (s), 3.16 (m), 3.41 (d), 3.51 (dd), 3.69 (dd), 3.92 (t), 4.07-4.12 (m), 6.45 (d), 6.47 (d), 6.57 (br. s.), 6.61 (br. s.), 6.82 (d), 7.25 (d), 7.26 (d); MS (ES+) m/z 366.0 [M+H]$^+$.

Separation of the isomers of 6'-bromo-5-methyl-5",6"-dihydro-4"H-dispiro[imidazole-2,4'-chromene-2',3"-pyran]-4-amine The diastereomeric mixture of 6'-bromo-5-methyl-5",6"-dihydro-4"H-dispiro[imidazole-2,4'-chromene-2',3"-pyran]-4-amine (Example 45 Step 4) was separated (3 separate injections) using preparative chromatography (Gilson Prep. system with a XBridge C18 10 μm 50×250 mm column applying a gradient of 15-55% B (100% MeCN) in A (95% 0.05 M NH$_4$OAc in MilliQ water and 5% MeCN) over 15 min at a flow rate of 100 mL/min) to give:
Isomer 1 (0.143 g, 11.5% yield) with undetermined absolute configuration and with retention time 12.5 min: $^1$H NMR (500 MHz, CDCl$_3$) δ ppm 1.54-1.61 (m, 1 H), 1.84 (ddd, 2 H), 1.96-2.06 (m, 1 H), 2.13-2.18 (m, 1 H), 2.36 (s, 3 H), 3.57 (ddd, 1 H), 3.70 (d, 1 H), 3.80-3.86 (m, 1 H), 4.03 (d, 1 H), 6.60 (d, 1 H), 6.88 (d, 1 H), 7.25 (dd, 1 H); MS (ES+) m/z 366.0 [M+H]$^+$.
Isomer 2 (0.109 g, 9% yield) with undetermined absolute configuration and with retention time 13.1 min: $^1$H NMR (500 MHz, CDCl$_3$) δ ppm 1.52-1.60 (m, 1 H), 1.72 (br. s., 2 H), 1.86 (ddd, 1 H), 1.95-2.06 (m, 1 H), 2.20-2.26 (m, 1 H), 2.37 (s, 3 H), 3.57 (ddd, 1 H), 3.66 (d, 1 H), 3.80-3.86 (m, 1 H), 3.95 (d, 1 H), 6.59 (d, 1 H), 6.88 (d, 1 H), 7.25 (dd, 1 H); MS (ES+) m/z 366.0 [M+H]$^+$.

Example 46a

6'-(3-Chlorophenyl)-5-methyl-5",6"-dihydro-4"H-dispiro[imidazole-2,4'-chromene-2',3"-pyran]-4-amine

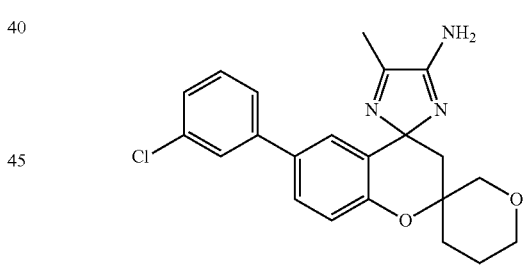

Isomer 1
A mixture of 6'-bromo-5-methyl-5",6"-dihydro-4"H-dispiro[imidazole-2,4'-chromene-2',3"-pyran]-4-amine (Example 45 Isomer 1, 116 mg, 0.32 mmol), 3-chlorophenylboronic acid (64.7 mg, 0.41 mmol), [1,1'-bis(diphenylphosphino)ferrocene]palladium(II) chloride (26.0 mg, 0.03 mmol), K$_2$CO$_3$ (2 M aq) (0.318 mL, 0.64 mmol) and 1,4-dioxane (2 mL) were added to a microwave vial. The vial was capped, evacuated and filled with argon. The vial was heated in a microwave reactor at 130° C. for 20 min. Brine was added and the residue was extracted with DCM (×3), dried with a phase separator and concentrated under reduced pressure. The crude product was purified by preparative chromatography. The desired fractions were concentrated. Water and DCM were added and the layers separated. The organic phase was dried with a phase separator and concentrated to give isomer 1 of the title compound (38.5 mg, 30% yield) with undetermined configuration: ¹H NMR (500 MHz, DMSO-d$_6$) δ ppm 1.44-1.53 (m, 1 H), 1.83-1.92 (m, 3 H), 2.01 (d, 2 H), 2.22 (s, 3 H), 3.41-3.48 (m, 1 H), 3.56 (d, 1 H), 3.67-3.73 (m, 1 H), 3.99 (d, 1 H), 6.58 (s, 1 H), 6.62 (s, 1 H), 6.95 (d, 1 H), 7.31-7.39 (m, 2 H), 7.39-7.47 (m, 3 H); MS (ES+) m/z 396 [M+H]⁺.

Isomer 2

6'-Bromo-5-methyl-5'',6''-dihydro-4''H-dispiro[imidazole-2,4'-chromene-2',3''-pyran]-4-amine (Example 45 Isomer 2, 102 mg, 0.28 mmol) was treated as described for Example 46a, Isomer 1, to give isomer 2 of the title compound (52 mg, 46% yield) with undetermined configuration: ¹H NMR (500 MHz, DMSO-d$_6$) δ ppm 1.45-1.51 (m, 1 H), 1.80-1.91 (m, 3 H), 2.04 (d, 1 H), 2.06-2.11 (m, 1 H), 2.25 (s, 3 H), 3.40-3.47 (m, 1 H), 3.54 (d, 1 H), 3.68-3.74 (m, 1 H), 3.94 (d, 1 H), 6.54 (s, 1 H), 6.59 (d, 1 H), 6.95 (d, 1 H), 7.32-7.36 (m, 1 H), 7.36-7.40 (m, 1 H), 7.41 (d, 1 H), 7.43-7.47 (m, 2 H); MS (ES+) m/z 396 [M+H]⁺.

Example 46b

6'-(3-Chloro-4-fluorophenyl)-5-methyl-5'',6''-dihydro-4''H-dispiro[imidazole-2,4'-chromene-2',3''-pyran]-4-amine

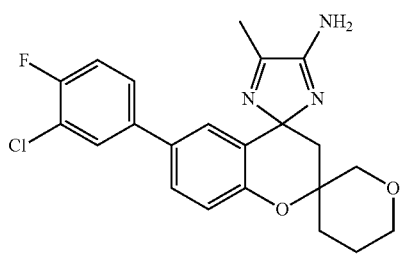 [SMILES: CC1=NC2(CC3(CCCOC3)Oc3ccc(-c4ccc(F)c(Cl)c4)cc32)N=C1N]

Isomer 1

6'-Bromo-5-methyl-5'',6''-dihydro-4''H-dispiro[imidazole-2,4'-chromene-2',3''-pyran]-4-amine (Example 45 Isomer 1, 77 mg, 0.21 mmol) and 3-chloro-4-fluorophenylboronic acid (47.9 mg, 0.27 mmol) were reacted using the conditions described for Example 46a Isomer 1, to give Isomer 1 of the title compound (33 mg, 38% yield) with undetermined configuration: ¹H NMR (500 MHz, DMSO-d$_6$) δ ppm 1.44-1.52 (m, 1 H), 1.81-1.92 (m, 3 H), 1.97-2.05 (m, 2 H), 2.22 (s, 3 H), 3.41-3.48 (m, 1 H), 3.56 (d, 1 H), 3.67-3.74 (m, 1 H), 3.98 (d, 1 H), 6.57 (s, 2H), 6.60 (d, 1 H), 6.94 (d, 1 H), 7.38-7.46 (m, 3 H), 7.60 (dd, 1 H); MS (ES+) m/z 414 [M+H]⁺.

Isomer 2

6'-Bromo-5-methyl-5'',6''-dihydro-4''H-dispiro[imidazole-2,4'-chromene-2',3''-pyran]-4-amine (Example 45 Isomer 2, 77 mg, 0.21 mmol), and 3-chloro-4-fluorophenylboronic acid (47.9 mg, 0.27 mmol) was reacted using the conditions described for Example 46a Isomer 1, to give isomer 2 of the title compound, (24 mg, 27% yield) with undetermined configuration: ¹H NMR (500 MHz, DMSO-d$_6$) δ ppm 1.41-1.54 (m, 1 H), 1.78-1.92 (m, 3 H), 1.99-2.13 (m, 2 H), 2.25 (s, 3 H), 3.40-3.47 (m, 1 H), 3.54 (d, 1 H), 3.68-3.74 (m, 1 H), 3.94 (d, 1 H), 6.53 (br. s, 2 H), 6.58 (d, 1 H), 6.94 (d, 1 H), 7.39-7.46 (m, 3 H), 7.58-7.63 (m, 1 H); MS (ES+) m/z 414 [M+H]⁺.

Example 47

6-Bromo-5'-methyl-2-(tetrahydro-2H-pyran-3-yl)spiro[chromane-4,2'-imidazole]-4'-amine Step 1: N-(6-Bromo-2-(tetrahydro-2H-pyran-3-yl)chroman-4-ylidene)-2-methylpropane-2-sulfinamide

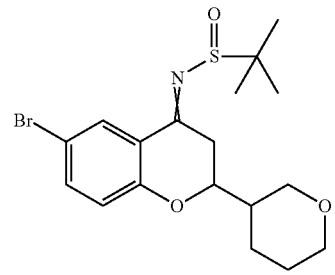 [SMILES: CC(C)(C)S(=O)N=C1CC(C2CCCOC2)Oc2ccc(Br)cc21]

6-Bromo-2-(tetrahydro-2H-pyran-3-yl)chroman-4-one (Intermediate 27, 1.5 g, 4.82 mmol) and 2-methylpropane-2-sulfinamide (1.052 g, 8.68 mmol) were dissolved in dry 2-methyl-tetrahydrofuran (12 mL). Neat titanium ethoxide (1.788 mL, 8.68 mmol) was added. The resulting mixture was heated by MW at 130° C. for 60 min. The mixture was diluted with EtOAc (150 mL) and water (40 mL) was added dropwise during vigorous stirring of the reaction mixture. The stirring was continued for 15 min. The solid was decanted and the mixture filtered through a pad of diatomaceous earth. The organic layer was separated, dried over MgSO$_4$ and vacuum filtered directly through a pad of silica (approx. 10 g) and concentrated in vacuo to give the title compound (1.8 g, 90% yield). MS (ES+) m/z 414 [M+H]⁺.

Step 2: 6-Bromo-4'-methyl-2-(tetrahydro-2H-pyran-3-yl)spiro[chroman-4,2'-imidazole]-5'(1'H)-thione

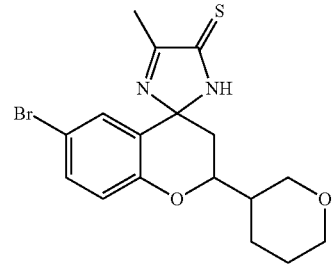 [SMILES: CC1=NC2(CC(C3CCCOC3)Oc3ccc(Br)cc32)NC1=S]

N-(6-Bromo-2-(tetrahydro-2H-pyran-3-yl)chroman-4-ylidene)-2-methylpropane-2-sulfinamide (Example 47 Step 1, 0.5 g, 1.21 mmol) and 2-oxopropanethioamide (Intermediate 2, 0.373 g, 3.62 mmol) were dissolved in dry acetonitrile (4.0 mL) in a dry microwave vial. The vial was sealed and heated with MW for 20 min. at 130° C. The solvent was evaporated to give the crude title compound that was used directly in the next reaction. MS (ES+) m/z 395 [M+H]+.

Step 3: 6-Bromo-5'-methyl-2-(tetrahydro-2H-pyran-3-yl)spiro[chroman-4,2'-imidazol]-4'-amine

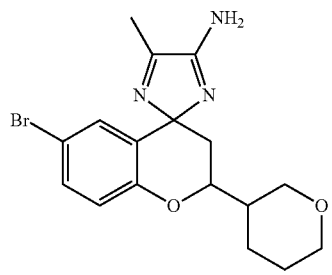 [SMILES: CC1=NC2(CC(C3CCCOC3)Oc3ccc(Br)cc32)N=C1N]

6-Bromo-4'-methyl-2-(tetrahydro-2H-pyran-3-yl)spiro[chroman-4,2'-imidazole]-5'(1'H)-thione (Example 47 Step 2, 3.78 g, 9.56 mmol) was dissolved in 7N solution of ammonia in MeOH (30.1 mL, 210 mmol) and heated with MW at 100° C. for 1 hr. The reaction mixture was concentrated, the residue re-dissolved in DCM, washed with brine, dried over $Na_2SO_4$ and concentrated at reduced pressure. Two isomeric mixtures were separated using a Gilson RP HPLCsystem with a X-Bridge C18, 50×250 mm column with gradient elution of acetonitrile in 0.05 M aq. ammonium acetate to give:
Isomeric mixture 1 (241 mg, 7% yield) with retention time 13.75 min: MS (ES+) m/z 378 [M+H]+, and
Isomeric mixture 2 (206 mg, 6% yield) with retention time 14.53 min: MS (ES+) m/z 378 [M+H]+.

Step 4: Separation of the isomers of 6-bromo-5'-methyl-2-(tetrahydro-2H-pyran-3-yl)spiro[chroman-4,2'-imidazol]-4'-amine The isomers in Isomeric mixture 1 from Example 47 Step 3, 60 mg, were separated on chiral SFC using a Chiralcel OD-H, 4.6*250 mm; 5 μm column and a mobile phase consisting of 10% MeOH (containing 0.1% diethylamine) and 90% $CO_2$ at a flow rate of 3 mL/min to give the following stereoisomers of undetermined absolute configuration:
Isomer 1 (13.7 mg, 11% yield) with retention time 7.63 min: $^1$H NMR (400 MHz, CDCl$_3$) δ ppm 1.48 (m, 2 H), 1.66 (m, 2 H), 1.83 (dt, 1 H), 1.98 (ddt, 1 H), 2.41 (s, 3 H), 2.48 (m, 1 H), 3.38 (m, 2 H), 3.92 (d, 1 H), 4.25 (m, 1 H), 4.33 (ddd, 1 H), 6.55 (d, 1 H), 6.79 (d, 1 H), 7.22 (dd, 1 H); MS (ES+) m/z 378 [M+H]+.
Isomer 2 (15.7 mg, 13% yield) with retention time 8.67 min: $^1$H NMR (500 MHz, CDCl$_3$) δ ppm 1.46 (m, 1 H), 1.53 (dd, 1 H), 1.67 (m, 2 H), 1.83 (dt, 1 H), 1.99 (dtd, 1 H), 2.44 (s, 3 H), 2.50 (m, 1 H), 3.38 (m, 2 H), 3.92 (d, 1 H), 4.25 (dd, 1 H), 4.32 (ddd, 1 H), 6.56 (d, 1 H), 6.79 (d, 1 H), 7.24 (dd, 1 H); MS (ES+) m/z 378 [M+H]+.
Isomer 3 (7.6 mg, 6% yield) with retention time 10.60 min: $^1$H NMR (500 MHz, CDCl$_3$) δ ppm 1.46 (m, 1 H), 1.56 (dd, 1 H), 1.67 (m, 2 H), 1.83 (dt, 1 H), 1.97 (dtd, 1 H), 2.35 (s, 3 H), 2.40 (t, 1 H), 3.38 (m, 2 H), 3.93 (d, 1 H), 4.26 (dd, 1 H), 4.47 (ddd, 1 H), 6.72 (d, 1 H), 6.79 (d, 1 H), 7.24 (dd, 1 H); MS (ES+) m/z 378 [M+H]+.
Isomer 4 (7.8 mg, 6.5% yield) with retention time 11.64 min: $^1$H NMR (500 MHz, CDCl$_3$) δ ppm 1.45 (m, 1 H), 1.55 (dd, 1 H), 1.67 (m, 2 H), 1.83 (dt, 1 H), 1.97 (dtd, 1 H), 2.34 (s, 3 H), 2.40 (m, 1 H), 3.38 (m, 2 H), 3.93 (d, 1 H), 4.26 (dd, 1 H), 4.47 (ddd, 1 H), 6.71 (d, 1 H), 6.79 (d, 1 H), 7.24 (dd, 1 H); MS (ES+) m/z 378 [M+H]+.

The isomers in Isomeric mixture 2 from Example 47 Step 3, 60 mg, were separated on chiral SFC using a Chiralpak AD-H; 20*250 mm; 5 μm column; and a mobile phase consisting of 15% IPA (containing 0.1% diethylamine) and 85% $CO_2$ at a flow rate of 50 mL/min to give the following stereoisomers of undetermined absolute configuration:
Isomer 5 (14.2 mg, 11% yield) with retention time 5.49 min: $^1$H NMR (500 MHz, CDCl$_3$) δ ppm 1.44 (d, 1 H), 1.66 (m, 3 H), 1.98 (m, 2 H), 2.43 (s, 3 H), 2.57 (m, 1 H), 3.45 (m, 2 H), 3.92 (m, 2H), 4.41 (m, 1 H), 6.57 (d, 1 H), 6.80 (d, 1 H), 7.24 (dd, 1 H); MS (ES+) m/z 378 [M+H]+.
Isomer 6 (4.4 mg, 4% yield) with retention time 6.27 min: $^1$H NMR (500 MHz, CDCl$_3$) δ ppm 1.49 (d, 1 H), 1.64 (m, 3 H), 1.97 (m, 2 H), 2.39 (s, 3 H), 2.48 (m, 1 H), 3.43 (m, 2 H), 3.93 (m, 2 H), 4.53 (ddd, 1 H), 6.74 (d, 1 H), 6.80 (m, 1 H), 7.25 (m, 1 H); MS (ES+) m/z 378 [M+H]+.
Isomer 7 (14.3 mg, 12% yield) with retention time 7.17 min: $^1$H NMR (500 MHz, CDCl$_3$) δ ppm 1.44 (d, 1 H), 1.66 (m, 3 H), 1.99 (m, 2 H), 2.43 (s, 3 H), 2.57 (m, 1 H), 3.45 (m, 2 H), 3.93 (m, 2 H), 4.41 (m, 1 H), 6.57 (d, 1 H), 6.80 (d, 1 H), 7.24 (dd, 1 H); MS (ES+) m/z 378 [M+H]+.
Isomer 8 (4.5 mg; 4% yield) with retention time 8.98 min: $^1$H NMR (500 MHz, CDCl$_3$) δ ppm 1.43 (m, 1 H), 1.63 (m, 3 H), 1.94 (m, 1 H), 2.04 (m, 1 H), 2.31 (m, 3 H), 2.47 (t, 1 H), 3.43 (m, 2 H), 3.94 (m, 2 H), 4.53 (m, 1 H), 6.71 (d, 1 H), 6.78 (d, 1 H), 7.23 (dd, 1 H); MS (ES+) m/z 378 [M+H]+.

Example 48a 6-(3-Chlorophenyl)-5'-methyl-2-(tetrahydro-2H-pyran-3-yl)spiro[chroman-4,2'-imidazol]-4'-amine

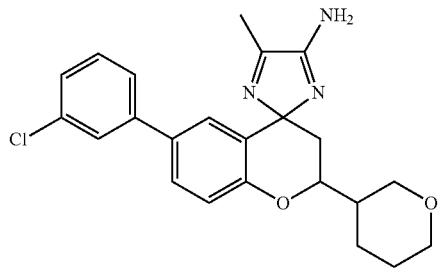 [SMILES: CC1=NC2(CC(C3CCCOC3)Oc3ccc(-c4cccc(Cl)c4)cc32)N=C1N]

A mixture of 6-bromo-5'-methyl-2-(tetrahydro-2H-pyran-3-yl)spiro[chroman-4,2'-imidazol]-4'-amine (Isomeric mixture 1 from Example 47 Step 3, 0.181 g, 0.48 mmol), 3-chlorophenylboronic acid (0.112 g, 0.72 mmol), [1,1'-bis(diphenylphosphino)ferrocene]palladium(II) chloride (0.035 g, 0.04 mmol), $K_2CO_3$ (2 M aq.) (0.479 mL, 0.96 mmol) and 1,4-dioxane (4 mL) were mixed in a vial and heated in a microwave reactor at 130° C. for 15 min. When cooled to r.t. the mixture was diluted with brine (3 mL) and extracted with DCM (3×3 mL). The combined organics were concentrated and the resulting residue was taken up in MeOH (1.5 mL), filtered and purified by preparative chromatography. The stereoisomers were separated using chiral SFC HPLC on a Phenomenex Lux C4; 4.6*250 mm; 5 μm column, and a mobile phase consisting of 20% MeOH (containing 0.1% diethylamine) and 80% $CO_2$ and a flow rate of 50 mL/min to give: Isomer 1 (2S,4R)-6-(3-chlorophenyl)-5'-methyl-2-[(3R)-tetrahydro-2H-pyran-3-yl]-2,3-dihydrospiro[chromene-4,2'-imidazol]-4'-amine:

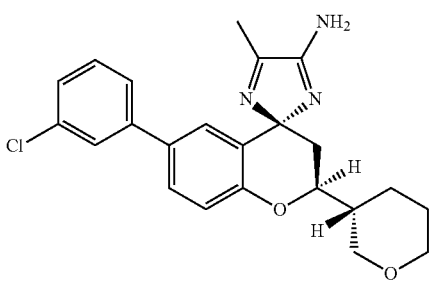 [SMILES: CC1=N[C@]2(C[C@@H]([C@@H]3CCCOC3)Oc3ccc(-c4cccc(Cl)c4)cc32)N=C1N]

(23 mg, 12% yield) with retention time 6.77 min: $^1$H NMR (500 MHz, CDCl$_3$) δ ppm 1.70 (m, 4 H), 1.86 (m, 1 H), 2.02 (ddt, 1 H), 2.45 (s, 3 H), 2.57 (t, 1 H), 3.40 (m, 2 H), 3.94 (d, 1 H), 4.30 (dd, 1 H), 4.39 (ddd, 1 H), 6.59 (d, 1 H), 6.98 (d, 1 H), 7.24 (m, 1 H), 7.29 (m, 2 H), 7.34 (dd, 1 H), 7.39 (s, 1 H); MS (ES+) m/z 410 [M+H]$^1$.

Isomer 2 with undetermined absolute configuration (19 mg, 10% yield) with retention time 7.85 min: $^1$H NMR (500 MHz, CDCl$_3$) δ ppm 1.69 (m, 4 H), 1.86 (m, 1 H), 2.02 (m, 1 H), 2.44 (s, 3 H), 2.57 (t, 1 H), 3.40 (m, 2 H), 3.94 (d, 1 H), 4.30 (dd, 1 H), 4.40 (ddd, 1 H), 6.59 (d, 1 H), 6.98 (d, 1 H), 7.24 (qd, 1 H), 7.28 (m, 2 H), 7.33 (dd, 1 H), 7.39 (m, 1 H); MS (ES+) m/z 410 [M+H]$^1$ Isomer 3 with undetermined absolute configuration (12 mg, 6% yield) with retention time 10.03 min: $^1$H NMR (500 MHz, CDCl$_3$) δ ppm 1.68 (m, 4 H), 1.86 (m, 1 H), 2.01 (m, 1 H), 2.34 (s, 3 H), 2.47 (t, 1 H), 3.40 (m, 2 H), 3.94 (m, 1 H), 4.31 (dd, 1 H), 4.54 (m, 1 H), 6.75 (d, 1 H), 6.98 (m, 1 H), 7.23 (m, 1 H), 7.30 (m, 2 H), 7.34 (dd, 1 H), 7.40 (m, 1 H); MS (ES+) m/z 410 [M+H]$^1$ Isomer 4 (2R,4R)-6-(3-chlorophenyl)-5'-methyl-2-[(3S)-tetrahydro-2H-pyran-3-yl]-1',2,3,3'-tetrahydro spiro[chromene-4,2'-imidazol]-4'-amine:

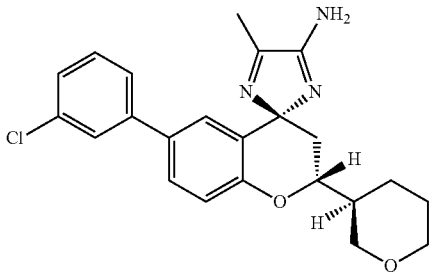 [SMILES: CC1=N[C@]2(C[C@H]([C@H]3CCCOC3)Oc3ccc(-c4cccc(Cl)c4)cc32)N=C1N]

(10 mg, 5% yield) with retention time 11.65 min: $^1$H NMR (500 MHz, CDCl$_3$) δ ppm 1.69 (m, 4 H), 1.86 (d, 1 H), 2.01 (m, 1 H), 2.34 (s, 3 H), 2.47 (t, 1 H), 3.40 (m, 2 H), 3.95 (d, 1 H), 4.31 (dd, 1 H), 4.54 (ddd, 1 H), 6.76 (d, 1 H), 6.97 (d, 1 H), 7.23 (m, 1 H), 7.30 (m, 2 H), 7.34 (dd, 1 H), 7.40 (m, 1 H); MS (ES+) m/z 410 [M+H]$^1$.

6-Bromo-5'-methyl-2-(tetrahydro-2H-pyran-3-yl)spiro[chroman-4,2'-imidazol]-4'-amine (Isomeric mixture 2 from Example 47 Step 3, 0.146 g, 0.39 mmol) was reacted with 3-chlorophenylboronic acid (0.091 g, 0.58 mmol) as described above. The isomers were separated using chiral HPLC methods:

Method 1: SFC HPLC with a OD-H; 20*250 mm; 5 μm column and a mobile phase consisting of 15% (IPA/EtOH 50:50 containing 0.1% diethylamine) and 85% CO$_2$ at a flow rate of 50 mL/min to give:

Isomer 5 with undetermined absolute configuration (29 mg, 15% yield) with retention time 8.94 min: $^1$H NMR (500 MHz, CDCl$_3$) δ ppm 1.67 (m, 4 H), 2.02 (m, 2 H), 2.46 (s, 3 H), 2.65 (t, 1 H), 3.44 (td, 1 H), 3.52 (t, 1 H), 3.95 (m, 2 H), 4.46 (m, 1 H), 6.60 (d, 1 H), 6.99 (d, 1 H), 7.24 (m, 1 H), 7.29 (d, 2 H), 7.35 (dd, 1 H), 7.39 (s, 1 H); MS (ES+) m/z 410 [M+H]$^+$. and Isomer 6 with undetermined absolute configuration (9 mg, 5% yield) with retention time 11.11 min: $^1$H NMR (500 MHz, CDCl$_3$) δ ppm 1.60 (m, 4 H), 1.98 (td, 1 H), 2.07 (d, 1 H), 2.36 (s, 3 H), 2.56 (t, 1 H), 3.43 (m, 1 H), 3.51 (t, 1 H), 3.96 (m, 2 H), 4.60 (dd, 1 H), 6.76 (d, 1 H), 6.98 (d, 1 H), 7.24 (m, 1 H), 7.30 (m, 2 H), 7.36 (dd, 1 H), 7.41 (s, 1 H); MS (ES+) m/z 410 [M+H]$^+$. and Isomeric mixture 1 was further separated using Method 2: SFC HPLC with a Phenomenex Lux C4; 20*250 mm; 5 μm column, and a mobile phase consisting of 20% MeOH (containing 0.1% diethylamine) and 80% CO$_2$ at a flow rate of 50 mL/min to give:

Isomer 7 (2R,4R)-6-(3-chlorophenyl)-5'-methyl-2-[(3R)-tetrahydro-2H-pyran-3-yl]-1',2,3,3'-tetrahydrospiro[chromene-4,2'-imidazol]-4'-amine:

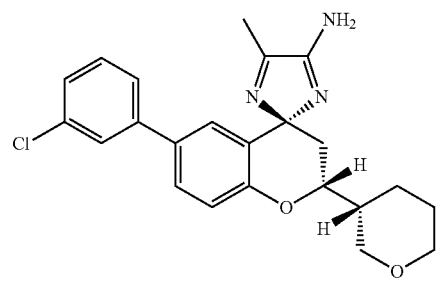 [SMILES: CC1=N[C@]2(C[C@H]([C@@H]3CCCOC3)Oc3ccc(-c4cccc(Cl)c4)cc32)N=C1N]

(8 mg, 4% yield) with retention time 6.64 min: $^1$H NMR (500 MHz, CDCl$_3$) δ ppm 1.65 (m, 4 H), 1.98 (dd, 1 H), 2.08 (d, 1 H), 2.32 (s, 3 H), 2.55 (t, 1 H), 3.43 (td, 1 H), 3.51 (t, 1 H), 3.96 (m, 2 H), 4.61 (m, 1 H), 6.76 (d, 1 H), 6.97 (d, 1 H), 7.23 (m, 1 H), 7.30 (m, 2 H), 7.34 (dd, 1 H), 7.41 (s, 1 H); MS (ES+) m/z 410 [M+H]$^+$. and Isomer 8 (2S,4R)-6-(3-chlorophenyl)-5'-methyl-2-[(3S)-tetrahydro-2H-pyran-3-yl]-1',2,3,3'-tetrahydro spiro[chromene-4,2'-imidazol]-4'-amine:

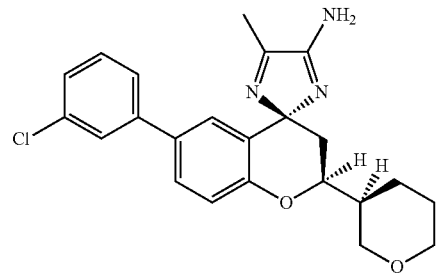 [SMILES: CC1=N[C@]2(C[C@@H]([C@H]3CCCOC3)Oc3ccc(-c4cccc(Cl)c4)cc32)N=C1N]

(25 mg, 13% yield) with retention time 10.30 min: $^1$H NMR (500 MHz, CDCl$_3$) δ ppm 1.68 (m, 4 H), 2.01 (m, 2 H), 2.43 (s, 3 H), 2.64 (t, 1 H), 3.45 (td, 1 H), 3.52 (t, 1 H), 3.95 (m, 2 H), 4.47 (m, 1 H), 6.60 (d, 1 H), 6.98 (d, 1 H), 7.24 (m, 1 H), 7.28 (d, 2 H), 7.33 (dd, 1 H), 7.39 (s, 1 H); MS (ES+) m/z 410 [M+H]$^+$.

Example 49

6-Bromo-2-(2,2-dimethyltetrahydro-2H-pyran-4-yl)-5'-methyl-spiro[chromane-4,2'-imidazole]-4'-amine Step 1: N-(6-Bromo-2-(2,2-dimethyltetrahydro-2H-pyran-4-yl)chroman-4-ylidene)-2-methylpropane-2-sulfinamide

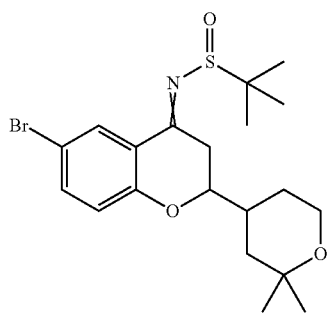 [SMILES: CC1(C)CC(C2CC(=NS(=O)C(C)(C)C)c3cc(Br)ccc3O2)CCO1]

Titanium (IV) ethoxide (6.18 mL, 29.48 mmol) was added to a solution of 6-bromo-2-(2,2-dimethyltetrahydro-2H-pyran-4-yl)chroman-4-one (Intermediate 28, 4 g, 11.79 mmol) in dry THF (150 mL) under argon. The solution was stirred 5 min before addition of 2-methylpropane-2-sulfinamide (1.715 g, 14.15 mmol) was made in one portion. The reaction was refluxed over the weekend (~70 h) with a heating bath temperature of 80° C. The reaction was cooled to r.t., and diluted with EtOAc (300 mL). Saturated NaHCO$_3$ (150 mL) was added under vigorous stirring. After 5 min diatomaceous earth was added and the mixture was stirred for another 10 min. The slurry was filtered through diatomaceous earth (washed with EtOAc) and the filtrate was evaporated at reduced pressure. Purification by flash chromatography (EtOAc/heptane) on silica gel gave the title compound (4.93 g, 95% yield): MS (ES+) m/z 442 [M+H]$^+$.

Step 2: 6-Bromo-2-(2,2-dimethyltetrahydro-2H-pyran-4-yl)-4'-methylspiro[chroman-4,2'-imidazole]-5'(1'H)-thione

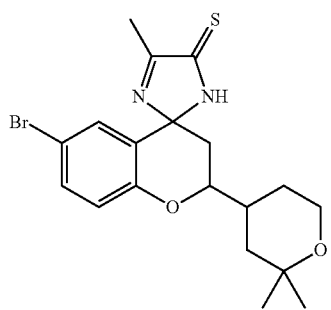 [SMILES: CC1=NC2(CC(C3CCOC(C)(C)C3)Oc3ccc(Br)cc32)NC1=S]

A solution of 2-oxopropanethioamide (Intermediate 2, 3.29 g, 31.94 mmol) in dry DMF (15 mL) was added to N-(6-bromo-2-(2,2-dimethyltetrahydro-2H-pyran-4-yl)chroman-4-ylidene)-2-methylpropane-2-sulfinamide (Example 49 Step 1, 4.71 g, 10.65 mmol) in a dried microwave vial under argon. The vial was sealed and heated at 120° C. for 30 min. The product was not isolated but used directly in the solution in the next reaction: MS (ES−) m/z 421 [M−H]$^-$.

Step 3: 6-Bromo-2-(2,2-dimethyltetrahydro-2H-pyran-4-yl)-5'-methylspiro[chroman-4,2'-imidazol]-4'-amine

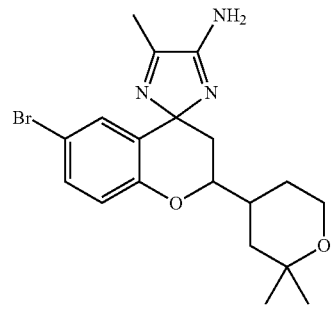 [SMILES: CC1=NC2(CC(C3CCOC(C)(C)C3)Oc3ccc(Br)cc32)N=C1N]

6-Bromo-2-(2,2-dimethyltetrahydro-2H-pyran-4-yl)-4'-methylspiro[chroman-4,2'-imidazole]-5'(1'H)-thione (Example 49 Step 2), directly from the previous step was dissolved in dry DMF (4 mL) in a microwave vial. Ammonia, 7M in MeOH (18 mL, 126 mmol) was added. The vial was sealed and the reaction was heated at 100° C. for 60 min in a microwave reactor (fixed hold time). The mixture was concentrated and the residue was dissolved in ammonia (7M in MeOH, 18 mL, 126 mmol) and heated at 120° C. for 30 min in a microwave reactor. This cycle was repeated three more times. After evaporation of the solvent, the remaining product was subjected to flash chromatography (0-7% of MeOH (NH$_3$) in DCM) to give the title compound as a mixture of isomers (1.29 g, 30% yield over two steps): MS (ES+) m/z 406 [M+H]$^+$.

Step 4: Separation of the isomers of 6-bromo-2-(2,2-dimethyltetrahydro-2H-pyran-4-yl)-5'-methylspiro[chroman-4,2'-imidazol]-4'-amine 6-Bromo-2-(2,2-dimethyltetrahydro-2H-pyran-4-yl)-5'-methylspiro[chroman-4,2'-imidazol]-4'-amine (Example 49 Step 3, 1.28 g, 3.15 mmol) was purified using a Gilson RP HPLC system with a X-Bridge C18, 50×250 mm column with gradient elution of acetonitrile in 0.05 M aq. ammonium acetate. The purification yielded two mixtures of isomers:
Isomeric mixture 1: (182 mg, 14% yield) with retention time 8.11 min: MS (ES+) m/z 406 [M+H]$^1$.
Isomeric mixture 2: (608 mg, 47% yield) with retention time 8.68 min: MS (ES+) m/z 406 [M+H]$^1$.

Example 50

6-(3-Chlorophenyl)-2-(2,2-dimethyltetrahydro-2H-pyran-4-yl)-5'-methylspiro[chroman-4,2'-imidazol]-4'-amine

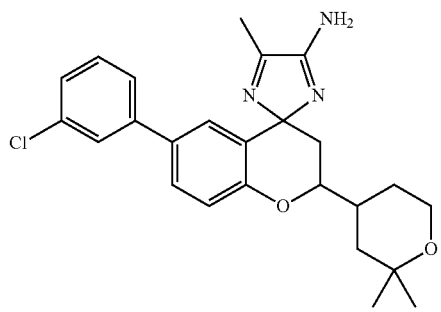 [SMILES: CC1=NC2(CC(C3CCOC(C)(C)C3)Oc3ccc(-c4cccc(Cl)c4)cc32)N=C1N]

6-Bromo-2-(2,2-dimethyltetrahydro-2H-pyran-4-yl)-5'-methylspiro[chroman-4,2'-imidazol]-4'-amine (Isomeric mixture 1 from Example 49 Step 4, 0.08 g, 0.20 mmol), 3-chlorophenylboronic acid (0.046 g, 0.30 mmol), [1,1'-bis(diphenylphosphino)ferrocene]palladium(II) chloride (0.015 g, 0.02 mmol), 2 M aq. K$_2$CO$_3$ solution (0.197 mL, 0.39 mmol) and 1,4-dioxane (1.5 mL) were mixed in a vial and heated in a microwave reactor at 130° C. for 20 min. When cooled to r.t. the mixture was diluted with DCM, washed with water and dried over Na$_2$SO$_4$. The filtrate was concentrated and the product purified by preparative chromatography to yield Isomeric mixture 1 of the title compound (30 mg, 35% yield): $^1$H NMR (500 MHz, CDCl$_3$) δ ppm 1.28 (m, 7 H), 1.48 (m, 3 H), 1.64 (d, 1 H), 1.91 (t, 1 H), 2.11 (m, 1 H), 2.40 (s, 3 H), 2.51 (t, 1 H), 3.74 (td, 1 H), 3.85 (td, 1 H), 4.48 (dd, 1 H), 6.81 (d, 1 H), 7.01 (d, 1 H), 7.26 (m, 1 H), 7.32 (d, 2 H), 7.40 (m, 2 H); MS (ES+) m/z 438 [M+H]$^1$.

Using the same procedure as above but starting from 6-bromo-2-(2,2-dimethyltetrahydro-2H-pyran-4-yl)-5'-methylspiro[chroman-4,2'-imidazol]-4'-amine (Isomeric mixture 2 from Example 49 Step 4, 0.102 g, 0.25 mmol) gave Isomeric mixture 2 of the title compound (35 mg, 32% yield): $^1$H NMR (500 MHz, CDCl$_3$) δ ppm 1.29 (m, 6 H), 1.50 (m, 3 H), 1.66 (d, 1 H), 1.90 (d, 1 H), 2.17 (m, 1 H), 2.51 (s, 3 H), 2.62 (m, 1 H), 3.74 (td, 1 H), 3.86 (dd, 1 H), 4.29 (dd, 1 H), 6.64 (d, 1 H), 7.03 (d, 1 H), 7.27 (m, 1 H), 7.32 (m, 2 H), 7.40 (m, 2 H), 8.18 (s, 1 H); MS (ES+) m/z 438 [M+H]$^+$.

Example 51

7'-Bromo-5-methyl-3',4'-dihydro-2'H-spiro[imidazole-2,1'-naphthalen]-4-amine

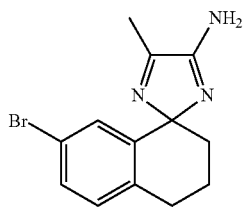 [SMILES: CC1=NC2(CCCc3ccc(Br)cc32)N=C1N]

Step 1: N-(7-Bromo-3,4-dihydronaphthalen-1(2 H)-ylidene)-2-methylpropane-2-sulfinamide

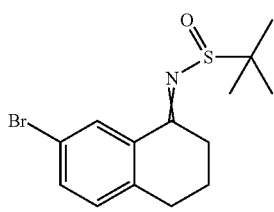 [SMILES: CC(C)(C)S(=O)N=C1CCCc2ccc(Br)cc21]

7-Bromo-3,4-dihydronaphthalen-1(2 H)-one (5 g, 22.21 mmol), 2-methylpropane-2-sulfinamide (4.04 g, 33.32 mmol) and titanium ethoxide (9.15 mL, 44.43 mmol) were dissolved in 2-Me THF (50 mL) and heated to reflux for 22 h. The reaction was left to cool down to r.t. EtOAc (20 mL), NaHCO$_3$ (sat, 5 mL) and water was added under stirring. The mixture was left to stand without stirring for 1 h. The organic phase was collected by filtration, dried over MgSO$_4$ and concentrated in vacuo to give the title compound (7.29 g) that was used without purification in the next step: $^1$H NMR (500 MHz, CDCl$_3$) δ ppm 1.34 (s, 9 H), 2.00-2.10 (m, 2 H), 2.77-2.86 (m, 2 H), 3.01-3.12 (m, 1 H), 3.28 (ddd, 1 H), 7.09 (d, 1 H), 7.50 (dd, 1 H), 8.25 (d, 1 H), MS (ES+) m/z 328[M+H]$^+$.

Step 2: 7-Bromo-3,4-dihydronaphthalen-1(2 H)-imine

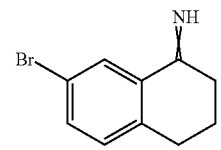

HCl (4M in 1,4-dioxane) (6.75 mL, 222.07 mmol) was added to a suspension of N-(7-bromo-3,4-dihydronaphthalen-1(2 H)-ylidene)-2-methylpropane-2-sulfinamide (Example 51 Step 1, 7.29 g, 22.2 mmol) in anhydrous 1,4-dioxane (50 mL). The resulting mixture was stirred under a nitrogen atmosphere at r.t. for 1 h. The formed precipitate was filtered off and washed with Et$_2$O. The solid was then dissolved in DCM and sat. aq. NaHCO$_3$. The mixture was poured into a phase separator, the organic layer was collected and concentrated. The product was used directly in the next step.

Step 3: 7'-Bromo-4-methyl-3',4'-dihydro-2'H-spiro[imidazole-2,1'-naphthalene]-5(1 H)-thione

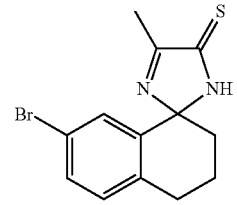

7-Bromo-3,4-dihydronaphthalen-1(2 H)-imine (Example 51 Step 2, 3 g, 13.39 mmol) was dissolved in MeOH (70 mL) and THF (10 mL). 2-Oxopropanethioamide (4.14 g, 40.16 mmol, Intermediate 2) was added. The solution was heated at 60° C. overnight. The reaction was allowed to cool to r.t. The formed precipitate was filtered off, washed with cold MeOH and dried in vacuo. The mother liquor was concentrated. The combined precipitate and concentrated mother liquor was purified using two subsequent flash chromatography (1: 40 g SiO$_2$, 0-30% 0.2 NH$_3$ in MeOH in DCM, 2: 80 g SiO$_2$, 0-10% 0.2 M NH$_3$ in MeOH in DCM) to yield the title compound (1.05 g, 25% yield). MS (ES+) m/z 309 [M+H]$^+$.

Step 4: 7'-Bromo-5-methyl-3',4'-dihydro-2'H-spiro[imidazole-2,1'-naphthalen]-4-amine

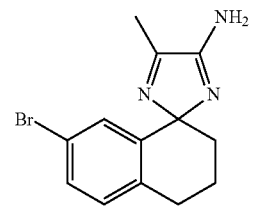

7'-Bromo-4-methyl-3',4'-dihydro-2'H-spiro[imidazole-2,1'-naphthalene]-5(1 H)-thione (Example 51 Step 3, 1 g, 3.23 mmol) was taken up in ammonia (7M in MeOH, 15 mL, 105 mmol) and the resulting mixture was heated in the microwave reactor at 110° C. for 30 min. The solvent was evaporated. Ammonia (7M in MeOH, 15 mL, 105 mmol) was added and the reaction was heated again using MW for 30 min at 110° C. The solvent was evaporated. Ammonia (7M in MeOH, 15 mL, 105 mmol) was added and the reaction was heated again using MW for 30 min at 110° C. The solvent was evaporated and the residue was dissolved in EtOAc (20 mL). The resulting mixture was extracted with 0.1 M citric acid (2×10 mL). The organic layer was discarded while the aqueous phase was basified to pH 12 by addition of 50% NaOH (aq) and extracted with iii DCM (3×20 mL). The organic phase was dried with a phase separator and concentrated in vacuo to give the title compound (0.619 g, 65% yield). 20 mg of the product was purified using flash chromatography (4 g SiO$_2$, DCM in 0.1M NH$_3$ in MeOH) to give the title compound (10 mg). $^1$H NMR (500 MHz, CDCl$_3$) δ ppm 1.88-1.99 (m, 2 H), 2.07-2.16 (m, 1 H), 2.20 (dqd, 1 H), 2.31-2.37 (m, 3 H), 2.92 (t, 2 H), 6.68 (d, 1 H), 7.04 (d, 1 H), 7.25 (dd, 1 H); $^1$H NMR (500 MHz, CD$_3$OD) δ ppm 1.84 (ddd, 1 H), 1.94 (ddd, 1 H), 2.03-2.12 (m, 1 H), 2.15 (dtd, 1 H), 2.34 (s, 3 H), 2.91 (t, 2 H), 6.69 (d, 1 H), 7.11 (d, 1 H), 7.29 (dd, 1 H), MS (ES+) m/z 292 [M+H]$^1$.

Example 52

7'-(5-Chloropyridin-3-yl)-5-methyl-3',4'-dihydro-2'H-spiro[imidazole-2,1'-naphthalen]-4-amine

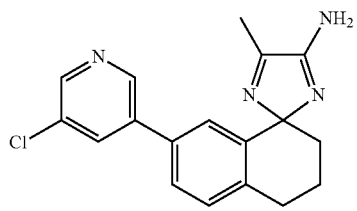 [SMILES: CC1=NC2(CCCc3ccc(-c4cncc(Cl)c4)cc32)N=C1N]

Sodium tetrachloropalladate(II) (3.52 mg, 0.01 mmol), 3-(di-tert-butylphosphonium)propane sulfonate (6.43 mg, 0.02 mmol), 5-chloropyridin-3-ylboronic acid (51.6 mg, 0.31 mmol) and 7'-bromo-5-methyl-3',4'-dihydro-2'H-spiro[imidazole-2,1'-naphthalen]-4-amine (Example 51 Step 4, 70 mg, 0.24 mmol) were added to a vial. 2-Methyl-tetrahydrofuran (1 mL) and K$_2$CO$_3$ (2M aq.) (0.359 mL, 0.72 mmol) were added and the mixture was degassed by bubbling N$_2$ (g). The vial was sealed and heated in a microwave reactor at 90° C. for 30 min. EtOAc (5 mL) and water (5 mL) were added and the phases were separated. The aqueous phase was extracted with EtOAc twice and the combined organic layers were dried over MgSO$_4$, filtered and concentrated in vacuo. The crude product was purified by flash chromatography (4 g SiO$_2$, O-10% MeOH containing 0.1M NH$_3$ in DCM). The fractions containing product were combined and concentrated, yielding the title compound (26 mg, 33% yield). $^1$H NMR (500 MHz, CD$_3$OD) δ ppm 1.85-1.94 (m, 1 H), 2.01 (ddd, 1 H), 2.08-2.17 (m, 1 H), 2.17-2.27 (m, 1 H), 2.35 (s, 3 H), 3.02 (t, 2 H), 6.84 (d, 1 H), 7.34 (d, 1 H), 7.48 (dd, 1 H), 7.97 (t, 1 H), 8.48 (d, 1 H), 8.57 (d, 1 H); MS (ES+) m/z 325 [M+H]$^+$.

Example 53

5-Methyl-7'-(5-(prop-1-ynyl)pyridin-3-yl)-3',4'-dihydro-2'H-spiro[imidazole-2,1'-naphthalen]-4-amine

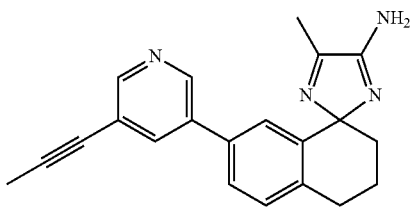 [SMILES: CC#Cc1cncc(-c2ccc3c(c2)C2(CCC3)N=C(C)C(N)=N2)c1]

The title compound (19 mg, 22% yield), was prepared as described for Example 52 starting from 5-(prop-1-ynyl)pyridin-3-ylboronic acid (Intermediate 15, 66 mg, 0.33 mmol) and 7'-bromo-5-methyl-3',4'-dihydro-2'H-spiro[imidazole-2,1'-naphthalen]-4-amine (Example 51, 75 mg, 0.26 mmol). $^1$H NMR (500 MHz, CD$_3$OD) δ ppm 1.86-1.93 (m, 1 H), 2.01 (ddd, 1 H), 2.08 (s, 3 H), 2.09-2.17 (m, 1 H), 2.17-2.26 (m, 1 H), 2.34 (s, 3 H), 3.02 (t, 2 H), 6.80 (d, 1 H), 7.33 (d, 1 H), 7.45 (dd, 1 H), 7.85 (t, 1 H), 8.44 (d, 1 H), 8.52 (d, 1 H); MS (ES+) m/z 329 [M+H]$^+$.

Example 54

6'-Bromo-5''-methyl-3'H-dispiro[cyclobutane-1,2'-indene-1',2''-imidazol]-4''-amine Step 1: N-(5'-Bromospiro[cyclobutane-1,2'-indene]-3'(1'H)-ylidene)-2-methylpropane-2-sulfinamide

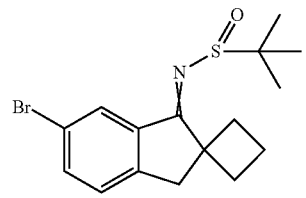 [SMILES: CC(C)(C)S(=O)N=C1c2cc(Br)ccc2CC12CCC2]

6'-Bromospiro[cyclobutane-1,2'-inden]-1'(3'H)-one (Intermediate 38, 1.1 g, 4.38 mmol), 2-methylpropane-2-sulfinamide (0.96 g, 7.88 mmol), and titanium ethoxide (1.805 mL, 8.76 mmol) were dissolved in methyl THF (20 mL), and heated to reflux overnight. The reaction was allowed to cool to r.t., then it was diluted with EtOAc (150 mL). Water (22 mL) was added dropwise over 10 min under vigorous stirring and then the mixture was left standing without stirring for 1.5 h. The solids were filtered off and the organics were evaporated to give a crude product which was purified by flash chromatography (eluent: heptane/ethylacetate 8:1) to afford the title compound (2.1 g, 77% yield), used as such in the next step: MS (ES+) m/z 354 [M+H]$^+$.

Step 2: 6'-Bromospiro[cyclobutane-1,2'-inden]-1'(3'H)-imine

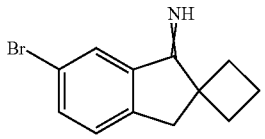 [SMILES: N=C1c2cc(Br)ccc2CC12CCC2]

Hydrochloric acid (4M in 1,4-dioxane, 14.89 mL, 59.55 mmol) was added to a solution of N-(5'-bromospiro[cyclobutane-1,2'-indene]-3'(1'H)-ylidene)-2-methylpropane-2-sulfinamide (Example 54 Step 1, 2.11 g, 5.96 mmol) in anhydrous 1,4-dioxane (60 mL), and the resulting mixture was stirred under an argon atmosphere for 3 h. Et$_2$O (4 mL) was added and the precipitate was filtered off and washed with Et$_2$O, then partitioned between DCM (100 mL), and sat. aq. NaHCO$_3$ (100 mL). The phases were separated and the organic layer concentrated to afford the title compound that was used as such without further purification.

Step 3: 6'-Bromo-5"-methyl-3'H-dispiro[cyclobutane-1,2'-indene-1,2"-imidazole]-4"(3"H)-thione

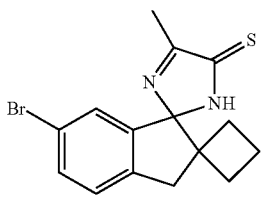 [SMILES: CC1=NC2(NC1=S)c1cc(Br)ccc1CC21CCC1]

6'-Bromospiro[cyclobutane-1,2'-inden]-1'(3'H)-imine (Example 54 Step 2, 1.49 g, 5.96 mmol) and 2-oxopropanethioamide (Intermediate 2, 1.844 g, 17.88 mmol) were dissolved in dry MeOH (12 mL), and the resulting solution was heated at 60° C. under an argon atmosphere overnight. The reaction was allowed to cool to r.t and was then concentrated to give a crude product which was purified by flash chromatography (eluent: heptane/EtOAc 12:1 to 10:1) to afford the title compound (1.62 g, 81% yield): NMR: $^1$H NMR (500 MHz, CDCl$_3$) δ ppm 1.73-2.07 (m, 6 H), 2.42 (s, 3 H), 3.13-3.38 (m, 2 H), 7.10 (s, 1 H), 7.21 (d, 1 H), 7.42-7.47 (m, 1 H), 9.15 (br. s., 1 H); MS (ES+) m/z 337 [M+H]$^+$.

Step 4: 6'-Bromo-5"-methyl-3'H-dispiro[cyclobutane-1,2'-indene-1',2"-imidazol]-4"-amine

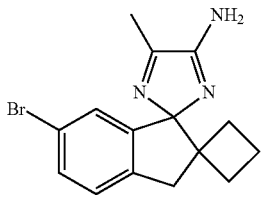 [SMILES: CC1=NC2(N=C1N)c1cc(Br)ccc1CC21CCC1]

6'-Bromo-5"-methyl-3'H-dispiro[cyclobutane-1,2'-indene-1',2"-imidazole]-4"(3"H)-thione (Example 54 Step 3, 1.62 g, 4.83 mmol) and ammonia (7M in MeOH, 15.2 mL, 106 mmol) were mixed together in a microwave vial. The vial was sealed and the reaction was heated at 90° C. for 30 min in a microwave reactor. The mixture was concentrated and the residue was dissolved in ammonia (7M in MeOH, 15.2 mL, 106 mmol), and heated once more at 90° C. for 30 min in a microwave reactor. This cycle was repeated four more times. After evaporation of the solvent, the crude was acidified with 2 M aq. hydrochloric acid, and washed with EtOAc. The aqueous phase was treated with 2M NaOH until basic pH was reached and then it was extracted with EtOAc. The organic phase was dried over MgSO$_4$ and concentrated. The organic phase was then acidified with 2M citric acid. The aqueous phase was treated with 2M NaOH until basic pH was reached and then it was extracted with EtOAc. The organic phases containing the title compound were combined, dried over MgSO$_4$ and concentrated. The residue was dissolved in EtOAc and was washed with 50% aq. NaOH The organic layer was dried over MgSO$_4$ and concentrated to afford the title compound (1.0 g, 65% yield): NMR: $^1$H NMR (500 MHz, DMSO-d$_6$) δ ppm 1.48-1.67 (m, 4 H), 1.73-1.86 (m, 1 H), 2.08-2.17 (m, 1 H), 2.19 (s, 3 H), 3.06-3.20 (m, 2 H), 6.65 (br. s., 2 H), 6.71 (d, 1 H), 7.26 (d, 1 H), 7.35 (dd, 1 H); MS (ES+) m/z 318 [M+H]$^+$.

Example 55

6'-(5-Chloropyridin-3-yl)-5"-methyl-3'H-dispiro[cyclobutane-1,2'-indene-1',2"-imidazol]-4"-amine

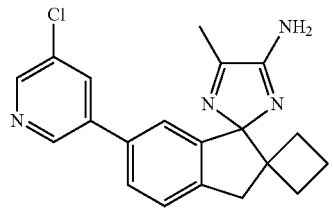 [SMILES: CC1=NC2(N=C1N)c1cc(-c3cncc(Cl)c3)ccc1CC21CCC1]

Sodium tetrachloropalladate (II) (2.77 mg, 9.43 μmol), 3-(di-tert-butylphosphonium)propane sulfonate (5.06 mg, 0.02 mmol), 5-chloropyridin-3-ylboronic acid (40.6 mg, 0.25 mmol) and 6'-bromo-5"-methyl-3'H-dispiro[cyclobutane-1,2'-indene-1',2"-imidazol]-4"-amine (Example 54, 60 mg, 0.19 mmol), was added to a vial. 2-Methyl-tetrahydrofuran (1 mL) and 2 M aq. K$_2$CO$_3$ (0.283 mL, 0.57 mmol) was added and the mixture was degassed by bubbling N$_2$ (g). The vial was sealed and heated in a microwave reactor at 90° C. for 30 min. EtOAc (5 mL) and water (5 mL) were added and the phases were separated. The aq phase was extracted with EtOAc and the combined organic layers were dried over MgSO$_4$, filtered and concentrated in vacuo. Purification by flash chromatography using a gradient of 0-10% MeOH, containing 1.2% 7M NH$_3$ in MeOH, in DCM, afforded 51 mg of the title compound (77% yield). $^1$H NMR (500 MHz, DMSO-d$_6$) δ ppm 1.62 (m, 4 H) 1.83 (d, 1 H) 2.16 (s, 1 H) 2.21 (s, 3 H) 3.23 (d, 2 H) 6.60 (s, 2 H) 6.94 (d, 1 H) 7.43 (d, 1 H) 7.58 (dd, 1 H) 8.10 (t, 1 H) 8.57 (d, 1 H) 8.71 (d, 1 H); MS (ES+) m/z 351 [M+H]$^+$.

Example 56

5"-Methyl-6'-[5-(prop-1-yn-1-yl)pyridin-3-yl]-3'H-dispiro[cyclobutane-1,2'-indene-1',2"-imidazol]-4"-amine

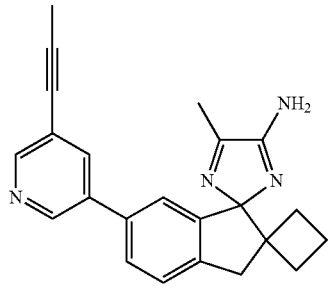

The title compound (60 mg, 68% yield) was prepared by the method described in Example 55, starting from 6'-bromo-5"-methyl-3'H-dispiro[cyclobutane-1,2'-indene-1',2"-imidazol]-4"-amine (Example 54) (80 mg, 0.25 mmol) and 5-(prop-1-ynyl)pyridin-3-ylboronic acid (Intermediate 15, 53 mg, 0.33 mmol). $^1$H NMR (500 MHz, DMSO-d$_6$) δ ppm 1.59 (m, 4 H) 1.83 (d, 1 H) 2.09 (s, 3 H) 2.16 (d, 1 H) 2.21 (s, 3 H) 3.23 (m, 2 H) 6.60 (s, 2 H) 6.89 (d, 1 H) 7.41 (d, 1 H) 7.54 (dd, 1 H) 7.91 (t, 1 H) 8.52 (d, 1 H) 8.67 (d, 1 H). MS (ES+) m/z 355 [M+H]$^+$.

Example 57

Separation of the isomers of 5"-methyl-6'-[5-(prop-1-yn-1-yl)pyridin-3-yl]-3'H-dispiro[cyclobutane-1,2'-indene-1',2"-imidazol]-4"-amine The isomers of 5"-methyl-6'-[5-(prop-1-yn-1-yl)pyridin-3-yl]-3'H-dispiro[cyclobutane-1,2'-indene-1',2"-imidazol]-4"-amine (Example 56, 47 mg, 0.13 mmol) were separated using a SFC Berger Multigram II preparative HPLC, with a Chiralcel OD-H; 20*250 mm; 5 μm column, and a mobile phase consisting of 30% MeOH (containing 0.1% DEA) and 70% CO$_2$ at a flow rate of 50 mL/min to give:
Isomer 1 with undetermined absolute configuration (16 mg, 34% yield) with retention time 2.4 min: $^1$H NMR (500 MHz, DMSO-d$_6$) δ ppm 1.58 (m, 4 H), 1.83 (m, 1 H), 2.09 (s, 3 H), 2.16 (m, 1 H), 2.21 (s, 3 H), 3.23 (m, 2 H), 6.59 (m, 2 H), 6.89 (m, 1 H), 7.41 (m, 1 H), 7.55 (m, 1 H), 7.91 (m, 1 H), 8.52 (m, 1 H), 8.67 (m, 1 H); MS (APCI+) m/z 355 [M+H]$^+$; and
Isomer 2 with undetermined absolute configuration (15 mg, 33% yield) with retention time 7.2 min: $^1$H NMR (500 MHz, DMSO-d$_6$) δ ppm 1.61 (br. s., 4 H), 1.82 (m, 1 H), 2.09 (s, 3 H), 2.16 (m, 1 H), 2.21 (s, 3 H), 3.23 (d, 2 H), 6.60 (s, 2 H), 6.89 (d, 1 H), 7.41 (d, 1 H), 7.54 (d, 1 H), 7.91 (t, 1 H), 8.52 (d, 1 H), 8.67 (d, 1 H); MS (APCI+) m/z 355 [M+H]$^+$.

Example 58

6'-(Cyclopropylethynyl)-5"-methyl-3'H-dispiro[cyclobutane-1,2'-indene-1',2"-imidazol]-4"-amine

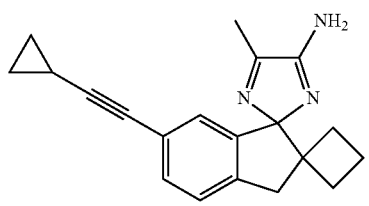

To a solution of 6'-bromo-5"-methyl-3'H-dispiro[cyclobutane-1,2'-indene-1',2"-imidazol]-4"-amine (Example 54, 0.10 g, 0.31 mmol) in DMF (10 mL) under argon was added ethynylcyclopropane (0.031 g, 0.47 mmol), tetrakis(triphenylphosphine)palladium(0) (0.036 g, 0.03 mmol) and triethylamine (1.31 mL, 9.43 mmol). The reaction mixture was stirred at r.t. for 5 min before addition of cuprous iodide (8.98 mg, 0.05 mmol). The reaction mixture was stirred overnight at 65° C. The reaction mixture was partitioned between sat aq. NaHCO$_3$ and EtOAc. The organic phase was dried over MgSO$_4$ and concentrated to give a crude product which was purified by preparative chromatography to afford the title compound (0.046 g, 48% yield): $^1$H NMR (500 MHz, DMSO-d$_6$) δ ppm 0.60-0.73 (m, 2 H), 0.77-0.89 (m, 2 H), 1.46 (tt, 1 H), 1.50-1.65 (m, 4 H), 1.72-1.85 (m, 1 H), 2.08-2.16 (m, 1 H), 2.18 (s, 3 H), 3.07-3.23 (m, 2 H), 6.54 (d, 1 H), 6.60 (s, 2 H), 7.16 (dd, 1 H), 7.20-7.27 (m, 1 H); MS (ES+) m/z 304 [M+H]$^+$.

Example 59

6'-(3,3-Dimethylbut-1-yn-1-yl)-5"-methyl-3'H-dispiro[cyclobutane-1,2'-indene-1',2"imidazol]-4"-amine

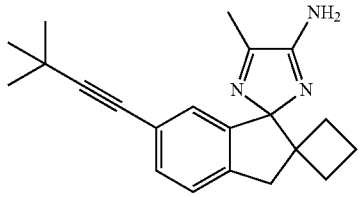

To a solution of 6'-bromo-5"-methyl-3'H-dispiro[cyclobutane-1,2'-indene-1',2"-imidazol]-4"-amine (Example 54, 0.100 g, 0.31 mmol) in DMF (10 mL) under argon was added 3,3-dimethyl-but-1-yne (0.039 g, 0.47 mmol), tetrakis(triphenylphosphine)palladium(0) (0.036 g, 0.03 mmol) and triethylamine (1.31 mL, 9.43 mmol). The reaction mixture was stirred at r.t. for 5 min before addition of cuprous iodide (8.98 mg, 0.05 mmol). The reaction mixture was stirred overnight at 65° C. and then partitioned between sat aq. NaHCO$_3$ and EtOAc. The organic phase was dried over MgSO$_4$ and concentrated to give a crude product which was purified by preparative chromatography to afford the title compound (0.039 g, 38% yield): $^1$H NMR (500 MHz, DMSO-d$_6$) δ ppm 1.24 (s, 9 H), 1.47-1.66 (m, 4 H), 1.73-1.84 (m, 1 H), 2.09-2.17 (m, 1 H), 2.18 (s, 3 H), 3.16 (d, 2 H), 6.53 (d, 1 H), 6.60 (s, 2 H), 7.14 (dd, 1 H), 7.24 (d, 1 H); MS (ES+) m/z 320 [M+H]$^+$.

Example 60

(1r,4r)-6'-(5-Chloro-6-methylpyridin-3-yl)-4-methoxy-5"-methyl-3'H-dispiro[cyclohexane-1,2'-indene-1',2"-imidazol]-4"-amine

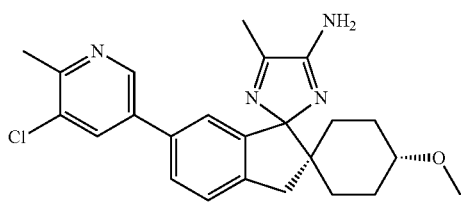

4,4,4',4',5,5,5',5'-Octamethyl-2,2'-bi(1,3,2-dioxaborolane) (287 mg, 1.13 mmol), (1r,4r)-6'-bromo-4-methoxy-5"-methyl-3'H-dispiro[cyclohexane-1,2'-indene-1',2"-imidazol]-4"-amine (Example 19, 213 mg, 0.57 mmol) and potassium acetate (167 mg, 1.70 mmol) and dioxane (3 mL) were added and the mixture was degassed with a stream of argon (g) for a couple of min. PdCl$_2$(dppf) CH$_2$Cl$_2$ (32.4 mg, 0.04 mmol) was added and the mixture was heated to reflux for 1.5 h under N$_2$ atmosphere. 4,4,4',4',5,5,5',5'-Octamethyl-2,2'-bi(1,3,2-dioxaborolane) (120 mg, 0.47 mmol) was added and the reaction was heated to reflux overnight. The volatiles were removed in vacuo and 80 mg of the residue ((1r,4r)-4-methoxy-5"-methyl-6'-(4,4,5,5-tetramethyl-1,3,2-dioxaborolan-2-yl)-3'H-dispiro[cyclohexane-1,2'-indene-1',2"-imidazol]-4"-amine (MS (ES+) m/z 424 [M+H]$^+$) was mixed with 5-bromo-3-chloro-2-methylpyridine (Intermediate 43, 47 mg, 0.23 mmol), K$_2$CO$_3$ (0.38 mL, 0.76 mmol) and dioxane (2 mL). The mixture was degassed with a stream of argon (g) for a couple of min. PdCl$_2$(dppf) CH$_2$Cl$_2$ adduct (138 mg, 0.19 mmol) was added. The vial was sealed and heated in a microwave reactor at 140° C. for 30 min. EtOAc was added and the mixture was washed with brine and water. The organic phase was dried with MgSO$_4$, filtered and concentrated in vacuo. The crude product was purified by flash chromatography (12 g SiO$_2$, 0-20% MeOH containing 0.1 M NH$_3$ in DCM). The crude product was purified with preparative chromatography. The fractions containing product were combined and concentrated. The water phase was extracted with DCM and the phases were separated using a phase separator. The organic phase was concentrated in vacuo yielding the title compound (5 mg, 6% yield): $^1$H NMR (CD$_3$OD) δ ppm 1.11 (td, 1 H), 1.24-1.43 (m, 2 H), 1.49 (td, 1 H), 1.63 (td, 2 H), 1.90-2.00 (m, 2 H), 2.32 (s, 3 H), 2.61 (s, 3 H), 3.04-3.12 (m, 1 H), 3.15 (d, 1 H), 3.25 (d, 1 H), 3.33 (s, 3 H), 6.99 (d, 1 H), 7.47 (d, 1 H), 7.55 (dd, 1 H), 7.99 (d, 1 H), 8.51 (d, 1 H); MS (MM−ES+APCI)+ m/z 423 [M+H]$^+$.

Example 61

(1r,1'R,4R)-6'-(5-Chloro-6-methylpyridin-3-yl)-4-methoxy-5"-methyl-3'H-dispiro[cyclohexane-1,2'-indene-1',2"-imidazol]-4"-amine

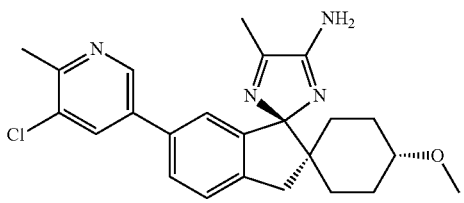

(1r,1'R,4R)-6'-Bromo-4-methoxy-5"-methyl-3'H-dispiro[cyclohexane-1,2'-indene-1',2"-imidazol]-4"-amine as the D(+)-10-camphor sulfonic acid salt (Example 19 Step 5, 0.4 g, 0.66 mmol) was dissolved in 2-methyl-tetrahydrofuran (5 mL). KOH (0.4 g, 7.13 mmol) in water (3 mL) was added. The reaction mixture was stirred for 30 min before the water phase was removed and the residue was washed with 2M K$_2$CO$_3$ solution (3 mL). The aqueous phase was removed and the organic phase was transferred to a microwave vial. 3-chloro-2-methyl-5-(4,4,5,5-tetramethyl-1,3,2-dioxaborolan-2-yl)pyridine (Intermediate 44, 0.200 g, 0.79 mmol) was added followed by K$_2$CO$_3$ (2.0 M, 0.986 mL, 1.97 mmol). Ar (g) was bubbled through the mixture. Sodium tetrachloropalladate(II) (9.67 mg, 0.03 mmol) and 3-(di-tert-butylphosphonium)propane sulfonate (0.018 g, 0.07 mmol) were added and the vial was closed and heated with MW for 30 min at 100° C. After cooling to r.t., water and 2-Me THF were added and the water phase was eliminated. The organic phase was washed with brine and water and concentrated in vacuo. The product was purified using flash chromatography (40 g SiO$_2$, gradient elution 0-100% EtOAc in heptane) followed by flash chromatography (40 g SiO$_2$, gradient elution 0-10% MeOH (containing 0.2 M NH$_3$) in DCM) to give the title compound (0.065 g, 23% yield): $^1$H NMR (500 MHz, DMSO-d$_6$) δ ppm 0.90-1.02 (m, 1 H), 1.09-1.31 (m, 2 H), 1.35-1.55 (m, 3 H), 1.83 (d, 2 H), 2.17 (s, 3 H), 2.52-2.59 (m, 3 H), 2.89-3.03 (m, 2 H), 3.03-3.13 (m, 1 H), 3.19 (s, 3 H), 6.54 (br. s., 2 H), 6.84 (s, 1 H), 7.40 (d, 1 H), 7.54 (d, 1 H), 8.00 (s, 1 H), 8.58 (s, 1 H); MS (ES+) m/z 423 [M+H]$^+$.

Example 62

(1r,4r)-6'-(5-Chloro-2-methylpyridin-3-yl)-4-methoxy-5"-methyl-3'H-dispiro[cyclohexane-1,2'-indene-1',2"-imidazol]-4"-amine

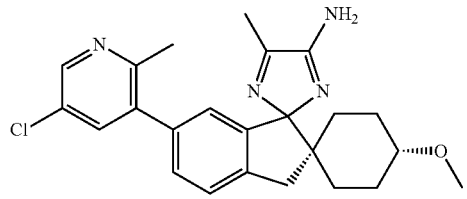

3-Bromo-5-chloro-2-methylpyridine (Intermediate 41, 47 mg, 0.23 mmol), (1r,4r)-4-methoxy-5"-methyl-6'-(4,4,5,5-tetramethyl-1,3,2-dioxaborolan-2-yl)-3'H-dispiro[cyclohexane-1,2'-indene-1',2"-imidazol]-4"-amine (prepared in Example 60, 80 mg, 0.19 mmol), K$_2$CO$_3$ (2 M aq. solution, 0.38 mL, 0.76 mmol) and dioxane (2 mL) were added and the mixture was degassed with a stream of argon for a couple of min. PdCl$_2$(dppf) CH$_2$Cl$_2$ adduct (138 mg, 0.19 mmol) was added. The vial was sealed and heated in a microwave reactor at 140° C. for 30 min. EtOAc was added and the reaction was washed with brine and water. The organic phase was dried with MgSO$_4$, filtered and concentrated in vacuo. The crude product was purified by flash chromatography (12 g SiO$_2$, 0-20% MeOH containing 0.1 M NH$_3$ in DCM). The crude product was purified with preparative chromatography. The fractions containing product were combined, concentrated and freeze dried yielding the title compound (5 mg, 6% yield): $^1$H NMR (CD$_3$OD) δ ppm 1.07-1.19 (m, 1 H), 1.29-1.44 (m, 2 H), 1.49 (td, 1 H), 1.57-1.72 (m, 2 H), 1.92-2.00 (m, 2 H), 2.30 (s, 3 H), 2.37 (s, 3 H), 3.04-3.13 (m, 1 H), 3.17 (d, 1 H), 3.26 (d, 1 H), 3.34 (s, 3 H), 6.66-6.72 (m, 1 H), 7.26 (dd, 1 H), 7.46 (d, 1 H), 7.60 (d, 1 H), 8.38 (d, 1 H); MS (MM−ES+APCI)+ m/z 423 [M+H]$^1$.

Example 63

1r,4r)-4-Methoxy-5"-methyl-6'-[4-methyl-5-(prop-1-yn-1-yl)pyridin-3-yl]-3'H-dispiro[cyclohexane-1,2'-indene-1',2"-imidazol]-4"-amine

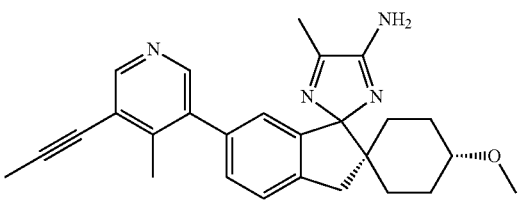

A suspension of 4,4,4',4',5,5,5',5'-octamethyl-2,2'-bi(1,3,2-dioxaborolane) (160 mg, 0.63 mmol), 3-bromo-4-methyl-5-(prop-1-ynyl)pyridine (Intermediate 45, 66 mg, 0.31 mmol) and potassium acetate (93 mg, 0.94 mmol) in dioxane (3 mL) was degassed with a stream of argon for a couple of min. PdCl₂(dppf)CH₂Cl₂ (13 mg, 0.02 mmol) was added and the mixture was heated at reflux under N₂ for 4 h. The mixture was allowed to cool, filtered and concentrated in vacuo. The obtained residue (80 mg, 4-methyl-3-(prop-1-ynyl)-5-(4,4,5,5-tetramethyl-1,3,2-dioxaborolan-2-yl)pyridine) was mixed with sodium tetrachloropalladate(II) (4 mg, 0.01 mmol), 3-(di-tert-butylphosphonium)propane sulfonate (6 mg, 0.02 mmol), and (1r,4r)-6'-bromo-4-methoxy-5''-methyl-3'H-dispiro[cyclohexane-1,2'-indene-1',2''-imidazol]-4''-amine (Example 19, 90 mg, 0.24 mmol) in dioxane (3 mL). The mixture was degassed with a stream of argon for a couple of min. and then heated at reflux. The reaction mixture was allowed to cool and the solvent was removed in vacuo. The residue was partitioned between water and EtOAc. The organic phase was dried (Na₂SO₄) and evaporated to give a crude product which was purified by flash chromatography (4 g SiO₂, heptane-(EtOAc/MeOH/NH₃ 90:10:1) gradient. The obtained material was purified by preparative chromatography. Fractions containing the product were pooled and the organic solvent was removed in vacuo. The residue was partitioned between 1 M NaOH and EtOAc. The organic phase was dried (Na₂SO₄) and evaporated to give an oily residue which was solidified by co-evaporation with acetonitrile to give the title compound (15 mg, 15% yield) after drying in vacuo at 40° C.: ¹H NMR (400 MHz, DMSO-d₆) δ ppm 0.98 (t, 1 H), 1.11-1.34 (m, 2 H), 1.34-1.57 (m, 3 H), 1.83 (d, 2 H), 2.13 (m, 9 H), 2.87-3.13 (m, 3 H), 3.20 (s, 3 H), 6.50 (d, 3 H), 7.18 (d, 1 H), 7.39 (d, 1 H), 8.16 (br. s., 1 H), 8.46 (br. s., 1 H); MS (APCI⁺) m/z 427 [M+H]⁺.

Example 64

(1r,4r)-6'-Bromo-5''-ethyl-4-methoxy-3'H-dispiro[cyclohexane-1,2'-indene-1',2''-imidazol]-4''-amine Step 1: (1r,4r)-6'-Bromo-5''-ethyl-4-methoxy-3'H-dispiro[cyclohexane-1,2'-indene-1',2''-imidazole]-4''(3''H)-thione

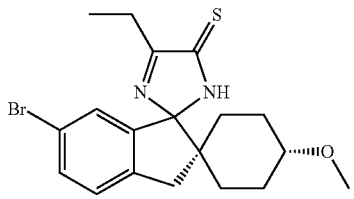

HCl (4M in 1,4-dioxane, 1.807 mL, 7.23 mmol) was added to a solution of N-((1r,4r)-5'-bromo-4-methoxyspiro[cyclohexane-1,2'-indene]-3'(1'H)-ylidene)-2-methylpropane-2-sulfinamide (Example 19 Method B Step 1, 0.60 g, 1.45 mmol) in anhydrous 1,4-dioxane (3 mL) and the resulting mixture was stirred under a nitrogen atmosphere at r.t. for 90 min. A precipitate had formed. Et₂O (15 mL) was added and the solid was filtered off and washed with Et₂O (10 mL). The solid was partitioned between DCM (20 mL) and sat. aq. NaHCO₃ (20 mL). The phases were separated and the organic layer was dried over Na₂SO₄ and concentrated to give crude (1r,4r)-6'-bromo-4-methoxyspiro[cyclohexane-1,2'-inden]-1'(3'H)-imine (1.658 g) that was mixed with 2-oxobutanethioamide (Intermediate 29, 1.891 g, 16.14 mmol) in MeOH (50 mL). The resulting mixture was refluxed for 18 h. The reaction mixture was concentrated and the product was purified by flash chromatography on silica gel, (gradient elution 0 to 50% EtOAc in n-heptane) to give the title compound (1.8 g, 82% yield): ¹H NMR (500 MHz, CDCl₃) δ ppm 1.17 (td, 1 H), 1.33 (m, 6 H), 1.63 (m, 1 H), 1.75 (m, 1 H), 2.02 (m, 2 H), 2.80 (m, 2 H), 3.09 (m, 3 H), 3.35 (s, 3 H), 7.04 (d, 1 H), 7.21 (d, 1 H), 7.45 (dd, 1 H), 8.97 (br. s., 1 H); MS (ES+) m/z 407 [M+H]⁺.

Step 2: (1r,4r)-6'-Bromo-5''-ethyl-4-methoxy-3'H-dispiro[cyclohexane-1,2'-indene-1',2''-imidazol]-4''-amine

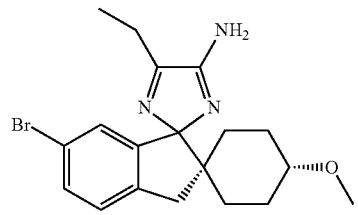

(1r,4r)-6'-Bromo-5''-ethyl-4-methoxy-3'H-dispiro[cyclohexane-1,2'-indene-1',2''-imidazole]-4''(3''H)-thione (Example 64 step 1, 0.32 g, 0.80 mmol) was dissolved in ammonia (7M solution in MeOH, 7.04 mL, 49.31 mmol) and the mixture was heated in a microwave oven at 90° C. for 2 h. The mixture was concentrated, re-dissolved in ammonia (7M solution in MeOH, 7.04 mL, 49.31 mmol) and heated at 90° C. for 30 min. This procedure was repeated one more time. The solvent was concentrated in vacuo and the residue was partitioned between citric acid (2 M aq. solution, 10 mL) and EtOAc (5 mL). The aqueous layer was neutralized with solid NaHCO₃ until gas evolution ceased and the product was extracted with EtOAc (50 mL). The organic layer washed with brine, dried over Na₂SO₄ and concentrated at reduced pressure to give the title compound (0.168 g, 54% yield): ¹H NMR (500 MHz, CDCl₃) δ ppm 1.08 (td, 1 H), 1.38 (m, 6 H), 1.67 (m, 2 H), 1.96 (m, 2 H), 2.62 (m, 2 H), 3.06 (m, 1 H), 3.12 (m, 2 H), 3.34 (s, 3 H), 6.87 (d, 1 H), 7.20 (d, 1 H), 7.36 (dd, 1 H); MS (ES+) m/z 390 [M+H]¹.

Example 65

1r,4r)-6'-(5-Chloropyridin-3-yl)-5''-ethyl-4-methoxy-3'H-dispiro[cyclohexane-1,2'-indene-1',2''-imidazol]-4''-amine

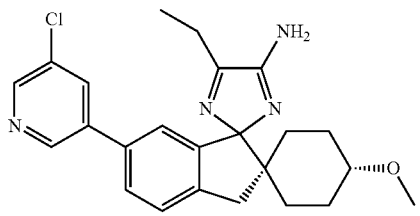

A mixture of (1r,4r)-6'-bromo-5''-ethyl-4-methoxy-3'H-dispiro[cyclohexane-1,2'-indene-1',2''-imidazol]-4''-amine (Example 64, 0.084 g, 0.22 mmol), 5-chloropyridin-3-ylboronic acid (0.034 g, 0.22 mmol), [1,1'-bis(diphenylphosphino)ferrocene]palladium(II) chloride (0.016 g, 0.02 mmol), K₂CO₃ (2 M aq. solution, 0.215 mL, 0.43 mmol) and 1,4-dioxane (2 mL) were mixed in a vial and heated in a microwave reactor at 130° C. for 20 min. When cooled to r.t. the mixture was diluted with DCM, washed with water, dried over Na₂SO₄, and concentrated. The product was purified by preparative chromatography to give the title compound (46 mg, 51% yield): ¹H NMR (500 MHz, CDCl₃) δ ppm 1.12 (td, 1 H), 1.38 (m, 6 H), 1.72 (m, 2 H), 2.03 (m, 2 H), 2.74 (q, 2 H), 3.11 (m, 1 H), 3.23 (d, 1 H), 3.30 (d, 1 H), 3.35 (s, 3 H), 6.99 (s, 1 H), 7.50 (m, 2 H), 7.79 (t, 1 H), 8.35 (s, 1 H), 8.52 (d, 1 H), 8.63 (m, 1 H); MS (ES+) m/z 423 [M+H]⁺.

Example 66

Separation of the isomers of (1r,4r)-6'-(5-chloropyridin-3-yl)-5"-ethyl-4-methoxy-3'H-dispiro[cyclohexane-1,2'-indene-1',2"-imidazol]-4"-amine (1r,4r)-6'-(5-Chloropyridin-3-yl)-5"-ethyl-4-methoxy-3'H-dispiro[cyclohexane-1,2'-indene-1',2"-imidazol]-4"-amine (Example 65, 39 mg, 0.09 mmol) was subjected to chiral HPLC separation using a SFC Berger Multigram II system with a Chiralcel OD-H column (4.6*250 mm; 5 μm) and a mobile phase consisting of 25% MeOH (containing 0.1% DEA) and 75% CO₂ at a flow rate of 50 mL/min to give:
Isomer 1 with undetermined absolute configuration (15 mg, 39% yield) with retention time 3.2 min: ¹H NMR (600 MHz) δ ppm 1.12 (td, 1 H), 1.32 (t, 3 H), 1.42 (m, 3 H), 1.71 (t, 2 H), 1.97 (d, 2 H), 2.63 (m, 2 H), 3.08 (m, 1 H), 3.24 (m, 2 H), 3.35 (s, 3 H), 6.90 (s, 1 H), 7.44 (s, 2 H), 7.78 (s, 1 H), 8.49 (m, 1 H), 8.62 (s, 1 H); MS (MM–ES+APCI)+ m/z 423 [M+H]⁺.
and
Isomer 2 with undetermined absolute configuration (11 mg, 29% yield) with retention time 8.9 min: ¹H NMR (600 MHz, CDCl₃) δ ppm 1.11 (m, 1 H) 1.32 (t, 3 H) 1.39 (m, 2 H) 1.50 (m, 1 H) 1.72 (t, 2 H) 1.97 (d, 2 H) 2.61 (dquin, 2 H) 3.08 (m, 1 H) 3.24 (m, 2 H) 3.35 (s, 3 H) 6.89 (s, 1 H) 7.43 (m, 2 H) 7.78 (s, 1 H) 8.49 (m, 1 H) 8.62 (s, 1 H); MS (MM–ES+APCI)+ m/z 423 [M+H]⁺.

Example 67

(1r,4r)-5"-Ethyl-4-methoxy-6'-[5-(prop-1-yn-1-yl)pyridin-3-yl]-3'H-dispiro[cyclohexane-1,2'-indene-1', 2"-imidazol]-4"-amine

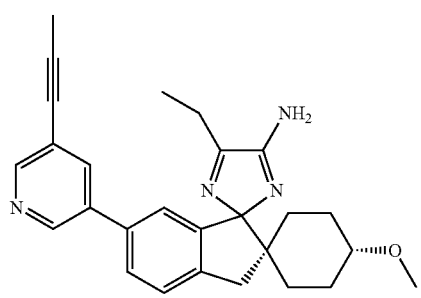

The title compound (40 mg, 43% yield) was prepared by the method described in Example 65 starting from (1r,4r)-6'-bromo-5"-ethyl-4-methoxy-3'H-dispiro[cyclohexane-1,2'-indene-1',2"-imidazol]-4"-amine (Example 64, 84 mg, 0.22 mmol), and 5-(prop-1-ynyl)pyridin-3-ylboronic acid (Intermediate 15, 35 mg, 0.22 mmol): ¹H NMR (500 MHz, CDCl₃) δ ppm 1.12 (td, 1 H), 1.34 (t, 3 H), 1.41 (m, 3 H), 1.70 (dd, 1 H), 1.77 (d, 1 H), 2.05 (m, 2 H), 2.09 (s, 3 H), 2.80 (q, 2 H), 3.11 (m, 1 H), 3.22 (d, 1 H), 3.30 (d, 1 H), 3.35 (s, 3 H), 7.03 (s, 1 H), 7.46 (m, 1 H), 7.52 (m, 1 H), 7.79 (s, 1 H), 8.54 (m, 1 H), 8.64 (m, 1 H); MS (ES+) m/z 427 [M+H]⁺.

Example 68

Separation of the isomers of (1r,4r)-5"-ethyl-4-methoxy-6'-[5-(prop-1-yn-1-yl)pyridin-3-yl]-3'H-dispiro[cyclohexane-1,2'-indene-1',2"-imidazol]-4"-amine (1r,4r-5"-Ethyl-4-methoxy-6'-[5-(prop-1-yn-1-yl)pyridin-3-yl]-3'H-dispiro[cyclohexane-1,2'-indene-1',2"-imidazol]-4"-amine (Example 67, 29 mg, 0.07 mmol) was subjected to chiral HPLC separation using a SFC Berger Multigram II system with a Chiralcel OD-H column (4.6*250 mm; 5 μm) and a mobile phase consisting of 25% MeOH (containing 0.1% DEA) and 75% CO₂ at a flow rate of 50 mL/min to give:
Isomer 1 with undetermined absolute configuration (11 mg, 39% yield) with retention time 3.4 min: ¹H NMR (600 MHz, CDCl₃) δ ppm 1.12 (m, 1 H), 1.32 (t, 3 H), 1.41 (m, 3 H), 1.72 (m, 2 H), 1.99 (br. s., 2 H), 2.09 (s, 3 H), 2.66 (m, 2 H), 3.09 (m, 1 H), 3.24 (m, 2 H), 3.35 (s, 3 H), 6.93 (s, 1 H), 7.44 (q, 2 H), 7.77 (s, 1 H), 8.53 (br. s., 1 H), 8.62 (br. s., 1 H); MS (MM–ES+APCI)+ m/z 427 [M+H]⁺.
and
Isomer 2 with undetermined absolute configuration (11 mg, 39% yield) with retention time 8.7 min: ¹H NMR (600 MHz, CDCl₃) δ ppm 1.11 (m, 1 H), 1.32 (t, 3 H), 1.39 (m, 2 H), 1.49 (m, 1 H), 1.72 (m, 2 H), 1.97 (d, 2 H), 2.09 (s, 3 H), 2.61 (m, 2 H), 3.08 (m, 1 H), 3.23 (m, 2 H), 3.35 (s, 3 H), 6.89 (s, 1 H), 7.43 (m, 2 H), 7.77 (s, 1 H), 8.53 (s, 1 H), 8.61 (s, 1 H); MS (MM–ES+APCI)+ m/z 427 [M+H]⁺.

Example 69

5-[(1r,4r)-4"-Amino-5"-ethyl-4-methoxy-3'H-dispiro[cyclohexane-1,2'-indene-1',2"-imidazol]-6'-yl]pyridine-3-carbonitrile

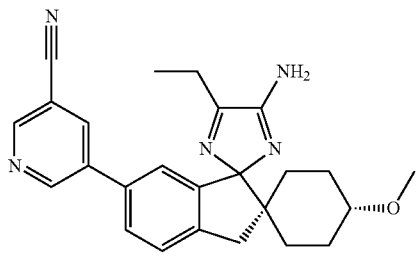

The title compound (44 mg, 52% yield) was prepared by the method described in Example 65 starting from (1r,4r)-6'-bromo-5"-ethyl-4-methoxy-3'H-dispiro[cyclohexane-1,2'-indene-1',2"-imidazol]-4"-amine (Example 64, 80 mg, 0.20 mmol), and 5-cyanopyridin-3-ylboronic acid (0.030 g, 0.20 mmol): ¹H NMR (500 MHz, CDCl₃) δ ppm 1.14 (td, 1 H), 1.37 (m, 6 H), 1.72 (m, 2 H), 2.04 (m, 2 H), 2.73 (q, 2 H), 3.10

(m, 1 H), 3.24 (d, 1 H), 3.31 (d, 1 H), 3.36 (s, 3 H), 7.00 (s, 1 H), 7.52 (m, 2 H), 8.06 (t, 1 H), 8.83 (d, 1 H), 8.95 (d, 1 H); MS (ES+) m/z 414 [M+H]+.

Example 70

3-[(1r,4r)-4"-amino-5"-ethyl-4-methoxy-3'H-dispiro[cyclohexane-1,2'-indene-1',2"-imidazol]-6'-yl]benzonitrile

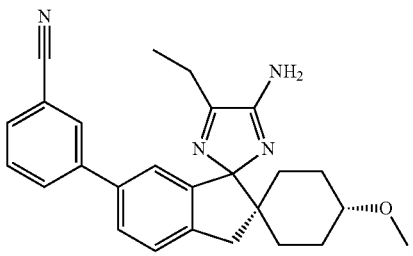

The title compound (73 mg, 85% yield) was prepared by the method described in Example 65 starting from (1r,4r)-6'-bromo-5"-ethyl-4-methoxy-3'H-dispiro[cyclohexane-1,2'-indene-1',2"-imidazol]-4"-amine (Example 64, 81 mg, 0.21 mmol), and 3-cyanophenylboronic acid (30 mg, 0.21 mmol): $^1$H NMR (500 MHz, CDCl$_3$) δ ppm 1.13 (td, 1 H), 1.38 (m, 6 H), 1.72 (m, 2 H), 2.05 (m, 2 H), 2.76 (q, 2 H), 3.11 (m, 1 H), 3.22 (d, 1 H), 3.30 (d, 1 H), 3.35 (s, 3 H), 7.00 (s, 1 H), 7.46 (m, 1 H), 7.52 (m, 2 H), 7.61 (d, 1 H), 7.73 (d, 1 H), 7.78 (s, 1 H), 8.32 (br. s., 1 H); MS (ES+) m/z 413 [M+H]+.

Example 71

Separation of the isomers of 3-[(1r,4r)-4"-amino-5"-ethyl-4-methoxy-3'H-dispiro-[cyclohexane-1,2'-indene-1',2"-imidazol]-6'-yl]benzonitrile 3-[(1r,4r)-4"-Amino-5"-ethyl-4-methoxy-3'H-dispiro[cyclohexane-1,2'-indene-1',2"-imidazol]-6'-yl]benzonitrile (Example 70, 34 mg, 0.08 mmol) was subjected to chiral HPLC separation using a SFC Berger Multigram II system with a Chiralcel OD-H column (4.6*250 mm; 5 μm) and a mobile phase consisting of 25% MeOH (containing 0.1% DEA) and 75% CO$_2$ at a flow rate of 50 mL/min to give:

Isomer 1 with undetermined absolute configuration (22 mg, 65% yield) with retention time 3.4 min: $^1$H NMR (600 MHz, CDCl$_3$) δ ppm 1.12 (td, 1 H), 1.33 (t, 3 H), 1.42 (m, 3 H), 1.72 (m, 2 H), 1.98 (d, 2 H), 2.63 (m, 2 H), 3.08 (m, 1 H), 3.24 (m, 2 H), 3.35 (s, 3 H), 6.90 (s, 1 H), 7.43 (m, 2 H), 7.48 (t, 1 H), 7.57 (d, 1 H), 7.73 (d, 1 H), 7.78 (s, 1 H); MS (MM–ES+APCI)+ m/z 413 [M+H]+.

and

Isomer 2 with undetermined absolute configuration (19 mg, 56% yield) with retention time 11.6 min: $^1$H NMR (600 MHz, CDCl$_3$) δ ppm 1.11 (m, 1 H), 1.32 (t, 3 H), 1.39 (m, 2 H), 1.48 (m, 2 H), 1.72 (t, 2 H), 1.97 (d, 2 H), 2.62 (dquin, 2 H), 3.08 (m, 1 H), 3.23 (m, 2 H) 3.35 (s, 3 H), 6.89 (s, 1 H), 7.42 (s, 2 H), 7.47 (t, 1 H), 7.57 (d, 1 H), 7.72 (d, 1 H), 7.78 (s, 1 H); MS (MM–ES+APCI)+ m/z 413 [M+H]+.

Example 72

(1r,4r)-6'-[5-(But-1-yn-1-yl)pyridin-3-yl]-4-methoxy-5"-methyl-3'H-dispiro[cyclohexane-1,2'-indene-1',2"-imidazol]-4"-amine

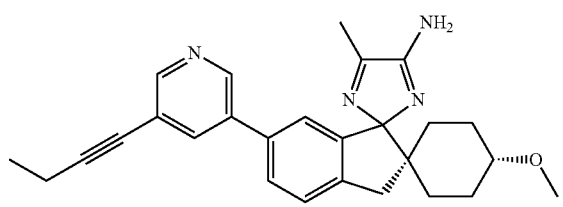

(1r,4r)-6'-Bromo-4-methoxy-5"-methyl-3'H-dispiro[cyclohexane-1,2'-indene-1',2"-imidazol]-4"-amine (Example 19 Method B Step 4, 83 mg, 0.22 mmol), PdCl$_2$(dppf)-CH$_2$Cl$_2$ adduct (9.0 mg, 0.01 mmol), 5-(but-1-ynyl)pyridin-3-ylboronic acid (60 mg, 0.34 mmol) and Cs$_2$CO$_3$ (144 mg, 0.44 mmol) were weighed into a microwave vial. A mixture of DME, water and EtOH (6:3:1) (5 mL) was added and the vial was flushed with argon. The resulting mixture was heated to 120° C. in a microwave reactor for 1 h. The mixture was diluted with EtOAc and filtered. The solvents were evaporated and the residue was purified by preparative chromatography to give 37 mg (39% yield) of the title compound: $^1$H NMR (500 MHz, CDCl$_3$) δ ppm 1.12 (td, 1 H), 1.27 (t, 2 H), 1.29-1.44 (m, 2 H), 1.50 (td, 1 H), 1.65-1.77 (m, 2 H), 1.92-2.01 (m, 2 H), 2.31 (s, 3 H), 2.45 (q, 2 H), 3.02-3.15 (m, 1 H), 3.17-3.28 (m, 2 H), 3.34 (s, 3 H), 6.90 (s, 1 H), 7.41 (s, 2 H), 7.78 (t, 1 H), 8.53 (d, 1 H), 8.61 (d, 1 H); MS (APCI+) m/z 427 [M+H]+.

Example 73

(1r,1'R,4R)-4"-Amino-5"-methyl-6'-[5-(prop-1-yn-1-yl)pyridin-3-yl]-3'H-dispiro[cyclohexane-1,2'-indene-1',2"-imidazol]-4-ol

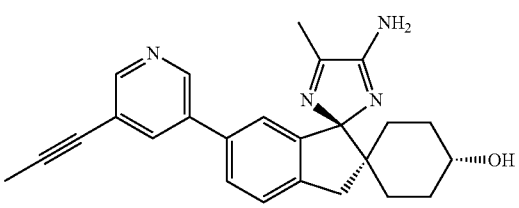

(1r,1'R,4R)-4-Methoxy-5"-methyl-6'-[5-(prop-1-yn-1-yl)pyridin-3-yl]-3'H-dispiro[cyclohexane-1,2'-indene-1',2"-imidazol]-4"-amine (Example 20a Isomer 1, 519 mg, 1.26 mmol) was added to (methylthio)trimethylsilane (1.249 mL, 8.81 mmol) in 1,2-dichloroethane (8 mL), followed by zinc iodide (2.0 g, 6.29 mmol) and tetrabutylammonium iodide (697 mg, 1.89 mmol). The suspension was stirred at 60° C. for 2 days. The reaction mixture was filtered and the filtrate was washed with a 5% aq solution of barium hydroxide then with water. After evaporation of the solvent, the residue was subjected to flash chromatography (0-7% MeOH (containing NH₃) in DCM) to give the title compound (100 mg, 20% yield): ¹H NMR (500 MHz, DMSO-d₆) δ ppm 0.89-1.02 (m, 1 H) 1.13-1.35 (m, 2 H) 1.41 (br. s., 3 H) 1.66 (br. s., 2 H) 2.09 (s, 3 H) 2.17 (s, 3 H) 3.04 (dd, 2 H) 3.18-3.27 (m, 1 H) 4.55 (br. s, 1 H) 6.53 (br. s., 2 H) 6.82 (s, 1 H) 7.41 (d, 1 H) 7.53 (dd, 1 H) 7.90 (s, 1 H) 8.51 (d, 1 H) 8.66 (d, 1 H); MS (ES+) m/z 399 [M+H]⁺.

Example 74

3-[(1r,4r)-4"-Amino-4-methoxy-5"-methyl-3'H-dispiro[cyclohexane-1,2'-indene-1',2"-imidazol]-6'-yl]-5-methylbenzonitrile

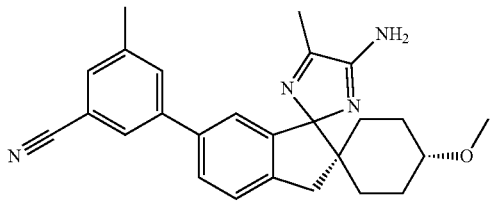

(1r,4r)-6'-Bromo-4-methoxy-5"-methyl-3'H-dispiro[cyclohexane-1,2'-indene-1',2"-imidazol]-4"-amine (Example 19 Method B Step 4, 414 mg, 1.10 mmol), potassium acetate (216 mg, 2.20 mmol), bis(pinacolato)diboron (307 mg, 1.21 mmol) and PdCl₂(dppf)-dichloromethane adduct (44.9 mg, 0.06 mmol) were taken up in dioxane (8 mL) in a Biotage 10-20 mL microwave vial. The reaction vessel was sealed and heated at 130° C. for 35+20 min in a Biotage Initiator. The obtained mixture containing (1r,4r)-4-methoxy-5"-methyl-6'44,4,5,5-tetramethyl-1,3,2-dioxaborolan-2-yl)-3'H-dispiro [cyclohexane-1,2'-indene-1',2"-imidazol]-4"-amine mixture was used directly. K₂CO₃ (2 M aq., 2.20 mL, 4.41 mmol), Pd(Ph₃P)₄ (63.7 mg, 0.06 mmol) and 3-bromo-5-methylbenzonitrile (Intermediate 50, 216 mg, 1.10 mmol) in dioxane (2 mL) were added. The reaction vessel was sealed and heated at 130° C. for 20 min in a Biotage Initiator. After cooling, the vessel was uncapped, the mixture was diluted with DCM, washed with brine, dried over MgSO₄, filtered and concentrated in vacuo. The product was purified by preparative chromatography to give the title product compound (62 mg, 16% yield): ¹H NMR (600 MHz, DMSO-d₆) δ ppm 0.97 (td, 1 H) 1.11-1.30 (m, 2 H) 1.35-1.52 (m, 3 H) 1.83 (d, 2 H) 2.18 (s, 3 H) 2.39 (s, 3 H) 2.90-2.97 (m, 1 H) 2.97-3.11 (m, 2 H) 3.20 (s, 3 H) 6.53 (br. s, 2 H) 6.82 (s, 1 H) 7.39 (d, 1 H) 7.52 (d, 1 H) 7.59 (s, 1 H) 7.67 (s, 1 H) 7.77 (s, 1 H); MS (ES+) m/z 413 [M+H]¹.

Example 75

3-[(1r,4r)-4"-Amino-4-methoxy-5"-methyl-3'H-dispiro[cyclohexane-1,2'-indene-1',2"-imidazol]-6'-yl]-5-fluorobenzonitrile

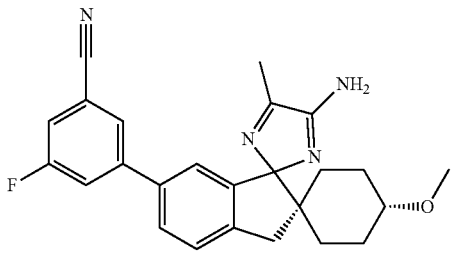

A mixture of (1r,4r)-6'-bromo-4-methoxy-5"-methyl-3'H-dispiro[cyclohexane-1,2'-indene-1',2"-imidazol]-4"-amine (Example 19 Method B Step 4, 300 mg, 0.80 mmol), 3-cyano-5-fluoro-phenylboronic acid (145 mg, 0.88 mmol), [1,1'-bis (diphenylphosphino)ferrocene]palladium(II) chloride (59.0 mg, 0.07 mmol), K₂CO₃, 2 M aq. solution (0.797 mL, 1.59 mmol) and 1,4-dioxane (5 mL) were mixed in a vial and heated in a microwave reactor at 130° C. for 20 min. When cooled to r.t. the mixture was diluted with DCM, washed with water and dried over Na₂SO₄. The filtrate was concentrated and the product purified by preparative chromatography to give the title compound (190 mg, 57% yield): ¹H NMR (400 MHz, DMSO-d₆) δ ppm 0.90-1.03 (m, 1 H) 1.11-1.31 (m, 2 H) 1.36-1.53 (m, 3 H) 1.82 (d, 2 H) 2.18 (s, 3 H) 2.88-2.98 (m, 1 H) 2.96-3.12 (m, 2 H) 3.19 (s, 3 H) 6.56 (br. s, 2 H) 6.90 (d, 1 H) 7.40 (d, 1 H) 7.58 (dd, 1 H) 7.73-7.84 (m, 2 H) 7.90 (t, 1 H); MS (ES+) m/z 417 [M+H]⁺.

Example 76

Separation of the isomers of 3-[(1r,4r)-4"-amino-4-methoxy-5"-methyl-3'H-dispiro[cyclohexane-1,2'-indene-1',2"-imidazol]-6'-yl]-5-fluorobenzonitrile 3-[(1r,4r)-4"-Amino-4-methoxy-5"-methyl-3'H-dispiro [cyclohexane-1,2'-indene-1',2"-imidazol]-6'-yl]-5-fluorobenzonitrile (Example 75, 157 mg, 0.378 mmol) was dissolved in MeOH/DEA and the resulting solution was injected (2 separate injections) on a SFC Berger Multigram II system equipped with a LuxC4 (4.6*250 mm; 5 μm) column using a mobile phase consisting of 30% MeOH (containing 0.1% DEA) and 70% CO₂ at a flowrate of 50 mL/min to give:
Isomer 1 with undetermined absolute configuration (56 mg, 36% yield) with retention time 4.8 min: ¹H NMR (500 MHz, DMSO-d₆) δ ppm 0.88-1.05 (m, 1 H) 1.09-1.30 (m, 2 H) 1.35-1.52 (m, 3 H) 1.83 (d, 2 H) 2.18 (s, 3 H) 2.88-2.98 (m, 1 H) 3.04 (q, 2 H) 3.19 (s, 3 H) 6.53 (br. s, 2 H) 6.90 (s, 1 H) 7.41 (d, 1 H) 7.59 (d, 1 H) 7.74-7.84 (m, 2 H) 7.90 (s, 1 H); MS (ES+) m/z 417 [M+H]⁺; and
Isomer 2 with undetermined absolute configuration (56 mg, 36% yield) with retention time 13 min: ¹H NMR (500 MHz, DMSO-d₆) δ ppm 0.92-1.06 (m, 1 H) 1.11-1.30 (m, 2 H) 1.36-1.56 (m, 3 H) 1.83 (d, 2 H) 2.18 (s, 3 H) 2.89-2.97 (m, 1 H) 3.04 (q, 2 H) 3.20 (s, 3 H) 6.53 (br. s., 2 H) 6.90 (s, 1 H) 7.41 (d, 1 H) 7.59 (d, 1 H) 7.73-7.83 (m, 2 H) 7.91 (s, 1 H); MS (ES+) m/z 417 [M+H]⁺.

Example 77

6'-Bromo-5"-methyl-3'H-dispiro[cyclopropane-1,2'-indene-1',2"-imidazol]-4"-amine Step 1: N-(5'-Bromospiro[cyclopropane-1,2'-indene]-3'(1'H)-ylidene)-2-methylpropane-2-sulfinamide

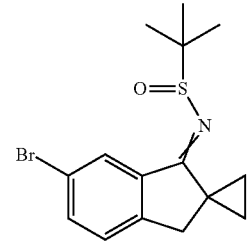 [SMILES: CC(C)(C)S(=O)N=C1c2cc(Br)ccc2CC12CC2]

The title compound was prepared in quantitative yield as described for Example 19 Method A Step 1 starting from 6'-bromospiro[cyclopropane-1,2'-inden]-1'(3'H)-one (Intermediate 52, 1.41 g, 5.96 mmol): MS (ES+) m/z 342 [M+H]+.

Step 2: 6'-Bromospiro[cyclopropane-1,2'-inden]-1'(3'H)-imine

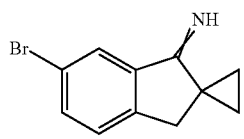

The title compound (0.61 g, 44% yield) was prepared as described for Example 19 Method A Step 2 starting from N-(5'-bromospiro[cyclopropane-1,2'-indene]-3'(1'H)-ylidene)-2-methylpropane-2-sulfinamide (Example 77 Step 1, 2.0 g, 5.88 mmol): MS (ES+) m/z 236 [M+H]+.

Step 3: 6'-Bromo-5"-methyl-3'H-dispiro[cyclopropane-1,2'-indene-1',2"-imidazole]-4"(3"H)-thione

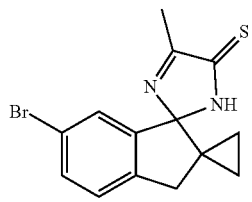 [SMILES: CC1=NC2(NC1=S)c1cc(Br)ccc1CC21CC1]

The title compound (0.51 g, 63% yield) was prepared as described for Example 19 Method A Step 3 starting from 6'-bromospiro[cyclopropane-1,2'-inden]-1'(3'H)-imine (Example 77 Step 2, 0.61 g, 2.54 mmol). $^1$H NMR (500 MHz, CDCl$_3$) δ ppm 0.55-0.62 (m, 1 H), 0.64-0.73 (m, 2 H), 0.79-0.87 (m, 1 H), 2.39 (s, 3 H), 2.91 (d, 1 H), 3.36 (d, 1 H), 7.09 (d, 1 H), 7.21 (d, 1 H), 7.48 (dd, 1 H), MS (ES+) m/z 321 [M+H]+.

Step 4

6'-Bromo-5"-methyl-3'H-dispiro[cyclopropane-1,2'-indene-1',2"-imidazol]-4"-amine

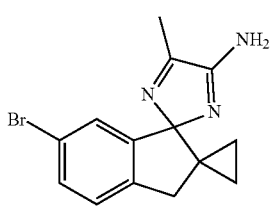 [SMILES: CC1=NC2(N=C1N)c1cc(Br)ccc1CC21CC1]

The title compound (0.33 g, 68% yield) was prepared as described for Example 19 Method A Step 4 starting from 6'-bromo-5"-methyl-3'H-dispiro[cyclopropane-1,2'-indene-1',2"-imidazole]-4"(3"H)-thione (Example 77 step 3, 0.51 g, 1.59 mmol): $^1$H NMR (500 MHz, CDCl$_3$) δ ppm 0.23 (ddd, 1 H), 0.42-0.57 (m, 1 H), 0.65 (dt, 1 H), 0.79 (ddd, 1 H), 2.29 (s, 3 H), 2.87 (d, 1 H), 3.42 (d, 1 H), 6.90 (d, 1 H), 7.19 (d, 1 H), 7.37 (dd, 1 H), MS (ES+) m/z 304 [M+H]+.

Example 78

3-(4"-Amino-5"-methyl-3'H-dispiro[cyclopropane-1,2'-indene-1',2"-imidazol]-6'-yl)-5-chlorobenzonitrile

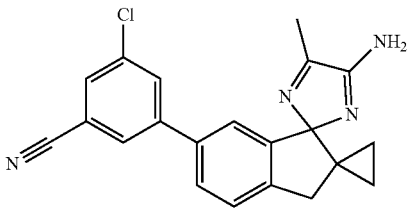 [SMILES: CC1=NC2(N=C1N)c1cc(-c3cc(Cl)cc(C#N)c3)ccc1CC21CC1]

6'-Bromo-5"-methyl-3'H-dispiro[cyclopropane-1,2'-indene-1',2"-imidazol]-4"-amine (Example 77, 0.10 g, 0.33 mmol), 3-chloro-5-(4,4,5,5-tetramethyl-1,3,2-dioxaborolan-2-yl)benzonitrile (Intermediate 35, 0.121 g, 0.46 mmol), [1,1'-bis(diphenylphosphino)ferrocene]palladium(II) chloride (0.048 g, 0.07 mmol), 2M aq. K$_2$CO$_3$ (0.493 mL, 0.99 mmol) and THF (1 mL) were added to microwave vial. The mixture was degassed by bubbling N$_2$ (g) through it. The vial was sealed and heated in a microwave reactor at 130° C. for 30 min. [1,1'-Bis(diphenylphosphino)-ferrocene]palladium(II) chloride (0.048 g, 0.07 mmol) was added and the mixture was degassed by bubbling N$_2$ (g) through it. The vial was sealed and heated in a microwave reactor at 130° C. for 30 min. The residue was dissolved in EtOAc and the mixture was extracted with 1.0 M HCl (2×10 mL). The organic layer was discarded while the aq phase was basified to pH 12 by addition of 1 M NaOH (aq). The basic water phase was extracted with DCM (2×20 mL). The organic phase was dried through a phase separator and concentrated in vacuo. The crude product was purified by flash chromatography (0-10% 0.1 M NH$_3$ in MeOH, in DCM, 25 g SiO$_2$ column). The product was purified by a second flash chromatography (0-100% EtOAc in heptane, 25 g SiO$_2$ column) followed by preparative chromatography. The fractions containing pure product were combined and concentrated. DCM was added and the organic phase was collected and dried through a phase separator and concentrated in vacuo, yielding the title compound (10 mg, 0.028 mmol, 8% yield): $^1$H NMR (500 MHz, CD$_3$OD) δ ppm 0.14-0.23 (m, 1 H), 0.50-0.58 (m, 1 H), 0.62-0.70 (m, 1 H), 0.80 (ddd, 1 H), 2.30 (s, 3 H), 2.96 (d, 1 H), 3.49 (d, 1 H), 7.02-7.08 (m, 1 H), 7.47 (d, 1 H), 7.59 (dd, 1 H), 7.73 (s, 1 H), 7.88 (s, 2 H); MS (MM–ES+APCI)+ m/z 361 [M+H]+.

Example 79

(1r,4r)-4"-Amino-4-methoxy-5"-methyl-3'H-dispiro[cyclohexane-1,2'-indene-1',2"-imidazole]-6'-carbonitrile Step 1: Tert-butyl [(1r,4r)-6'-bromo-4-methoxy-5"-methyl-3'H-dispiro[cyclohexane-1,2'-indene-1',2"-imidazol]-4"-yl]carbamate

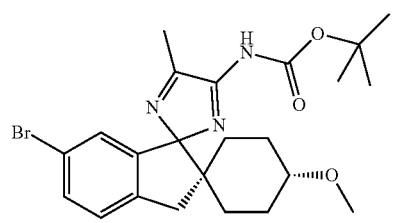

Di-tert-butyl dicarbonate (87 mg, 0.40 mmol) was added to a stirred solution of (1r,4r)-6'-bromo-4-methoxy-5"-methyl-3'H-dispiro[cyclohexane-1,2'-indene-1',2"-imidazol]-4"-amine (Example 19 Method B Step 4, 100 mg, 0.27 mmol) in DMF (5 mL). The reaction was stirred at r.t. overnight. The mixture was then partitioned between water (10 mL) and EtOAc (10 mL). The organic phase was washed with brine (10 mL), dried over MgSO$_4$ and concentrated in vacuo to give the title compound (112 mg, 88% yield): MS (ES−) m/z 474 [M−H]$^-$. The position of the tBuOC(O)-group was not established with certainty.

Step 2: (1r,4r)-4"-Amino-4-methoxy-5"-methyl-3'H-dispiro[cyclohexane-1,2'-indene-1',2"-imidazole]-6'-carbonitrile

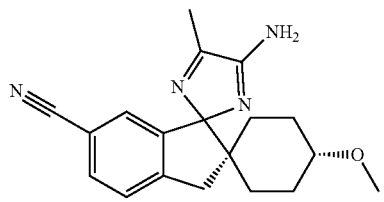

A mixture of tert-butyl [(1r,4r)-6'-bromo-4-methoxy-5"-methyl-3'H-dispiro[cyclohexane-1,2'-indene-1',2"-imidazol]-4"-yl]carbamate (Example 79 step 1, 112 mg, 0.24 mmol), zinc cyanide (33 mg, 0.28 mmol) and tetrakis(triphenylphosphine)palladium(0) (14 mg, 0.01 mmol) in anhydrous DMF (2.1 mL) was irradiated at 170° C. in a microwave oven for 60 min and was then left at r.t. overnight. The mixture was diluted with conc NH$_3$ (10 mL) and extracted with DCM (2×10 mL), dried through a phase separator column and concentrated in vacuo. The product was purified using preparative chromatography to give the title compound (5 mg, 6% yield): 1H NMR (500 MHz, CDCl$_3$) δ ppm 1.16 (m, 1 H) 1.34 (m, 3 H) 1.66 (m, 2 H) 2.04 (m, 2 H) 2.45 (s, 3 H) 2.66 (s, 2 H) 3.04-3.15 (m, 1 H) 3.35 (s, 3 H) 7.17 (s, 1 H) 7.48 (d, J=7.88 Hz, 1 H) 7.63 (d, J=7.57 Hz, 1 H) 8.23 (br. s., 1 H) MS (ES+) m/z 323 [M+H]$^+$.

Example 80

(1r,4r)-4-Methoxy-6'-[3-(methoxymethyl)phenyl]-5"-methyl-3'H-dispiro[cyclohexane-1,2'-indene-1', 2"-imidazol]-4"-amine

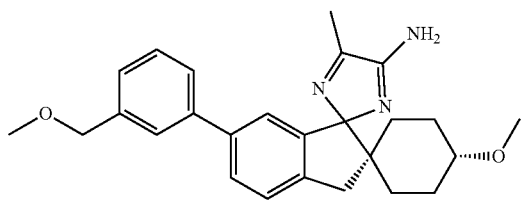

(1r,4r)-6'-Bromo-4-methoxy-5"-methyl-3'H-dispiro[cyclohexane-1,2'-indene-1',2"-imidazol]-4"-amine (Example 19 Step 4 Method B, 183 mg, 0.49 mmol), PdCl$_2$(dppf)-CH$_2$Cl$_2$ adduct (20 mg, 0.02 mmol) and Cs$_2$CO$_3$ (317 mg, 0.97 mmol) were placed in a microwave vial. A solution of 3-(methoxymethyl)phenylboronic acid (105 mg, 0.63 mmol) in a 6:3:1 mixture of DME, water and EtOH (5 mL) was added, and the tube was capped and flushed with argon. The mixture was heated to 120° C. in a microwave reactor for 1 h. The reaction mixture was filtered through a plug of diatomaceous earth and MgSO$_4$. The solvents were evaporated and the residue was purified by preparative chromatography to give 54 mg (26% yield) of the title compound: $^1$H NMR (500 MHz, DMSO-d$_6$) δ ppm 0.94 (td, 1 H), 1.12-1.31 (m, 2 H), 1.43-1.52 (m, 3 H), 1.83 (m, 2 H), 2.16 (s, 3 H), 2.91-3.01 (m, 2 H), 3.05-3.11 (m, 1 H), 3.20 (s, 3 H), 3.30 (s, 3 H), 4.45 (s, 2 H), 6.56 (s, 2 H), 6.75 (d, 1 H), 7.25 (m, 1 H), 7.35-7.40 (m, 2 H), 7.40-7.44 (m, 2 H), 7.44-7.47 (m, 1 H); MS (ES+) m/z 418 [M+H]$^+$.

Example 81

(1r,4r)-6'-[3-Fluoro-5-(methoxymethyl)phenyl]-4-methoxy-5"-methyl-3'H-dispiro[cyclohexane-1,2'-indene-1',2"-imidazol]-4"-amine

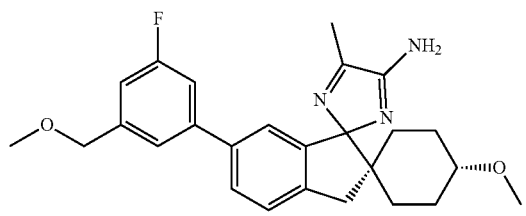

1-Bromo-3-fluoro-5-(methoxymethyl)benzene (Intermediate 53, 139 mg, 0.63 mmol), 4,4,4',4',5,5,5',5'-octamethyl-2,2'-bi(1,3,2-dioxaborolane) (177 mg, 0.70 mmol), PdCl$_2$(dppf)-CH$_2$Cl$_2$ adduct (26 mg, 0.03 mmol) and potassium acetate (187 mg, 1.90 mmol) were weighed into a microwave vial. 2-Me THF (2 mL) was added and the vial was flushed with argon. The mixture was heated to 100° C. in a microwave reactor for 30 min. From this reaction mixture, as an assumed 0.3 M solution in dioxane, was taken the formed 2-(3-fluoro-5-(methoxymethyl)-phenyl)-4,4,5,5-tetramethyl-1,3,2-dioxaborolane (0.945 mL, 0.28 mmol). The solution was added to a mixture of (1r,4r)-6'-bromo-4-methoxy-5"-methyl-3'H-dispiro[cyclohexane-1,2'-indene-1',2"-imidazol]-4"-amine (Example 19 Method B Step 4, 82 mg, 0.22 mmol), sodium tetrachloropalladate(II) (7 mg, 0.02 mmol), 3-(di-tert-butylphosphino)propane-1-sulfonic acid (13 mg, 0.05 mmol), K$_2$CO$_3$ (0.33 mL, 0.65 mmol) and dioxane (2 mL) in a microwave tube. The tube was flushed with argon and the mixture was heated to 120° C. in a microwave reactor for 2 h. The reaction mixture was partitioned between EtOAc and water. The aqueous phase was extracted with EtOAc. The combined organic layers were washed with water and dried over MgSO$_4$. It was then treated with active charcoal for 5 min, filtered and concentrated in vacuo. The residue was purified by HPLC to give 19 mg (20% yield) of the title compound: $^1$H NMR (500 MHz, DMSO-d$_6$) δ ppm 0.94 (m, 1 H), 1.12-1.30 (m, 2 H), 1.40-1.51 (m, 3 H), 1.83 (m, 2 H), 2.17 (s, 3 H), 2.91-3.02 (m, 2 H), 3.05-3.11 (m, 1 H), 3.20 (s, 3 H), 3.31 (s, 3 H), 4.46 (s, 2 H), 6.56 (br. s., 2 H), 6.79 (s, 1 H), 7.07 (d, 1 H), 7.23-7.30 (m, 2 H), 7.38 (d, 1 H), 7.47-7.51 (m, 1 H); MS (ES+) m/z 436 [M+H]$^+$.

Example 82

(1r,4r)-4-Methoxy-5''-methyl-6'-{5-[(2,2,2-trifluoroethoxy)methyl]pyridin-3-yl}-3'H-dispiro[cyclohexane-1,2'-indene-1',2''-imidazol]-4''-amine

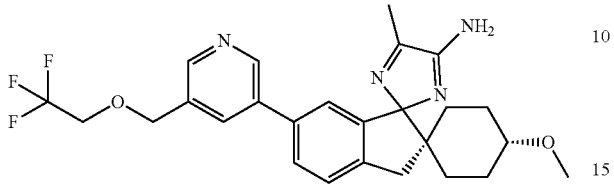

The title compound (37 mg, 19% yield) was prepared as described for Example 81 starting from 3-bromo-5-((2,2,2-trifluoroethoxy)methyl)pyridine (Intermediate 54, 222 mg, 0.82 mmol) and (1r,4r)-6'-Bromo-4-methoxy-5''-methyl-3'H-dispiro[cyclohexane-1,2'-indene-1',2''-imidazol]-4''-amine (Example 19 Method B Step 4, 149 mg, 0.40 mmol): $^1$H NMR (500 MHz, DMSO-$d_6$) δ ppm 0.91-1.01 (m, 1 H), 1.13-1.31 (m, 2 H), 1.44-1.52 (m, 3 H), 1.83 (m, 2 H), 2.17 (s, 3 H), 2.90-3.04 (m, 2 H), 3.05-3.14 (m, 1 H), 3.20 (s, 3 H), 4.16 (q, 2 H), 4.76 (s, 2 H), 6.56 (s, 2 H), 6.80-6.85 (m, 1 H), 7.42 (d, 1 H), 7.50-7.56 (m, 1 H), 7.83-7.90 (m, 1 H), 8.48-8.52 (m, 1 H), 8.70 (m, 1 H); MS (ES+) m/z 487 [M+H]$^+$.

Example 83

(1r,1'R,4R)-4-Methoxy-5''-methyl-6'-(5-methylpyridin-3-yl)-3'H-dispiro[cyclohexane-1,2'-indene-1',2''-imidazol]-4''-amine

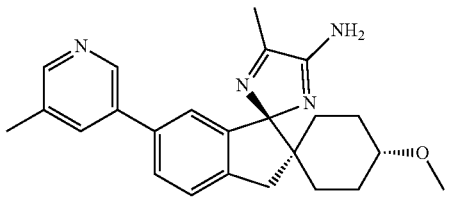

(1r,1'R,4R)-6'-Bromo-4-methoxy-5''-methyl-3'H-dispiro[cyclohexane-1,2'-indene-1',2''-imidazol]-4''-amine as the D(+)-10-camphor sulfonic acid salt (Example 19 Step 5, 130 mg, 0.21 mmol) was treated with 2-methyl-tetrahydrofuran (3 mL). Aq. KOH solution (1 M, 3 mL) was added, and the mixture was stirred for 1 h. The water phase was removed and the suspension was washed with aq. $K_2CO_3$ solution (2 M, 3 mL). The phases were separated, and to the organic layer was added to a mixture of (5-methyl-3-pyridinyl)-boronic acid (40.5 mg, 0.30 mmol), sodium tetrachloropalladate(II) (8.80 mg, 0.03 mmol), and 3-(di-tert-butylphosphonium)propane sulfonate (16.05 mg, 0.06 mmol) in a microwave vial. $K_2CO_3$ (2.0 M, 0.320 mL, 0.64 mmol) was added, the vial was closed, and the atmosphere was exchanged for argon. The reaction mixture was heated to 100° C. for 30 min by microwave irradiation. The reaction mixture was cooled to r.t., diluted with EtOAc, and washed with brine. The organic layer was dried over $MgSO_4$, filtered, and concentrated in vacuo. The residue was purified by preparative chromatography to give the title compound (18 mg, 19% yield): $^1$H NMR (500 MHz, DMSO-$d_6$) δ ppm 0.96 (td, 1 H) 1.12-1.29 (m, 2 H) 1.41-1.52 (m, 3 H) 1.83 (d, 2 H) 2.17 (s, 3 H) 2.33 (s, 3 H) 2.89-2.98 (m, 1 H) 3.04 (q, 2 H) 3.20 (s, 3 H) 6.55 (br. s., 2 H) 6.80 (s, 1 H) 7.40 (d, 1 H) 7.50 (dd, 1 H) 7.72 (s, 1 H) 8.35 (s, 1 H) 8.52 (d, 1 H); MS (ES+) m/z 389 [M+H]$^+$.

Example 84

(1r,1'R,4R)-4-Methoxy-5''-methyl-6'-[5-(trifluoromethyl)pyridin-3-yl]-3'H-dispiro[cyclohexane-1,2'-indene-1',2''-imidazol]-4''-amine

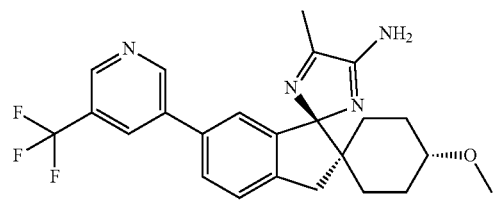 [SMILES: CO[C@H]1CC[C@]2(CC1)Cc1ccc(-c3cncc(C(F)(F)F)c3)cc1[C@@]21N=C(C)C(N)=N1]

The title compound (35 mg 32% yield) was prepared as described for Example 83 starting from (1r,1'R,4R)-6'-bromo-4-methoxy-5''-methyl-3'H-dispiro[cyclohexane-1,2'-indene-1',2''-imidazol]-4''-amine as the D(+)-10-camphor sulfonic acid salt (Example 19 Step 5, 130 mg, 0.21 mmol), and 5-trifluoromethyl-pyridine-3-boronic acid (56.5 mg, 0.30 mmol): $^1$H NMR (500 MHz, DMSO-$d_6$) δ ppm 0.87-1.06 (m, 1 H) 1.11-1.31 (m, 2 H) 1.38-1.54 (m, 3 H) 1.83 (d, 2 H) 2.17 (s, 3 H) 2.96 (m, 1 H) 3.06 (q, 2 H) 3.20 (s, 3 H) 6.55 (br. s, 2 H) 6.93 (d, 1 H) 7.45 (d, 1 H) 7.63 (dd, 1 H) 8.28 (s, 1 H) 8.91 (d, 1 H) 9.05 (d, 1 H); MS (ES+) m/z 443 [M+H]$^+$.

Example 85

3-[(1r,1'R,4R)-4''-Amino-4-methoxy-5''-methyl-3'H-dispiro[cyclohexane-1,2'-indene-1',2''-imidazol]-6'-yl]-5-(trifluoromethyl)benzonitrile

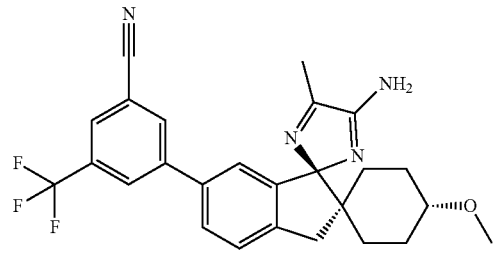 [SMILES: CO[C@H]1CC[C@]2(CC1)Cc1ccc(-c3cc(C#N)cc(C(F)(F)F)c3)cc1[C@@]21N=C(C)C(N)=N1]

The title compound (34 mg, 34% yield) was prepared as described in Example 83 starting from (1r,1'R,4R)-6'-bromo-4-methoxy-5''-methyl-3'H-dispiro[cyclohexane-1,2'-indene-1',2''-imidazol]-4''-amine as the D(+)-10-camphor sulfonic acid salt (Example 19 Step 5, 130 mg, 0.21 mmol)) and 3-(4,4,5,5-tetramethyl-1,3,2-dioxaborolan-2-yl)-5-(trifluoromethyl)benzonitrile (Intermediate 55, 70 mg, 0.23 mmol): $^1$H NMR (500 MHz, DMSO-$d_6$) δ ppm 0.97 (br. s., 1 H) 1.12-1.29 (m, 2 H) 1.40-1.50 (m, 3 H) 1.83 (d, 2 H) 2.18 (s, 3 H) 2.91-3.13 (m, 3 H) 3.20 (s, 3 H) 6.55 (br. s., 2 H) 6.94 (s, 1 H) 7.44 (m, 1 H) 7.64 (m, 1 H) 8.14 (s, 1 H) 8.27 (s, 1 H) 8.35 (s, 1 H); MS (ES+) m/z 467 [M+H]+.

Example 86

3-[(1r,1'R,4R)-4''-Amino-4-methoxy-5''-methyl-3'H-dispiro[cyclohexane-1,2'-indene-1',2''-imidazol]-6'-yl]-5-(difluoromethyl)benzonitrile

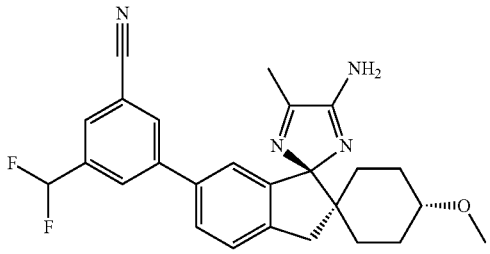 [SMILES: CO[C@H]1CC[C@]2(CC1)Cc1ccc(-c3cc(C#N)cc(C(F)F)c3)cc1[C@@]21N=C(C)C(N)=N1]

The title compound (50 mg, 49% yield) was prepared according to the procedure described in Example 83 starting from (1r,1'R,4R)-6'-bromo-4-methoxy-5''-methyl-3'H-dispiro[cyclohexane-1,2'-indene-1',2''-imidazol]-4''-amine as the D(+)-10-camphor sulfonic acid salt (Example 19 Step 5, 130 mg, 0.21 mmol) and 3-(difluoromethyl)-5-(4,4,5,5-tetramethyl-1,3,2-dioxaborolan-2-yl)benzonitrile (Intermediate 56, 71.5 mg, 0.26 mmol): $^1$H NMR (500 MHz, DMSO-$d_6$) δ ppm 0.96 (d, 1 H) 1.19-1.30 (m, 2 H) 1.38-1.50 (m, 3 H) 1.83 (d, 2 H) 2.18 (s, 3 H) 2.91-3.12 (m, 3 H) 3.20 (s, 3 H) 6.55 (br. s., 2 H) 6.89 (d, 1 H) 7.01-7.26 (m, 1 H) 7.43 (d, 1 H) 7.60 (dd, 1 H) 8.01 (d, 2 H) 8.22 (s, 1 H); MS (ES+) m/z 449 [M+H]+ and (ES−) m/z 447 [M−H]−.

Example 87

5-[(1r,1'R,4R)-4''-Amino-4-methoxy-5''-methyl-3'H-dispiro[cyclohexane-1,2'-indene-1',2''-imidazol]-6'-yl]-2-fluoro-3-methoxybenzonitrile

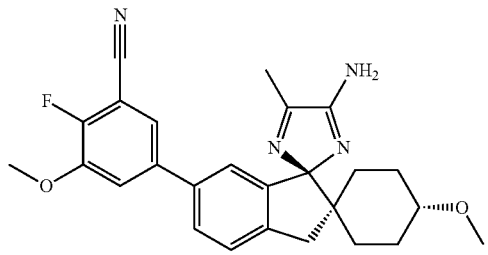

The title compound (13 mg, 12% yield) was prepared according to the procedure described in Example 83 starting from (1r,1'R,4R)-6'-bromo-4-methoxy-5''-methyl-3'H-dispiro[cyclohexane-1,2'-indene-1',2''-imidazol]-4''-amine as the D(+)-10-camphor sulfonic acid salt (Example 19 Step 5, 0.150 g, 0.25 mmol) and 2-fluoro-3-methoxy-5-(4,4,5,5-tetramethyl-1,3,2-dioxaborolan-2-yl)benzonitrile (Intermediate 79, 0.082 g, 0.30 mmol) except that the reaction time was 1 h: $^1$H NMR (500 MHz, DMSO-$d_6$) δ ppm 0.97 (td, 1 H), 1.22 (m, 2 H), 1.43 (m, 3 H), 1.83 (d, 2 H), 2.17 (s, 3 H), 2.95 (m, 2 H), 3.08 (d, 1 H), 3.20 (s, 3 H), 3.97 (s, 3 H), 6.53 (s, 2 H), 6.84 (d, 1 H), 7.40 (d, 1 H), 7.54 (m, 2 H), 7.58 (dd, 1 H); MS (APCI+) m/z 447.2 [M+H]+.

Example 88

(1r,1'R,4R)-6'-(3,5-difluorophenyl)-4-methoxy-5''-methyl-3'H-dispiro[cyclohexane-1,2'-indene-1',2''-imidazol]-4''-amine

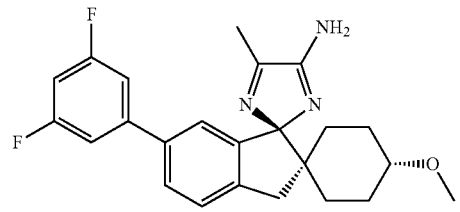 [SMILES: CO[C@H]1CC[C@]2(CC1)Cc1ccc(-c3cc(F)cc(F)c3)cc1[C@@]21N=C(C)C(N)=N1]

The title compound (49 mg, 48% yield) was prepared according to the procedure described in Example 83 starting from (1r,1'R,4R)-6'-bromo-4-methoxy-5''-methyl-3'H-dispiro[cyclohexane-1,2'-indene-1',2''-imidazol]-4''-amine as the D(+)-10-camphor sulfonic acid salt (Example 19 Step 5, 153 mg, 0.25 mmol) and 3,5-difluorophenylboronic acid (48 mg, 0.30 mmol) except that the reaction temperature was 120° C.: $^1$H NMR (500 MHz, DMSO-$d_6$) δ ppm 1.0 (td, 1 H), 1.1-1.3 (m, 2 H), 1.4-1.5 (m, 3 H), 1.8 (m, 2 H), 2.2 (s, 3 H), 2.9-3.0 (m, 2 H), 3.0-3.1 (m, 1 H), 3.2 (s, 3 H), 6.5 (s, 2 H), 6.8 (s, 1 H), 7.1-7.2 (m, 1 H), 7.2-7.3 (m, 2 H), 7.4 (d, 1 H), 7.5-7.6 (m, 1 H); MS (ES+) m/z 410 [M+H]+.

Example 89

1s (1r,1'R,4R)-6'-(2-Fluoro-3-methoxyphenyl)-4-methoxy-5''-methyl-3'H-dispiro[cyclohexane-1,2'-indene-1',2''-imidazol]-4''-amine

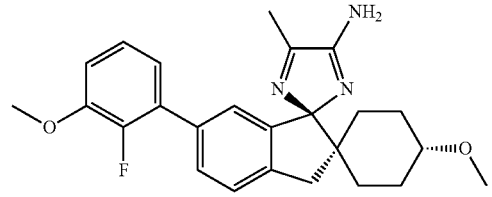

The title compound (49 mg, 47% yield) was prepared according to the procedure described in Example 83 starting from (1r,1'R,4R)-6'-bromo-4-methoxy-5''-methyl-3'H-dispiro[cyclohexane-1,2'-indene-1',2''-imidazol]-4''-amine as the D(+)-10-camphor sulfonic acid salt (Example 19 Step 5, 153 mg, 0.25 mmol) and 2-(2-fluoro-3-methoxyphenyl)-4,4,5,5-tetramethyl-1,3,2-dioxaborolane (76 mg, 0.30 mmol): $^1$H NMR (400 MHz, DMSO-$d_6$) δ ppm 0.94 (td, 1 H), 1.10-1.33 (m, 2 H), 1.39-1.54 (m, 3 H), 1.83 (m, 2 H), 2.15 (s, 3 H), 2.90-3.03 (m, 2 H), 3.04-3.13 (m, 1 H), 3.20 (s, 3 H), 3.84 (s, 3 H), 6.55 (s, 2 H), 6.64 (s, 1 H), 6.89 (td, 1 H), 7.08-7.19 (m, 2 H), 7.31 (m, 1 H), 7.38 (d, 1 H); MS (ES+) m/z 422 [M+H]⁺.

Example 90

(1r,1'R,4R)-4-Methoxy-5"-methyl-6'-phenyl-3'H-dispiro[cyclohexane-1,2'-indene-1',2"-imidazol]-4"-amine

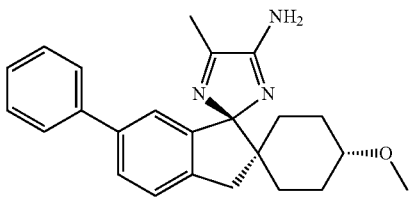 [SMILES: CO[C@H]1CC[C@]2(CC1)Cc1ccc(-c3ccccc3)cc1[C@@]21N=C(C)C(N)=N1]

The title compound (41 mg, 44% yield) was prepared according to the procedure described in Example 83 starting from (1r,1'R,4R)-6'-bromo-4-methoxy-5"-methyl-3'H-dispiro[cyclohexane-1,2'-indene-1',2"-imidazol]-4"-amine as the D(+)-10-camphor sulfonic acid salt (Example 19 Step 5, 149 mg, 0.24 mmol) and phenylboronic acid (30+6 mg, 0.24+0.05 mmol), except that the reaction time was 30+15 min: ¹H NMR (500 MHz, DMSO-d₆) δ ppm 0.95 (td, 1 H) 1.12-1.30 (m, 2 H) 1.43-1.51 (m, 3 H) 1.83 (d, 2 H) 2.16 (s, 3 H) 2.91-2.96 (m, 1 H) 2.96-3.00 (m, 1 H) 3.06-3.10 (m, 1 H) 3.20 (s, 3 H) 6.54 (br. s., 2 H) 6.75 (d, 1 H) 7.28-7.33 (m, 1 H) 7.35-7.47 (m, 4 H) 7.47-7.52 (m, 2 H); MS (ES+) m/z 374 [M+H]⁺.

Example 91

3-[(1r,4r)-4"-Amino-4-methoxy-5"-methyl-3'H-dispiro[cyclohexane-1,2'-indene-1',2"-imidazol]-6'-yl]-5-methoxybenzonitrile

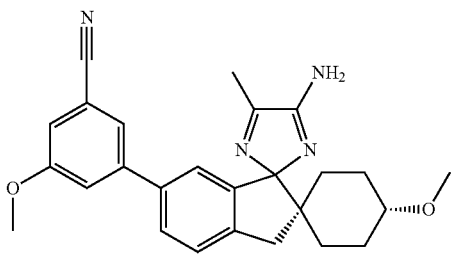

A mixture of (1r,4r)-6'-bromo-4-methoxy-5"-methyl-3'H-dispiro[cyclohexane-1,2'-indene-1',2"-imidazol]-4"-amine (Example 19 Method B Step 4, 87 mg, 0.23 mmol), 3-cyano-5-methoxy-phenylboronic acid (45 mg, 0.25 mmol), [1,1'-bis(diphenylphosphino)ferrocene]palladium(II) chloride (17 mg, 0.02 mmol), K₂CO₃ (2 M aq. solution, 0.231 mL, 0.46 mmol) and 1,4-dioxane (2 mL) were mixed in a vial and heated in a microwave reactor at 130° C. for 20 min. When cooled to r.t. the mixture was diluted with DCM, washed with water, dried over Na₂SO₄, and concentrated in vacuo. The product was purified by preparative chromatography to give the title compound (37 mg, 37% yield): ¹H NMR (400 MHz, DMSO-d₆) δ ppm 0.97 (m, 1 H), 1.22 (m, 2 H), 1.44 (m, 3 H), 1.83 (d, 2 H), 2.18 (s, 3 H), 2.99 (m, 3 H), 3.19 (s, 3 H), 3.85 (s, 3 H), 6.83 (d, 1 H), 7.37 (m, 3 H), 7.54 (m, 2 H), 8.18 (s, 1 H); MS (ES+) m/z 430 [M+H]⁺.

Example 92

Separation of the isomers of 3-[(1r,4r)-4"-amino-4-methoxy-5"-methyl-3'H-dispiro[cyclohexane-1,2'-indene-1',2"-imidazol]-6'-yl]-5-methoxybenzonitrile The racemic mixture of 3-[(1r,4r)-4"-Amino-4-methoxy-5"-methyl-3'H-dispiro[cyclohexane-1,2'-indene-1',2"-imidazol]-6'-yl]-5-methoxybenzonitrile from Example 91 (19 mg, 0.04 mmol) was separated using a SFC Berger Multigram II system with a Chiralcel OD-H column (4.6*250 mm; 5 μm) and a mobile phase consisting of 25% MeOH (containing 0.1% DEA) and 75% CO₂ at a flowrate of 50 mL/min to give:

Isomer 1: 3-[(1r,1'R,4R)-4"-Amino-4-methoxy-5"-methyl-3'H-dispiro[cyclohexane-1,2'-indene-1',2"-imidazol]-6'-yl]-5-methoxybenzonitrile (2 mg 10% yield) with retention time 3.5 min:

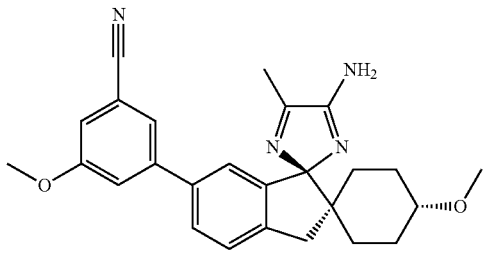

¹H NMR (500 MHz, CDCl₃) δ ppm 1.04 (td, 1 H), 1.29 (m, 2 H), 1.42 (td, 1 H), 1.63 (m, 2 H), 1.89 (d, 2 H), 2.25 (s, 3 H), 3.01 (m, 1 H), 3.14 (m, 2 H), 3.27 (s, 3 H), 3.78 (s, 3 H), 6.80 (s, 1 H), 6.98 (s, 1 H), 7.16 (m, 1 H), 7.29 (s, 1 H), 7.33 (s, 2 H); MS (MM−ES+APCI)+ m/z 429 [M+H]⁺; and Isomer 2: 3-[(1r,1'S,4S)-4"-amino-4-methoxy-5"-methyl-3'H-dispiro[cyclohexane-1,2'-indene-1',2"-imidazol]-6'-yl]-5-methoxybenzonitrile (1 mg, 5% yield) with retention time 9.5 min:

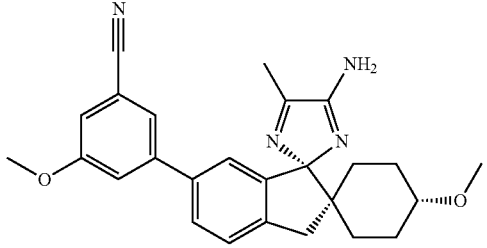

¹H NMR (500 MHz, CDCl₃) δ ppm 1.05 (m, 1 H), 1.29 (m, 3 H), 1.43 (m, 1 H), 1.63 (m, 2 H), 1.89 (d, 2 H), 2.25 (s, 3 H), 3.00 (m, 1 H), 3.14 (m, 2 H), 3.27 (s, 3 H), 3.78 (s, 3 H), 6.80 (s, 1 H), 6.98 (s, 1 H), 7.16 (s, 1 H), 7.29 (s, 1 H), 7.33 (s, 2 H); MS (MM−ES+APCI)+ m/z 429 [M+H]⁺.

Example 92

Isomer 1 (Alternative Method)

3-[(1r,1'R,4R)-4"-Amino-4-methoxy-5"-methyl-3'H-dispiro[cyclohexane-1,2'-indene-1',2"-imidazol]-6'-yl]-5-methoxybenzonitrile

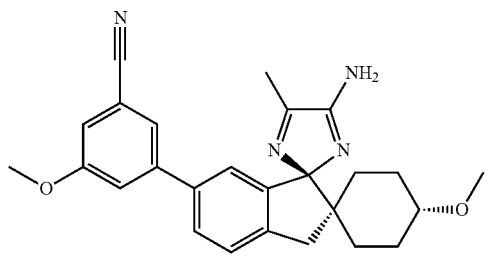

The title compound (26 mg, 24% yield) was prepared according to the procedure described in Example 83 starting from (1r,1'R,4R)-6'-bromo-4-methoxy-5"-methyl-3'H-dispiro[cyclohexane-1,2'-indene-1',2"-imidazol]-4"-amine as the D(+)-10-camphor sulfonic acid salt (Example 19 Step 5, 151 mg, 0.25 mmol) and 3-cyano-5-methoxyphenylboronic acid (44 mg, 0.25 mmol), except that the reaction time was 30+30 min: $^1$H NMR (500 MHz, CDCl$_3$) δ ppm 1.16 (td, 1 H), 1.42 (m, 3 H), 1.74 (m, 2 H), 2.02 (m, 2 H), 2.39 (s, 3 H), 3.11 (m, 1 H), 3.25 (q, 2 H), 3.37 (s, 3 H), 3.88 (s, 3 H), 6.93 (s, 1 H), 7.09 (s, 1 H), 7.26 (m, 1 H), 7.39 (s, 1 H), 7.46 (m, 2 H); MS (MM–ES+APCI)+ m/z 429 [M+H]$^+$.

Example 93

3-[(1r,4r)-4"-Amino-4-methoxy-5"-methyl-3'H-dispiro[cyclohexane-1,2'-indene-1',2"-imidazol]-6'-yl]-5-bromobenzonitrile

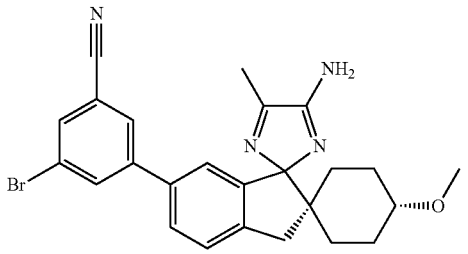

A mixture of (1r,4r)-6'-bromo-4-methoxy-5"-methyl-3'H-dispiro[cyclohexane-1,2'-indene-1',2"-imidazol]-4"-amine (Example 19 Method B Step 4, 120 mg, 0.32 mmol), potassium acetate (63 mg, 0.64 mmol), bis(pinacolato)diboron (89 mg, 0.35 mmol) and PdCl$_2$(dppf)-CH$_2$Cl$_2$ adduct (13 mg, 0.02 mmol) in dioxane (2 mL) were mixed in a vial and heated in a microwave reactor at 130° C. for 35 min. Formation of (1r,4r)-4-methoxy-5"-methyl-6'-(4,4,5,5-tetramethyl-1,3,2-dioxaborolan-2-yl)-3'H-dispiro[cyclohexane-1,2'-indene-1',2"-imidazol]-4"-amine was observed by LCMS (MS (ES+) m/z 342, 425 [M+H]$^+$, masses corresponding to both the boronic ester and the hydrolysed boronic acid were detected). The obtained mixture was used as is. K$_2$CO$_3$ (2 M aq. solution, 0.319 mL, 0.64 mmol), Pd(Ph$_3$P)$_4$ (18 mg, 0.02 mmol) and 3,5-dibromobenzonitrile (125 mg, 0.48 mmol) in dioxane (1 mL) were added to the above mixture containing (1r,4r)-4-methoxy-5"-methyl-6'-(4,4,5,5-tetramethyl-1,3,2-dioxaborolan-2-yl)-3'H-dispiro[cyclohexane-1,2'-indene-1',2"-imidazol]-4"-amine. The reaction vessel was sealed and heated in a microwave reactor at 130° C. for 20 min. When cooled to r.t. the mixture was diluted with DCM, washed with brine, dried over MgSO$_4$, and concentrated in vacuo. The product was purified by preparative chromatography to give the title compound (45 mg, 30% yield): $^1$H NMR (400 MHz, DMSO-d$_6$) δ ppm 0.97 (m, 1 H), 1.21 (m, 2 H), 1.44 (m, 3 H), 1.83 (d, 2 H), 2.18 (s, 3 H), 2.94 (m, 1 H), 3.00 (d, 1 H), 3.09 (d, 1 H), 3.20 (s, 3 H), 6.56 (br. s., 1 H), 6.88 (d, 1 H), 7.41 (d, 1 H), 7.58 (dd, 1 H), 8.07 (m, 3 H); MS (ES+) m/z 477 [M+H]$^+$.

Example 94

Separation of the isomers of 3-[(1r,4r)-4"-Amino-4-methoxy-5"-methyl-3'H-dispiro[cyclohexane-1,2'-indene-1',2"-imidazol]-6'-yl]-5-bromobenzonitrile The racemic mixture of 3-[(1r,4r)-4"-Amino-4-methoxy-5"-methyl-3'H-dispiro[cyclohexane-1,2'-indene-1',2"-imidazol]-6'-yl]-5-bromobenzonitrile from Example 93 (60 mg, 0.13 mmol) was separated using a SFC Berger Multigram II system with a Chiralcel OD-H column (20*250 mm; 5 μm) and a mobile phase consisting of 35% MeOH (containing 0.1% DEA) and 65% CO$_2$ at a flowrate of 50 mL/min to give Isomer 1 with undetermined absolute configuration (13 mg, 22% yield) with retention time 2.0 min: $^1$H NMR (500 MHz, CDCl$_3$) δ ppm 1.12 (td, 1 H), 1.37 (m, 2 H), 1.50 (m, 1 H), 1.70 (m, 2 H), 1.97 (d, 2 H), 2.34 (s, 3 H), 3.08 (m, 1 H), 3.22 (m, 2 H), 3.35 (s, 3 H), 6.87 (m, 1 H), 7.41 (m, 2 H), 7.70 (dt, 2 H), 7.87 (t, 1 H); MS (MM–ES+APCI)+ m/z 477 [M+H]$^+$; and
Isomer 2 with undetermined absolute configuration (15 mg, 25% yield) with retention time 4.9 min: $^1$H NMR (500 MHz, CDCl$_3$) δ ppm 1.12 (td, 1 H), 1.38 (m, 2 H), 1.51 (td, 1 H), 1.70 (m, 2 H), 1.97 (d, 2 H), 2.34 (s, 3 H), 3.09 (t, 1 H), 3.23 (m, 2 H), 3.35 (s, 3 H), 6.87 (s, 1 H), 7.41 (m, 2 H), 7.70 (m, 2 H), 7.87 (t, 1 H); MS (MM–ES+APCI)+ m/z 477 [M+H]$^+$.

Example 95

3-[(1r,4r)-4"-Amino-4-methoxy-5"-methyl-3'H-dispiro[cyclohexane-1,2'-indene-1',2"-imidazol]-6'-yl]-5-ethylbenzonitrile

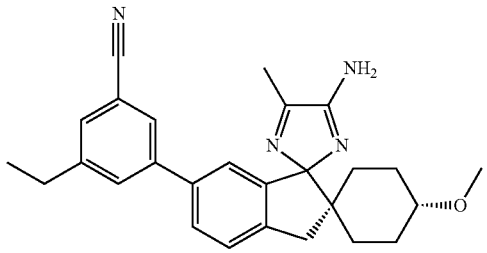

The title compound (38 mg, 17% yield) was prepared as described for Example 93 starting from 3-bromo-5-ethylbenzonitrile (Intermediate 58, 0.124 g, 0.59 mmol) and (1r,4r)-6'-bromo-4-methoxy-5"-methyl-3'H-dispiro[cyclohexane-1,2'-indene-1',2"-imidazol]-4"-amine) (Example 19 Method B Step 4, 200 mg, 0.53 mmol): $^1$H NMR (400 MHz, CDCl$_3$) δ ppm 1.14 (td, 1 H) 1.27 (t, 3 H) 1.36 (m, 3 H) 1.71 (m, 2 H) 2.00 (m, 2 H) 2.39 (s, 3 H) 2.72 (q, 2 H) 3.10 (m, 1 H) 3.23 (m, 2 H) 3.35 (s, 3 H) 6.95 (m, 1 H) 7.45 (m, 3 H) 7.54 (s, 1 H) 7.59 (m, 1 H) 8.49 (s, 1 H); MS (ES+) m/z 427 [M+H]$^+$.

Example 96

3-[(1r,4r)-4''-Amino-4-methoxy-5''-methyl-3'H-dispiro[cyclohexane-1,2'-indene-1',2''-imidazol]-6'-yl]-5-(methoxymethyl)benzonitrile

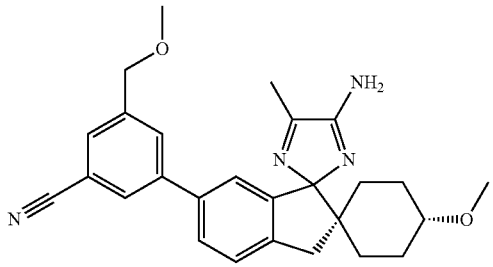

The title compound (52 mg, 40% yield) was prepared as described for Example 93 starting from 3-bromo-5-(methoxymethyl)benzonitrile (Intermediate 59, 66 mg, 0.29 mmol) and (1r,4r)-6'-bromo-4-methoxy-5''-methyl-3'H-dispiro[cyclohexane-1,2'-indene-1',2''-imidazol]-4''-amine (Example 19 Method B Step 4, 109 mg, 0.29 mmol): $^1$H NMR (500 MHz, CDCl$_3$) δ ppm 1.15 (td, 1 H), 1.39 (m, 3 H), 1.72 (m, 2 H), 2.02 (m, 2 H), 2.43 (s, 3 H), 3.10 (m, 1 H), 3.20 (d, 1 H), 3.28 (d, 1 H), 3.35 (s, 3 H), 3.44 (s, 3 H), 4.52 (s, 2 H), 6.99 (s, 1 H), 7.48 (m, 2 H), 7.58 (s, 1 H), 7.69 (d, 2 H), 8.41 (br. s., 1 H); MS (MM–ES+APCI)+ m/z 443 [M+H]$^+$.

Example 97

Separation of the isomers of 3-[(1r,4r)-4''-Amino-4-methoxy-5''-methyl-3'H-dispiro-[cyclohexane-1,2'-indene-1',2''-imidazol]-6'-yl]-5-(methoxymethyl)benzonitrile The racemic mixture from Example 96 (40 mg, 0.09 mmol) was separated using a SFC Berger Multigram II system with a Chiralcel OD-H column (20*250 mm; 5 μm) and a mobile phase consisting of 30% MeOH (containing 0.1% DEA) and 70% CO$_2$ at a flow rate of 50 mL/min to give:

Isomer 1 with undetermined absolute configuration (14 mg, 35% yield) with retention time 2.5 min: $^1$H NMR (500 MHz, CDCl$_3$) δ ppm 1.12 (td, 1 H), 1.37 (m, 2 H), 1.51 (td, 1 H), 1.72 (td, 2 H), 1.97 (d, 2 H), 2.34 (s, 3 H), 3.09 (m, 1 H), 3.23 (m, 2 H), 3.35 (s, 3 H), 3.43 (s, 3 H), 4.50 (s, 2 H), 6.91 (s, 1 H), 7.43 (m, 2 H), 7.54 (s, 1 H), 7.70 (s, 2 H); MS (MM–ES+APCI)+ m/z 443 [M+H]$^+$; and Isomer 2 with undetermined absolute configuration (13 mg, 33% yield) with retention time 7.5 min: $^1$H NMR (500 MHz, CDCl$_3$) δ ppm 1.12 (td, 1 H), 1.38 (m, 2 H), 1.51 (m, 1 H), 1.72 (m, 2 H), 1.97 (d, 2 H), 2.34 (s, 3 H), 3.09 (m, 1 H), 3.23 (m, 2 H), 3.35 (s, 3 H), 3.43 (s, 3 H), 4.50 (s, 2 H), 6.91 (s, 1 H), 7.43 (m, 2 H), 7.54 (s, 1 H), 7.70 (s, 2 H); MS (MM–ES+APCI)+ m/z 443 [M+H]$^+$.

Example 98

(1r,1'R,4R)-6'-(2-Fluoro-5-methoxyphenyl)-4-methoxy-5''-methyl-3'H-dispiro[cyclohexane-1,2'-indene-1',2''-imidazol]-4''-amine

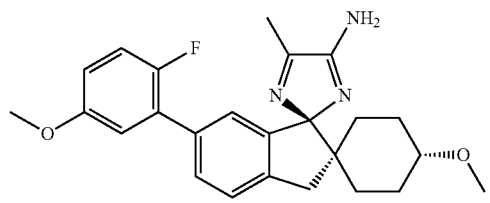

The title compound was prepared according to the procedure described in Example 83 starting from (1r,1'R,4R)-6'-bromo-4-methoxy-5''-methyl-3'H-dispiro[cyclohexane-1,2'-indene-1',2''-imidazol]-4''-amine as the D(+)-10-camphor sulfonic acid salt (Example 19 Step 5, 150 mg, 0.25 mmol) and 2-fluoro-5-methoxyphenylboronic acid (42+21 mg, 0.25 mmol), except that the reaction time was 30+30 min. The resulting material was combined with a product from an identical reaction run starting with 80 mg (0.13 mmol) of (1r,1'R,4R)-6'-bromo-4-methoxy-5''-methyl-3'H-dispiro[cyclohexane-1,2'-indene-1',2''-imidazo 1]-4''-amine as the D(+)-10-camphor sulfonic acid salt and purified by preparative chromatography to afford 38 mg (24% yield) of the title compound: $^1$H NMR (500 MHz, DMSO-d$_6$) δ ppm 0.94 (m, 1 H) 1.21 (m, 2 H) 1.47 (m, 3 H) 1.83 (m, 2 H) 2.15 (s, 3 H) 2.94 (m, 1 H) 3.04 (m, 2 H) 3.20 (s, 3 H) 3.76 (s, 3 H) 6.54 (s, 2 H) 6.67 (s, 1 H) 6.88 (m, 2 H) 7.17 (t, 1 H) 7.36 (m, 2 H); MS (ES+) m/z 422 [M+H]$^+$.

Example 99

(1r,1'R,4R)-6'-(2,5-Difluorophenyl)-4-methoxy-5''-methyl-3'H-dispiro[cyclohexane-1,2'-indene-1',2''-imidazol]-4''-amine

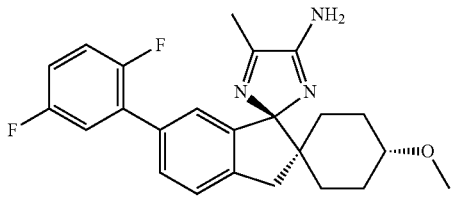 [SMILES: CO[C@H]1CC[C@]2(CC1)Cc1ccc(-c3cc(F)ccc3F)cc1[C@@]21N=C(C)C(N)=N1]

The title compound (24.4 mg, 16% yield) was prepared according to the procedure described in Example 83 starting from (1r,1'R,4R)-6'-bromo-4-methoxy-5''-methyl-3'H-dispiro[cyclohexane-1,2'-indene-1',2''-imidazol]-4''-amine as the D(+)-10-camphor sulfonic acid salt (Example 19 Step 5, 230 mg, 0.38 mmol) and 2,5-difluorophenylboronic acid (87 mg, 0.56 mmol): $^1$H NMR (500 MHz, DMSO-d$_6$) δ ppm 0.94 (m, 1 H) 1.21 (m, 2 H) 1.46 (m, 3 H) 1.83 (m, 2 H) 2.15

(s, 3 H) 2.94 (m, 1 H) 3.05 (dd, 2 H) 3.20 (s, 3 H) 6.54 (s, 2 H) 6.70 (s, 1 H) 7.20 (m, 1 H) 7.29 (m, 2 H) 7.38 (d, 2 H); MS (ES+) m/z 410 [M+H]

Example 100

5-[(1r,1'R,4R)-4"-amino-4-methoxy-5"-methyl-3'H-dispiro[cyclohexane-1,2'-indene-1',2"-imidazol]-6'-yl]-3-chloro-2-fluorobenzonitrile

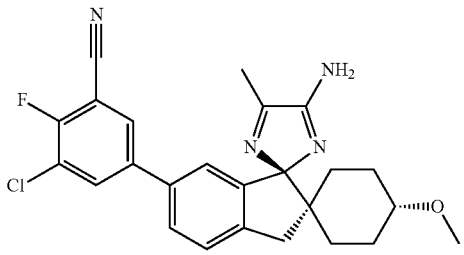 [SMILES: CO[C@H]1CC[C@]2(CC1)Cc1ccc(-c3cc(Cl)c(F)c(C#N)c3)cc1[C@@]21N=C(C)C(N)=N1]

The title compound (22 mg, 20% yield) was prepared according to the procedure described in Example 83 starting from (1r,1'R,4R)-6'-bromo-4-methoxy-5"-methyl-3'H-dispiro[cyclohexane-1,2'-indene-1',2"-imidazol]-4"-amine as the D(+)-10-camphor sulfonic acid salt (Example 19 Step 5, 150 mg, 0.25 mmol) and 3-chloro-2-fluoro-5-(4,4,5,5-tetramethyl-1,3,2-dioxaborolan-2-yl)benzonitrile (Intermediate 57, 90 mg, 0.32 mmol): $^1$H NMR (500 MHz, CDCl$_3$) δ ppm 1.07-1.17 (m, 1 H), 1.29-1.44 (m, 3 H), 1.50 (br. s., 2 H), 1.65-1.75 (m, 4 H), 1.98 (d, 2 H), 2.36 (s, 3 H), 3.04-3.13 (m, 1 H), 3.23 (d, 2 H), 3.35 (s, 3 H), 6.85 (d, 1 H), 7.35-7.39 (m, 1 H), 7.41-7.45 (m, 1 H), 7.63 (dd, 1 H), 7.77 (dd, 2.36 Hz, 1 H); MS (ES+) m/z 451 [M+H]$^+$.

Example 101

(1r,1'R,4R)-6'-(2,3-Difluorophenyl)-4-methoxy-5"-methyl-3'H-dispiro[cyclohexane-1,2'-indene-1',2"-imidazol]-4"-amine

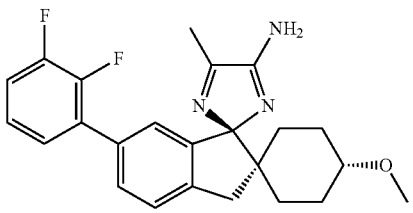 [SMILES: CO[C@H]1CC[C@]2(CC1)Cc1ccc(-c3cccc(F)c3F)cc1[C@@]21N=C(C)C(N)=N1]

(1r,1'R,4R)-6'-bromo-4-methoxy-5"-methyl-3'H-dispiro[cyclohexane-1,2'-indene-1',2"-imidazol]-4"-amine as the D(+)-10-camphor sulfonic acid salt (Example 19 Step 5, 150 mg, 0.40 mmol) was treated with 2-Me THF (2 mL) and aq. KOH solution (0.4 g KOH in 3 mL water). The reaction was stirred for 30 min before the water phase was removed and the remaining suspension was washed with 2 M aq. Na$_2$CO$_3$ solution (3 mL). The water solution was removed, and the organic phase was transferred to a microwave vial. 2,3-difluorophenylboronic acid (126 mg, 0.80 mmol) was added, followed by Na$_2$CO$_3$ (598 μL, 1.20 mmol). The solution was degassed by bubbling argon through it. 1,1'-Bis(diphenylphosphino)ferrocene-palladium dichloride (16.4 mg, 0.02 mmol) was added, and the reaction was irradiated in the microwave reactor for 30 min at 120° C. Water/EtOAc was added, the phases were separated. The organic phase was washed with brine and water and dried over Na$_2$SO$_4$ and then concentrated in vacuo. The product was purified using preparative chromatography to give the title compound (61 mg, 60% yield): $^1$H NMR (500 MHz, CDCl$_3$) δ ppm 1.14 (d, 1 H) 1.42 (d, 3 H) 1.67-1.81 (m, 2 H) 1.94-2.12 (m, 2 H) 2.41 (s, 3 H) 3.11 (m, 1 H) 3.16 20 (m, 1 H) 3.29 (m, 1 H) 3.36 (s, 3 H) 6.97 (s, 1 H) 7.06-7.15 (m, 3 H) 7.44 (m, 1 H) 7.50 (m, 1 H) 8.35 (s, 1 H); MS (ES+) m/z 410 [M+H]$^1$.

Example 102

3-[(1r,1'R,4R)-4"-Amino-4-methoxy-5"-methyl-3'H-dispiro[cyclohexane-1,2'-indene-1',2"-imidazol]-6'-yl]-4-fluorobenzonitrile

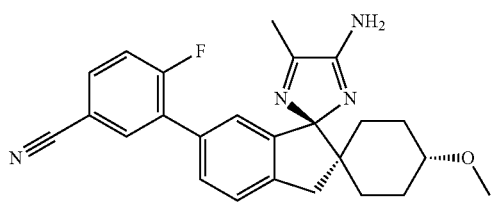 [SMILES: CO[C@H]1CC[C@]2(CC1)Cc1ccc(-c3cc(C#N)ccc3F)cc1[C@@]21N=C(C)C(N)=N1]

The title compound (20 mg, 19% yield) was prepared using the procedure described in Example 101 starting from (1r,1'R,4R)-6'-bromo-4-methoxy-5"-methyl-3'H-dispiro[cyclohexane-1,2'-indene-1',2"-imidazol]-4"-amine as the D(+)-10-camphor sulfonic acid salt (Example 19 Step 5, 150 mg, 0.40 mmol) and 5-cyano-2-fluorophenylboronic acid (131 mg, 0.80 mmol): $^1$H NMR (500 MHz, CDCl$_3$) δ ppm 1.15 (td, 1 H) 1.31-1.47 (m, 3 H) 1.67-1.79 (m, 2 H) 1.95-2.11 (m, 2 H) 2.43 (s, 3 H) 3.12 (m, 1 H) 3.22 (m, 1 H) 3.30 (m, 1 H) 3.36 (s, 3 H) 6.95 (s, 1 H) 7.23 (dd, 1 H) 7.41-7.52 (m, 2 H) 7.61 (ddd, 1 H) 7.70 (dd, 1 H) 8.38 (br. s., 1 H); MS (ES+) m/z 417 [M+H]$^+$.

Example 103

(1r,1'R,4R)-6'-(2,4-Difluorophenyl)-4-methoxy-5"-methyl-3'H-dispiro[cyclohexane-1,2'-indene-1',2"-imidazol]-4"-amine

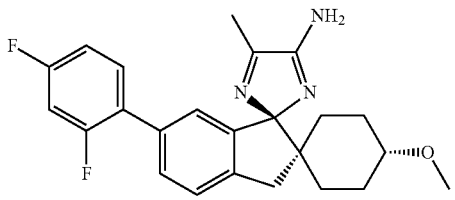 [SMILES: CO[C@H]1CC[C@]2(CC1)Cc1ccc(-c3ccc(F)cc3F)cc1[C@@]21N=C(C)C(N)=N1]

The title compound (56 mg, 53% yield) was prepared according to the procedure described in Example 83 starting from (1r,1'R,4R)-6'-bromo-4-methoxy-5"-methyl-3'H-dispiro[cyclohexane-1,2'-indene-1',2"-imidazol]-4"-amine as the D(+)-10-camphor sulfonic acid salt (Example 19 Step 5, 155 mg, 0.25 mmol) and 2,4-difluorophenylboronic acid (48.3 mg, 0.31 mmol). The title compound was recrystallized from CHCl$_3$/MeOH: $^1$H NMR (500 MHz, DMSO-d$_6$) δ ppm 0.95 (m, 1 H), 1.12-1.32 (m, 2 H), 1.39-1.55 (m, 3 H), 1.84 (d, 2 H), 2.16 (s, 3 H), 2.91-3.01 (m, 2 H), 3.11 (d, 1 H), 3.21 (s, 3 H), 6.55 (s, 2 H), 6.65 (s, 1 H), 7.14 (td, 1 H), 7.26-7.35 (m, 2 H), 7.40 (d, 1 H), 7.45 (m, 1 H); MS (ES+) m/z 410.1 [M+H]$^1$.

Example 104

(1r,1'R,4R)-6'-(2,3-dichlorophenyl)-4-methoxy-5''-methyl-3'H-dispiro[cyclohexane-1,2'-indene-1',2''-imidazol]-4''-amine

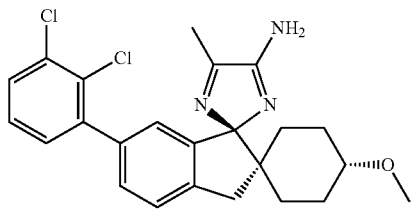 [SMILES: CO[C@H]1CC[C@]2(CC1)Cc1ccc(-c3cccc(Cl)c3Cl)cc1[C@@]21N=C(C)C(N)=N1]

The title compound (19 mg, 11% yield) was prepared using the procedure described in Example 101 starting from (1r,1'R,4R)-6'-bromo-4-methoxy-5''-methyl-3'H-dispiro[cyclohexane-1,2'-indene-1',2''-imidazol]-4''-amine as the D(+)-10-camphor sulfonic acid salt (Example 19 Step 5, 150 mg, 0.40 mmol) and 2,3-dichlorophenylboronic acid (114 mg, 0.60 mmol): $^1$H NMR (500 MHz, DMSO-d$_6$) δ ppm 1.01 (m, 1 H) 1.13-1.34 (m, 2 H) 1.41 (t, 1 H) 1.49 (d, 2 H) 1.84 (d, 2 H) 2.17 (s, 3 H) 2.95 (m, 1 H) 3.03 (m, 1 H) 3.12 (m, 1 H) 3.20 (s, 3 H) 6.61 (s, 1 H) 7.25 (dd, 2 H) 7.35-7.41 (m, 2 H) 7.61 (dd, 1 H); MS (ES+) m/z 442 [M+H]$^+$.

Example 105

3-[(1r,4r)-4''-Amino-4-(difluoromethoxy)-5''-methyl-3'H-dispiro[cyclohexane-1,2'-indene-1',2''-imidazol]-6'-yl]-5-fluorobenzonitrile

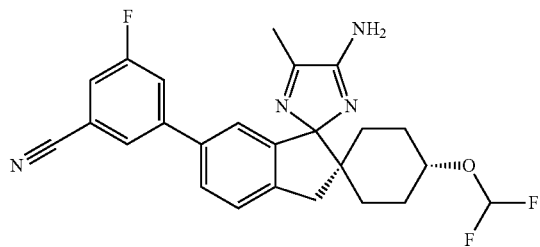

3-Cyano-5-fluorophenylboronic acid (54 mg, 0.33 mmol) was added to (1r,4r)-6'-bromo-4-(difluoromethoxy)-5''-methyl-3'H-dispiro[cyclohexane-1,2'-indene-1',2''-imidazol]-4''-amine (Example 15 Step 3, 90 mg, 0.22 mmol) in dry 2-methyl-tetrahydrofuran (2 mL). K$_2$CO$_3$ (2.0 M aq., 0.327 mL, 0.65 mmol) was added. The mixture was degassed by bubbling Ar (g) through it (1 min). Then sodium tetrachloropalladate(II) (3.2 mg, 10.92 µmol) and 3-(di-tert-butylphosphonium)propane sulfonate (5.9 mg, 0.02 mmol) were added and the mixture was microwaved for 40 min at 100° C. 3-Cyano-5-fluorophenylboronic acid (54 mg, 0.33 mmol), sodium tetrachloropalladate(II) (3.2 mg, 10.92 µmol) and 3-(di-tert-butylphosphonium)propane sulfonate (5.9 mg, 0.02 mmol) were added and the mixture was microwaved for 1 h at 120° C. Water, 2-methyl-tetrahydrofuran and EtOAc were added to the mixture and the phases were separated. The organic phase was washed once with brine and water. The organic phase was dried (Na$_2$SO$_4$), filtered and concentrated in vacuo. Purification by flash chromatography using a gradient of CHCl$_3$/MeOH (30:1-20:1) followed by preparative chromatography gave the title compound (13 mg, 13% yield): $^1$H NMR (500 MHz, DMSO-d$_6$) δ ppm 1.05 (m, 1 H), 1.37-1.58 (m, 5 H), 1.81 (d, 2 H), 2.19 (s, 3 H), 3.03 (d, 1 H), 3.12 (d, 1 H), 3.88 (m, 1 H), 6.56 (s, 2 H), 6.66 (t, 1 H), 6.91 (s, 1 H), 7.42 (d, 1 H), 7.60 (dd, 1 H), 7.79 (m, 2 H), 7.91 (s, 1 H); MS (ES+) m/z 453.0 [M+H]$^+$.

Example 106

3-[(1r,4r)-4''-Amino-4-(difluoromethoxy)-5''-methyl-3'H-dispiro[cyclohexane-1,2'-indene-1',2''-imidazol]-6'-yl]-5-methoxybenzonitrile

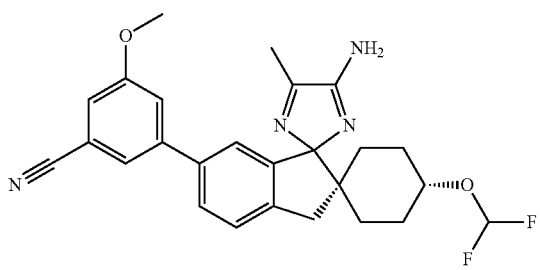

The title compound (45 mg, 22% yield) was prepared using the procedure described in Example 105 starting from 3-methoxy-5-(4,4,5,5-tetramethyl-1,3,2-dioxaborolan-2-yl)benzonitrile (139+139 mg, 0.54+0.54 mmol) and (1r,4r)-6'-bromo-4-(difluoromethoxy)-5''-methyl-3'H-dispiro-[cyclohexane-1,2'-indene-1',2''-imidazol]-4''-amine (Example 15 Step 3, 184 mg, 0.45 mmol). The reaction mixture was run in a microwave reactor at 100° C. for 40 min followed by a total of 3 h at 120° C.: $^1$H NMR (500 MHz, DMSO-d$_6$) δ ppm 1.04 (m, 1 H), 1.38-1.58 (m, 5 H), 1.81 (m, 2 H), 2.18 (s, 3 H), 3.02 (d, 1 H), 3.12 (d, 1 H), 3.81-3.93 (m, 4 H), 6.56 (s, 2 H), 6.66 (t, 1 H), 6.83 (d, 1 H), 7.33-7.43 (m, 3 H), 7.50-7.59 (m, 2 H); MS (ES+) m/z 465.1 [M+H]$^+$.

Example 107

(1r,4r)-4-(Difluoromethoxy)-5''-methyl-6'-[5-(trifluoromethyl)pyridin-3-yl]-3'H-dispiro[cyclohexane-1,2'-indene-1',2''-imidazol]-4''-amine

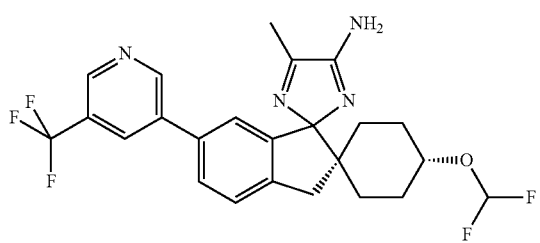

The title compound (68.5 mg, 59% yield) was prepared using the procedure described in Example 105 starting from 3-(4,4,5,5-tetramethyl-1,3,2-dioxaborolan-2-yl)-5-(trifluoromethyl)pyridine (99+99 mg, 0.36+0.36 mmol) and (1r,4r)-6'-bromo-4-(difluoromethoxy)-5"-methyl-3'H-dispiro[cyclohexane-1,2'-indene-1',2"-imidazol]-4"-amine (Example 15 Step 3, 100 mg, 0.24 mmol). The reaction was heated in a microwave reactor at 120° C. for 40+30 min: $^1$H NMR (500 MHz, DMSO-$d_6$) δ ppm 0.96-1.11 (m, 1 H), 1.39-1.47 (m, 1 H), 1.47-1.60 (m, 4 H), 1.82 (m, 2 H), 2.18 (s, 3 H), 3.05 (d, 1 H), 3.14 (d, 1 H), 3.89 (m, 1 H), 6.58 (br. s., 2 H), 6.66 (t, 1 H), 6.94 (d, 1 H), 7.46 (d, 1 H), 7.64 (dd, 1 H), 8.28 (s, 1 H), 8.91 (s, 1 H), 9.05 (d, 1 H); MS (ES+) m/z 479.1 [M+H]$^+$.

Example 108

3-[(1r,4r)-4"-Amino-4-(difluoromethoxy)-5"-methyl-3'H-dispiro[cyclohexane-1,2'-indene-1',2"-imidazol]-6'-yl]-5-chlorobenzonitrile

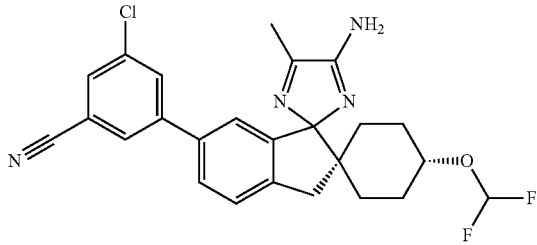

The title compound (20 mg, 17% yield) was prepared using the procedure described in Example 105 starting from 3-chloro-5-(4,4,5,5-tetramethyl-1,3,2-dioxaborolan-2-yl)benzonitrile (Intermediate 35, 96 mg, 0.36 mmol) and (1r,4r)-6'-bromo-4-(difluoromethoxy)-5"-methyl-3'H-dispiro[cyclohexane-1,2'-indene-1',2"-imidazol]-4"-amine (Example 15 Step 3, 100 mg, 0.24 mmol). The reaction was heated in a microwave reactor at 120° C. for 40+30+30 min: $^1$H NMR (500 MHz, DMSO-$d_6$) δ ppm 1.05 (m, 1 H), 1.38-1.57 (m, 5 H), 1.81 (m, 2 H), 2.19 (s, 3 H), 3.03 (d, 1 H), 3.12 (d, 1 H), 3.88 (m, 1 H), 6.56 (s, 2 H), 6.66 (t, 1 H), 6.90 (s, 1 H), 7.42 (d, 1 H), 7.59 (dd, 1 H), 7.95 (m, 2 H), 8.02 (s, 1 H); MS (ES+) m/z 469.1 [M+H]$^+$.

Example 109

(1r,4r)-4-(Difluoromethoxy)-6'-(3,5-difluorophenyl)-5"-methyl-3'H-dispiro[cyclohexane-1,2'-indene-1',2"-imidazol]-4"-amine

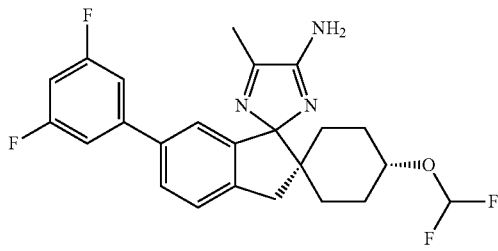

The title compound was prepared using the procedure described in Example 105 starting from 2-(3,5-difluorophenyl)-4,4,5,5-tetramethyl-1,3,2-dioxaborolane (62+34+34 mg, 0.26+0.14+0.14 mmol) and (1r,4r)-6'-bromo-4-(difluoromethoxy)-5"-methyl-3'H-dispiro[cyclohexane-1,2'-indene-1',2"-imidazol]-4"-amine (Example 15 Step 3, 97 mg, 0.24 mmol). The reaction was heated in a microwave reactor at 120° C. for respectively 30+30+20 min. Purification by preparative chromatography (2 separate injections) using a XBridge C18; 21*250 mm; 5 μm column and 40-80% MeCN/0.1% aq. NH$_3$ as mobile phase with a flow rate of 20 mL/min gave the title compound with retention time 12.4 min. The desired fractions were pooled, the acetonitrile was evaporated and the remaining aqueous phase was extracted with DCM. The organic layer was washed with water, concentrated and dried in vacuo at 45° C. overnight to give the title compound (44.5 mg, 42% yield): $^1$H NMR (500 MHz, DMSO-$d_6$) δ ppm 0.98-1.08 (m, 1 H) 1.40-1.46 (m, 1 H) 1.46-1.56 (m, 4 H) 1.77-1.85 (m, 2 H) 2.18 (s, 3 H) 3.01 (d, 1 H) 3.11 (d, 1 H) 3.84-3.93 (m, 1 H) 6.56 (s, 2 H) 6.83 (s, 1 H) 7.17 (tt, 1 H) 7.27 (d, 2 H) 7.39 (d, 1 H) 7.52-7.57 (m, 1 H); MS (ES+) m/z 446.0 [M+H]$^+$.

Example 110

5-[(1r,4r)-4"-Amino-4-(difluoromethoxy)-5"-methyl-3'H-dispiro[cyclohexane-1,2'-indene-1',2"-imidazol]-6'-yl]-2-fluoro-3-methoxybenzonitrile

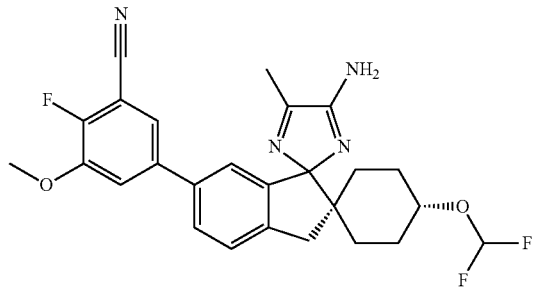

The title compound (22 mg, 21% yield) was prepared using the procedure described in Example 105 starting from 2-fluoro-3-methoxy-5-(4,4,5,5-tetramethyl-1,3,2-dioxaborolan-2-yl)benzo-nitrile (Intermediate 79, 89+30 mg, 0.32+011 mmol) and (1r,4r)-6'-bromo-4-(difluoromethoxy)-5"-methyl-3'H-dispiro[cyclohexane-1,2'-indene-1',2"-imidazol]-4"-amine (Example 15 Step 3, 88 mg, 0.21 mmol). The reaction mixture was heated with MW at 120° C. for 30+30+15 min. Purification by preparative chromatography (3 separate injections) using a XBridge C18; 4.6*250 mm; 5 μm column and 30-70% MeCN/0.1% aqueous NH$_3$ as mobile phase with a flow rate of 20 mL/min gave the title compound with retention time 16.2 min: $^1$H NMR (500 MHz, DMSO-$d_6$) δ ppm 0.98-1.08 (m, 1 H) 1.40-1.55 (m, 5 H) 1.76-1.86 (m, 2 H) 2.18 (s, 3 H) 3.02 (d, 1 H) 3.11 (d, 1 H) 3.83-3.93 (m, 1 H) 3.97 (s, 3 H) 6.56 (s, 2 H) 6.66 (t, 1 H) 6.85 (s, 1 H) 7.41 (d, 1 H) 7.53-7.57 (m, 2 H) 7.58 (dd, 1 H); MS (ES+) m/z 483.0 [M+H]$^+$.

Example 111

(1r,4r)-4-Methoxy-4,5"-dimethyl-6'-[5-(prop-1-yn-1-yl)pyridin-3-yl]-3'H-dispiro[cyclohexane-1,2'-indene-1',2"-imidazol]-4"-amine

Step 1: N-[(1r,4r)-6'-Bromo-4-methoxy-4-methylspiro[cyclohexane-1,2'-inden]-1'(3'H)-ylidene]-2-methylpropane-2-sulfinamide

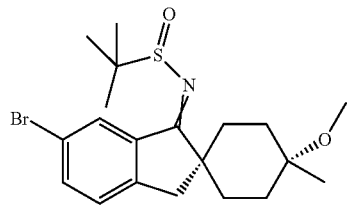 [SMILES: CO[C@]1(C)CC[C@@]2(CC1)Cc1ccc(Br)cc1C2=NS(=O)C(C)(C)C]

(1r,4r)-6'-Bromo-4-methoxy-4-methylspiro[cyclohexane-1,2'-inden]-1'(3'H)-one (Intermediate 61, 0.613 g, 1.90 mmol), 2-methylpropane-2-sulfinamide (0.919 g, 7.59 mmol) and titanium(IV) ethoxide (2.163 mL, 10.43 mmol) were dissolved in 2-Me THF (6 mL) and heated at reflux for 6 days. The reaction was allowed to cool to r.t. and thereafter it was diluted with EtOAc (30 mL). Water (20 mL) was added under vigorous stirring, and the obtained mixture was stirred for 10 min. Diatomaceous earth was added and the mixture was left standing without stirring for 1 h. The mixture was filtered through a pad of diatomaceous earth. The organic layer was separated, dried over MgSO$_4$ and concentrated in vacuo. The crude title compound (0.7 g, 87% yield) was used in the next step without further purification: MS (ES+) m/z 428 [M+H]$^+$.

Step 2: (1r,4r)-6'-Bromo-4-methoxy-4-methylspiro[cyclohexane-1,2'-inden]-1'(3'H)-imine

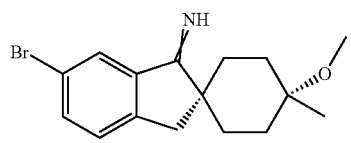 [SMILES: CO[C@]1(C)CC[C@@]2(CC1)Cc1ccc(Br)cc1C2=N]

HCl (4M in 1,4-dioxane, 1.9 mL, 7.60 mmol) was added to a solution of N-((1r,4O-5'-bromo-4-methoxy-4-methylspiro[cyclohexane-1,2'-indene]-3'(1'H)-ylidene)-2-methylpropane-2-sulfinamide (0.648 g, 1.52 mmol, Example 111 Step 1) in anhydrous 1,4-dioxane (4 mL) and the resulting mixture was stirred under a nitrogen atmosphere at r.t. for 90 min. A precipitate was formed. Et$_2$O (5 mL) was added and the solid was filtered off and washed with Et$_2$O (5 mL). The solid was partitioned between DCM (20 mL) and sat. aq. NaHCO$_3$ (20 mL). The phases were separated, the organic layer dried over Na$_2$SO$_4$ and concentrated in vacuo to yield the crude title compound that was used directly in the next step: GCMS (CI) m/z 322 [M+H]$^+$.

Step 3: (1r,4r)-6'-Bromo-4-methoxy-4,5"-dimethyl-3'H-dispiro[cyclohexane-1,2'-indene-1',2"-imidazole]-4"(3"H)-thione

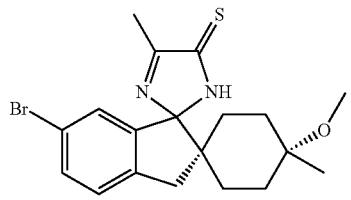

(1r,4r)-6'-Bromo-4-methoxy-4-methylspiro[cyclohexane-1,2'-inden]-1'(3'H)-imine (0.515 g, 1.60 mmol, Example 111 Step 2) and 2-oxopropanethioamide (Intermediate 2, 0.495 g, 4.79 mmol) were dissolved in MeOH (6 mL) and refluxed for 18 h. The reaction was concentrated and the residue was dissolved in DCM (10 mL). The organic layer was washed with water (10 mL), dried over Na$_2$SO$_4$, and filtered. The filtrate was passed through a pad of silica gel and eluted with DCM (removal of side products) and with DCM:MeOH (9:1) (to elute the product). The product solution was concentrated to give the title compound (0.536 g, 82% yield): $^1$H NMR (500 MHz, CDCl$_3$) δ ppm 1.16 (s, 3 H), 1.35 (m, 3 H), 1.60 (m, 8 H), 2.40 (s, 3 H), 3.08 (s, 2 H), 3.23 (s, 3 H), 7.06 (d, 1 H), 7.20 (d, 1 H), 7.45 (dd, 1 H); MS (ES+) m/z 407 [M+H]$^+$.

Step 4: (1r,4r)-6'-Bromo-4-methoxy-4,5"-dimethyl-3'H-dispiro[cyclohexane-1,2'-indene-1',2"-imidazol]-4"-amine

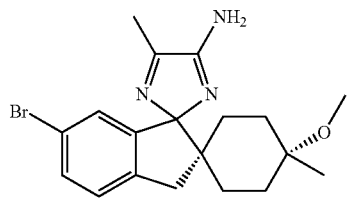

(1r,4r)-6'-Bromo-4-methoxy-4,5"-dimethyl-3'H-dispiro[cyclohexane-1,2'-indene-1',2"-imidazole]-4"(3"H)-thione (0.535 g, 1.31 mmol Example 111 Step 3) was dissolved in ammonia (7 M in MeOH, 16.89 mL, 118.2 mmol) and the mixture was heated with microwaves at 90° C. for 60 min. The mixture was concentrated, dissolved in ammonia (7M in MeOH, 18.76 ml, 131.3 mmol) and it was heated again with microwaves for 30 min at 90° C. This procedure (concentration and ammonia treatment in microwave reactor) was repeated once more. The mixture was concentrated and the product purified by flash chromatography with a gradient of 0-6% MeOH in DCM (containing 6% 7N NH$_3$ in MeOH): $^1$H NMR (500 MHz, CDCl$_3$) δ ppm 1.12 (s, 3 H), 1.56 (m, 8 H), 2.32 (s, 3 H), 3.11 (d, 2 H), 3.22 (s, 3 H), 6.84 (d, 1 H), 7.17 (d, 1 H), 7.33 (dd, 1 H); MS (ES+) m/z 392 [M+H]$^+$.

Step 5: (1r,4r)-4-Methoxy-4,5"-dimethyl-6'-[5-(prop-1-yn-1-yl)pyridin-3-yl]-3'H-dispiro[cyclohexane-1,2'-indene-1',2"-imidazol]-4"-amine

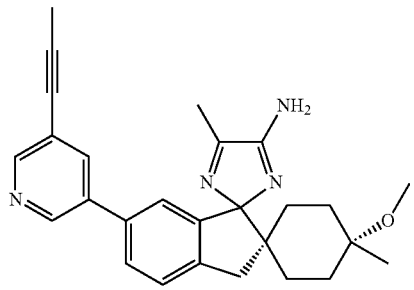

A mixture of (1r,4r)-6'-bromo-4-methoxy-4,5"-dimethyl-3'H-dispiro[cyclohexane-1,2'-indene-1',2"-imidazol]-4"-amine (Example 111, Step 4, 84 mg, 0.22 mmol), 5-(prop-1-ynyl)pyridin-3-ylboronic acid (Intermediate 15, 45 mg, 0.28 mmol) [1,1'-bis(diphenylphosphino)ferrocene]-palladium(II) chloride (17.7 mg, 0.02 mmol), $K_2CO_3$ (2 M aq. solution, 0.215 mL, 0.43 mmol) and 1,4-dioxane (1 mL) was heated in a microwave reactor at 130° C. for 20 min. When cooled to r.t. the mixture was diluted with DCM, washed with water, dried over $Na_2SO_4$ and concentrated in vacuo. The product was purified by preparative chromatography to give the title compound (53 mg, 58% yield): $^1$H NMR (CDCl$_3$) δ ppm 1.15 (s, 3 H), 1.29 (d, 1 H), 1.65 (m, 7 H), 2.10 (s, 3 H), 2.39 (s, 3 H), 3.20 (m, 1 H), 3.24 (s, 3 H), 3.27 (m, 1 H), 6.94 (d, 1 H), 7.45 (m, 2 H), 7.78 (t, 1 H), 8.55 (d, 1 H), 8.62 (d, 1 H); MS (MM−ES+APCI)+ m/z 427 [M+H]$^+$.

Example 112

(1r,4r)-6'-(Cyclobutylethynyl)-4-methoxy-5"-methyl-3'H-dispiro[cyclohexane-1,2'-indene-1',2"-imidazol]-4"-amine

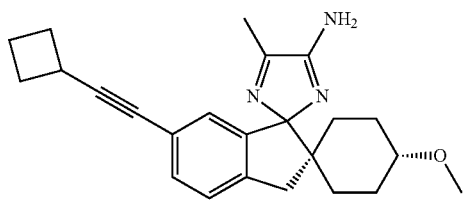

To a mixture of (1r,4r)-6'-bromo-4-methoxy-5"-methyl-3'H-dispiro[cyclohexane-1,2'-indene-1',2"-imidazol]-4"-amine (Example 19 Method B Step 4, 0.168 g, 0.45 mmol), $K_2CO_3$ (0.093 g, 0.67 mmol), copper(I) iodide (5.10 mg, 0.03 mmol), tetrakis(triphenylphosphine)palladium(0) (0.031 g, 0.03 mmol) in DMF (10 mL) was added (cyclobutylethynyl)trimethylsilane (0.102 g, 0.67 mmol) (see Kozhushkov, S. I.; Wagner-Gillen, K.; Khlebnikov A. F.; de Meijere, A. Synthesis 2010 (23), 3967-3973). The atmosphere over the reaction mixture was exchanged to argon and the mixture was heated to 70° C. overnight. The reaction was allowed to reach r.t. EtOAc and brine were added. The organic phase was dried over MgSO$_4$, filtered and concentrated in vacuo. The residue was purified by preparative chromatography to give the title compound (73 mg, 44% yield): $^1$H NMR (500 MHz, DMSO-d$_6$) δ ppm 1.28 (d, 1 H), 1.49 (d, 2 H), 1.70-1.83 (m, 3 H), 2.10-2.21 (m, 3 H), 2.21-2.31 (m, 1 H), 2.41 (td, 2 H), 2.50 (s, 3 H), 2.55-2.65 (m, 2 H), 3.23-3.42 (m, 3 H), 3.50-3.59 (m, 4 H), 6.85 (s, 1 H), 6.88 (s, 2 H), 7.51 (dd, 1 H), 7.59 (d, 1 H); MS (ES+) m/z 376 [M+H]$^+$.

Example 113

(1r,4r)-4-Methoxy-5"-methyl-6'-(3-methylbut-1-yn-1-yl)-3'H-dispiro[cyclohexane-1,2'-indene-1',2"-imidazol]-4"-amine

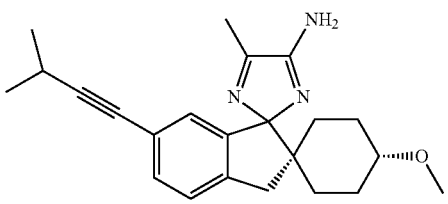

To a solution of (1r,4r)-6'-bromo-4-methoxy-5"-methyl-3'H-dispiro[cyclohexane-1,2'-indene-1',2"-imidazol]-4"-amine (Example 19 Method B Step 4, 0.153 g, 0.41 mmol) in DMF (8 mL) under argon was added 3-methylbut-1-yne (0.028 g, 0.41 mmol), tetrakis(triphenylphosphine)-palladium(0) (0.047 g, 0.04 mmol) and triethylamine (1.70 mL, 12.2 mmol). The reaction mixture was stirred at r.t. for 5 min, then cuprous iodide (0.012 g, 0.06 mmol) was added and the reaction mixture was heated at 65° C. for 18 h. The reaction mixture was partitioned between brine and EtOAc. The organic phase was dried over MgSO$_4$ and concentrated in vacuo. The residue was purified by preparative chromatography to give the title compound (0.035 g, 24% yield): $^1$H NMR (500 MHz, DMSO-d$_6$) δ ppm 0.87-0.98 (m, 1 H), 1.09-1.26 (m, 8 H), 1.35-1.48 (m, 3 H), 1.81 (d, 2 H), 2.15 (s, 3 H), 2.73 (dt, 1 H), 2.88-3.08 (m, 3 H), 3.18 (s, 3 H), 6.49 (s, 1 H), 6.54 (s, 2 H), 7.15 (dd, 1 H), 7.24 (d, 1 H); MS (ES+) m/z 364 [M+H]$^+$.

Example 114

(1r,1'R,4R)-4-Methoxy-5"-methyl-6'-{5-[($^2$H$_3$)prop-1-yn-1-yl]pyridin-3-yl}-3'H-dispiro[cyclohexane-1,2'-indene-1',2"-imidazol]-4"-amine

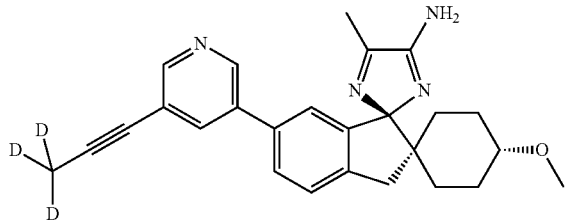 [SMILES: [2H]C([2H])([2H])C#Cc1cncc(-c2ccc3c(c2)[C@@]2(N=C(C)C(N)=N2)[C@]2(CC[C@H](OC)CC2)C3)c1]

A solution of (1r,1'R,4R)-6'-bromo-4-methoxy-5"-methyl-3'H-dispiro[cyclohexane-1,2'-indene-1',2"-imidazol]-4"-amine as the D(+)-10-camphor sulfonic acid salt (Example 19 Step 5, 135 mg, 0.22 mmol) in 2-Me THF (3 mL) was treated with KOH (1 M aq, 3.5 mL). The mixture was stirred for 30 min, the organic layer separated, washed with water, dried over Na$_2$SO$_4$ and concentrated. The residue was dissolved in 1,4-dioxane (2 mL) and bis(pinacolato)diboron (62 mg, 0.24 mmol), potassium acetate (44 mg, 0.44 mmol) and PdCl$_2$(dppf)-CH$_2$Cl$_2$ adduct (9 mg, 0.01 mmol) were added. The obtained mixture was heated with microwaves at 130° C. for 40 min. After cooling, the vessel was uncapped, and K$_2$CO$_3$ (2 M aq, 0.22 mL, 0.44 mmol), Pd(Ph$_3$P)$_4$ (13 mg, 0.01 mmol) and 3-bromo-5-[($^2$H$_3$)prop-1-yn-1-yl]pyridine (Intermediate 70, 53 mg, 0.27 mmol) in dioxane (1 mL) were added. The reaction vessel was sealed and heated with microwaves at 130° C. for 20 min. The mixture was diluted with DCM, washed with brine, dried over MgSO$_4$, filtered, and concentrated in vacuo. The product was purified by preparative chromatography (XBridge column 19×250 mm, 5 μm, with a mobile phase of 20-60% MeCN in 0.1% aq. ammonia, at a flow rate of 15 mL/min) to yield the title compound (15 mg, 16% yield, retention time 14 min): $^1$H NMR (500 MHz, CDCl$_3$) δ ppm 1.12 (td, 1 H), 1.37 (m, 2 H), 1.50 (m, 1 H), 1.72 (m, 2 H), 1.98 (m, 2 H), 2.34 (s, 3 H), 3.09 (m, 1 H), 3.23 (m, 2 H), 3.35 (s, 3 H), 6.92 (s, 1 H), 7.43 (s, 2 H), 7.77 (t, 1 H), 8.54 (d, 1 H), 8.62 (d, 1 H); MS (MM−ES+APCI)+ m/z 416 [M+H]$^+$.

Example 115

3-(4"-Amino-5"-methyl-4-oxodispiro[cyclohexane-1,2'-[1H]indene-1'(3'H),2"-[211]imidazol]-6'-yl)-5-fluorobenzonitrile Step 1: N-(6"-Bromodispiro[1,3-dioxolane-2,1'-cyclohexane-4',2"-inden]-1"(3" H)-ylidene)-2-methylpropane-2-sulfinamide

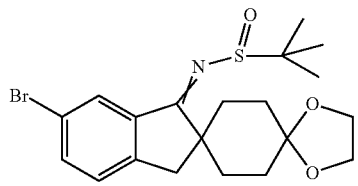 [SMILES: CC(C)(C)S(=O)N=C1c2cc(Br)ccc2CC12CCC1(CC2)OCCO1]

6"-Bromodispiro[1,3-dioxolane-2,1'-cyclohexane-4',2"-inden]-1"(3"H)-one (Intermediate 71, 320 mg, 0.95 mmol), 2-methylpropane-2-sulfinamide (173 mg, 1.42 mmol) and titanium ethoxide (0.391 mL, 1.90 mmol) were dissolved in 2-Me THF (5 mL) and heated to reflux overnight. The reaction was stopped and was left to cool down to r.t. EtOAc and water were added under stirring. The mixture was left to stand still for 2 h. The organic phase was collected by filtration, dried using a phase separator and concentrated in vacuo. The crude product was purified by flash chromatography using a gradient of 0-30% EtOAc in heptane to give the title compound (290 mg, 69% yield): $^1$H NMR (500 MHz, CDCl$_3$) δ ppm 1.35 (s, 9 H) 1.48-1.54 (m, 1 H) 1.61 (dd, 1 H) 1.67-1.77 (m, 2 H) 1.81-1.90 (m, 2 H) 2.10 (br. s., 2 H) 2.95-3.05 (m, 2 H) 3.95-4.02 (m, 4 H) 7.25 (s, 1 H) 7.60 (dd, 1 H) 8.62 (br. s., 1 H); MS (ES+) m/z 440.0 [M+H]$^1$.

Step 2: 6'-Bromo-1'-imino-1',3'-dihydrospiro[cyclohexane-1,2'-inden]-4-one

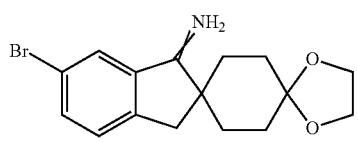

To N-(6"-bromodispiro[1,3-dioxolane-2,1'-cyclohexane-4',2"-inden]-1"(3"H)-ylidene)-2-methylpropane-2-sulfinamide (Example 115, Step 1, 288 mg, 0.65 mmol) in 1,4-dioxane (2 mL) under N$_2$ (g) was added HCl (4 M in 1,4-dioxane, 1.635 mL, 6.54 mmol). The mixture was stirred at r.t overnight and was then concentrated. The crude product was dissolved in DCM and was washed with NaHCO$_3$ (sat. aq). The aqueous phase was extracted with DCM. The combined organics were dried using a phase separator and concentrated to give the title compound (220 mg, quantitative yield) that was used directly in the next step: $^1$H NMR (400 MHz, DMSO-d$_6$) δ ppm 1.13-1.24 (m, 2 H) 1.25-1.35 (m, 2 H) 1.66-1.75 (m, 2 H) 1.83-1.93 (m, 2 H) 2.86 (s, 2 H) 5.83 (s, 1 H) 7.40 (d, 1 H) 7.64 (dd, 1 H) 7.69 (d, 1 H); MS (ES+) m/z 292 [M+H]$^1$.

Step 3: 6'-Bromo-4"-methyl-5"-thioxo-1",5"-dihydro-3'H,4H-dispiro[cyclohexane-1,2'-indene-1',2"-imidazol]-4-one

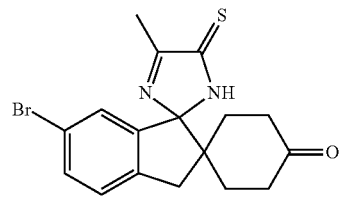 [SMILES: CC1=NC2(NC1=S)c1cc(Br)ccc1CC21CCC(=O)CC1]

6'-Bromo-1'-imino-1',3'-dihydrospiro[cyclohexane-1,2'-inden]-4-one (Example 115, Step 2, 2.37 g, 8.11 mmol) and trimethyl orthoformate (2.5 mL, 22.8 mmol) in 2-propanol (25 mL) was heated to 80° C. 2-Oxopropanethioamide (Intermediate 2, 1.673 g, 16.2 mmol) dissolved in 2-propanol (10 mL) was added. The mixture was heated at 80° C. overnight. The mixture was allowed to cool to r.t. before concentrated. The crude product was purified by flash chromatography using a gradient of 0-100% EtOAc in heptane. The desired fractions were concentrated to give the title compound (0.563 g, 18% yield): $^1$H NMR (500 MHz, CDCl$_3$) δ 1.69 (ddd, 1 H), 1.74-1.81 (m, 1 H), 1.90-1.96 (m, 1 H), 2.00-2.05 (m, 1 H), 2.40 (s, 4 H), 2.42-2.55 (m, 3 H), 3.25-3.35 (m, 2 H), 7.11 (d, 1 H), 7.26 (br. s., 1 H), 7.50 (dd, 1 H), 8.67 (br. s., 1 H); MS (ES+) m/z 377 [M+H]$^+$.

Step 4: 6"-Bromo-5'"-methyl-3"H-trispiro[1,3-dioxolane-2,1'-cyclohexane-4',2"-indene-1",2'"-imidazole]-4'"(3'"H)-thione

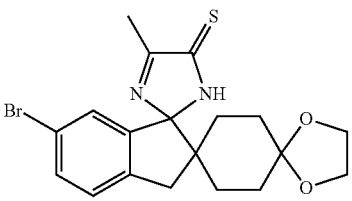 [SMILES: CC1=NC2(NC1=S)c1cc(Br)ccc1CC21CCC2(CC1)OCCO2]

Ethane-1,2-diol (0.074 mL, 1.33 mmol), 6'-bromo-4"-methyl-5"-thioxo-1",5"-dihydro-3'H,4H-dispiro[cyclohexane-1,2'-indene-1',2"-imidazol]-4-one (Example 115 Step 3, 0.5 g, 1.33 mmol) and p-toluenesulfonic acid monohydrate (0.013 g, 0.07 mmol) in toluene (8 mL) were heated to reflux overnight. The mixture was cooled to r.t and then washed with NaHCO₃ (sat aq). The aqueous phase was extracted with EtOAc. The combined organic phases were dried with MgSO₄, filtered and concentrated in vacuo to yield the title compound (0.506 g, 91% yield): MS [ES+] m/z 423 [M+H]⁺.

Step 5: 6"-Bromo-5'"-methyl-3"H-trispiro[1,3-dioxolane-2,1'-cyclohexane-4',2"-indene-1",2'"-imidazol]-4'"-amine

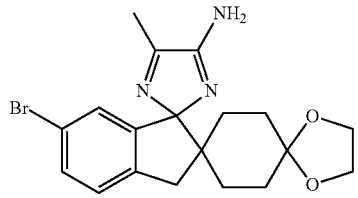 [SMILES: CC1=NC2(N=C1N)c1cc(Br)ccc1CC21CCC2(CC1)OCCO2]

6"-Bromo-5'"-methyl-3"H-trispiro[1,3-dioxolane-2,1'-cyclohexane-4',2"-indene-1",2'"-imidazole]-4"(3'"H)-thione (Example 115 Step 4, 0.5 g, 1.19 mmol) was taken up in ammonia (7 M in MeOH, 15 mL, 105 mmol) and the resulting mixture was heated in the microwave reactor at 110° C. for 30 min. The solvent was evaporated in vacuo and the same procedure (addition of ammonia, heating and evaporation) was repeated 3 times. The solvent was evaporated to yield the title compound (0.568 g, quantitative yield) that was used without further purification: ¹H NMR (500 MHz, CDCl₃) δ ppm 1.35-1.49 (m, 2 H), 1.61 (d, 2 H), 1.69-1.81 (m, 2 H), 2.33 (s, 3 H), 3.14 (s, 2 H), 3.87-3.98 (m, 4 H), 6.88 (d, 1 H), 7.19 (d, 1 H), 7.35 (dd, 1 H); MS (ES+) m/z 404 [M+H]⁺.

Step 6: 4"-Amino-6'-bromo-5"-methyl-3'H,4H-dispiro[cyclohexane-1,2'-indene-1,2"-imidazol]-4-one

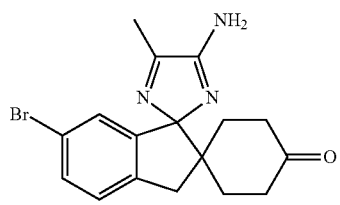 [SMILES: CC1=NC2(N=C1N)c1cc(Br)ccc1CC21CCC(=O)CC1]

6"-Bromo-5'"-methyl-3"H-trispiro[1,3-dioxolane-2,1'-cyclohexane-4',2"-indene-1",2'"-imidazol]-4'"-amine (Example 115 Step 5, 0.568 g, 1.40 mmol) was dissolved in HCl (1.25 M in MeOH, 15 mL, 18.8 mmol) and water (5 mL). The mixture was stirred at 60° C. for 1.5 h. and then at 80° C. for 3 h. EtOAc was added and the aqueous phase was extracted. The aqueous phase was discarded. Aq. citric acid solution (0.1 M) was added to the organic phase and the phases were separated. The organic phase was extracted once more with citric acid (0.1 M aq.). The combined citric acid phases were basified with 1 M NaOH and extracted with DCM twice. The combined organic phases were dried with a phase separator and evaporated to dryness in vacuo. The crude product was purified by flash chromatography (24 g SiO₂, gradient elution 0-20% (0.1 M NH₃ in MeOH) in DCM) to yield the title compound (0.116 g, 23% yield): ¹H NMR (500 MHz, CD₃OD) δ ppm 1.24 (t, 1 H), 1.55 (td, 1 H), 1.88 (dd, 2 H), 2.15-2.30 (m, 2 H), 2.30-2.38 (m, 3 H), 2.42-2.60 (m, 2 H), 3.27 (s, 1 H), 3.33-3.41 (m, 1 H), 6.88 (d, 1 H), 7.31 (d, 1 H), 7.42 (dd, 1 H); MS (MM–ES+APCI)+ m/z 360.0 [M+H]⁺.

Step 7: 3-(4"-Amino-5"-methyl-4-oxodispiro[cyclohexane-1,2'-[1H]indene-1'(3'H),2"-[2H]imidazol]-6'-yl)-5-fluorobenzonitrile

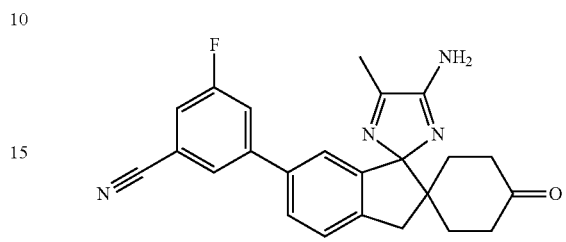

4"-Amino-6'-bromo-5"-methyl-3'H,4H-dispiro[cyclohexane-1,2'-indene-1',2"-imidazol]-4-one (Example 115 step 6, 92 mg, 0.26 mmol), 3-cyano-5-fluorophenylboronic acid (42 mg, 0.26 mmol), 3-(di-tert-butylphosphonium)propane sulfonate (6.8 mg, 0.03 mmol), sodium tetrachloropalladate(II) (3.8 mg, 0.01 mmol), 2-Me THF (2 mL) and K₂CO₃ (2 M aq., 0.383 mL, 0.77 mmol) were added to a microwave vial. The vial was sealed and heated in the MW for 30 min at 100° C. EtOAc and water were added and the organic phase was collected, dried through a phase separator and evaporated to dryness in vacuo. The crude product was purified using preparative chromatography to yield the title compound (39 mg, 38% yield): ¹H NMR (500 MHz, DMSO-d₆) δ ppm 1.45 (td, 1 H), 1.67-1.78 (m, 2 H), 1.78-1.90 (m, 1 H), 2.08 (d, 1 H), 2.14-2.23 (m, 4 H), 2.34-2.48 (m, 2 H), 3.20-3.32 (m, 2 H), 6.61 (br. s., 2 H), 6.94 (s, 1 H), 7.45 (d, 1 H), 7.63 (d, 1 H), 7.74-7.87 (m, 2 H), 7.93 (s, 1 H); MS (MM–ES+APCI)+ m/z 401 [M+H]⁺.

Example 116

(1r,4r)-4-Methoxy-5"-methyl-6'-(3-methyl-1H-pyrrolo[2,3-b]pyridin-5-yl)-3'H-dispiro[cyclohexane-1,2'-indene-1',2"-imidazol]-4"-amine

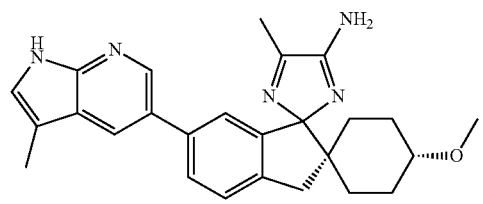

An analogous procedure to the procedure described for Example 81 was followed using 3-methyl-5-(4,4,5,5-tetramethyl-1,3,2-dioxaborolan-2-yl)-1H-pyrrolo[2,3-b]pyridine (98 mg, 0.38 mmol) and (1r,4r)-6'-bromo-4-methoxy-5"-methyl-3'H-dispiro[cyclohexane-1,2'-indene-1',2"-imidazol]-4"-amine (Example 19 Method B Step 4, 130 mg, 0.35 mmol). The product was purified by flash chromatography on silica using gradient elution with 0-10% of 0.2 M methanolic ammonia in DCM to give 65 mg (44% yield) of the title compound: ¹H NMR (500 MHz, DMSO-d₆) δ ppm 0.90-1.01 (m, 1 H), 1.13-1.33 (m, 2 H), 1.46-1.54 (m, 3 H), 1.84 (m, 2 H), 2.18 (s, 3 H), 2.28 (s, 3 H), 2.91-3.03 (m, 2 H), 3.05-3.12

(m, 1 H), 3.20 (s, 3 H), 6.56 (br. s., 2 H), 6.81 (s, 1 H), 7.23 (s, 1 H), 7.38 (d, 1 H), 7.47-7.53 (m, 1 H), 7.93-7.98 (m, 1 H), 8.31 (m, 1 H), 11.31 (s, 1 H); MS (ES+) m/z 428 [M+H]⁺.

Example 117

(1r,4r)-6'-Bromo-5"-methyl-4-[(²H₃)methyloxy]-3'H-dispiro[cyclohexane-1,2'-indene-1',2"-imidazol]-4"-amine Step 1: (1r,4r)-N-{6'-Bromo-4-[(²H₃)methyloxy]spiro[cyclohexane-1,2'-inden]-1'(3'H)-ylidene}-2-methylpropane-2-sulfinamide

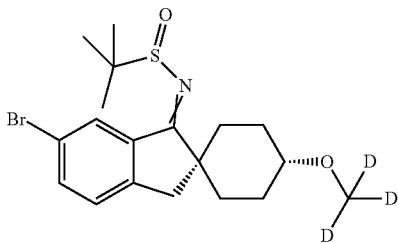 [SMILES: [2H]C([2H])([2H])O[C@H]1CC[C@]2(CC1)Cc1ccc(Br)cc1C2=NS(=O)C(C)(C)C]

6'-Bromo-4-[(²H₃)methyloxy]spiro[cyclohexane-1,2'-inden]-1'(3'H)-one (Intermediate 72, 1.66 g, 5.32 mmol), 2-methylpropane-2-sulfinamide (1.20 g, 9.57 mmol) and titanium ethoxide (2.19 mL, 10.6 mmol) were dissolved in 2-Me THF (12 mL) and heated to reflux over the weekend. The mixture was allowed to cool to r.t. whereafter it was diluted with EtOAc (20 mL). Water (15 mL) was added dropwise under vigorous stirring. After 10 min the mixture was left standing still without stirring for 1 h. The solids were filtered off and the organic layer was concentrated. Purification by flash chromatography using 0-25% EtOAc in heptane as eluent afforded 1.44 g (65% yield) of the title compound as a mixture of isomers (1r,4r) major and (1s,4s) minor. Major isomer (1r,4r): ¹H NMR (500 MHz, CDCl₃) δ 1.31-1.36 (m, 9 H), 1.38 (m, 1 H), 1.52-1.68 (m, 4 H), 1.96-2.07 (m, 1 H), 2.13 (dt, 2 H), 2.97 (d, 2 H), 3.20-3.33 (m, 1 H), 7.22-7.26 (m, 1 H), 7.61 (dd, 1 H), 8.46-8.71 (m, 1 H). MS (ES+) m/z 415 [M+H]⁺.

Step 2: (1r,4r)-6'-Bromo-4-[(2H₃)methyloxy]spiro[cyclohexane-1,2'-inden]-1'(3'H)-imine

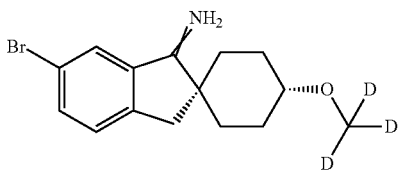 [SMILES: [2H]C([2H])([2H])O[C@H]1CC[C@]2(CC1)Cc1ccc(Br)cc1C2=N]

HCl (4 M in 1,4-dioxane, 8.67 mL, 34.7 mmol) was added to a solution of N-{6'-Bromo-4-[(²H₃)methyloxy]spiro[cyclohexane-1,2'-inden]-1'(3'H)-ylidene}-2-methylpropane-2-sulfinamide (Example 117 step 1, 1.44 g, 3.47 mmol) in anhydrous 1,4-dioxane (5 mL). A white precipitate was formed immediately and the resulting cloudy mixture was stirred under an argon atmosphere at r.t. for 45 min. Et₂O (30 mL) was added and the solid was filtered off and washed with Et₂O. The solid was partitioned between DCM and sat. aq. NaHCO₃. The phases were separated and the organic layer dried over Na₂SO₄ and concentrated to afford 999 mg (93% yield) of the title compound as a mixture of isomers (1r,4r) (major) and (1s,4s) (minor) which was used directly in the next step: MS (ES+) m/z 311 [M+H]⁺.

Step 3: (1r,4r)-6'-Bromo-5"-methyl-4-[(²H₃)methyloxy]-3'H-dispiro[cyclohexane-1,2'-indene-1',2"-imidazole]-4"(3"H)-thione

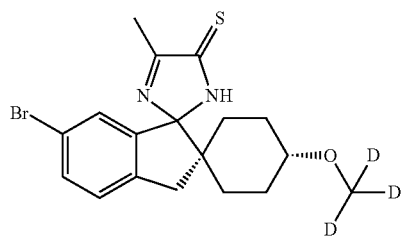

6'-Bromo-4-[(²H₃)methyloxy]spiro[cyclohexane-1,2'-inden]-1'(3'H)-imine (Example 117 step 2, 0.999 g, 3.21 mmol) and trimethyl orthoformate (1.06 mL, 9.63 mmol) in 2-propanol (10 mL) was heated to 80° C. 2-Oxopropanethioamide (Intermediate 2, 0.828 g, 8.02 mmol) dissolved in 2-propanol (6 mL) was added dropwise over ~10 min and the resulting orange mixture was stirred at 80° C. under N₂. After 3 h the mixture was concentrated to approximately ½ the volume and left at 4° C. overnight. The formed solid was filtered off, washed with cold MeOH and dried in vacuo, yielding 0.701 g (55% yield) of the title compound as a mixture of isomers (83:27 of (1r,4r) and (1s,4s)). The mother liquor was concentrated and the crude product was purified by flash chromatography using a gradient of 0-40% EtOAc in heptane to afford another 0.181 g (14% yield) of the title compound as a mixture of isomers (94:6 of (1r,4r) and (1s,4s)). Major isomer (1r,4r): ¹H NMR (500 MHz, DMSO-d₆) δ 1.16-1.32 (m, 4 H), 1.47 (dd, 2 H), 1.81-1.92 (m, 2 H), 2.23-2.29 (m, 3 H), 2.95-3.09 (m, 3 H), 6.98 (d, 1 H), 7.34 (d, 1 H), 7.51 (dd, 1 H), 12.35 (s, 1 H); MS (ES+) m/z 396 [M+H]⁺.

Step 4: (1r,4r)-6'-Bromo-5"-methyl-4-[(²H₃)methyloxy]-3'H-dispiro[cyclohexane-1,2'-indene-1',2"-imidazol]-4"-amine

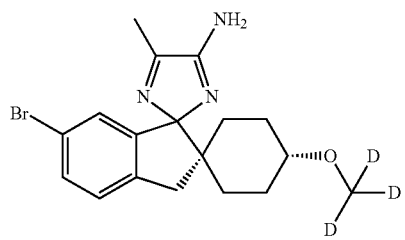

(1r,4r)-6'-Bromo-5"-methyl-4-[(²H₃)methyloxy]-3'H-dispiro[cyclohexane-1,2'-indene-1',2"-imidazole]-4"(3"H)-thione (Example 117 step 3, 0.701 g, 1.77 mmol) and ammonia (7 M in MeOH, 12 mL, 84 mmol) were mixed in a microwave vial. The vial was sealed and the reaction was heated at 100° C. for 30 min in a microwave reactor (fixed hold time). The mixture was concentrated and the residue was dissolved in new ammonia (7 M in MeOH, 12 mL, 84 mmol)

and heated again at 100° C. for 30 min in a microwave reactor. This, concentration, addition of ammonia and heating, was repeated once more (3 runs in total). After evaporation of the solvent, the residue was partitioned between EtOAc and 2 M citric acid. The phases were separated and the organic layer was extracted with 2 M citric acid. The organic layer was discarded while the combined aqueous phases were basified to pH 12 by addition of 50% NaOH (aq) and extracted with EtOAc ×2. The combined organic layers were treated with charcoal and filtered through diatomaceous earth. The filter pad was rinsed with EtOAc and the organic phase was concentrated, yielding 0.521 g (78% yield) of the title compound as a mixture of isomers (75:25 of (1r,4r) and (1s,4s)). A pure sample of (1r,4r)-6'-bromo-5"-methyl-4-[($^2$H$_3$)methyloxy]-3'H-dispiro[cyclohexane-1,2'-indene-1',2"-imidazol]-4"-amine was obtained using a Waters FractionLynx preparative HPLC, with an XBridge C18 (150*19 mm; 5 μm) column, and a mobile phase consisting of 5-40% MeCN in 0.1M aq. NH$_4$OAc over 18 min at a flow rate of 20 mL/min and a temperature at 45° C.: $^1$H NMR (500 MHz, DMSO-d$_6$) δ 0.88-0.98 (m, 1 H), 1.09-1.26 (m, 2 H), 1.35-1.46 (m, 3 H), 1.81 (d, 2 H), 2.16 (s, 3 H), 2.86-3.04 (m, 3 H), 6.59 (br. s., 2 H), 6.65 (s, 1 H), 7.25 (d, 1 H), 7.34 (dd, 1 H). MS (ES+) m/z 379 [M+H]$^+$.

Example 118

3-{(1r,4r)-4"-Amino-5"-methyl-4-[($^2$H$_3$)methyloxy]-3'H-dispiro[cyclohexane-1,2'-indene-1',2"-imidazol]-6'-yl}-5-fluorobenzonitrile

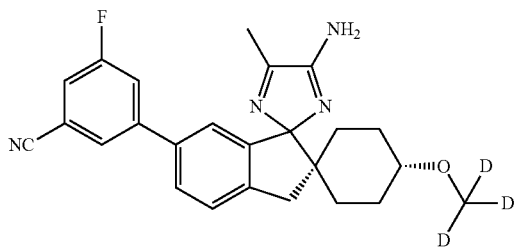

(1r,4r)-6'-Bromo-5"-methyl-4-[($^2$H$_3$)methyloxy]-3'H-dispiro[cyclohexane-1,2'-indene-1',2"-imidazol]-4"-amine (Example 117, 0.100 g, 0.26 mmol), 3-cyano-5-fluorophenylboronic acid (65 mg, 0.40 mmol), sodium tetrachloropalladate(II) (3.8 mg, 0.01 mmol) and 3-(di-tert-butyl-phosphonium)propane sulfonate (7.1 mg, 0.03 mmol) were put in a microwave vial. 2-Me THF (2 mL) was added followed by K$_2$CO$_3$ (2.0 M, 0.395 mL, 0.79 mmol) and the mixture was degassed. The mixture was then heated at 100° C. in a microwave reactor for 30 min. Water and EtOAc were added and the phases were separated. The aqueous phase was extracted with EtOAc and the combined organic layers were dried over MgSO$_4$ and concentrated. The crude product was purified by preparative chromatography followed by flash chromatography using a gradient of 5% MeOH (containing 0.1M NH$_3$) in EtOAc to obtain 40 mg (37% yield) of the title compound: $^1$H NMR (500 MHz, DMSO-d$_6$) δ 0.94-1.03 (m, 1 H), 1.13-1.28 (m, 2 H), 1.36-1.50 (m, 3 H), 1.82 (d, 2 H), 2.18 (s, 3 H), 2.90-2.98 (m, 1 H), 2.98-3.11 (m, 2 H), 6.53 (s, 2 H), 6.90 (s, 1 H), 7.41 (d, 1 H), 7.59 (dd, 1 H), 7.79 (dd, 2 H), 7.91 (s, 1 H); MS (ES+) m/z 420 [M+H]$^+$.

Example 119

(1r,4r)-6'-(5-Chloropyridin-3-yl)-5"-methyl-4-[($^2$H$_3$) methyloxy]-3'H-dispiro[cyclohexane-1,2'-indene-1',2"-imidazol]-4"-amine

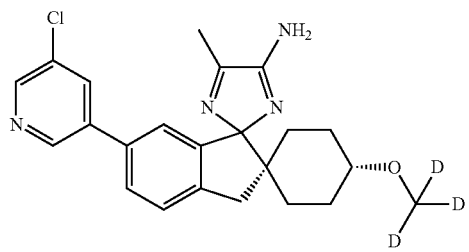

The title compound (23 mg, 21% yield) was prepared using the procedure described for Example 118 starting from (1r,4r)-6'-bromo-5"-methyl-4-[($^2$H$_3$)methyloxy]-3'H-dispiro[cyclohexane-1,2'-indene-1',2"-imidazol]-4"-amine (Example 117, 0.100 g, 0.26 mmol) and 5-chloropyridin-3-ylboronic acid (0.054 g, 0.34 mmol): $^1$H NMR (500 MHz, DMSO-d$_6$) δ 0.93-1.02 (m, 1 H), 1.13-1.29 (m, 2 H), 1.40-1.50 (m, 3 H), 1.80-1.85 (m, 2 H), 2.17 (s, 3 H), 2.91-2.98 (m, 1 H), 2.98-3.13 (m, 2 H), 6.54 (s, 2 H), 6.87 (d, 1 H), 7.42 (d, 1 H), 7.57 (dd, 1 H), 8.09 (t, 1 H), 8.56 (d, 1 H), 8.71 (d, 1 H). MS (ES+) m/z 412 [M+H]$^+$.

Example 120

(1r,4r)-6'-[5-(Difluoromethyl)pyridin-3-yl]-4-methoxy-5"-methyl-3'H-dispiro[cyclohexane-1,2'-indene-1',2"-imidazol]-4"-amine

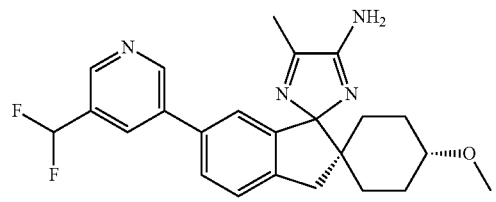

(1r,4r)-6'-Bromo-4-methoxy-5"-methyl-3'H-dispiro[cyclohexane-1,2'-indene-1',2"-imidazol]-4"-amine (Example 19 Method B Step 4, 400 mg, 1.06 mmol) was dissolved in 2-Me THF (3 mL) in a MW-vial. 3-(Difluoromethyl)-5-(4,4,5,5-tetramethyl-1,3,2-dioxaborolan-2-yl)pyridine (Intermediate 74, 184 mg, 0.72 mmol) was added followed by K$_2$CO$_3$ (2.0 M aq.) (1.595 mL, 3.19 mmol). Then sodium tetrachloropalladate(II) (44 mg, 0.15 mmol) and 3-(di-tert-butylphosphonium)propane sulfonate (80 mg, 0.30 mmol) were added, the system was closed and run in the MW reactor for 30 min at 100° C. The Water and 2-Me THF were added. The water phase was eliminated. The organic phase was washed once with brine and water. The organic phase was concentrated in vacuo and the product was purified by preparative chromatography to give 7 mg (1.5% yield) of the title compound: $^1$H NMR (500 MHz, DMSO-d$_6$) δ ppm 0.96 (m, 1 H) 1.12-1.31 (m, 2 H) 1.38-1.55 (m, 3 H) 1.83 (d, 2 H) 2.17 (s, 3 H) 2.91-2.99 (m, 1 H) 3.05 (q, 2 H) 3.20 (s, 3 H) 6.56 (br. s, 2 H) 6.87 (s, 1 H) 7.18 (t, 1 H) 7.44 (d, 1 H) 7.59 (dd, 1 H) 8.09 (s, 1 H) 8.73 (s, 1 H) 8.92 (s, 1 H); MS (ES+) m/z 425 [M+H]$^+$.

Example 121

(1r,4r)-4-Methoxy-5"-methyl-6'-(3-methyl-1H-indol-5-yl)-3'H-dispiro[cyclohexane-1,2'-indene-1',2"-imidazol]-4"-amine

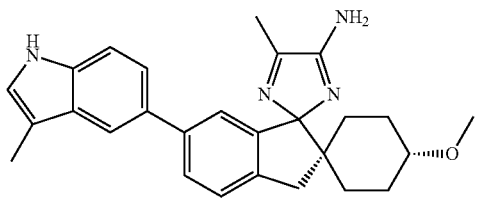

(1r,4r)-6'-Bromo-4-methoxy-5"-methyl-3'H-dispiro[cyclohexane-1,2'-indene-1',2"-imidazol]-4"-amine (Example 19 Method B Step 4, 110 mg, 0.29 mmol), 4,4,4',4',5,5,5',5'-octamethyl-2,2'-bi(1,3,2-dioxaborolane) (82 mg, 0.32 mmol), PdCl$_2$(dppf)-CH$_2$Cl$_2$ adduct (11.9 mg, 0.01 mmol) and potassium acetate (86 mg, 0.88 mmol) were placed in a microwave vial. 2-Me THF (5 mL) was added and the vial was evacuated and refilled with argon. The mixture was heated to 100° C. in a microwave apparatus for 30 min. To the resulting mixture was added 5-bromo-3-methyl-1H-indole (74 mg, 0.35 mmol), sodium tetrachloropalladate(II) (4.3 mg, 0.01 mmol), 3-(di-tert-butylphosphino)propane-1-sulfonic acid (7.8 mg, 0.03 mmol) and 2 M aq. K$_2$CO$_3$ (0.438 mL, 0.88 mmol). The vial was evacuated and refilled with argon. The reaction mixture was heated to 120° C. in a microwave reactor for 30 min. The reaction mixture was diluted with EtOAc and DCM, washed with water, dried over MgSO$_4$, filtered and concentrated. The residue was purified by flash chromatography on silica using gradient elution with 0-10% (0.2 M ammonia in MeOH) in DCM to give 56 mg (44% yield) of the title compound: $^1$H NMR (500 MHz, DMSO-d$_6$) δ ppm 0.94 (m, 1 H), 1.12-1.32 (m, 2 H), 1.49 (m, 3 H), 1.84 (m, 2 H), 2.17 (s, 3 H), 2.27 (s, 3 H), 2.90-3.01 (m, 2 H), 3.03-3.12 (m, 1 H), 3.20 (s, 3 H), 6.55 (s, 2 H), 6.77 (s, 1 H), 7.11 (s, 1 H), 7.20 (m, 1 H), 7.30-7.38 (m, 2 H), 7.46 (m, 1 H), 7.54 (s, 1 H), 10.75 (s, 1 H); MS (ES+) m/z 427 [M+H]$^+$.

Example 122

(1r,4r)-5"-methyl-4-[($^2$H$_3$)methyloxy]-6'-[5-(prop-1-yn-1-yl)pyridin-3-yl]-3'H-dispiro[cyclohexane-1,2'-indene-1',2"-imidazol]-4"-amine

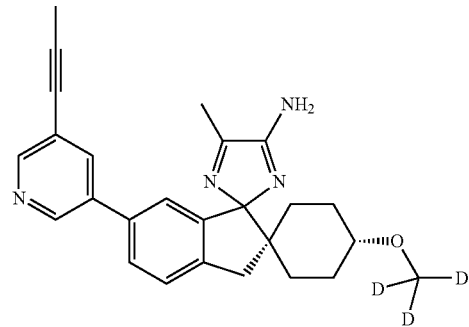

(1r,4r)-6'-Bromo-5"-methyl-4-[($^2$H$_3$)methyloxy]-3'H-dispiro[cyclohexane-1,2'-indene-1',2"-imidazol]-4"-amine (Example 117, 0.100 g, 0.26 mmol), 5-(prop-1-ynyl)pyridin-3-ylboronic acid (Intermediate 15, 55 mg, 0.34 mmol), sodium tetrachloropalladate(II) (3.88 mg, 0.01 mmol) and 3-(di-tert-butylphosphonium)propane sulfonate (7.07 mg, 0.03 mmol) were placed in a microwave vial. 2-Me THF (2 mL) was added followed by aq. K$_2$CO$_3$ (2.0 M, 0.395 mL, 0.79 mmol). The mixture was degassed, the atmosphere was exchanged to argon, and the mixture was heated at 100° C. in a microwave reactor for 30 min. The reaction mixture was allowed to reach r.t., and EtOAc and brine were added. The organic phase was dried over MgSO$_4$, filtered and concentrated in vacuo. The residue was purified by preparative chromatography (XBridge C18 (150×19 mm, 5 μm) column and a gradient of 10-40% MeCN in 50 mM aq. NH$_4$OAc over 18 min at 45° C. with a flow rate of 20 mL/min) to give the title compound (55 mg, 50% yield): $^1$H NMR (500 MHz, DMSO-d$_6$) δ ppm 0.90-1.04 (m, 1 H), 1.11-1.31 (m, 2 H), 1.37-1.55 (m, 3 H), 1.83 (d, 2 H), 2.09 (s, 3 H), 2.17 (s, 3 H), 2.89-3.14 (m, 3 H), 6.53 (br. s., 2 H), 6.83 (s, 1 H), 7.41 (d, 1 H), 7.54 (d, 1 H), 7.90 (s, 1 H), 8.51 (s, 1 H), 8.67 (d, 1 H); MS (ES+) m/z 416 [M+H]$^+$.

Example 123

(1r,4r)-6'-[2-Chloro-3-(prop-1-yn-1-yl)phenyl]-4-methoxy-5"-methyl-3'H-dispiro[cyclohexane-1,2'-indene-1',2"-imidazol]-4"-amine

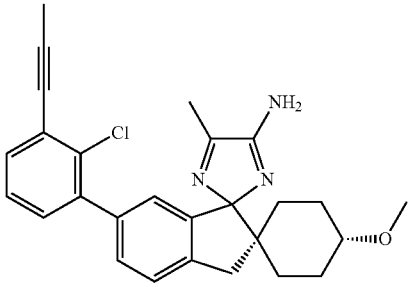

In a microwave vial were (1r,4r)-6'-bromo-4-methoxy-5"-methyl-3'H-dispiro[cyclohexane-1,2'-indene-1',2"-imidazol]-4"-amine (Example 19 Method B Step 4, 0.218 g, 0.58 mmol), 4,4,4',4',5,5,5',5'-octamethyl-2,2'-bi(1,3,2-dioxaborolane) (0.162 g, 0.64 mmol), 1,1'-bis-(diphenylphosphino)ferrocene-palladium dichloride (24 mg, 0.03 mmol) and potassium acetate (0.114 g, 1.16 mmol) were dissolved in dioxane (7 mL) and was irradiated at 130° C. for 40 min in a microwave reactor. To the mixture was added K$_2$CO$_3$ (2 M aq., 0.578 mL, 1.16 mmol), tetrakis(triphenylphosphine)palladium (33 mg, 0.03 mmol) and a solution of 1-bromo-2-chloro-3-(prop-1-ynyl)benzene (Intermediate 75, 146 mg, 0.64 mmol) in dioxane (2 mL). The vial was sealed and heated at 130° C. for 20 min in a microwave reactor. After cooling, the mixture was diluted with DCM, washed with brine, dried over MgSO$_4$, filtered and concentrated in vacuo. The product was isolated using preparative chromatography to give 25 mg (10% yield) of the title compound: $^1$H NMR (500 MHz, CDCl$_3$) δ ppm 1.15 (td, J=13.40, 2.84 Hz, 1 H) 1.30-1.47 (m, 3 H) 1.67-1.75 (m, 1 H) 1.79 (d, J=8.51 Hz, 1 H) 1.96-2.10 (m, 2 H) 2.12 (s, 3 H) 2.42 (s, 3 H) 3.11 (br. s., 1 H) 3.20 (m, 1 H)

3.29 (m, 1 H) 3.35 (s, 3 H) 6.87 (s, 1 H) 7.18 (q, J=7.99 Hz, 2 H) 7.35-7.44 (m, 3 H) 8.33 (br. s., 2 H); MS (ES+) m/z 446 [M+H]$^+$.

Example 124

6'-Bromo-5''-methyl-4-(trifluoromethyl)-3'H-dispiro[cyclohexane-1,2'-indene-1',2''-imidazol]-4''-amine Step 1: N-(5'-Bromo-4-(trifluoromethyl)spiro[cyclohexane-1,2'-indene]-3'(1'H)-ylidene)-2-methylpropane-2-sulfinamide

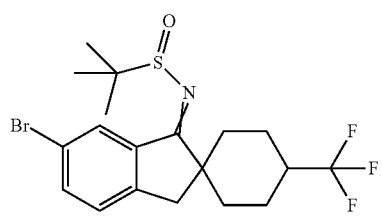 [SMILES: CC(C)(C)S(=O)N=C1c2cc(Br)ccc2CC12CCC(C(F)(F)F)CC2]

Titanium ethoxide (2.03 mL, 9.85 mmol), 2-methyl-2-propanesulfinamide (0.895 g, 7.39 mmol) and 6'-bromo-4-(trifluoromethyl)spiro[cyclohexane-1,2'-inden]-1'(3'H)-one (Intermediate 78, 1.71 g, 4.93 mmol) in dry 2-Me THF (30 mL) were heated to 100° C. to give an azeotrope at 74° C. The azeotropic distillation was continued for 5 h and then the mixture was refluxed for 2 days. The mixture was cooled to r.t. Water (10 mL) and EtOAc (20 mL) were added, under continuous stirring, while a solid formed. The reaction mixture was stirred at r.t. for 2 h, and then the formed solid was left to sediment for 1 h. The mixture was filtered, and the solid was washed with EtOAc. The filtrate was concentrated in vacuo to give a residue that was purified by flash chromatography (eluent heptane/EtOAc 65/35) to give the title compound (400 mg, 18% yield): $^1$H NMR (400 MHz, CDCl$_3$) δ ppm 1.34-1.37 (m, 9 H) 1.56 (s, 4 H) 1.73-1.82 (m, 2 H) 2.13 (br. s., 5 H) 2.89 (d, 2 H) 7.22 (d, 1 H) 7.60 (dd, 1 H) 8.53 (d, 1 H); MS (ES+) 451 [M+H]$^+$.

Step 2: 6'-Bromo-5''-methyl-4-(trifluoromethyl)-3'H-dispiro[cyclohexane-1,2'-indene-1',2''-imidazole]-4''(3''H)-thione

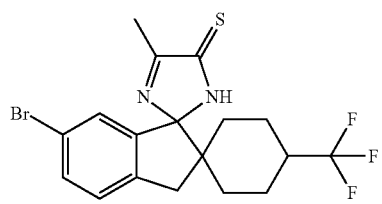 [SMILES: CC1=NC2(NC1=S)c1cc(Br)ccc1CC21CCC(C(F)(F)F)CC1]

N-(5'-Bromo-4-(trifluoromethyl)spiro[cyclohexane-1,2'-indene]-3'(1'H)-ylidene)-2-methyl-propane-2-sulfinamide (Example 124 Step 1, 400 mg, 0.89 mmol) was dissolved in dioxane (10 mL). The atmosphere was exchanged to argon. Hydrochloric acid (4 M in dioxane) (2.22 mL, 8.88 mmol) was added. The reaction mixture was stirred at 21° C. for 2.5 h. The mixture was concentrated and the residue was dissolved in DCM (~4-6 mL). Et$_2$O (14 mL) was added and the solid was filtered off and washed with Et$_2$O. The solid was partitioned between DCM (10 mL) and sat. aq. NaHCO$_3$ (8 mL). The phases were separated and the organic layer concentrated in vacuo. The acquired solid (340 mg), trimethyl orthoformate (0.292 mL, 2.67 mmol), and N-ethyldiisopropylamine (0.307 mL, 1.78 mmol) in i-PrOH (20 mL) were heated to 80° C. for 10 min, and then 2-oxopropanethioamide (Intermediate 2, 183 mg, 1.78 mmol) was added. The reaction mixture was refluxed for 6 h. The mixture was cooled to r.t., and concentrated in vacuo. The residue was diluted with EtOAc, and washed with brine. The organic layer was dried over MgSO$_4$, filtered, and purified by flash chromatography (eluent heptane/EtOAc 80/20) to give the title compound (40 mg, 10% yield): $^1$H NMR (400 MHz, CDCl$_3$) δ ppm 1.37-1.50 (m, 6 H) 1.66-1.83 (m, 6 H) 1.89-2.04 (m, 4 H) 2.07-2.22 (m, 2 H) 2.44 (s, 4 H) 3.00 (d, 2 H) 7.01 (d, 1 H) 7.18 (d, 1 H) 7.45 (dd, 1 H) 9.04-9.13 (m, 1 H); MS (ES+) m/z 433 [M+H]$^+$ and (ES–) m/z 431 [M–H]$^-$.

Step 3: 6'-Bromo-5''-methyl-4-(trifluoromethyl)-3'H-dispiro[cyclohexane-1,2'-indene-1',2''-imidazol]-4''-amine

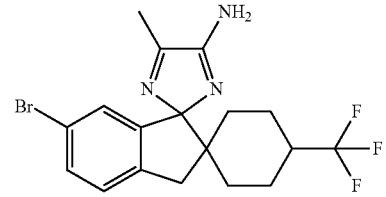 [SMILES: CC1=NC2(N=C1N)c1cc(Br)ccc1CC21CCC(C(F)(F)F)CC1]

6'-Bromo-5''-methyl-4-(trifluoromethyl)-3'H-dispiro[cyclohexane-1,2'-indene-1',2''-imidazole]-4''(3''H)-thione (Example 124 Step 2, 40 mg, 0.09 mmol) was dissolved in ammonia (7 M in MeOH) (2 mL, 14.0 mmol) in a microwave vial. The vial was capped, and heated to 110° C. for 30 min in a microwave reactor. The solution was concentrated, and the residue dissolved in ammonia (7 M in MeOH) (2 mL, 14.0 mmol) and heated to 110° C. in a microwave reactor. This cycle (concentration, addition of ammonia and heating) was repeated until all starting material was converted to product (6 times). The reaction mixture was cooled to r.t., concentrated in vacuo and purified by preparative chromatography to give the title compound (8 mg, 21% yield): $^1$H NMR (400 MHz, DMSO-d$_6$) δ ppm 1.19-1.38 (m, 4 H) 1.42-1.59 (m, 3 H) 1.84-1.92 (m, 1 H) 1.98 (m, 1 H) 2.20 (s, 3 H) 2.76-2.94 (m, 2 H) 6.55-6.62 (m, 3 H) 7.22 (m, 1 H) 7.34 (m, 1 H); MS (APCI+) 416 [M+H]$^+$.

Example 125

3-{(1r,4r)-4''-Amino-5''-methyl-4-[($^2$H$_3$)methyloxy]-3'H-dispiro[cyclohexane-1,2'-indene-1',2''-imidazol]-6'-yl}-5-chlorobenzonitrile

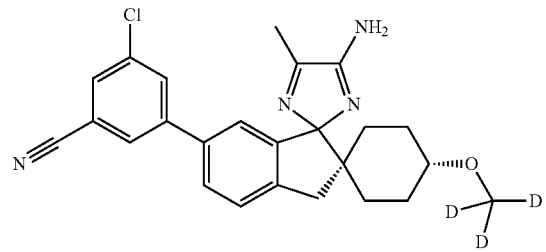

The title compound (40 mg, 35% yield) was prepared using the procedure described for Example 118 starting from (1r,4r)-6'-bromo-5"-methyl-4-[($^2$H$_3$)methyloxy]-3'H-dispiro[cyclohexane-1,2'-indene-1',2"-imidazol]-4"-amine (Example 117, 0.100 g, 0.26 mmol) and 3-chloro-5-(4,4,5,5-tetramethyl-1,3,2-dioxaborolan-2-yl)benzonitrile (Intermediate 35, 0.114 g, 0.29 mmol): $^1$H NMR (500 MHz, DMSO-d$_6$) δ 0.91-1.04 (m, 1 H), 1.11-1.30 (m, 2 H), 1.35-1.51 (m, 3 H), 1.82 (d, 2 H), 2.18 (s, 3 H), 2.90-2.96 (m, 1 H), 2.96-3.12 (m, 2 H), 6.54 (br. s., 2 H), 6.89 (s, 1 H), 7.41 (d, 1 H), 7.58 (dd, 1 H), 7.95 (d, 2 H), 8.01 (s, 1 H). MS (APCI+) m/z 436 [M+H]$^+$.

Example 126

(1r,4r)-6'-(Cyclobutylmethoxy)-4-methoxy-5"-methyl-3'H-dispiro[cyclohexane-1,2'-indene-1',2"-imidazol]-4"-amine Step 1: N-((1r,40-5'-(cyclobutylmethoxy)-4-methoxyspiro[cyclohexane-1,2'-indene]-3'(1'H)-ylidene)-2-methylpropane-2-sulfinamide

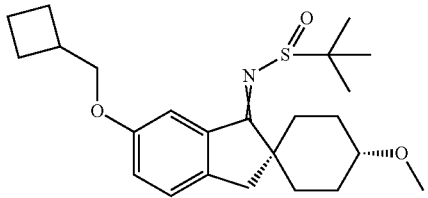 [SMILES: CO[C@H]1CC[C@]2(CC1)Cc1ccc(OCC3CCC3)cc1C2=NS(=O)C(C)(C)C]

(1r,4r)-6'-(Cyclobutylmethoxy)-4-methoxyspiro[cyclohexane-1,2'-inden]-1'(3'H)-one (Intermediate 46, 1.48 g, 4.71 mmol) and 2-methylpropane-2-sulfinamide (1.027 g, 8.47 mmol) were dissolved in 2-Me THF (17 mL) and titanium (IV) ethoxide (1.97 mL, 9.41 mmol) was added. The resulting mixture was heated to reflux overnight. 2-Methylpropane-2-sulfinamide (0.560 g, 4.62 mmol) was added and the reaction was refluxed for 6 h. Additional 2-methylpropane-2-sulfinamide (0.560 g, 4.62 mmol) and titanium(IV) ethoxide (1 mL, 4.79 mmol) were added and the mixture was refluxed overnight. Additional 2-methylpropane-2-sulfinamide (0.560 g, 4.62 mmol) and titanium(IV) ethoxide (1 mL, 4.79 mmol) were added and the mixture was refluxed overnight by the time the reaction had reached 80% conversion. EtOAc (10 mL) and sat aq. NaHCO$_3$ (2 mL) were added under stirring. The mixture was left to stand still for 1 h. The organic phase was collected by filtration through diatomaceous earth, dried over MgSO$_4$ and concentrated. The crude product was purified on a silica gel column (gradient elution 0-100% EtOAc in n-heptane) to give the title compound (1.12 g, 57% yield) containing 30% of the (1s,4s)-isomer. It was used as such in the next step: $^1$H NMR (500 MHz, DMSO-d$_6$) δ ppm 1.26 (m, 11 H), 1.50 (m, 3 H), 1.87 (m, 5 H), 2.06 (m, 4 H), 2.73 (m, 1 H), 2.96 (m, 2 H), 3.17 (m, 1 H), 3.26 (s, 3 H), 3.95 (d, 2 H), 7.22 (m, 1 H), 7.40 (m, 1 H), 7.83 (m, 1 H); MS (ES+) m/z 418.2 [M+H]$^+$.

Step 2: (1r,4r)-6'-(Cyclobutylmethoxy)-4-methoxyspiro[cyclohexane-1,2'-inden]-1'(3'H)-imine

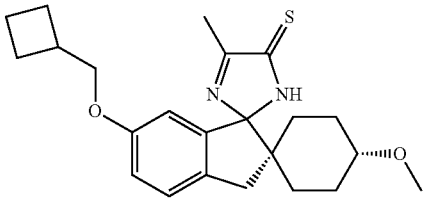

HCl (4 M in 1,4-dioxane) (6.70 mL, 26.8 mmol) was added to a solution of N-((1r,4r)-5'-(cyclobutylmethoxy)-4-methoxyspiro[cyclohexane-1,2'-indene]-3'(1'H)-ylidene)-2-methylpropane-2-sulfinamide (Example 126 Step 1, 1.12 g, 2.68 mmol) in anhydrous 1,4-dioxane (8 mL). The reaction mixture was stirred under a nitrogen atmosphere at r.t. for 90 min. DCM (20 mL) and sat aq. NaHCO$_3$ (15 mL) were added to the reaction mixture. The phases were separated and the organic layer concentrated to give the title compound (0.840 g, quantitative yield), that was used directly in next step: MS (ES+) m/z 314.15 [M+H]$^+$.

Step 3: (1r,4r)-6'-(Cyclobutylmethoxy)-4-methoxy-5"-methyl-3'H-dispiro[cyclohexane-1,2'-indene-1',2"-imidazole]-4"(3"H)-thione (1r,4r)-6'-(Cyclobutylmethoxy)-4-methoxyspiro[cyclohexane-1,2'-inden]-1'(3'H)-imine (Example 126 Step 2, 0.84 g, 2.68 mmol) and 2-oxopropanethioamide (Intermediate 2, 0.829 g, 8.04 mmol) were dissolved in dry MeOH (12 mL) and the resulting orange solution was heated at 60° C. under N$_2$ (g) overnight. Additional 2-oxopropanethioamide (Intermediate 2, 0.829 g, 8.04 mmol) was added to the reaction mixture and it was heated to 60° C. for 6 h, but there was no desired product in the mixture. The reaction mixture was concentrated and the solvent was changed to 2-propanol (12 mL) and trimethyl orthoformate (0.880 mL, 8.04 mmol) was added. The reaction mixture was heated to 80° C. for approximately 2 days (20% conversion). The mixture was concentrated. The residue was dissolved in EtOAc and then washed with water. The organic phase was concentrated and the residue was purified on a silica gel column (0-100% EtOAc in n-heptane) to give the title compound (0.140 g, 13% yield). The product contained 15% of the (1s,4s)-isomer and was used as such in the next step: $^1$H NMR (500 MHz, DMSO-d$_6$) δ ppm 1.09 (m, 1 H) 1.24 (m, 3 H) 1.49 (m, 2 H) 1.85 (m, 6 H) 2.03 (m, 2 H) 2.26 (s, 3 H) 2.64 (dt, 1 H) 2.97 (m, 3 H) 3.20

(s, 3 H) 3.85 (m, 2 H) 6.30 (d, 1 H) 6.87 (dd, 1 H) 7.23 (d, 1 H) 12.29 (s, 1 H); MS (ES+) m/z 399.1 [M+H]⁺.

Step 4: (1r,4r)-6'-(Cyclobutylmethoxy)-4-methoxy-5"-methyl-3'H-dispiro[cyclohexane-1,2'-indene-1', 2"-imidazol]-4"-amine

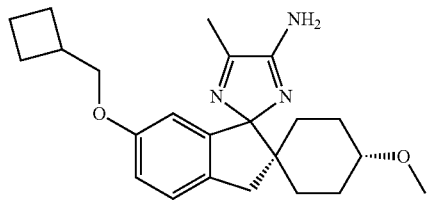

(1r,4r)-6'-(Cyclobutylmethoxy)-4-methoxy-5"-methyl-3'H-dispiro[cyclohexane-1,2'-indene-1',2"-imidazole]-4" (3"H)-thione (Example 126 Step 3, 140 mg, 0.35 mmol) and ammonia (7 M in MeOH) (1.5 mL, 10.5 mmol) was microwaved for 40 min. at 100° C. The mixture was concentrated and then re-dissolved in ammonia (7 M in MeOH) (1.5 mL, 10.5 mmol). The mixture was microwaved for 40 min. at 110° C. This procedure (concentration, dissolution in ammonia and heating) was repeated 4 times. The crude product was purified on a silica gel column (4 g $SiO_2$, gradient elution of 0-100% (7 M $NH_3$ in MeOH/DCM 1:9) in DCM) followed by preparative chromatography to give the title compound (44.0 mg, 28% yield): ¹H NMR (500 MHz, DMSO-$d_6$) δ ppm 0.90 (t, 1 H) 1.17 (m, 2 H) 1.41 (m, 3 H) 1.82 (m, 9 H) 2.01 (m, 2 H) 2.14 (s, 3 H) 2.62 (m, 1 H) 2.90 (m, 3 H) 3.18 (s, 3 H) 3.78 (m, 2 H) 6.05 (s, 1 H) 6.46 (br. s, 2 H) 6.70 (d, 1 H) 7.14 (d, 1 H); MS (APCI+) m/z 382.2 [M+H]⁺.

Example 127

5-[(1r,4r)-4"-Amino-4-methoxy-5"-methyl-3'H-dispiro[cyclohexane-1,2'-indene-1',2"-imidazol]-6'-yl]-2-fluoro-3-(methoxymethyl)benzonitrile

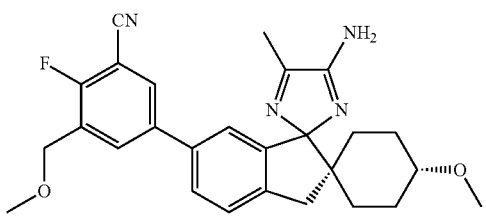

(1r,4r)-6'-Bromo-4-methoxy-5"-methyl-3'H-dispiro[cyclohexane-1,2'-indene-1',2"-imidazol]-4"-amine (Example 19 Method B Step 4, 328 mg, 0.87 mmol) was dissolved in 2-Me THF (5 mL). 2-Fluoro-3-(methoxymethyl)-5-(4,4,5,5-tetramethyl-1,3,2-dioxaborolan-2-yl)benzonitrile (Intermediate 86, 254 mg, 0.87 mmol) was added to the above solution followed by $K_2CO_3$ (2.0 M aq.) (1.3 mL, 2.61 mmol). Sodium tetrachloropalladate(II) (35.9 mg, 0.12 mmol) and 3-(di-tert-butylphosphonium)propane sulfonate (65.5 mg, 0.24 mmol) were added, the MW-vial was closed and heated in the microwave reactor for 30 min at 100° C. The mixture was transferred to a separation funnel, and water and 2-Me THF was added. The water phase was eliminated. The organic phase was washed once with brine and water. The organic phase was concentrated in vacuo and the product was purified by preparative chromatography to give (23 mg, 5% yield) of the title compound: ¹H NMR (500 MHz, CDCl₃) δ ppm 1.12 (td, 1 H), 1.31-1.45 (m, 2 H), 1.45-1.56 (m, 1 H), 1.71 (t, 2 H), 1.98 (d, 2 H), 2.36 (s, 3 H), 3.04-3.15 (m, 1 H), 3.22 (q, 2 H), 3.35 (s, 3 H), 3.45 (s, 3 H), 4.56 (s, 2 H), 6.89 (s, 1 H), 7.36-7.45 (m, 2 H), 7.65 (d, 1 H), 7.81 (d, 1 H); (ES+) m/z 461 [M+H]⁺.

Example 128

6'-Bromo-4-(difluoromethyl)-5"-methyl-3'H-dispiro[cyclohexane-1,2'-indene-1',2"-imidazol]-4"-amine Step 1: N-(5'-Bromo-4-(difluoromethyl)spiro[cyclohexane-1,2'-indene]-3'(1'H)-ylidene)-2-methylpropane-2-sulfinamide

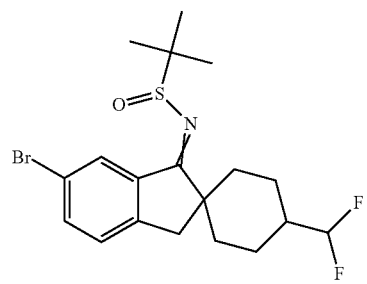 [SMILES: CC(C)(C)S(=O)N=C1c2cc(Br)ccc2CC12CCC(C(F)F)CC2]

Titanium ethoxide (0.893 mL, 4.33 mmol), 2-methylpropane-2-sulfinamide (0.315 g, 2.60 mmol) and 6'-bromo-4-(difluoromethyl)spiro[cyclohexane-1,2'-inden]-1'(3'H)-one (Intermediate 91, 0.713 g, 2.17 mmol) were dissolved in 2-Me THF (5 mL) and heated to 90° C. overnight. 2-Methylpropane-2-sulfinamide (0.315 g, 2.60 mmol) and titanium ethoxide (0.893 mL, 4.33 mmol) were added and the reaction was refluxed for 7 h. Another portion of reagents was added and the mixture was refluxed overnight. The reaction was allowed to attain r.t. EtOAc (50 mL) was added followed by dropwise addition of NaHCO₃ (10 mL). The mixture was stirred at r.t. for 2 h. The crude product was purified using flash chromatography (40 g $SiO_2$, 0-40% EtOAc in heptane) to give the title compound (564 mg, 60% yield): MS (ES+) m/z 432 [M+H]⁺.

Step 2: 6'-Bromo-4-(difluoromethyl)spiro[cyclohexane-1,2'-inden]-1'(3'H)-imine

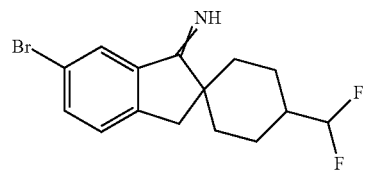 [SMILES: N=C1c2cc(Br)ccc2CC12CCC(C(F)F)CC2]

HCl (4 M in 1,4-dioxane) (3.26 mL, 13.0 mmol) was added to a suspension of N-(5'-bromo-4-(difluoromethyl)spiro[cyclohexane-1,2'-indene]-3'(1'H)-ylidene)-2-methylpropane-2-sulfinamide (Example 128 Step 1, 0.564 g, 1.30 mmol) in 1,4-dioxane (5 mL) and the resulting mixture was stirred under a nitrogen atmosphere at r.t. overnight. The formed precipitate was filtered off and washed with Et₂O. The solid was then dissolved in DCM and sat. aq. NaHCO$_3$. The mixture was poured into a phase separator, the organic layer was collected and concentrated to yield the title compound that was used as such in the next step: MS (CI) m/z 328 [M+H]$^+$.

Step 3: 6'-Bromo-4-(difluoromethyl)-5''-methyl-3'H-dispiro[cyclohexane-1,2'-indene-1',2''-imidazole]-4''(3''H)-thione

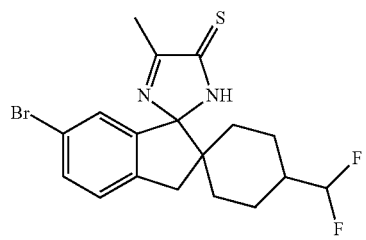 [SMILES: CC1=NC2(NC1=S)c1cc(Br)ccc1CC21CCC(C(F)F)CC1]

6'-Bromo-4-(difluoromethyl)spiro[cyclohexane-1,2'-inden]-1'(3'H)-imine (Example 128 Step 2, 0.310 g, 0.94 mmol), trimethyl orthoformate (0.209 mL, 1.89 mmol) and 2-propanol (4 mL) was heated to 80° C. 2-Oxopropanethioamide (Intermediate 2, 0.244 g, 2.36 mmol) in 2-propanol (1 mL) was added and the mixture was heated for 3.5 h. The mixture was concentrated and then MeOH was added. The reaction was left standing in a refrigerator over a weekend. The solvent was evaporated and the crude product was purified using flash chromatography (40 g SiO$_2$, 0-100% EtOAc in heptane) to give the title compound (300 mg, 77% yield): MS (ES+) m/z 413 [M+H]$^+$.

Step 4: 6'-Bromo-4-(difluoromethyl)-5''-methyl-3'H-dispiro[cyclohexane-1,2'-indene-1',2''-imidazol]-4''-amine

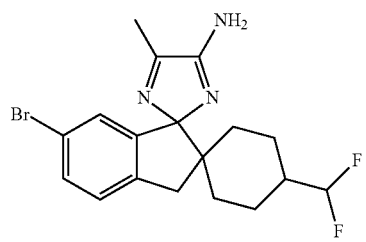 [SMILES: CC1=NC2(N=C1N)c1cc(Br)ccc1CC21CCC(C(F)F)CC1]

6'-Bromo-4-(difluoromethyl)-5''-methyl-3'H-dispiro[cyclohexane-1,2'-indene-1',2''-imidazole]-4''(3''H)-thione (Example 128 Step 3, 0.3 g, 0.73 mmol) was taken up in ammonia (7 M in MeOH) (6.22 mL, 43.6 mmol) and the resulting mixture was heated in the microwave reactor at 110° C. for 30 min. The solvent was evaporated. The same amount of ammonia was added and the mixture was heated and concentrated (5 times). The crude material was dissolved in EtOAc. Aq. citric acid solution (0.1 M) was added and the phases were separated. The citric acid phase was basified with 1 M NaOH and extracted with DCM twice. The combined DCM extracts were concentrated to give the title compound (0.120 g, 42% yield). 20 mg of the product was purified by preparative chromatography to give 11 mg of the title compound: $^1$H NMR (500 MHz, DMSO-d$_6$) δ ppm 1.19-1.31 (m, 3 H), 1.34-1.48 (m, 3 H), 1.66-1.82 (m, 2 H), 1.90 (d, 1 H), 2.20 (s, 3 H), 2.80-2.95 (m, 2 H), 5.53-5.97 (m, 1 H), 6.53 (s, 2 H), 6.59 (s, 1 H), 7.21 (d, 1 H), 7.33 (d, 1 H); MS (ES+) m/z 396 [M+H]$^+$.

Example 129

6'-(5-Chloropyridin-3-yl)-4-(difluoromethyl)-5''-methyl-3'H-dispiro[cyclohexane-1,2'-indene-1',2''-imidazol]-4''-amine

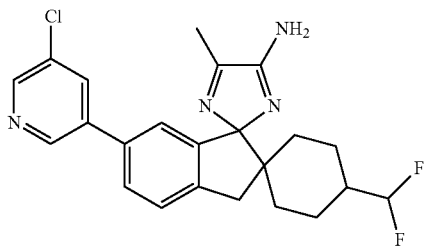 [SMILES: CC1=NC2(N=C1N)c1cc(-c3cncc(Cl)c3)ccc1CC21CCC(C(F)F)CC1]

6'-Bromo-4-(difluoromethyl)-5''-methyl-3'H-dispiro[cyclohexane-1,2'-indene-1',2''-imidazol]-4''-amine (Example 128, 0.1 g, 0.25 mmol), 5-chloropyridin-3-yl boronic acid (0.048 g, 0.30 mmol), 3-(di-tert-butylphosphonium)propane sulfonate (6.77 mg, 0.03 mmol), sodium tetrachloro-palladate(II) (3.71 mg, 0.01 mmol), 2-Me THF (2 mL) and aq. K$_2$CO$_3$ (2.0 M, 0.379 mL, 0.76 mmol) were added to a microwave vial. The vial was sealed and evacuated and refilled with Ar (g) and then heated in the microwave reactor for 30 min at 100° C. The same amount of Pd-catalyst, ligand and boronic ester were added and the vial was sealed and evacuated and refilled with Ar (g). The vial was heated in the microwave reactor for 30 min at 100° C. EtOAc and water were added and the organic phase was extracted, dried through a phase separator and evaporated to dryness. The crude product was purified using preparative chromatography to give the title compound (12 mg, 11% yield): $^1$H NMR (500 MHz, CD$_3$CN) δ ppm 1.24-1.41 (m, 4 H), 1.45-1.54 (m, 3 H), 1.71-1.86 (m, 1 H), 2.00 (dt, 1 H), 2.24 (s, 3 H), 2.98 (d, 1 H), 3.07 (d, 1 H), 5.32 (br. s., 2 H), 5.64 (d, 1 H), 6.86 (d, 1 H), 7.38 (d, 1 H), 7.50 (dd, 1 H), 7.93 (t, 1 H), 8.49 (d, 1 H), 8.65 (d, 1 H); MS (MM−ES+APCI)+ m/z 429 [M+H]$^+$.

Example 130

(1r,4r)-6'-Bromo-4-ethoxy-5''-methyl-3'H-dispiro[cyclohexane-1,2'-indene-1',2''-imidazol]-4''-amine Step 1: N-[(1r,1'E,4r)-6'-Bromo-4-ethoxyspiro[cyclohexane-1,2'-inden]-1'(3'H)-ylidene]-2-methylpropane-2-sulfinamide

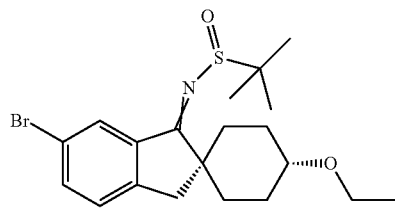 [SMILES: CCO[C@H]1CC[C@]2(CC1)Cc1ccc(Br)cc1C2=NS(=O)C(C)(C)C]

6'-Bromo-4-ethoxyspiro[cyclohexane-1,2'-inden]-1'(3'H)-one (Intermediate 80, 3.7 g, 11.4 mmol, as a 2:1 mixture of isomers), 2-methylpropane-2-sulfinamide (2.77 g, 22.9 mmol) and titanium ethoxide (8.26 mL, 40.1 mmol) were dissolved in 2-Me THF (30 mL) and heated to reflux for 48 h. The reaction was left to cool down. EtOAc (100 mL) and NaHCO$_3$ (aq. Sat, 30 mL) were added under stirring. The mixture was allowed to stand still for 1 h. The organic phase was collected by filtration, dried over MgSO$_4$ and concentrated. Flash chromatography (twice) using 0-20% EtOAc in n-heptane gave the title compound (1.48 g, 30% yield): $^1$H NMR (500 MHz, DMSO-d$_6$) δ ppm 1.10 (t, 3 H) 1.24 (s, 9 H) 1.30 (m, 2 H) 1.44-1.57 (m, 2 H) 1.66 (br. s, 2 H) 1.99 (d, 2 H) 3.01 (s, 2 H) 3.23-3.32 (m, 1 H) 3.48 (q, 2 H) 7.48 (d, 1 H) 7.78 (d, 1 H) 8.53 (br. s, 1 H); MS (ES+) m/z 426 [M+H]$^+$.

Step 2: (1r,4r)-6'-Bromo-4-ethoxyspiro[cyclohexane-1,2'-inden]-1'(3'H)-imine

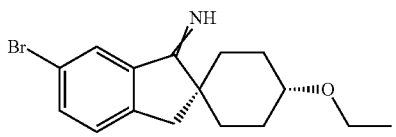 [SMILES: CCO[C@H]1CC[C@]2(CC1)Cc1ccc(Br)cc1C2=N]

HCl (4 M in 1,4-dioxane) (12.7 mL, 50.9 mmol) was added to a solution of N-((1r,40-5'-bromo-4-methoxyspiro[cyclohexane-1,2'-indene]-3'(1'H)-ylidene)-2-methylpropane-2-sulfinamide (Example 130 Step 1, 2.17 g, 5.09 mmol) in anhydrous 1,4-dioxane (25 mL) and the resulting mixture was stirred under a nitrogen atmosphere at rt for 90 min. A white precipitate formed. Et$_2$O (30 mL) was added and the solid was filtered off and washed with Et$_2$O (10 mL). The solid was partitioned between DCM (20 mL) and sat. aq. NaHCO$_3$ (20 mL). The phases were separated and the organic layer dried over Na$_2$SO$_4$ and concentrated. The crude product (1.2 g, 73% yield) was used directly in the next step: MS (EI) m/z 322 M$^+$.

Step 3: (1r,4r)-6'-Bromo-4-ethoxy-5''-methyl-3'H-dispiro[cyclohexane-1,2'-indene-1',2''-imidazole]-4''(3''H)-thione

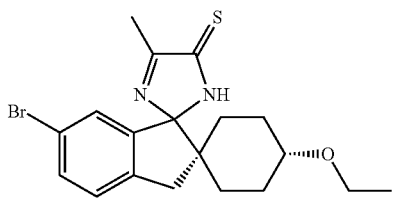

(1r,4r)-6'-Bromo-4-ethoxyspiro[cyclohexane-1,2'-inden]-1'(3'H)-imine (Example 130 Step 2, 1.2 g, 3.72 mmol) and 2-oxobutanethioamide (Intermediate 2, 1.15 g, 11.2 mmol) were dissolved in MeOH (80 mL) and was heated at 60° C. overnight. The reaction was concentrated and the obtained product was used as such in the next step: MS (ES+) m/z 407 [M+H]$^+$.

Step 4: (1r,4r)-6'-Bromo-4-ethoxy-5''-methyl-3'H-dispiro[cyclohexane-1,2'-indene-1',2''-s imidazol]-4''-amine

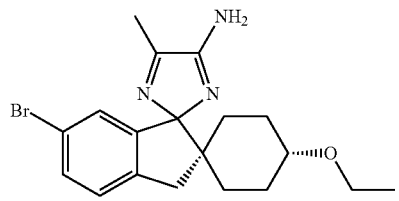

(1r,4r)-6'-Bromo-4-ethoxy-5''-methyl-3'H-dispiro[cyclohexane-1,2'-indene-1',2''-imidazole]-4''(3''H)-thione (Example 130 Step 3) was dissolved in ammonia (7 M in MeOH) (18 mL, 126 mmol) and placed in a microwave vial. The vial was sealed and the reaction was heated at 120° C. for 30 min in a microwave reactor. The mixture was concentrated and the residue was dissolved in ammonia (7 M in MeOH) (18 mL, 126 mmol) and heated once more at 120° C. for 30 min in a microwave reactor. This procedure (concentration, addition of ammonia and heating) was repeated 3 more times. After evaporation of the solvent was the residue subjected to flash chromatography using 0-7% of MeOH(containing NH$_3$) in DCM as eluent followed by purification by preparative chromatography to give the title compound (600 mg, 41% yield over two steps): $^1$H NMR (500 MHz, DMSO-d$_6$) δ ppm 0.87-0.98 (m, 1 H), 1.06 (t, 3 H), 1.11-1.32 (m, 2 H), 1.35-1.48 (m, 3 H), 1.78 (dt, 2 H), 2.16 (s, 3 H), 2.90 (d, 1 H), 2.97-3.08 (m, 2 H), 3.39 (q, 2 H), 6.58 (br. s, 2 H), 6.64 (d, 1 H), 7.25 (d, 1 H), 7.34 (dd, 1 H); MS (ES+) m/z 390 [M+H]$^+$.

Example 131

(1r,4r)-4-ethoxy-5''-methyl-6'-[5-(trifluoromethyl)pyridin-3-yl]-3'H-dispiro[cyclohexane-1,2'-indene-1',2''-imidazol]-4''-amine

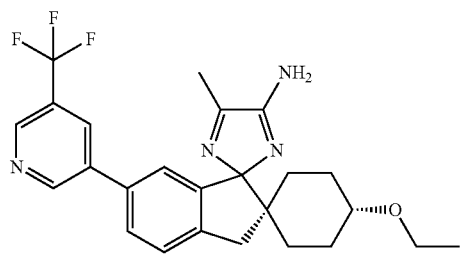

(1r,4r)-6'-Bromo-4-ethoxy-5''-methyl-3'H-dispiro[cyclohexane-1,2'-indene-1',2''-imidazol]-4''-amine (Example 130, 100 mg, 0.26 mmol) was dissolved in 2-Me THF (5 mL) and 5-(trifluoro-methyl)pyridin-3-ylboronic acid (73.4 mg, 0.38 mmol) was added to the above solution followed by K$_2$CO$_3$ (2.0M aq, 0.384 mL, 0.77 mmol). Then, sodium tetrachloropalladate(II) (10.5 mg, 0.04 mmol) and 3-(di-tert-butylphosphonium)propane sulfonate (19 mg, 0.07 mmol) were added, the system closed (MW vial) and run in the microwave reactor for 30 min at 100° C. The reaction mixture was cooled to r.t., diluted with EtOAc, and washed with brine. The organic layer was collected, dried over MgSO₄, filtered, and concentrated in vacuo. The residue was purified by preparative chromatography, providing 25 mg (21% yield) of the title compound: $^1$H NMR (500 MHz, DMSO-d₆) δ ppm 0.97 (td, 1 H), 1.07 (t, 3 H), 1.14-1.34 (m, 2 H), 1.37-1.51 (m, 3 H), 1.81 (dt, 2 H), 2.17 (s, 3 H), 2.96-3.18 (m, 3 H), 3.41 (q, 2 H), 6.55 (br. s, 2 H), 6.93 (d, 1 H), 7.45 (d, 1 H), 7.63 (dd, 1 H), 8.28 (s, 1 H), 8.91 (s, 1 H), 9.05 (d, 1 H); MS (ES+) m/z 457 [M+H]⁺.

Example 132

3-[(1r,4r)-4"-amino-4-ethoxy-5"-methyl-3'H-dispiro[cyclohexane-1,2'-indene-1',2"-imidazol]-6'-yl]-5-fluorobenzonitrile

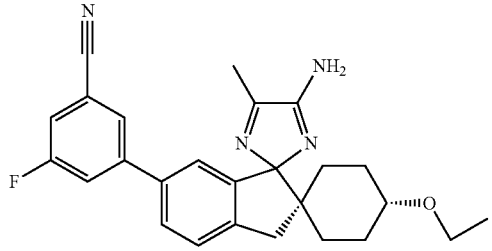

The title compound (9 mg, 9% yield) was prepared using the method described in Example 131 starting from (1r,4r)-6'-Bromo-4-ethoxy-5"-methyl-3'H-dispiro[cyclohexane-1,2'-indene-1',2"-imidazol]-4"-amine (Example 130, 0.86 mg, 0.22 mmol) and 3-cyano-5-fluorophenylboronic acid (44 mg, 0.26 mmol): $^1$H NMR (500 MHz, DMSO-d₆) δ ppm 0.91 (m, 1 H), 1.00 (t, 3 H), 1.06-1.27 (m, 2 H), 1.27-1.43 (m, 3 H), 1.67-1.82 (m, 2 H), 2.11 (s, 3 H), 2.88-3.07 (m, 3 H), 3.34 (q, 2 H), 6.46 (s, 2 H), 6.83 (s, 1 H), 7.34 (d, 1 H), 7.52 (dd, 1 H), 7.65-7.80 (m, 2 H), 7.84 (s, 1 H); MS (ES+) m/z 431 [M+H]⁺.

Example 133

(1r,4r)-6'-(5-chloropyridin-3-yl)-4-ethoxy-5"-methyl-3'H-dispiro[cyclohexane-1,2'-indene-1',2"-imidazol]-4"-amine

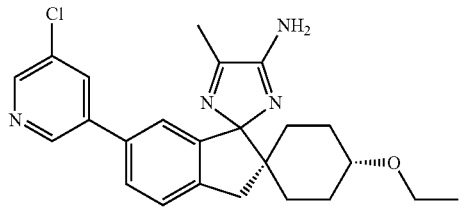

The title compound (34 mg, 36% yield) was prepared using the method described in Example 26a starting from (1r,4r)-6'-bromo-4-ethoxy-5"-methyl-3'H-dispiro[cyclohexane-1,2'-indene-1',2"-imidazol]-4"-amine (Example 130, 88 mg, 0.23 mmol) and 5-chloropyridin-3-ylboronic acid (53.2 mg, 0.34 mmol), with the exception that the reaction time was 30 min and that the product was purified by preparative chromatography: $^1$H NMR (500 MHz, DMSO-d₆) δ ppm 0.97 (td, 1 H), 1.06 (t, 3 H), 1.13-1.32 (m, 2 H), 1.35-1.49 (m, 3 H), 1.74-1.86 (m, 2 H), 2.17 (s, 3 H), 2.96-3.14 (m, 3 H), 3.40 (q, 2 H), 6.53 (br. s, 2 H), 6.87 (d, 1 H), 7.42 (d, 1 H), 7.57 (dd, 1 H), 8.08 (t, 1 H), 8.56 (d, 1 H), 8.70 (d, 1 H); MS (ES+) m/z 423 [M+H]⁺.

Example 134

3-[(1r,4r)-4"-Amino-4-ethoxy-5"-methyl-3'H-dispiro[cyclohexane-1,2'-indene-1',2"-imidazol]-6'-yl]-5-(difluoromethyl)benzonitrile

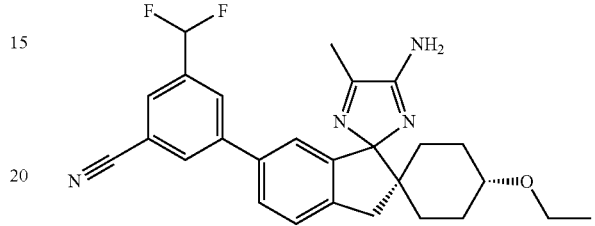

The title compound (50 mg, 48% yield) was prepared using the method described in Example 26a starting from (1r,4r)-6'-bromo-4-ethoxy-5"-methyl-3'H-dispiro[cyclohexane-1,2'-indene-1',2"-imidazol]-4"-amine (Example 130, 88 mg, 0.23 mmol) and 3-(difluoromethyl)-5-(4,4,5,5-tetramethyl-1,3,2-dioxaborolan-2-yl)benzonitrile (Intermediate 56, 88 mg, 0.23 mmol), with the exception that the reaction was heated for 30 min and that the product was purified by preparative chromatography: $^1$H NMR (500 MHz, DMSO-d₆) δ ppm 0.96 (m, 1 H), 1.07 (t, 3 H), 1.14-1.33 (m, 2 H), 1.40-1.50 (m, 3 H), 1.80 (m, 2 H), 2.17 (s, 3 H), 2.96-3.14 (m, 3 H), 3.41 (q, 2 H), 6.55 (br. s, 2 H), 6.90 (s, 1 H), 7.13 (t, 1 H), 7.43 (d, 1 H), 7.60 (dd, 1 H), 8.01 (d, 2 H), 8.22 (s, 1 H); MS (ES+) m/z 463 [M+H]⁺.

Example 135

(1r,4r)-4-Ethoxy-5"-methyl-6'-[5-(prop-1-yn-1-yl)pyridin-3-yl]-3'H-dispiro[cyclohexane-1,2'-indene-1',2"-imidazol]-4"-amine

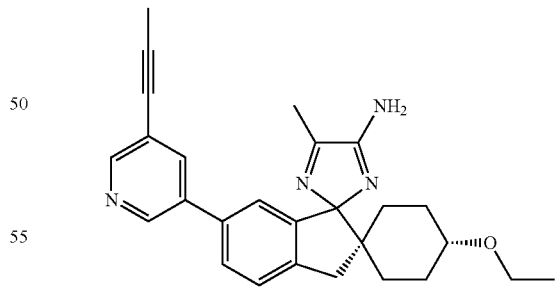

The title compound (50 mg, 40% yield) was prepared as described for Example 26a starting from (1r,4r)-6'-bromo-4-ethoxy-5"-methyl-3'H-dispiro[cyclohexane-1,2'-indene-1',2"-imidazol]-4"-amine (Example 130, 113 mg, 0.29 mmol) and 5-(prop-1-ynyl)pyridin-3-ylboronic acid (Intermediate 15, 56 mg, 0.35 mmol), with the exception that the reaction was heated for 30 min and the product purified by preparative chromatography: $^1$H NMR (500 MHz, DMSO-d₆) δ ppm 0.97 (td, 1 H), 1.06 (t, 3 H), 1.13-1.33 (m, 2 H), 1.35-1.51 (m, 3 H), 1.80 (dd, 2 H), 2.09 (s, 3H), 2.17 (s, 3 H), 2.94-3.13 (m, 3 H), 3.41 (q, 2 H), 6.53 (br. s., 2 H), 6.83 (s, 1 H), 7.40 (d, 1 H), 7.54 (dd, 1 H), 7.90 (s, 1 H), 8.51 (d, 1 H), 8.67 (d, 1 H); MS (ES+) m/z 427 [M+H]+.

Biological Assays

The level of activity of the compounds was tested using the following methods:

TR-FRET Assay

The β-secretase enzyme used in the TR-FRET is prepared as follows:

The cDNA for the soluble part of the human β-Secretase (AA 1-AA 460) was cloned using the ASP2-Fc10-1-IRES-GFP-neoK mammalian expression vector. The gene was fused to the Fc domain of IgG1 (affinity tag) and stably cloned into HEK 293 cells. Purified sBACE-Fc was stored in −80° C. in Tris buffer, pH 9.2 and had a purity of 40%.

The enzyme (truncated form) was diluted to 6 μg/mL (stock 1.3 mg/mL) and the substrate (Europium) CEVNLDAEFK(Qsy7) to 200 nM (stock 120 μM) in reaction buffer (NaAcetate, chaps, triton x-100, EDTA pH4.5). The robotic systems Biomek FX and Velocity 11 were used for all liquid handling and the enzyme and substrate solutions were kept on ice until they were placed in the robotic system. Enzyme (9 μl) was added to the plate then 1 μl of compound in dimethylsulphoxide was added, mixed and pre-incubated for 10 minutes. Substrate (10 μl) was then added, mixed and the reaction proceeded for 15 minutes at r.t. The reaction was stopped with the addition of Stop solution (7 μl, NaAcetate, pH 9). The fluorescence of the product was measured on a Victor II plate reader with an excitation wavelength of 340 nm and an emission wavelength of 615 nm. The assay was performed in a Costar 384 well round bottom, low volume, non-binding surface plate (Corning #3676). The final concentration of the enzyme was 2.7 μg/ml; the final concentration of substrate was 100 nM (Km of ~250 nM). The dimethylsulphoxide control, instead of test compound, defined the 100% activity level and 0% activity was defined by wells lacking enzyme (replaced with reaction buffer). A control inhibitor was also used in dose response assays and had an IC50 of ~150 nM.

Diluted TR-FRET Assay

Compounds with a high affinity were further tested in a diluted TR-FRET assay, conditions as described above for the TR-FRET assay, but with 50 times less enzyme and a 6.5 h long reaction time at r.t. in the dark.

sAP1V Release Assay

SH-SY5Y cells were cultured in DMEM/F-12 with Glutamax, 10% FCS and 1% non-essential amino acids and cryopreserved and stored at −140° C. at a concentration of 7.5-9.5×10$^6$ cells per vial. Thaw cells and seed at a conc. of around 10000 cells/well in DMEM/F-12 with Glutamax, 10% FCS and 1% non-essential amino acids to a 384-well tissue culture treated plate, 1004, cell susp/well. The cell plates were then incubated for 7-24 h at 37° C., 5% $CO_2$. The cell medium was removed, followed by addition of 30 L compound diluted in DMEM/F-12 with Glutamax, 10% FCS, 1% non-essential amino acids and 1% PeSt to a final conc. of 1% DMSO. The compounds were incubated with the cells for 17 h (overnight) at 37° C., 5% $CO_2$. Meso Scale Discovery (MSD) plates were used for the detection of sAPPβ release. MSD sAPPβ plates were blocked in 1% BSA in Tris wash buffer (40 μL/well) for 1 h on shake at r.t. and washed 1 time in Tris wash buffer (40 μL/well). 20 μL of medium was transferred to the pre-blocked and washed MSD sAPPβ microplates, and the cell plates were further used in an ATP assay to measure cytotoxicity. The MSD plates were incubated with shaking at r.t. for 2 h and the media discarded. 10 μL detection antibody was added (1 nM) per well followed by incubation with shaking at r.t. for 2 h and then discarded. 40 μL Read Buffer was added per well and the plates were read in a SECTOR Imager.

ATP assay

As indicated in the sAPPβ release assay, after transferring 20 μL medium from the cell plates for sAPPβ detection, the plates were used to analyse cytotoxicity using the ViaLight™ Plus cell proliferation/cytotoxicity kit from Cambrex Bio-Science that measures total cellular ATP. The assay was performed according to the manufacture's protocol. Briefly, 10 μL cell lysis reagent was added per well. The plates were incubated at r.t. for 10 min. Two min after addition of 25 μL reconstituted ViaLight™ Plus ATP reagent, the luminescence was measured in a Wallac Victor2 1420 multilabel counter. Tox threshold is a signal below 75% of the control.

Results

Typical $IC_{50}$ values for the compounds of the present invention are in the range of about 0.1 to about 100,000 nM. Biological data on exemplified final compounds is given below in Table 2.

TABLE 2

| Example | $IC_{50}$ in TR-FRET assay (nM) | $IC_{50}$ in sAPPβ release assay (nM) | Example | $IC_{50}$ in TR-FRET assay (nM) | $IC_{50}$ in sAPPβ release assay (nM) |
| --- | --- | --- | --- | --- | --- |
| 1 | 157 | 587 | 2 | 743 | 941 |
| 3 | 1700 | 2880 | 4 | 3200 | — |
| 5 | 3640 | — | 6 | 4250 | — |
| 7 | 6710 | — | 8 | 16300 | — |
| 9 | 1680 | 2450 | 10 | 6850 | — |
| 11 | 1980 | — | 12 | 1800 | — |
| 13a | 1300 | 501 | 13c | 1890 | 463 |
| 13d | 112 | 239 | 13e | 22$^a$ | 106 |
| 13f | 6460 | — | 13i | 560 | 160 |
| 15 | 112 | 46 | | | |
| 19 Isomer 1 | 53$^a$ | 18 | 19 Isomer 2 | 10300 | |
| 19 Isomer 3 | 3330 | | 19 Isomer 4 | 16600 | |
| 20a | 2.2$^a$ | 0.28 | 20a Isomer 1 | 0.57$^a$ | 0.10 |
| 20a Isomer 2 | 7720 | — | 20b | 2.3$^a$ | 0.78 |
| 20c | 5.2$^a$ | 1.7 | 20d | 1.6$^a$ | 0.72 |
| 20d Isomer 1 | 0.63$^a$ | 0.26 | 20e | 2.3$^a$ | 0.67 |
| 20e Isomer 1 | 1.1$^a$ | 0.57 | 20f | 5.5$^a$ | 3.3 |
| 20g | 7.1$^a$ | 2.6 | 20h | 15$^a$ | 7.1 |
| 20g Isomer 1 | 2.5$^a$ | 1.8 | | | |
| 20h Isomer 1 | 1910 | 277 | 20h Isomer 2 | 21 | 5.0 |
| 20i | 4.8$^a$ | 4.6 | 20i Isomer 1 | 14500 | |
| 20i Isomer 2 | 2.2$^a$ | 2.3 | 20j | 47 | 91 |
| 20k | 34$^a$ | 8.6 | 20n | 17$^a$ | 3.7 |
| 20o | 28$^a$ | 9.2 | 20q | 20$^a$ | 3.8 |
| 20t | 20 | 0.56 | 20t Isomer 1 | 0.89$^a$ | 0.36 |
| 20t Isomer 2 | 8360 | — | 20u | 22 | 0.63 |
| 20v | 25 | 1.2 | | | |
| 20w | 18$^a$ | 5.7 | 20x | 121 | 29 |
| 20y | 4.9$^a$ | 1.2 | 20z | 1.4$^a$ | 5.2 |
| 20aa | 1.6$^a$ | 0.72 | 25 | 7530 | — |
| 26a | 100 | 53 | 26c | 145 | 140 |
| 27 | 1760 | 399 | 28c | 53 | 109 |
| 28d | 408 | 89 | | | |
| 28h | 7.3$^a$ | 18 | 29 | 674 | 848 |
| 30b | 5.3$^a$ | 284 | 30d | 5.2$^a$ | 97 |

TABLE 2-continued

| Example | IC$_{50}$ in TR-FRET assay (nM) | IC$_{50}$ in sAPPβ release assay (nM) | Example | IC$_{50}$ in TR-FRET assay (nM) | IC$_{50}$ in sAPPβ release assay (nM) |
|---|---|---|---|---|---|
| 30e | 1.4[a] | 2.2 | 46a | 124 | 419 |
| 46a Isomer 2 | 91 | 125 | 46b Isomer 1 | 180 | 426 |
| 46b Isomer 2 | 147 | 185 | 47 Isomer 1 | inactive | — |
| 47 Isomer 2 | 1030 | 657 | 47 Isomer 3 | inactive | — |
| 47 Isomer 4 | 65300 | — | 47 Isomer 5 | 19800 | — |
| 47 Isomer 6 | 1380 | — | 47 Isomer 7 | inactive | — |
| 47 Isomer 8 | 8100 | — | 48 Isomer 1 | 0.7[a] | 20 |
| 48 Isomer 2 | 2030 | — | 48 Isomer 3 | 7040 | — |
| 48 Isomer 4 | 803 | 689 | 48 Isomer 5 | 35700 | — |
| 48 Isomer 6 | 2570 | — | 48 Isomer 7 | 10[a] | 191 |
| 48 Isomer 8 | 14[a] | 204 | 49 Isomeric mixture 1 | 10.000 | — |
| 49 Isomeric mixture 2 | inactive | — | 50 Isomeric mixture 1 | 100 | 597 |
| 50 Isomeric mixture 2 | 5[a] | 17 | 51 | 75600 | — |
| 52 | 325 | 91 | 53 | 62 | 21 |
| 54 | 6610 | — | 55 | 284 | 118 |
| 56 | 31 | 24 | 57 Isomer 1 | 19[a] | 19 |
| 57 Isomer 2 | 27600 | — | | | |
| 58 | 523 | 219 | 59 | 2610 | — |
| 60 | 12[a] | 8.7 | 61 | 5.9[a] | 3.1 |
| 62 | 19[a] | 8.6 | 63 | 89 | 29 |
| 64 | 401 | 125 | 65 | 5.7[a] | 3.4 |
| 66 Isomer 1 | 2.9[a] | 1.6 | 66 Isomer 2 | 16300 | — |
| 67 | 2.0[a] | 0.81 | 68 Isomer 1 | 1.2[a] | 0.38 |
| 68 Isomer 2 | 9970 | — | 69 | 21[a] | 10 |
| 70 | 18[a] | 13 | 71 Isomer 1 | 7.4[a] | 5.2 |
| 71 Isomer 2 | 6720 | 763 | | | |
| 72 | 2.3[a] | 0.76 | 73 | 1.3[a] | 1.0 |
| 74 | 2.6[a] | 2.1 | 75 | 5.7[a] | 2.1 |
| 76 Isomer 1 | 3.4[a] | 1.2 | 76 Isomer 2 | 636 | — |
| 77 | 16300 | — | 78 | 101[a] | 56 |
| 79 | 188 | 171 | 80 | 22[a] | 13 |
| 81 | 23 | 20 | 82 | 66 | 36 |
| 83 | 21 | 2.9 | 84 | 2.1[a] | 0.99 |
| 85 | 3.1[a] | 0.80 | 86 | 1.5[a] | 1.1 |
| 87 | 2.2[a] | 0.93 | 88 | 2.8[a] | 4.8 |
| 89 | 3.3[a] | 1.7 | 90 | 13[a] | 14 |
| 91 | 2.2a | 0.62 | 92 Isomer 1 | 0.84[a] | 0.27 |
| 92 Isomer 2 | 5870 | — | 93 | 1.8[a] | 0.56 |
| 94 Isomer 1 | 0.7[a] | 0.17 | 94 Isomer 2 | 4950 | — |
| 95 | 5.3[a] | 3.6 | 96 | 6.1[a] | 3.5 |
| 97 Isomer 1 | 3.1[a] | 1.4 | 97 Isomer 2 | 15400 | — |
| 98 | 1.5[a] | 0.82 | 99 | 3.9[a] | 5.7 |
| 100 | 0.72[a] | 0.59 | 101 | 19.8 | 6.3 |
| 102 | 3.3[a] | 2.5 | 103 | 34 | 14 |
| 104 | 64 | 34 | 105 | 22 | 9.7 |
| 106 | 1.0[a] | 1.1 | 107 | 21 | 7.9 |
| 108 | 1.3[a] | 1.8 | 109 | 21 | 28 |
| 110 | 24 | 4.0 | 111 | 51 | 31 |
| 112 | 22 | 2.0 | 113 | 24 | 1.6 |
| 114 | 1.2[a] | 0.14 | 115 | 632 | 293 |
| 116 | 26 | 12 | 117 | 163 | 47 |
| 118 | 23 | 2.8 | 119 | 23 | 0.97 |
| 120 | 27 | 3.1 | 121 | 37 | 10 |
| 122 | 25 | 0.30 | 123 | 189 | 135 |
| 124 | 19300 | 6950 | 125 | 20 | 0.50 |
| 126 | 20 | 1.4 | 127 | 34 | 5.1 |
| 128 | 2610 | — | 129 | 748 | 417 |
| 130 | 842 | 148 | 131 | 44 | 24 |
| 132 | 21 | 17 | 133 | 25 | 5.5 |
| 134 | 28 | 7.7 | 135 | 22 | 0.85 |

[a]IC$_{50}$ from the diluted FRET assay.

X-ray Crystal Structure Determination of Example Compounds Cocrystallized with the BACE1 Protein Protein expression, purification and crystallization Human BACE, CID1328 14-453, was cloned, expressed, refolded, activated and purified according to previously published protocols (Patel, S., Vuillard, L., Cleasby, A., Murray, C. W., Yon, J. J Mol Biol 2004, 343, 407). The protein buffer was exchanged to 20 mM Tris pH 8.5, 150 mM NaCl and concentrated to 3.5 mg/mL. Concentrated protein was mixed 1:1 with a stock of 11% PEG6k, 100 mM Na acetate pH 5.0 at RT and crystallized using vapor diffusion techniques in combination with seeding. The crystals were soaked with 10 mM of an example compound, 10% DMSO, 18% PEG6000, 90 mM Na acetate pH 4.85, 18 mM Tris pH 8.5 and 135 mM NaCl for 24 hours and flash frozen in liquid nitrogen using 20% glycerol as a cryoprotectant.

Data Collection and Refinement

X-ray diffraction data of Example 48 Isomer 1, Example 48 Isomer 7 or Example 48 Isomer 8 soaked crystals were collected at the European Synchrotron Radiation Facility beamlines ID23-1 and ID29, Grenoble France, to resolutions between 1.35-1.45 Å. Data of the compound of Example 20d Isomer 1 was collected on a Rigaku FR-E+SuperBright rotating anode and a HTC imaging plate to a resolution of 1.80 Å. All data were indexed and integrated with MOSFLM (Leslie, A. G. W. Joint CCP4+ESF-EAMCB Newsletter on Protein Crystallography 1992, 26, 27) and scaled with SCALA (Collaborative Computational Project 4, 1994) in space group P212121, with cell dimensions of about [48,76,105], giving a Matthews coefficient of 2.2 Å$^3$/Da with one monomer per asymmetric unit. The structures of Example 48 Isomer 1, Example 48 Isomer 7 and Example 48 Isomer 8 were determined by rigid body refinement of a previously determined BACE-1 structure based on the published 1FKN structure (Hong, L., Koelsch, G., Lin, X., Wu, S., Terzyan, S., Ghosh, A. K., Zhang, X. C., Tang, J. Science 2000, 290, 5489, 150-153) using Refmac5 (Murshudov, G. N., Vagin, A. A., Dodson, E. J. Acta Crystallogr., Sect. D 1997, 53, 240). The initial models were further refined by alternative cycles of model rebuilding in Coot (Emsley, P., Cowtan, K. Acta Crystallogr., Sect. D 2004, 60, 2126) and refinement in Refmac5 and AutoBuster (Bricogne, G., Blanc, E., Brandl, M., Flensburg, C., Keller, P., Paciorek, W., Roversi, P., Sharff, A., Smart, O., Vonrhein, C., Womack, T. Global Phasing Ltd, Cambridge, UK 2010). Strong 5-15 sigma Fo-Fc density in the vicinity of the BACE active site indicated the location of the bound compound. Restraints for the isomers of Example 48 were generated by Writedict (Wlodek S., Skillman A. G., Nicholls A., Acta Crystallogr., Sect. D 2006, 62, 741-749) and used by Flynn (Wlodek S., Skillman A. G., Nicholls A., Acta Crystallogr., Sect. D 2006, 62, 741-749) to determine the absolute configuration of the compound of interest based on the refined omit maps. Final refinement of the BACE-inhibitor complexes was performed in Refmac5 and AutoBuster. Resulting 2Fo-Fc maps of Example 20d Isomer 1, Example 48 Isomer 1, Example 48 Isomer 7 and Example 48 Isomer 8 can be seen in FIGS. 1-4. Full data collection and refinement statistics can be found in Table 3.

TABLE 3

Data collection and refinement statistics

| | Example 20d Isomer 1 | Example 48 Isomer 1 | Example 48 Isomer 8 | Example 48 Isomer 7 |
|---|---|---|---|---|
| Data collection | | | | |
| Space group | $P2_12_12_1$ | $P2_12_12_1$ | $P2_12_12_1$ | $P2_12_12_1$ |
| Cell dimensions (Å) | 47.8, 76.7, 104.8 | 47.9, 76.2, 104.7 | 47.9, 75.9, 104.5 | 48.6, 74, 104.6 |
| Resolution (Å) | 1.80-35.58 | 1.40-38.1 | 1.45-34.82 | 1.35-34.92 |
| $R_{merge}$ | 0.047 (0.452) | 0.057 (0.769) | 0.107 (1.502) | 0.088 (1.128) |
| $<I/\sigma I>$ | 14.1 (2.3) | 11.7 (1.2) | 8.6 (1.2) | 7.1 (1.0) |
| Completeness (%) | 93.6 (83.4) | 98.8 (89.5) | 100 (100) | 98.9 (96.5) |
| Redundancy | 3.8 (3.9) | 3.7 (2.7) | 4.6 (4.5) | 3.7 (3.2) |
| Refinement | | | | |
| Resolution (Å) | 1.80-30.0 | 1.40-30.0 | 1.45-30.0 | 1.35-25.0 |
| Measured reflections | 129173 | 281786 | 318526 | 303172 |
| Unique reflections | 33553 | 75301 | 68326 | 82658 |
| $R_{work}/R_{free}$ | 0.193/0.235 | 0.189/0.216 | 0.200/0.231 | 0.192/0.218 |
| No. atoms | | | | |
| Protein | 3014 | 3064 | 2978 | 3017 |
| Water | 183 | 310 | 318 | 313 |
| Ligand | 31 | 29 | 29 | 29 |
| Average B-factors | | | | |
| Protein (Å$^2$) | 29.6 | 18.9 | 18.5 | 16.3 |
| Water (Å$^2$) | 35.1 | 29.2 | 28.5 | 26.6 |
| Ligand (Å$^2$) | 22.7 | 16.0 | 16.1 | 16.4 |
| Ramachandran outliers (%) | 0.97 | 1.69 | 1.64 | 0.96 |
| R.m.s deviations | | | | |
| Bond lengths (Å) | 0.012 | 0.015 | 0.016 | 0.016 |
| Bond angles (°) | 1.58 | 1.62 | 1.66 | 1.69 |

[1]Values in parentheses refer to highest-resolution shell.

The invention claimed is:

1. A compound which is (1r,1'R,4R)-4-methoxy-5"-methyl-6'-[5-(prop-1-yn-1-yl)pyridin-3-yl]-3'H-dispiro[cyclohexane-1,2'-indene-1',2"-imidazol]-4"-amine or a pharmaceutically acceptable salt thereof.

2. A compound which is 3-[(1r,1'R,4R)-4"-amino-4-methoxy-5"-methyl-3'H-dispiro[cyclohexane-1,2'-indene-1',2"-imidazol]-6'-yl]-5-chlorobenzonitrile, or a pharmaceutically acceptable salt thereof.

3. A pharmaceutical composition, wherein the composition comprises:
a therapeutically effective amount of a compound or a pharmaceutically acceptable salt thereof according to claim 1, and
at least one pharmaceutically acceptable excipient, carrier or diluent.

4. A method of treating Alzheimer's Disease in a patient in need thereof, wherein the method comprises administering to said patient a therapeutically effective amount of a compound or a pharmaceutically acceptable salt thereof according to claim 1.

5. A method of treating Alzheimer's Disease in a patient in need thereof, wherein the method comprises administering to said patient a therapeutically effective amount of a pharmaceutically composition according to claim 3.

6. A pharmaceutical composition, wherein the composition comprises:
a therapeutically effective amount of a compound or a pharmaceutically acceptable salt thereof according to claim 2, and
at least one pharmaceutically acceptable excipient, carrier or diluent.

7. A method of treating Alzheimer's Disease in a patient in need thereof, wherein the method comprises administering to said patient a therapeutically effective amount of a compound or a pharmaceutically acceptable salt thereof according to claim 2.

8. A method of treating Alzheimer's Disease in a patient in need thereof, wherein the method comprises administering to said patient a therapeutically effective amount of a pharmaceutically composition according to claim 6.

* * * * *